United States Patent
Rosales et al.

(10) Patent No.: US 7,468,376 B2
(45) Date of Patent: Dec. 23, 2008

(54) PYRAZOLOPYRIDINE DERIVATES

(75) Inventors: Carmen Almansa Rosales, Barcelona (ES); Marina Virgili Bernadó, Barcelona (ES)

(73) Assignee: Palau Pharma, S.A., Palau-solita i Plegamans (ES)

( * ) Notice: Subject to any disclaimer, the term of this patent is extended or adjusted under 35 U.S.C. 154(b) by 348 days.

(21) Appl. No.: 10/547,232

(22) PCT Filed: Feb. 27, 2004

(86) PCT No.: PCT/EP2004/001974

§ 371 (c)(1),
(2), (4) Date: Aug. 26, 2005

(87) PCT Pub. No.: WO2004/076450

PCT Pub. Date: Sep. 10, 2004

(65) Prior Publication Data

US 2006/0167040 A1    Jul. 27, 2006

(30) Foreign Application Priority Data

Feb. 27, 2003  (ES) ............... 200300640
Mar. 14, 2003  (ES) ............... 200300727
Oct. 27, 2003  (ES) ............... 200302504

(51) Int. Cl.
A01N 57/00 (2006.01)
A61K 31/66 (2006.01)
C07D 471/02 (2006.01)
C07D 491/02 (2006.01)
C07D 498/02 (2006.01)
C07D 513/02 (2006.01)
C07D 515/02 (2006.01)

(52) U.S. Cl. ...................... 514/303; 546/119
(58) Field of Classification Search .......... 546/119; 514/303

See application file for complete search history.

(56) References Cited

U.S. PATENT DOCUMENTS

| 4,264,603 | A | 4/1981 | Lesher et al. |
| 4,375,467 | A | 3/1983 | Lesher et al. |
| 6,693,102 | B2 | 2/2004 | Stasch et al. |
| 7,135,568 | B2 | 11/2006 | Gerlach et al. |
| 2002/0013328 | A1 | 1/2002 | Sherk et al. |
| 2005/0070542 | A1 | 3/2005 | Hodgetts et al. |

FOREIGN PATENT DOCUMENTS

| BR | 1104145 | 2/1968 |
| EP | 0 063 754 A1 | 11/1982 |
| WO | 9501980 A1 | 1/1995 |
| WO | WO 99/30710 A1 | 6/1999 |
| WO | 0026216 A1 | 5/2000 |
| WO | 0127113 A2 | 4/2001 |
| WO | 0130778 A1 | 5/2001 |
| WO | WO 01/44244 A1 | 6/2001 |
| WO | WO 01/53268 A2 | 7/2001 |
| WO | 0194353 A1 | 12/2001 |
| WO | 0216359 A1 | 2/2002 |
| WO | WO 02/24694 A1 | 3/2002 |
| WO | WO 02/062795 A2 | 8/2002 |
| WO | WO 03/033502 A1 | 4/2003 |
| WO | 03/068773 | * 8/2003 |
| WO | WO 03/068773 A1 | 8/2003 |
| WO | WO 2004/014368 A1 | 2/2004 |
| WO | 2004056827 A2 | 7/2004 |
| WO | 2004099203 A1 | 11/2004 |
| WO | WO 2004/096130 A2 | 11/2004 |

OTHER PUBLICATIONS

Chen et al., Diabetologia, 2005, vol. 48, pp. 486-495.*
Witherington, Jason, et al., "6-Aryl-pyrazolo[3,4-*b*]pyridines: Potent Inhibitors of Glycogen Synthase Kinase-3 (GSK-3)," *Bioorganic & Medicinal Chemistry Letters*, 13 (2003) 3055-3057.
Witherington, Jason, et al., "6-Heteroaryl-pyrazolo[3,4-*b*]pyridines: Potent and Selective Inhibitors of Glycogen Synthase Kinase-3 (GSK-3)," *Bioorganic & Medicinal Chemistry Letters*, 13 (2003) 3059-3062.

* cited by examiner

*Primary Examiner*—D. Margaret Seaman
*Assistant Examiner*—Niloofar Rahmani
(74) *Attorney, Agent, or Firm*—Rothwell, Figg, Ernst & Manbeck

(57) ABSTRACT

New compounds of formula (I) and the salts, solvates and prodrugs thereof, wherein the meanings for the various substituents are as disclosed in the description. These compounds are useful as p38 kinase inhibitors.

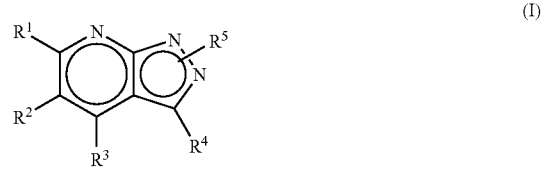

33 Claims, No Drawings

PYRAZOLOPYRIDINE DERIVATES

This application is a filing under 35 USC 371 of PCT/EP2004/001974, filed Feb. 27, 2004 and claims priority from Spanish patent application 2003 00640, filed Feb. 27, 2003, Spanish patent application 2003 00727, filed Mar. 14, 2003 and Spanish patent application 2003 02504, filed Oct. 27, 2003.

FIELD OF THE INVENTION

The present invention relates to a new series of pyrazolopyridine derivatives, a process to prepare them, pharmaceutical compositions containing these compounds and their application in medicine.

BACKGROUND OF THE INVENTION

Kinases are proteins involved in different cellular responses to external signals. In the Nineties, a new family of kinases called MAPK (mitogen-activated protein kinases) was discovered. MAPK activate their substrates by phosphorylation in serine and threonine residues.

MAPK are activated by other kinases in response to a wide range of signals including growth factors, pro-inflammatory cytokines, UV radiation, endotoxins and osmotic stress. Once they are activated, MAPK activate by phosphorylation other kinases or proteins, such as transcription factors, which, ultimately, induce an increase or a decrease in expression of a specific gene or group of genes.

The MAPK family includes kinases such as p38, ERK (extracellular-regulated protein kinase) and JNK (C-Jun N-terminal kinase).

Kinase p38 plays a crucial role in cellular response to stress and in the activation pathway in the synthesis of numerous cytokines, especially tumor necrosis factor (TNF-α), interleukin-1 (IL-1), interleukin-6 (IL-6) and interleukin-8 (IL-8).

IL-1 and TNF-α are produced by macrophages and monocytes and are involved in the mediation of immunoregulation processes and other physiopathological conditions. For example, elevated levels of TNF-α are associated with inflammatory and autoimmune diseases and with processes that trigger the degradation of connective and bone tissue such as rheumatoid arthritis, osteoarthritis, diabetes, inflammatory bowel disease and sepsis.

Thus, p38 kinase inhibitors could be useful to treat or prevent diseases mediated by cytokines such as IL-1 and TNF-α, as mentioned previously.

On the other hand, it has also been found that p38 inhibitors inhibit other pro-inflammatory proteins such as IL-6, IL-8, interferon-γ and GM-CSF (granulocyte-macrophage colony-stimulating factor). Moreover, in recent studies it has been found that p38 inhibitors not only block cytokine synthesis but also the cascade of signals that these induce, such as induction of the cyclooxygenase-2 enzyme (COX-2).

DESCRIPTION OF THE INVENTION

One aspect of the present invention relates to the new compounds of general formula I

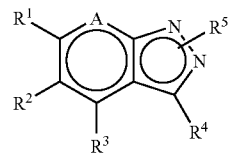

wherein:

A represents N or $N^+O^-$;

$R^1$ represents phenyl or Het optionally substituted with one or more substituents selected from $R^a$ and $R^b$;

$R^2$ represents Het optionally substituted with one or more substituents selected from $R^a$ and $R^b$;

$R^3$ represents H, Cy optionally substituted with one or more substituents selected from $R^a$ and $R^b$, or $R^3$ represents $C_{1-6}$alkyl optionally substituted with one or more substituents selected from $R^b$ and Cy*, wherein Cy* can be optionally substituted with one or more substituents selected from $R^b$ and $R^c$;

$R^4$ represents H, $R^a$, halogen, $-OR^{a'}$, $-OCOR^a$, $-OSO_2R^a$, $-OCONR^aR^{a'}$, $-NO_2$, $-CN$, $-COR^{a'}$, $-CO_2R^{a'}$, $-CONR^aR^{a'}$, $-NR^aR^{a'}$, $-NR^{a'}COR^{a'}$, $-NR^{a'}CONR^aR^{a'}$, $-NR^{a'}CO_2R^a$, $-NR^{a'}SO_2R^a$, $-SR^{a'}$, $-SOR^a$, $-SO_2R^a$ or $-SO_2NR^aR^{a'}$;

$R^5$ can be placed on any of the 2 N of the pyrazole ring of formula I and represents H or $R^f$;

each $R^a$ independently represents $C_{1-6}$alkyl, $C_{2-6}$alkenyl, $C_{2-6}$alkynyl or Cy, wherein the groups $C_{1-6}$alkyl, $C_{2-6}$alkenyl or $C_{2-6}$alkynyl can be optionally substituted with one or more substituents selected from $R^b$ and Cy*, and wherein any of the groups Cy or Cy* can be optionally substituted with one or more substituents selected from $R^b$ and $R^c$;

each $R^{a'}$ independently represents H or $R^a$;

each $R^b$ independently represents halogen, $-OR^{c'}$, $-OCOR^e$, $-OSO_2R^c$, $-OCONR^cR^{c'}$, $-NO_2$, $-CN$, $-COR^{c'}$, $-CO_2R^{c'}$, $-CONR^cR^{c'}$, $-CONR^{c'}NR^cR^{c'}$, $-NR^cR^{c'}$, $-NR^{c'}COR^{c'}$, $-NR^{c'}CONR^cR^{c'}$, $-NR^{c'}CO_2R^c$, $-NR^{c'}SO_2R^c$, $-SR^{c'}$, $-SOR^c$, $-SO_2R^c$, $-SO_2NR^cR^{c'}$, $-C(NR^{c'})NR^cR^{c'}$, $-C(NSO_2NR^{c'}R^{c'})NR^cR^{c'}$, $-C(NOR^{c'})R^{c'}$, $-C(NNR^cR^{c'})R^{c'}$, $-NR^{c'}C(NR^{c'})NR^cR^{c'}$ or $-NR^{c'}C(NCN)NR^cR^{c'}$;

each $R^c$ independently represents $C_{1-6}$alkyl, $C_{2-6}$alkenyl, $C_{2-6}$alkynyl or Cy, wherein all these groups can be optionally substituted with one or more substituents $R^d$;

each $R^{c'}$ independently represents H or $R^c$;

each $R^d$ independently represents halogen, $R^e$, $-OR^{e'}$, $-OCOR^e$, $-OSO_2R^e$, $-OCONR^eR^{e'}$, $-NO_2$, $-CN$, $-COR^{e'}$, $-CO_2R^{e'}$, $-CONR^eR^{e'}$, $CONR^{e'}NR^eR^{e'}$, $-NR^eR^{e'}$, $-NR^{e'}COR^{e'}$, $-NR^{e'}CONR^eR^{e'}$, $-NR^{e'}CO_2R^e$, $-NR^{e'}SO_2R^e$, $-SR^{e'}$, $-SOR^e$, $-SO_2R^e$, $-SO_2NR^eR^{e'}$, $-C(NR^{e'})NR^eR^{e'}$, $-C(NSO_2NR^{e'}R^{e'})NR^eR^{e'}$, $-C(NOR^{e'})R^{e'}$, $-C(NNR^eR^{e'})R^{e'}$, $-NR^{e'}C(NR^{e'})NR^eR^{e'}$ or Cy optionally substituted with one or more substituents selected from halogen, $R^e$, $-OR^{e'}$, $-OCOR^e$, $-OSO_2R^e$, $-OCONR^eR^{e'}$, $-NO_2$, $-CN$, $-COR^{e'}$, $-CO_2R^{a'}$, $-CONR^eR^{e'}$, $CONR^{e'}NR^eR^{e'}$, $-NR^eR^{e'}$, $-NR^{e'}COR^{e'}$, $-NR^{e'}CONR^eR^{e'}$, $-NR^{e'}CO_2R^e$, $-NR^{e'}SO_2R^e$, $-SR^{e'}$, $-SOR^e$, $-SO_2R^e$, $-SO_2NR^eR^{e'}$, $-C(NR^{e'})NR^eR^{e'}$, $-C(NSO_2NR^{e'}R^{e'})NR^eR^{e'}$, $-C(NOR^{e'})R^{e'}$, $-C(NNR^eR^{e'})R^{e'}$, $-NR^{e'}C(NR^{e'})NR^eR^{e'}$ and $-NR^{e'}C(NCN)NR^eR^{e'}$;

each $R^e$ independently represents $C_{1-6}$alkyl or halo$C_{1-6}$alkyl;
each $R^{e'}$ independently represents H or $R^e$;
$R^f$ represents $C_{1-6}$alkyl, $C_{2-6}$alkenyl, $C_{2-6}$alkynyl or Cy, wherein the groups $C_{1-6}$alkyl, $C_{2-6}$alkenyl or $C_{2-6}$alkynyl can be optionally substituted with one or more substituents selected from $R^g$ and Cy*, and wherein any of the groups Cy or Cy* can be optionally substituted with one or more substituents selected from $R^g$ and $R^a$;
each $R^g$ independently represents halogen, —$OR^{a'}$, —$OCOR^a$, —$OSO_2R^a$, —$OCONR^aR^{a'}$, —$NO_2$, —$CN$, —$COR^{a'}$, —$CO_2R^{a'}$, —$CONR^aR^{a'}$, —$CONR^{a'}NR^aR^{a'}$, —$NR^aR^{a'}$, —$NR^{a'}COR^{a'}$, —$NR^{a'}CONR^aR^{a'}$, —$NR^{a'}CO_2R^a$, —$NR^{a'}SO_2R^a$, —$SR^{a'}$, —$SOR^a$, —$SO_2R^a$, —$SO_2NR^aR^{a'}$, —$C(NR^{a'})NR^aR^{a'}$, —$C(NSO_2NR^aR^{a'})NR^aR^{a'}$, —$C(NOR^{a'})R^{a'}$, —$C(NNR^aR^{a'})R^{a'}$, —$NR^{a'}C(NR^{a'})NR^aR^{a'}$ or —$NR^{a'}C(NCN)NR^aR^{a'}$;

Het in the above definitions represents pyridine, pyrazine, pyrimidine, pyridazine, 2(1H)-pyridone, 2(1H)-pyrazinone, 2(1H)-pyrimidinone or 2(1H)-pyridazinone;

Cy or Cy* in the above definitions represent a partially unsaturated, saturated or aromatic 3- to 7-membered monocyclic or 8- to 12-membered bicyclic carbocyclic ring, which optionally contains from 1 to 4 heteroatoms selected from N, S and O, which can optionally contain 1 or 2 oxo groups when the ring is saturated or partially unsaturated, and wherein said ring or rings can be bonded to the rest of the molecule through a carbon or a nitrogen atom.

The present invention also relates to the addition salts of the compounds of the invention as well as their solvates and prodrugs. A prodrug is defined as any precursor of a compound of formula I that can be transformed in vivo into a compound of formula I.

Some compounds of formula I can have chiral centres that can give rise to various stereoisomers. The present invention relates to each of these stereoisomers and also mixtures thereof. Moreover, some of the compounds of the present invention can show cis/trans isomers. The present invention relates to each of the geometric isomers and mixtures thereof.

The compounds of formula I are selective p38 kinase inhibitors.

Thus, another aspect of this invention relates to the pharmaceutical compositions which comprise an effective amount of a compound of formula I or a pharmaceutically acceptable salt, solvate or prodrug thereof and one or more pharmaceutically acceptable excipients.

Another aspect of the present invention relates to the use of a compound of formula I or a pharmaceutically acceptable salt, solvate or prodrug thereof for the manufacture of a medicament for the treatment or prevention of diseases mediated by p38.

Another aspect of the present invention relates to the use of a compound of formula I or a pharmaceutically acceptable salt, solvate or prodrug thereof for the manufacture of a medicament for the treatment or prevention of diseases mediated by cytokines.

Another aspect of the present invention relates to the use of a compound of formula I or a pharmaceutically acceptable salt, solvate or prodrug thereof for the manufacture of a medicament for the treatment or prevention of diseases mediated by TNF-α, IL-1, IL-6 and/or IL-8.

Another aspect of the present invention relates to the use of a compound of formula I or a pharmaceutically acceptable salt, solvate or prodrug thereof for the manufacture of a medicament for the treatment or prevention of a disease selected from immune, autoimmune and inflammatory diseases, cardiovascular diseases, infectious diseases, bone resorption disorders, neurodegenerative diseases, proliferative diseases and processes associated with the induction of cyclooxygenase-2.

Another aspect of the present invention relates to the use of a compound of formula I or a pharmaceutically acceptable salt, solvate or prodrug thereof for the treatment or prevention of diseases mediated by p38.

Another aspect of the present invention relates to the use of a compound of formula I or a pharmaceutically acceptable salt, solvate or prodrug thereof for the treatment or prevention of diseases mediated by cytokines.

Another aspect of the present invention relates to the use of a compound of formula I or a pharmaceutically acceptable salt, solvate or prodrug thereof for the treatment or prevention of diseases mediated by TNF-α, IL-1, IL-6 and/or IL-8.

Another aspect of the present invention relates to the use of a compound of formula I or a pharmaceutically acceptable salt, solvate or prodrug thereof for the treatment or prevention of a disease selected from immune, autoimmune and inflammatory diseases, cardiovascular diseases, infectious diseases, bone resorption disorders, neurodegenerative diseases, proliferative diseases and processes associated with the induction of cyclooxygenase-2.

Another aspect of the present invention relates to a method of treating or preventing diseases mediated by p38 in a subject in need thereof, especially a human being, which comprises administering to said subject a therapeutically effective amount of a compound of formula I or a pharmaceutically acceptable salt, solvate or prodrug thereof.

Another aspect of the present invention relates to a method of treating or preventing diseases mediated by cytokines in a subject in need thereof, especially a human being, which comprises administering to said subject a therapeutically effective amount of a compound of formula I or a pharmaceutically acceptable salt, solvate or prodrug thereof.

Another aspect of the present invention relates to a method of treating or preventing diseases mediated by TNF-α, IL-1, IL-6 and/or IL-8 in a subject in need thereof, especially a human being, which comprises administering to said subject a therapeutically effective amount of a compound of formula I or a pharmaceutically acceptable salt, solvate or prodrug thereof.

Another aspect of the present invention relates to a method of treating or preventing a disease selected from immune, autoimmune and inflammatory diseases, cardiovascular diseases, infectious diseases, bone resorption disorders, neurodegenerative diseases, proliferative diseases and processes associated with the induction of cyclooxygenase-2 in a subject in need thereof, especially a human being, which comprises administering to said subject a therapeutically effective amount of a compound of formula I or a pharmaceutically acceptable salt, solvate or prodrug thereof.

Another aspect of the present invention relates to a process for the preparation of a compound of formula 1, which comprises:

(a) reacting a ketone of formula IV

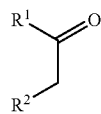

IV wherein $R^1$ and $R^2$ have the meaning described above, with an aminopyrazole of formula V and an aldehyde of formula VI

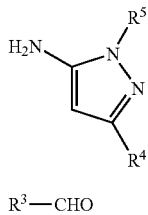

wherein $R^3$, $R^4$ and $R^5$ have the meaning described above; or (b) when in a compound of formula I, $R^5$ represents H and $R^3$ has the same meaning as $R^1$, reacting a ketone of formula IV or an enolate of formula VII

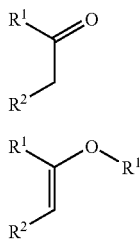

wherein $R^1$ and $R^2$ have the meaning described above, with an aminopyrazole of formula Va

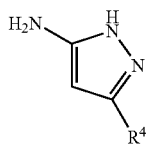

wherein $R^4$ has the meaning described above; or (c) when in a compound of formula I $R^4$ represents $NH_2$, treating a compound of formula XIX

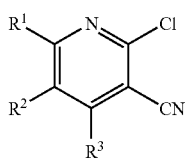

wherein $R^1$, $R^2$ and $R^3$ have the meaning described above, with a hydrazine of formula VIIIa $$NH_2\text{—}NHR^5 \qquad \text{VIIIa}$$

wherein $R^5$ has the meaning described above; or (d) converting, in one or a plurality of steps, a compound of formula I into another compound of formula I; and (e) if desired, after the previous steps, reacting a compound of formula I with a base or an acid to give the corresponding salt.

In the previous definitions, the term $C_{1-6}$alkyl, as a group or part of a group, means a straight or branched alkyl chain which contains from 1 to 6 carbon atoms. Examples include among others the groups methyl, ethyl, propyl, isopropyl, butyl, isobutyl, sec-butyl, tert-butyl, pentyl, isopentyl, neopentyl and hexyl.

A halo$C_{1-6}$alkyl group means a group resulting from the replacement of one or more hydrogen atoms from a $C_{1-6}$alkyl group with one or more halogen atoms (i.e. fluoro, chloro, bromo or iodo), which can be the same or different. Examples include, among others, trifluoromethyl, fluoromethyl, 1-chloroethyl, 2-chloroethyl, 1-fluoroethyl, 2-fluoroethyl, 2-bromoethyl, 2-iodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, nonafluorobutyl, 5-fluoropentyl and 6-fluorohexyl.

The term $C_{2-6}$alkenyl, as a group or part of a group, means a straight or branched alkyl chain which contains from 2 to 6 carbon atoms and that also contains one or more double bonds. Examples include, among others, the groups ethenyl, 1-propenyl, 2-propenyl, isopropenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl and 5-hexenyl.

The term $C_{2-6}$alkynyl, as a group or part of a group, means a straight or branched alkyl chain which contains from 2 to 6 carbon atoms and that also contains one or more triple bonds. Examples include the groups ethynyl, 1-propynyl, 2-propynyl, 1-butynyl, 2-butynyl, 3-butynyl, 1,3-butadiynyl, 1-pentynyl, 2-pentynyl, 3-pentynyl, 4-pentynyl, 1-hexynyl, 2-hexynyl, 3-hexynyl, 4-hexynyl and 5-hexynyl.

An oxo group means a carbonyl group (—CO—).

A halogen radical means fluoro, chloro, bromo or iodo.

Het in the definitions of $R^1$ and $R^2$ means pyridine, pyrazine, pyrimidine, pyridazine, 2(1H)-pyridone, 2(1H)-pyrazinone, 2(1H)-pyrimidinone or 2(1H)-pyridazinone. As mentioned previously, these groups can be optionally substituted with one or more substituents selected from $R^a$ and $R^b$, which can be placed on any available position of the Het group, and can be bonded to the rest of the molecule via any available carbon or nitrogen atom.

The term Cy or Cy*, as a group or part of a group, means a 3- to 7-membered monocyclic carbocyclic group or an 8- to 12-membered bicyclic carbocyclic group which can be partially unsaturated, saturated or aromatic and which can optionally contain from 1 to 4 heteroatoms selected from N, S and O. When the Cy or Cy* group is saturated or partially unsaturated, it can optionally contain 1 or 2 oxo groups. The Cy or Cy* ring or rings can be substituted as mentioned in the definition of general formula I, these substituents being placed on any available position, and can be bonded to the rest of the molecule through any available carbon or nitrogen atom. Examples of Cy or Cy* groups include, among others, cyclopropane, cyclobutane, cyclopentane, cyclohexane, cycloheptane, aziridine, oxirane, oxetane, imidazolidine, isothiazolidine, isoxazolidine, oxazolidine, pyrazolidine, pyrrolidine, thiazolidine, dioxane, morpholine, piperazine, piperidine, pyran, tetrahydropyran, azepine, oxazine, oxazoline, pyrroline, thiazoline, pyrazoline, imidazoline, isoxazoline, isothiazoline, phenyl, naphthyl, 1,2,4-oxadiazole, 1,2,4-thiadiazole, 1,3,4-oxadiazole, 1,3,4-thiadiazole, furan, imidazole, isoxazole, isothiazole, oxazole, pyrazole, pyrrole, thiazole, thiophene, 1,2,3-triazole, 1,2,4-triazole, pyrazine, pyridazine, pyridine, pyrimidine, benzimidazole, benzofuran, benzothiazole, benzothiophene, imidazopyrazine, imidazopyridazine, imidazopyridine, imidazopyrimidine, indazole, indole, isoindole, isoquinoline, tetrahydroisoquinoline, naphthyridine, pyrazolopyrazine, pyrazolopyridine, pyrazolopyrimidine, purine, quinazoline, quinoline, quinoxaline, cyclobutanone, cyclopentanone, cyclohexanone, cycloheptanone, pyrrolidin-2-one, piperidin-2-one, piperidin-4-one, 2(1H)-pyridone, 2(1H)-pyrazinone, 2(1H)-pyrimidinone, 2(1H)-pyridazinone and phthalimide.

The term heteroaryl, as a group or part of a group, means an aromatic 5- or 6-membered monocyclic or 8- to 12-membered bicyclic ring which contains from 1 to 4 heteroatoms selected from N, S and O and which can be optionally substituted as disclosed whenever this term is used, wherein said substituents can be placed on any available position. The heteroaryl group can be bonded to the rest of the molecule through any available carbon or nitrogen atom. Examples of heteroaryl groups include among others 1,2,4-oxadiazole, 1,2,4-thiadiazole, 1,3,4-oxadiazole, 1,3,4-thiadiazole, furan, imidazole, isoxazole, isothiazole, oxazole, pyrazole, pyrrole, thiazole, thiophene, 1,2,3-triazole, 1,2,4-triazole, pyrazine, pyridazine, pyridine, pyrimidine, benzimidazole, benzofuran, benzothiazole, benzothiophene, imidazopyrazine, imidazopyridazine, imidazopyridine, imidazopyrimidine, indazole, indole, isoindole, isoquinoline, naphthiridine, pyrazolopyrazine, pyrazolopyridine, pyrazolopyrimidine, purine, quinazoline, quinoline and quinoxaline.

In the previous definitions of Het, heteroaryl, Cy and Cy*, the term is meant to be the radical derived from the corresponding cycle.

In the previous definitions of heteroaryl, Cy and Cy*, when the specified examples refer to a bicycle in general terms, all possible dispositions of the atoms are included. For example, the term pyrazolopyridine is to be understood as including groups such as 1H-pyrazolo[3,4-b]pyridine, pyrazolo[1,5-a]pyridine, 1H-pyrazolo[3,4-c]pyridine, 1H-pyrazolo[4,3-c]pyridine and 1H-pyrazolo[4,3-b]pyridine; the term imidazopyrazine is to be understood as including groups such as 1H-imidazo[4,5-b]pyrazine, imidazo[1,2-a]pyrazine and imidazo[1,5-a]pyrazine and the term pyrazolopyrimidine is to be understood as including groups such as 1H-pyrazolo[3,4-d]pyrimidine, 1H-pyrazolo[4,3-d]pyrimidine, pyrazolo[1,5-a]pyrimidine and pyrazolo[1,5-c]pyrimidine.

The expression "optionally substituted with one or more" means that a group can be substituted with one or more, preferably with 1, 2, 3 or 4 substituents, provided that this group has 1, 2, 3 or 4 positions susceptible of being substituted.

In the previous definitions, when it is mentioned that $R^5$ can be placed on any one of the 2 N of the pyrazole ring this means that $R^5$ can be placed on the N at position 1 of the ring or on the N at position 2. Thus, the compounds of formula I include the following two types of compounds:

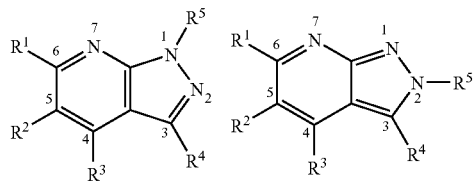

An embodiment of the invention are those compounds of formula I as defined above wherein A represents N.

Another embodiment of the invention are the compounds of formula I wherein A represents N and $R^5$ can be placed on any of the 2 N of the pyrazole ring of formula I and represents H or $R^a$.

Another embodiment of the invention are the compounds of formula I wherein when $R^3$ and $R^5$ both represent H and $R^2$ represents Het optionally substituted with one or more substituents selected from halogen, —CN, —CF$_3$, —OH, —NO$_2$, —OR$^6$, —NR$^6$R$^6$, —OCF$_3$, C$_{1-6}$alkyl, C$_{2-6}$alkenyl, C$_{2-6}$alkynyl and Cy can be optionally substituted with one or more substituents selected from $R^b$ and $R^c$, and wherein $R^6$ represents C$_{1-6}$alkyl, then $R^4$ is not —NR$^{a'}$COR$^a$, —NHCONHR$^a$ or —NHCO$_2$R$^a$.

Another embodiment of the invention are the compounds of formula I wherein when $R^3$ and $R^5$ both represent H, then $R^4$ is not —NR$^{a'}$COR$^a$, —NHCONHR$^a$ or —NHCO$_2$R$^a$.

Another embodiment of the invention are the compounds of formula I wherein A represents N; $R^4$ represents H, $R^a$, halogen, —OR$^a$, —OCOR$^a$, —OSO$_2$R$^a$, —OCONR$^{a'}$R$^{a'}$, —NO$_2$, —CN, —COR$^{a'}$, —CO$_2$R$^a$, —CONR$^{a'}$R$^a$, —NR$^{a'}$R$^{a'}$, —NR$^{a'}$SO$_2$R$^a$, —SR$^{a'}$, —SOR$^a$, —SO$_2$R$^a$ or —SO$_2$NR$^{a'}$R$^{a'}$; and $R^5$ can be placed on any of the 2 N of the pyrazole ring of formula I and represents H or $R^a$.

Another embodiment of the invention are the compounds of formula I wherein $R^1$ represents pyridine or phenyl, wherein all these groups can be optionally substituted with one or more substituents selected from $R^a$ and $R^b$.

Another embodiment of the invention are the compounds of formula I wherein $R^1$ represents phenyl optionally substituted with one or more substituents selected from $R^a$ and $R^b$.

Another embodiment of the invention are the compounds of formula I wherein $R^1$ represents phenyl optionally substituted with one or more substituents selected from halogen, —OR$^{c'}$, —NO$_2$, —CN, —CONR$^{c'}$R$^{c'}$, —NR$^{c'}$R$^{c'}$ and C$_{1-6}$alkyl optionally substituted with one or more substituents selected from halogen, —OR$^{c'}$, —COR$^{c'}$, —NR$^{c'}$R$^{c'}$ and —NR$^{c'}$COR$^{c'}$.

Another embodiment of the invention are the compounds of formula I wherein $R^1$ represents phenyl optionally substituted with one or more substituents selected from halogen and haloC$_{1-6}$alkyl.

Another embodiment of the invention are the compounds of formula I wherein $R^2$ represents pyridine or pyrimidine, wherein all these groups can be optionally substituted with one or more substituents selected from $R^a$ and $R^b$.

Another embodiment of the invention are the compounds of formula I wherein $R^2$ represents 4-pyridine or 4-pyrimidine, wherein all these groups can be optionally substituted with one or more substituents selected from $R^a$ and $R^b$.

Another embodiment of the invention are the compounds of formula I wherein $R^2$ represents 4-pyridine or 4-pyrimidine, wherein all these groups can be optionally substituted with one or more substituents selected from halogen, —OR$^{c'}$, —NR$^{c'}$R$^{c'}$, —SR$^{c'}$ and —SO$_2$R$^c$.

Another embodiment of the invention are the compounds of formula I wherein $R^2$ represents 4-pyridine.

Another embodiment of the invention are the compounds of formula I wherein $R^2$ represents 4-pyrimidine substituted with —NR$^{c'}$R$^{c'}$, wherein in $R^2$:
each $R^{c'}$ independently represents H or $R^c$;
each $R^c$ independently represents C$_{1-6}$alkyl optionally substituted with one or more substituents selected from Cy and —OR$^{e'}$; and
each $R^{e'}$ independently represents H or $R^e$.

Another embodiment of the invention are the compounds of formula I wherein $R^3$ represents H or Cy optionally substituted with one or more substituents selected from $R^a$ and $R^b$.

Another embodiment of the invention are the compounds of formula I wherein $R^3$ represents H, heteroaryl or phenyl, wherein all these groups can be optionally substituted with one or more substituents selected from $R^a$ and $R^b$.

Another embodiment of the invention are the compounds of formula I wherein $R^3$ represents heteroaryl or phenyl, wherein all these groups can be optionally substituted with one or more substituents selected from $R^a$ and $R^b$.

Another embodiment of the invention are the compounds of formula I wherein $R^3$ represents monocyclic heteroaryl or phenyl, wherein all these groups can be optionally substituted with one or more substituents selected from halogen, —$NO_2$, —$OR^{c'}$, $C_{1-6}$alkyl and Cy, wherein $C_{1-6}$alkyl can be optionally substituted with one or more substituents selected from $R^b$ and Cy*, and any of the groups Cy or Cy* can be optionally substituted with one or more substituents selected from $R^b$ and $R^c$.

Another embodiment of the invention are the compounds of formula I wherein $R^3$ represents monocyclic heteroaryl or phenyl, wherein all these groups can be optionally substituted with one or more substituents selected from halogen, —$NO_2$, —$OR^{c'}$, $C_{1-6}$alkyl, halo$C_{1-6}$alkyl and Cy; and wherein in $R^3$:
each $R^{c'}$ independently represents H or $R^c$;
each $R^c$ independently represents $C_{1-6}$alkyl optionally substituted with one or more substituents $R^d$; and
each $R^d$ independently represents Cy.

Another embodiment of the invention are the compounds of formula I wherein $R^4$ represents H, $R^a$, halogen, —$OR^{a'}$, —CN, —$CONR^a R^{a'}$, —$NR^a R^{a'}$ or —$NR^{a'}COR^{a'}$.

Another embodiment of the invention are the compounds of formula I wherein $R^4$ represents H.

Another embodiment of the invention are the compounds of formula I wherein $R^5$ represents H or $R^5$ represents $R^f$ and is placed on the N at position 2 of the pyrazole ring.

Another embodiment of the invention are the compounds of formula I wherein $R^5$ represents $R^f$ and is placed on the N at position 2 of the pyrazole ring.

Another embodiment of the invention are the compounds of formula I wherein $R^f$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^g$ and Cy*, and wherein any of the groups Cy or Cy* can be optionally substituted with one or more substituents selected from $R^g$ and $R^a$.

Another embodiment of the invention are the compounds of formula I wherein $R^f$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^g$ and CY*, and wherein any of the groups Cy or Cy* can be optionally substituted with one or more substituents selected from $R^g$ and $R^a$, wherein each $R^g$ independently represents halogen, —$OR^{a'}$, —$COR^{a'}$, —$CO_2R^{a'}$, —$CONR^a R^{a'}$, —$NR^a R^{a'}$, —$NR^{a'}COR^{a'}$, —$NR^{a'}CONR^a R^{a'}$, —$NR^{a'}SO_2R^{a'}$, —$SR^{a'}$, —$SOR^{a'}$ or —$SO_2R^{a'}$.

Another embodiment of the invention are the compounds of formula I wherein $R^f$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^g$ and Cy*, and wherein any of the groups Cy or Cy* can be optionally substituted with one or more substituents selected from $R^g$ and $R^a$, wherein in $R^f$:
each $R^g$ independently represents —$OR^{a'}$, —$COR^{a'}$, —$CONR^a R^{a'}$, —$NR^a R^{a'}$, —$NR^{a'}COR^{a'}$, —$NR^{a'}CONR^a R^{a'}$, —$NR^{a'}SO_2R^{a'}$, —$SOR^{a'}$ or —$SO_2R^{a'}$;
each $R^{a'}$ independently represents H or $R^a$;
each $R^a$ independently represents Cy or $C_{1-6}$alkyl, wherein $C_{1-6}$alkyl can be optionally substituted with one or more substituents selected from $R^b$ and Cy*, and any of the groups Cy or Cy* can be optionally substituted with one or more substituents selected from $R^b$ and $R^c$;
each $R^b$ independently represents —$OR^{c'}$, —$NR^c R^{c'}$, —CN, —$COR^{c'}$, —$SR^c$ or —$SOR^{c'}$;
each $R^{c'}$ independently represents H or $R^c$;
each $R^c$ independently represents $C_{1-6}$alkyl or Cy, wherein all these groups can be optionally substituted with one or more $R^d$.

Another embodiment of the invention are the compounds of formula I wherein $R^5$ is placed on the N at position 2 of the pyrazole ring and represents $R^f$, wherein $R^f$ represents $C_{1-6}$alkyl optionally substituted with one or more substituents selected from —$OR^{a'}$, —$COR^{a'}$, —$CONR^a R^{a'}$, —$NR^a R^{a'}$, —$NR^{a'}COR^{a'}$, —$NR^{a'}CONR^a R^{a'}$—$NR^{a'}SO_2R^{a'}$ and Cy* optionally substituted with one or more substituents selected from $R^a$; wherein in $R^f$:
each $R^{a'}$ independently represents H or $R^a$;
each $R^a$ independently represents Cy or $C_{1-6}$alkyl, wherein $C_{1-6}$alkyl can be optionally substituted with one or more substituents selected from $R^b$ and Cy*, and any of the groups Cy or Cy* can be optionally substituted with one or more substituents selected from $R^b$ and $R^c$;
each $R^b$ independently represents —$OR^{c'}$, —$NR^c R^{c'}$, —CN, —$COR^{c'}$, —$SR^{c'}$ or —$SOR^{c'}$;
each $R^{c'}$ independently represents H or $R^c$;
each $R^c$ independently represents $C_{1-6}$alkyl or Cy, wherein all these groups can be optionally substituted with one or more $R^d$; and
each $R^d$ independently represents —$OR^{e'}$.

Another embodiment of the invention are the compounds of formula I wherein $R^5$ represents H or $R^5$ represents $R^a$ and is placed on the N at position 2 of the pyrazole ring.

Another embodiment of the invention are the compounds of formula I wherein $R^5$ represents $R^a$ and is placed on the N at position 2 of the pyrazole ring.

Another embodiment of the invention are the compounds of formula I wherein $R^a$ in $R^5$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^b$ and Cy*, and wherein any of the groups Cy or Cy* can be optionally substituted with one or more substituents selected from $R^b$ and $R^c$.

Another embodiment of the invention are the compounds of formula I wherein $R^a$ in $R^5$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^b$ and Cy*, and wherein any of the groups Cy or Cy* can be optionally substituted with one or more substituents selected from $R^b$ and $R^c$, wherein each $R^b$ in $R^5$ independently represents halogen, —$OR^{c'}$, —$COR^{c'}$, —$CO_2R^{c'}$, —$CONR^c R^{c'}$, —$NR^c R^{c'}$, —$NR^{c'}COR^{c'}$, —$NR^{c'}CONR^c R^{c'}$, —$NR^{c'}SO_2R^{c'}$, —$SR^{c'}$, —$SOR^{c'}$ or —$SO_2R^{c'}$.

Another embodiment of the invention are the compounds of formula I wherein $R^a$ in $R^5$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^b$ and Cy*, and wherein any of the groups Cy or Cy* can be optionally substituted with one or more substituents selected from $R^b$ and $R^c$, wherein in $R^5$:
each $R^b$ independently represents —$OR^{c'}$, —$COR^{c'}$, —$CONR^c R^{c'}$, —$NR^c R^{c'}$, —$NR^{c'}COR^{c'}$, —$NR^{c'}CONR^c R^{c'}$, —$NR^{c'}SO_2R^{c'}$, —$SOR^{c'}$ or —$SO_2R^{c'}$;
each $R^{c'}$ independently represents H or $R^c$;
each $R^c$ independently represents Cy or $C_{1-6}$alkyl, wherein all these groups can be optionally substituted with one or more substituents selected from $R^d$;

each $R^d$ independently represents $R^e$, —$OR^{e'}$, —$NR^{e'}R^{e'}$, —CN, —$COR^{e'}$, —$SR^{e'}$, —$SOR^{e'}$ or Cy.

Another embodiment of the invention are the compounds of formula I wherein $R^5$ is placed on the N at position 2 of the pyrazole ring and represents $R^a$, wherein $R^a$ in $R^5$ represents $C_{1-6}$alkyl optionally substituted with one or more substituents selected from —$OR^{e'}$, —$COR^{e'}$, —$CONR^{e'}R^{e'}$, —$NR^{e'}R^{e'}$, —$NR^{e'}COR^{e'}$, —$NR^{e'}CONR^{e'}R^{e'}$, —$NR^{e'}SO_2R^{e'}$ and Cy* optionally substituted with one or more substituents selected from $R^c$; wherein in $R^5$:

each $R^{c'}$ independently represents H or $R^c$;
each $R^c$ independently represents Cy or $C_{1-6}$alkyl, wherein all these groups can be optionally substituted with one or more substituents selected from $R^d$;
each $R^d$ independently represents —$OR^{e'}$, —$NR^{e'}R^{e'}$, —CN, —$COR^{e'}$, —$SR^{e'}$, —$SOR^{e'}$ or Cy;
each $R^{e'}$ independently represents H or $R^e$; and
each $R^e$ independently represents $C_{1-6}$alkyl.

Furthermore, all possible combinations of the above-mentioned embodiments form also part of this invention.

The compounds of the present invention may contain one or more basic nitrogens and may, therefore, form salts with organic or inorganic acids that also form part of this invention. Examples of these salts include: salts with inorganic acids such as hydrochloric acid, hydrobromic acid, hydroiodic acid, nitric acid, perchloric acid, sulfuric acid or phosphoric acid, and salts with organic acids such as methanesulfonic acid, trifluoromethanesulfonic acid, ethanesulfonic acid, benzenesulfonic acid, p-toluenesulfonic acid, fumaric acid, oxalic acid, acetic acid or malic acid, among others. The compounds of the present invention may contain one or more acidic protons and, therefore, they may also form salts with bases, which also form part of the present invention. Examples of these salts include: salts with inorganic cations such as sodium, potassium, calcium, magnesium, lithium, aluminium, zinc, etc; and salts formed with pharmaceutically acceptable amines such as ammonia, alkylamines, hydroxylalkylamines, lysine, arginine, N-methylglucamine, procaine and the like b. There is no limitation on the type of salt that can be used provided that these are pharmaceutically acceptable when they are used for therapeutic purposes. Salts can be prepared by treating the compound of formula I with a sufficient amount of the desired acid or base to give a salt in the conventional manner. The compounds of formula I and their salts differ in some physical properties but they are equivalent for the purposes of the present invention.

Some of the compounds of the present invention can exist in solvated form, including hydrated forms. In general, the solvated forms with pharmaceutically acceptable solvents such as water, ethanol and the like are equivalent to the unsolvated form for the purposes of the invention.

Some of the compounds of the present invention may exist as several diastereoisomers and/or several optical isomers. Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on products of general formula I. Optically pure isomers can also be individually obtained using enantiospecific synthesis. The present invention covers all isomers and mixtures thereof (for example racemic mixtures) whether obtained by synthesis and also by physically mixing them.

Moreover, some compounds of the present invention may exhibit cis/trans isomers. The present invention includes each of the geometric isomers and its mixtures.

The compounds of formula I can be obtained by following the processes described below. As it is obvious to one skilled in the art the exact method used to prepare a given compound can vary depending on its chemical structure. Moreover, in some of the processes described below it may be necessary or advisable to protect the reactive or labile groups by conventional protective groups. Both the nature of these protective groups and the procedures followed to introduce or remove these are well known and form part of the state of the art (see for example Greene T. W. and Wuts P. G. M, "Protective Groups in Organic Synthesis", John Wiley & Sons, $3^{rd}$ edition, 1999). As an example, as protective groups of an amino function tert-butoxycarbonyl (Boc) or benzyl (Bn) can be used. The carboxyl groups can be protected for example in the form of $C_{1-6}$alkyl esters or arylalkyl esters, such as benzyl, while the hydroxyl groups can be protected for example with tetrahydropyranyl (THP). Whenever a protective group is present a later deprotection step will be required, which can be performed under standard conditions in organic synthesis, such as those described in the above-mentioned reference.

The compounds of formula I can be obtained in general by reaction of a compound of formula IV with an aminopyrazole of formula V and an aldehyde of formula VI, as shown in the following scheme:

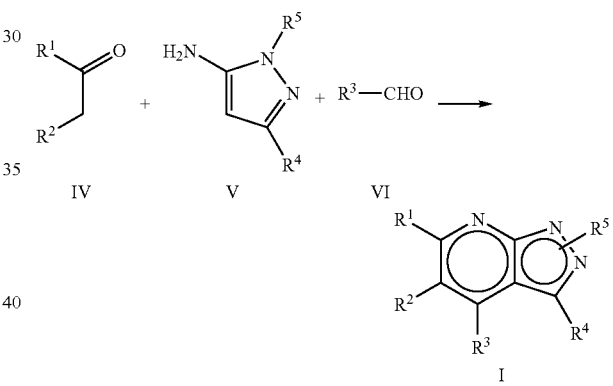

wherein $R^1$, $R^2$, $R^3$, $R^4$ and $R^5$ have the same meaning as in general formula I. This reaction is carried out preferably in the presence of an inorganic acid such as hydrochloric acid, in a suitable polar solvent such as 2-methoxyethanol or ethanol, and heating, preferably to reflux.

The compounds of formula I wherein $R^5$ represents $R^{5*}$ (i.e. compounds of formula Ia and Ib) are generally obtained by reaction of a compound of formula I wherein $R^5$ represents H (i.e. a compound of formula Ic) with an alkylating agent of formula $R^{5*}$—X (II), as shown in the following scheme:

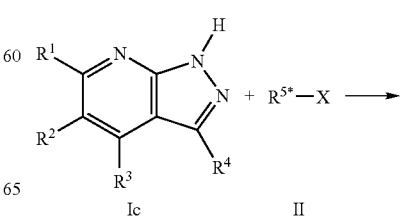

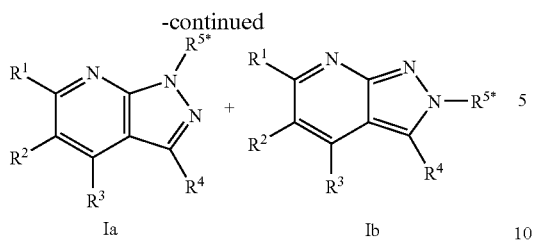

Ia    Ib

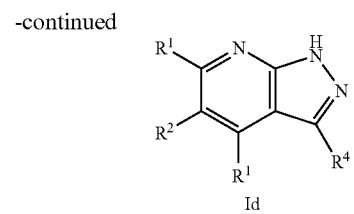

Id wherein $R^{5*}$ represents $R^a$ or $R^f$. $R^1$, $R^2$, $R^3$, $R^4$, $R^a$ and $R^f$ have the meaning described in general formula I and X represents a leaving group, for example an alkylsulfonate or an arylsulfonate such as mesylate or tosylate, or a halogen such as Cl, Br or I. This reaction is performed in the presence of a base such as KOH, $K_2CO_3$ or NaH in a suitable solvent, such as for example acetone, toluene, dimethylformamide, 1,2-dimethoxyethane or diglyme, and heating, preferably to reflux. In the case of using apolar solvents such as toluene this reaction can be carried out in the presence of a cation sequestering agent such as-crown ether 18-C-6 or a phase transfer agent such as a tetraalkylammonium salt.

Compounds of formula Ia and Ib wherein $R^a$ represents —$CH_2OH$ can be prepared by the reaction of a compound of formula Ic with formaldehyde in a suitable polar solvent, such as water, and heating, preferably to reflux.

Compounds of formula Ia and Ib wherein $R^a$ represents optionally substituted phenyl or optionally substituted heteroaryl can be prepared by reaction of a compound of formula Ic with a boronic acid of formula $R^a$—$B(OH)_2$ (III) wherein $R^a$ represents optionally substituted phenyl or heteroaryl in the presence of a base, such as pyridine and/or triethylamine, and in the presence of a catalyst, such as copper acetate (II), in a suitable solvent, such as an aprotic solvent such as dichloromethane.

Compounds of formula II and III are commercially available, are widely described in the literature or can be prepared by methods similar to those described, and can be conveniently protected as required.

Compounds of formula I wherein $R^5$ represents H and $R^3$ has the same meaning as $R^1$ (i.e., a compound Id) can be also prepared by reaction of a compound of formula IV with an aminopyrazole of formula Va, as shown in the following scheme:

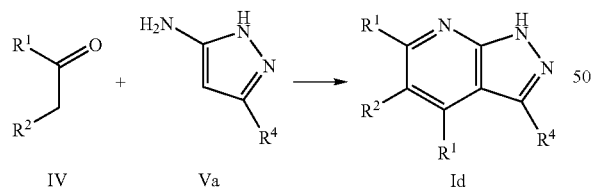

IV    Va    Id or alternatively by reaction of a compound of formula VII with a compound of formula Va

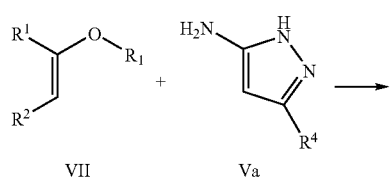

VII    Va wherein $R^1$, $R^2$ and $R^4$ have the meaning described in general formula I. This reaction is carried out preferably in the presence of an inorganic acid such as hydrochloric acid, in a suitable polar solvent such as 2-methoxyethanol or ethanol, and heating, preferably to reflux.

Aminopyrazoles of formula V and Va and aldehydes of formula VI, are commercially available and can be conveniently protected. Alternatively, compounds of formula Va can be conveniently prepared by reaction of a compound of formula VIII with a compound of formula IX, as shown in the following scheme:

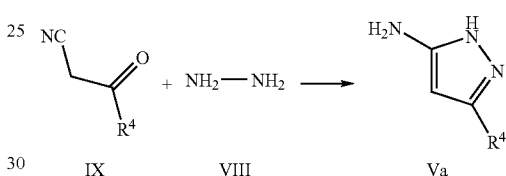

IX    VIII    Va wherein $R^4$ has the meaning described in general formula I. This reaction is carried out in a suitable polar solvent such as ethanol and by heating, preferably to reflux. Compounds of formula V can also be obtained by this method, starting from a compound of formula IX and a compound of formula $NH_2$—$NHR^5$ (VIIIa).

Compounds of formula IX are commercially available and can be conveniently protected or can be conveniently prepared by reaction of a compound of formula X

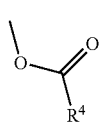

X with acetonitrile, in the presence of a base such as butyl lithium, in a suitable solvent such as tetrahydrofuran and at a suitable temperature, preferably −78° C.

Esters of formula X are commercially available or can be prepared by methods widely described in the literature and can be conveniently protected.

Enol ethers of formula VII can be conveniently prepared by reaction of a ketone of formula IV with a compound of formula $R^1$—COY (XI) wherein Y represents a halogen, preferably Cl, in the presence of a base, such as NaH, in a suitable polar solvent such as dimethylformamide.

Compounds of formula XI are commercially available or can be prepared by conventional reactions from the corresponding carboxylic acids of formula $R^1$—$CO_2H$ (XII).

Compounds of formula XII are commercially available or can be prepared by methods widely described in the literature and can be conveniently protected.

Compounds of formula IV can be prepared by reaction of a compound of formula R¹—H (XIII) with a compound of formula XIV

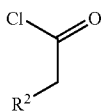

wherein R¹ and R² have the meaning described in general formula I, in the presence of a Lewis acid, such as AlCl₃, in a suitable halogenated solvent such as dichloromethane.

Compounds of formula XIV are commercially available or can be prepared readily from the corresponding carboxylic acid following conventional procedures.

Alternatively, compounds of formula IV can be conveniently prepared by reaction of a compound of formula R²—CH₃ (XV) with a compound of formula R¹—CN (XVI), wherein R¹ and R² have the meaning described in general formula I, in the presence of a base such as lithium diisopropylamide, generated from butyl lithium and N,N'-diisopropylamine, in an aprotic polar solvent, such as tetrahydrofuran and cooling, preferably to −78° C.

Alternatively, compounds of formula IV can be conveniently prepared by reaction of a compound of formula R²—CH₃ (XV) with a compound of formula R¹—CO₂R⁶ (XVII), wherein R¹ and R² have the meaning described in general formula I and R⁶ represents $C_{1-6}$alkyl, in the presence of a base such as sodium bis(trimethylsilyl)amide or sodium hydride, in an aprotic polar solvent, such as tetrahydrofuran or dimethylformamide and at a suitable temperature, preferably room temperature.

The compounds XIII, XV, XVI and XVII are commercially available or can be prepared by methods widely described in the literature.

Alternatively, compounds of formula IV can be conveniently prepared by reaction of a compound of formula R²—CH₃ (XV) with a compound of formula XVIII in the same conditions as those described previously for reaction of the compound of formula XV with a compound of formula XVI.

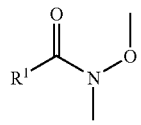

Compounds of formula XVIII can be conveniently prepared by reaction of a compound of formula XI with N,O-dimethylhydroxylamine hydrochloride in the presence of a base, such as triethylamine, in a suitable halogenated solvent such as dichloromethane and cooling, preferably to 0° C.

Alternatively, the compounds of formula XVIII can be prepared by reaction of a compound of formula XII with N,O-dimethylhydroxylamine hydrochloride in the presence of a suitable condensing agent such as for example N-(3-dimethylaminopropyl)-N'-ethylcarbodiimide or dicyclohexylcarbodiimide optionally in the presence of 1-hydroxybenzotriazole, or in the presence of a suitable base, such as pyridine, in a suitable solvent such as dimethylformamide.

The compounds of formula I can also be obtained from a compound of formula XIX, as shown in the scheme below.

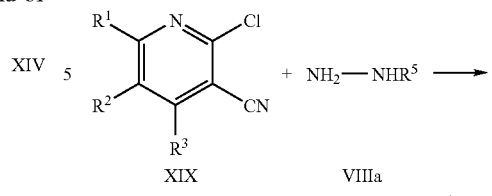

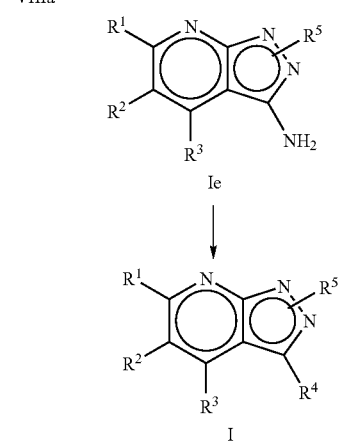

wherein R¹, R², R³, R⁴ and R⁵ have the meaning described in general formula I. The reaction of XIX with a compound of formula VIIIa gives rise to a compound of formula I wherein R⁴=NH₂ (Ie). This reaction is carried out in a suitable solvent such as ethanol and heating, preferably to reflux. Starting from these compounds of formula I wherein R⁴=NH₂, compounds of formula I wherein R⁴ is different from NH₂ can be generated by interconversion reactions, explained in more detail further on. This method is useful to prepare compounds of formula I wherein R³ represents H, optionally substituted $C_{1-6}$alkyl or Cy different from R¹.

Compounds of formula VIIIa are commercially available and can be conveniently protected.

Compounds of formula XIX can be conveniently prepared by reaction of a compound of formula XX

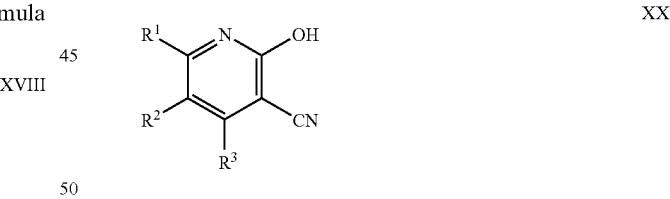

wherein R¹, R² and R³ have the meaning described in general formula I, with a chlorinating agent such as POCl₃ or PCl₃ without solvent or in a suitable solvent such as dimethylformamide and heating, preferably to reflux.

Compounds of formula XX are generally obtained by reaction of a compound of formula XXI with 2-cyanoacetamide, as shown in the following scheme:

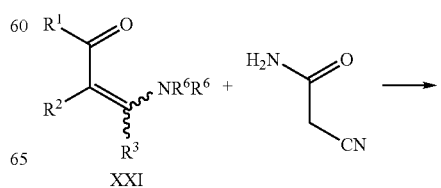

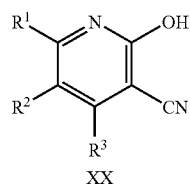

wherein $R^1$, $R^2$ and $R^3$ have the meaning described in general formula I and each $R^6$ independently represents $C_{1-6}$alkyl. This reaction is carried out in the presence of a base such as sodium methoxide, in a suitable solvent such as dimethylformamide and heating, preferably to reflux.

Compounds of formula XXI can be conveniently prepared by reaction of a compound of formula IV with a compound of formula XXII

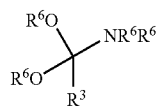

wherein $R^3$ and $R^6$ have the meaning previously described, in a suitable solvent such as tetrahydrofuran.

Compounds of formula XXII are commercially available or can be prepared by methods described in the literature, for example by reacting an amide of formula XXIII

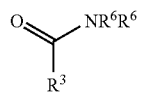

with triethyloxonium tetrafluoroborate in the presence of a base such as sodium ethoxide in a suitable solvent such as ethanol or a mixture of ethanol-diethyl ether.

Alternatively, compounds of the present invention can also be obtained by interconversion of another compound of formula I, in one or several steps, by using well-known reactions in organic chemistry under the reported standard experimental conditions.

Thus, $R^4$ can be transformed into another $R^4$, generating new compounds of formula I. For example, $R^4$=H can be transformed into $R^4$=Br by reaction with an appropriate brominating agent, such as $Br_2$, in a suitable solvent such as chloroform, and at an appropriate temperature comprised between room temperature and the boiling point of the solvent;

or $R^4$=H can be converted into $R^4$=Cl by reaction with an appropriate chlorinating agent such as N-chlorosuccinimide, in a suitable solvent such as dimethylformamide at an appropriate temperature comprised between room temperature and the boiling point of the solvent;

or $R^4$=$NH_2$ can be converted into $R^4$=halogen by formation of a diazonium salt with $NaNO_2$ followed by reaction with a copper halide such as CuBr or CuCl, in the presence of an acid such as for example HBr or HCl;

or $R^4$=$NH_2$ can be converted into $R^4$=H by forming a diazonium salt with $NaNO_2$ followed by reaction with $H_3PO_2$, in a suitable solvent such as water;

or $R^4$=halogen can be converted into $R^4$=CN by reaction with a cyanide salt such as CuCN, in a suitable solvent such as N-methylpyrrolidone and heating, preferably to reflux.

Other conversions of $R^4$, which can also be applied to $R^5$ and also to the substituents of the $R^1$, $R^2$ and $R^3$ groups to generate other compounds of formula I include, for example:

conversion of CN into $CONH_2$ by hydrolysis with a base such as KOH in a suitable solvent such as tert-butanol and heating, preferably to reflux;

conversion of CN into $CH_2NH_2$ by reaction with a reducing agent, such as $LiAlH_4$, in a suitable solvent such as diethyl ether;

conversion of a carboxylic acid group into an ester or an amide by reaction with an alcohol or an amine, respectively, in the presence of an activating agent such as N,N'-dicyclohexylcarbodiimide and 4-dimethylaminopyridine and in a suitable solvent such as diethyl ether;

conversion of an ester group into a carboxylic group by hydrolysis in the presence of a base, such as KOH, in a suitable solvent such as ethanol;

conversion of OH, SH or $NH_2$ into OR, SR and NHR or NRR, respectively, by reaction of an alkylating agent R—X wherein R represents $R^a$, $R^c$, $R^e$ or $R^f$ and X represents halogen, preferably chloro or bromo, in the presence of a base such as triethylamine, sodium hydroxide, sodium carbonate, potassium carbonate or sodium hydride in a suitable solvent such as dichloromethane, chloroform, dimethylformamide, ethanol or butanol, at a temperature comprised between room temperature and the temperature of the boiling point of the solvent;

alternatively, NHR can be converted into $NCH_3R$, wherein R represents $R^a$, $R^c$, $R^e$ or $R^f$, by reaction with formaldehyde in acid medium, such as formic acid and heating, preferably to reflux;

conversion of an amine into an amide by reaction of a carboxylic acid in the presence of an appropriate condensing agent such as N-(3-dimethylaminopropyl)-N'-ethylcarbodiimide or dicyclohexylcarbodiimide optionally in the presence of 1-hydroxybenzotriazole, or in the presence of an appropriate base such as pyridine, in a suitable solvent, such as dimethylformamide; or alternatively, an amine can be converted into an amide by reaction with an acyl chloride in pyridine or in the presence of a base such as triethylamine in a suitable solvent such as dichloromethane, and cooling, preferably to 0° C.;

conversion of an amine into a urea or a carbamate by a two step sequence that involves reacting the amine with an activating agent such as triphosgene, in the presence of a base such as diisopropylethylamine, triethylamine or N-methylmorpholine, in a suitable solvent such as acetonitrile or a halogenated hydrocarbon such as chloroform or dichloromethane, and then reacting the resulting compound with the second amine in the case of a urea or with an alcohol in the case of a carbamate, in a suitable solvent, such as the solvent used in the first step; or alternatively an amine can be converted into a urea or carbamate by reaction with an isocyanate or a chloroformate, respectively, in a suitable solvent, such as dimethylformamide, at a suitable temperature, preferably room temperature;

conversion of an amine into a sulfonamide by reaction with a sulfonyl halide, such as sulfonyl chloride, optionally in the presence of a base such as 4-dimethylaminopyridine, in a suitable solvent such as dioxane, chloroform, dichloromethane or pyridine;

conversion of a hydroxyl group into an ester group by reaction with a carboxylic acid in the standard conditions mentioned previously;

conversion of a sulfanyl group into a sulfinyl or sulfonyl group by reaction with 1 or 2 equivalents, respectively, of an appropriate oxidizing agent such as m-chloroperbenzoic acid in a suitable solvent such as for example dichloromethane;

conversion of a primary or secondary hydroxyl group into a leaving group, for example an alkylsulfonate or arylsulfonate such as mesylate or tosylate or a halogen such as Cl, Br or I, by reaction with a sulfonyl halide such as methanesulfonyl chloride, in the presence of a base, such as pyridine or triethylamine, in a suitable solvent such as dichloromethane or chloroform, or with a halogenating agent, such as $SOCl_2$, in a suitable solvent such as tetrahydrofuran;

the substitution of said leaving group by reaction with an alcohol, amine or thiol, optionally in the presence of a base, such as $K_2CO_3$, and in a suitable solvent such as dimethylformamide, 1,2-dimethoxyethane or acetonitrile;

the elimination of a leaving group bonded to an alkyl group to give an alkenyl group by reaction with a base, such as KOH, in a suitable solvent, such as toluene and heating, preferably to reflux;

conversion of a primary amide into a secondary amide by reaction with an alkylating agent in the presence of a strong base, such as sodium hydride, in a suitable solvent and at a temperature comprised between room temperature and the boiling point of the solvent;

conversion of CHO into an amine by reaction with an amine in the presence of a reducing agent such as sodium triacetoxyborohydride, in a suitable solvent such as for example 1,2-dichloroethane;

conversion of an acetal group into an aldehyde by reaction in acid medium, for example in HCl, at an appropriate temperature, preferably to reflux;

conversion of an ester group into an alcohol group by reaction with a reducing agent, such as $LiAlH_4$, in a suitable solvent, such as tetrahydrofuran;

conversion of a sulfonyl group bonded to an aromatic ring into an amino derivative by reaction with the corresponding amine, in a suitable solvent such as tetrahydrofuran or using the amine as a solvent, heating, preferably to a temperature comprised between room temperature and 100° C. and preferably carrying out the reaction in a closed vessel under atmospheric pressure;

conversion of a sulfonyl group bonded to an aromatic ring by displacement with an alkoxide to give the corresponding alkoxy derivative, in a suitable solvent such as tetrahydrofuran or using the corresponding alcohol as a solvent, heating, preferably to a temperature comprised between room temperature and 100° C. and preferably carrying out the reaction in a closed vessel under atmospheric pressure;

conversion of a vinylic or aromatic halogen into NHR, wherein R represents $R^a$, $R^c$, $R^e$ or $R^f$, by reacting with an amine of formula $H_2NR$ and preferably heating;

alternatively, a vinylic or aromatic halogen can be converted into NHR by reaction with an amine of formula $H_2NR$ in the presence of a base, such as $Cs_2CO_3$ or sodium tert-butoxide, in the presence of a palladium catalyst, such as palladium acetate (II), and a phosphine such as 2,2'-bis(diphenylphosphino)-1,1'-binaphthyl, in a solvent, such as toluene, and preferably heating;

conversion of a vinylic or aromatic halogen into a phenyl or heteroaryl group by treatment with a phenyl- or a heteroarylboronic acid in the presence of a catalyst, such as a palladium catalyst, such as palladium acetate (II) or tetraquis(triphenylphosphine) palladium (0) and of a base such as $Na_2CO_3$, $K_2CO_3$ or CsF, in a suitable polar solvent, such as 1,2-dimethoxyethane or toluene-water mixtures, and preferably heating;

conversion of an aromatic halogen into H by halogenolysis, with a reducing agent such as Zn, in a suitable solvent, such as acetic acid and heating, preferably to reflux; and oxidation of the N at position 7 of the pyrazolo[3,4-b] pyridine ring to give the corresponding N-oxide by reaction with an oxidizing agent, such as m-chloroperbenzoic acid, in a suitable solvent, such as for example dichloromethane.

Likewise, any of the aromatic rings of the compounds of the present invention can undergo electrophilic aromatic substitution reactions, widely described in the literature.

Many of these interconversion reactions are explained in greater detail in the examples.

As it will be obvious to those skilled in the art, these interconversion reactions can also be carried out on synthesis intermediates of compounds of formula I.

The present invention also includes the salts of the compounds of formula I. These salts can be prepared by conventional methods by treating a compound of formula I with an appropriate amount of an acid such as hydrochloric acid, sulfuric acid, nitric acid, oxalic acid or methanesulfonic acid. In the case of compounds of formula I that contain an acidic proton, salts can also be obtained by treatment with a base such as sodium hydroxide, potassium hydroxide, calcium hydroxide or calcium carbonate. Salts of the compounds of formula I can be converted in turn into other salts of compounds of formula I by ion exchange using a ionic exchange resin.

As mentioned previously, the compounds of the present invention act as p38 kinase inhibitors, inducing reduction of proinflammatory cytokines. Therefore, these compounds are expected to be useful to treat or prevent diseases in which kinase p38 plays a role. This includes diseases caused by overproduction of cytokines such as TNF-α, IL-1, IL-6 or IL-8. These diseases include, but are not limited to, immune, autoimmune and inflammatory diseases, cardiovascular diseases, infectious diseases, bone resorption disorders, neurodegenerative diseases, proliferative diseases and processes associated with cyclooxygenase-2 induction.

As an example, immune, autoimmune and inflammatory diseases that can be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), autoimmune hematologic disorders (e.g. hemolytic anemia, aplasic anemia, idiopathic thrombocytopenia and neutropenia), autoimmune gastritis and autoimmune inflammatory bowel diseases (e.g. ulcerative colitis and Crohn's disease), host versus graft disease, allograft rejection, chronic thyroiditis, Graves' disease, schleroderma, diabetes (type I and type II), active hepatitis (acute and chronic), primary biliary cirrhosis, myasthenia gravis, multiple sclerosis, systemic lupus erythematosus, psoriasis, atopic dermatitis, contact dermatitis, eczema, skin sunburns, chronic renal insufficiency, Stevens-Johnson syndrome, idiopathic sprue, sarcoidosis, Guillain-Barré syndrome, uveitis, conjunctivitis, keratoconjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive diseases of the airways.

Cardiovascular diseases that can be treated or prevented include, among others, myocardial infarction, cardiac hypertrophy, cardiac insufficiency, ischaemia-reperfusion disorders, thrombosis, thrombin-induced platelet aggregation, acute coronary syndromes, atherosclerosis and cerebrovascular accidents.

Infectious diseases that can be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that can be treated or prevented include osteoporosis, osteoarthritis, traumatic arthritis, gouty arthritis and bone disorders related with multiple myeloma, among others.

Neurodegenerative diseases that can be treated or prevented include Alzheimer's disease, Parkinson's disease, cerebral ischaemia and traumatic neurodegenerative disease, among others.

Proliferative diseases that can be treated or prevented include endometriosis, solid tumors, acute and chronic myeloid leukemia, Kaposi sarcoma, multiple myeloma, metastatic melanoma and angiogenic disorders such as ocular neovascularisation and infantile haemangioma.

p38 kinase inhibitors also inhibit the expression of proinflammatory proteins such as cyclooxygenase-2 (COX-2), the enzyme responsible for prostaglandin production. Therefore, the compounds of the present invention can also be used to treat or prevent diseases mediated by COX-2 and especially to treat processes with inflammation, fever and neuromuscular pain such as cephalea, pain caused by cancer, tooth pain and arthritic pain.

According to the activity of the products herein described, the present invention also relates to compositions which contain a compound of the present invention, together with an excipient or other auxiliary agents if necessary. The compounds of the present invention can be administered in the form of any pharmaceutical formulation, the nature of which, as it is well known, will depend upon the nature of the active compound and its route of administration. Any route of administration may be used, for example oral, parenteral, nasal, ocular, rectal and topical administration.

According to the present invention, solid compositions for oral administration include tablets, granulates and capsules. In any case the manufacturing method is based on a simple mixture, dry granulation or wet granulation of the active compound with excipients. These excipients can be, for example, diluents such as lactose, microcrystalline cellulose, mannitol or calcium hydrogenphosphate; binding agents such as for example starch, gelatin or povidone; disintegrants such as sodium carboxymethyl starch or sodium croscarmellose; and lubricating agents such as for example magnesium stearate, stearic acid or talc. Tablets can be additionally coated with suitable excipients by using known techniques with the purpose of delaying their disintegration and absorption in the gastrointestinal tract and thereby provide a sustained action over a longer period, or simply to improve their organoleptic properties or their stability. The active compound can also be incorporated by coating onto inert pellets using natural or synthetic film-coating agents. Soft gelatin capsules are also possible, in which the active compound is mixed with water or an oily medium, for example coconut oil, mineral oil or olive oil.

Powders and granulates for the preparation of oral suspensions by the additon of water can be obtained by mixing the active compound with dispersing or wetting agents; suspending agents and preservatives. Other excipients can also be added, for example sweetening, flavouring and colouring agents.

Liquid forms for oral administration include emulsions, solutions, suspensions, syrups and elixirs containing commonly-used inert diluents, such as purified water, ethanol, sorbitol, glycerol, polyethylene glycols (macrogols) and propylene glycol. Said compositions can also contain coadjuvants such as wetting, suspending, sweetening, flavouring agents, preservatives and buffers.

Injectable preparations, according to the present invention, for parenteral administration, comprise sterile solutions, suspensions or emulsions, in an aqueous or non-aqueous solvent such as propylene glycol, polyethylene glycol or vegetable oils. These compositions can also contain coadjuvants, such as wetting, emulsifying, dispersing agents and preservatives. They may be sterilized by any known method or prepared as sterile solid compositions which will be dissolved in water or any other sterile injectable medium immediately before use. It is also possible to start from sterile materials and keep them under these conditions throughout all the manufacturing process.

For the rectal administration, the active compound can be preferably formulated as a suppository on an oily base, such as for example vegetable oils or solid semisynthetic glycerides, or on a hydrophilic base such as polyethylene glycols (macrogol).

The compound can also be formulated for its topical application for the treatment of pathologies occurring in zones or organs accessible through this route, such as eyes, skin and the intestinal tract. Formulations include creams, lotions, gels, powders, solutions and patches wherein the compound is dispersed or dissolved in suitable excipients.

The compounds of the present invention can also be formulated as a solid form, dissolved or dispersed in a suitable vehicle, for inhalation in single or multidose container. Preparations to be administered as an aerosol (dispersion of solid or liquid particles in a gas) use suitable devices such as nebulisers, pressured metered-dose inhalers or dry-powder inhalers. Depending on this, the compound will be formulated with excipients such as propellants responsible for developing the proper pressure within the container to force the content out through the opening of the valve, solvents, emulsifying agents, viscosity-increasing agents, preservatives, stabilizing agents and lubricants to avoid the blockade of the valve.

The dosage and frequency of doses will depend upon the nature and severity of the disease to be treated, the age, the general condition and body weight of the patient, as well as the particular compound administered and the route of administration, among other factors. A representative example of a suitable dosage range is from about 0.01 mg/Kg to about 100 mg/Kg per day, which can be administered as a single or divided doses. However, the dosage administered is generally left to the discretion of the physician.

The activity of the compounds of this invention can be assessed using the following tests:

Test 1: Inhibition of TNF-α Release Induced by LPS in Human Histiocytic Lmphoma Cells, U-937

Maintenance and differentiation of U-937 cells: U-937 cells (ATCC N° CRL-159.2) are cultivated in RPMI 1640 medium supplemented with 10% inactivated fetal bovine serum (Gibco). A total of $0.5 \times 10^6$ cells are incubated in the presence of 20 ng/mL of PMA (phorbol 12-myristate 13-acetate) for 24 h to achieve complete monocytic differentiation. All the incubations are carried out at 37° C. in an atmosphere with 5% $CO_2$. The cells are centrifuged (200×g for 5 min) and resuspended in RPMI 1640 medium supplemented with 2% inactivated fetal bovine serum at a density of $2\times10^6$ cells/mL.

Inhibition of TNF-α release: 100 μL of cells U-937 ($2\times10^6$ cells/mL) are incubated with 100 μL of the test product (final concentration, 0.001-10 μM) for 30 min in 96-well plates. The mother solutions of the products (10 mM in DMSO) are diluted in culture medium to reach a final DMSO concentration equal to or less than 0.1%. A total of 20 μL of LPS (*E. coli* 055B5, Sigma) are added to a final concentration of 100 ng/mL and after incubation for 4 hours the amount of TNF-α released in the supernatant is quantified using a commercial ELISA kit (Biosource International).

Test 2: Inhibition of TNF-α Release Induced by LPS in Human Peripheral Blood Mononuclear Cells To obtain the mononuclear cells: heparinized venous blood, obtained from healthy volunteers, is diluted with an equal volume of saline phosphate buffer without calcium or magnesium. Aliquots of 30 mL of the mixture are transferred to 50 mL centrifuge tubes containing 15 mL of Ficoll-Hypaque (1.077 g/mL). The tubes are centrifuged at 1200×g for 20 min at room temperature without braking. Approximately two-thirds of the band of platelets lying above the mononuclear cells is removed with a pipette. The mononuclear cells are carefully transferred to a 50 mL tube, washed twice with saline phosphate buffer, centrifuged at 300×g for 10 min at room temperature and resuspended in RPMI supplemented with 1% inactivated fetal bovine serum at a cell density of $2\times10^6$ cells/mL.

Inhibition of TNF-α release: 100 μL of mononuclear cells ($2\times10^6$ cells/mL) are incubated on 96-well plates with 50 μL of the test product (final concentration, 0.001-10 μM) and 50 μL LPS (*E. coli* 055B5, Sigma) at a final concentration of 400 ng/mL for 19 h at 37° C. in an atmosphere with $CO_2$ at 5%. The amount of TNF-α released in the supernatant is quantified using a commercial ELISA kit (Biosource International).

Test 3: Inhibition of P38-α Kinase:

In a final volume of 25 μL, a total of 5 μL of the test product (final concentration, 0.001-10 μM), 5-10 mU of p38-α with 0.33 mg/mL of myelin basic protein, $Mg^{2+}$ acetate (10 mM) and [$\gamma^{33}$P-ATP] (100 μM, specific activity 500 cpm/pmol) in buffer Tris 25 mM pH7.5, EGTA 0.02 mM is incubated. The reaction is started by adding $Mg^{2+}$[$\gamma^{33}$P-ATP]. After incubation for 40 min at room temperature, the reaction is quenched by adding 5 μL of 3% phosphoric acid solution. The reaction mixture (10 μL) is passed through a filter (P30) and washed three times for 5 min with a 75 mM phosphoric acid solution and once with methanol before drying it and counting it, by liquid scintillation.

The following table shows the results obtained with representative compounds of the invention in test 2:

| Example | % Inhibition at 0.1 μM |
|---|---|
| 1 | 57.5 |
| 4 | 68.4 |
| 6 | 81.4 |
| 8 | 66.3 |
| 18 | 82.6 |
| 22 | 56.5 |
| 30 | 83.6 |
| 36 | 92.0 |

-continued

| Example | % Inhibition at 0.1 μM |
|---|---|
| 39 | 51.1 |
| 41 | 90.6 |
| 43 | 61.2 |
| 56 | 58.7 |
| 59 | 60.0 |
| 63 | 53.2 |
| 68 | 50.0 |
| 72 | 52.7 |
| 78 | 73.3 |
| 80 | 69.3 |
| 82 | 59.9 |
| 90 | 86.3 |
| 102 | 67.9 |
| 106 | 69.3 |
| 121 | 52.1 |
| 128 | 82.0 |
| 136 | 67.0 |
| 137 | 61.4 |
| 183 | 66.7 |
| 184 | 71.2 |
| 188 | 73.2 |
| 196 | 70.2 |
| 208 | 67.7 |
| 209 | 84.2 |
| 210 | 57.3 |
| 211 | 70.6 |
| 212 | 67.5 |
| 213 | 68.1 |
| 214 | 71.1 |
| 217 | 53.8 |
| 232 | 67.9 |
| 237 | 53.4 |
| 240 | 58.4 |
| 248 | 53.2 |
| 250 | 67.0 |
| 268 | 69.1 |
| 272 | 65.6 |
| 279 | 100.0 |
| 282 | 65.2 |
| 283 | 52.4 |
| 287 | 71.2 |
| 289 | 51.3 |
| 290 | 65.8 |

The following examples illustrate, but do not limit, the scope of the invention.

The following abbreviations have been used in the examples:
AcOH: acetic acid
EtOAc: ethyl acetate
$NH_4OAc$: ammonium acetate
BuLi: butyl lithium
$^t$BuOH: tert-butanol
conc.: concentrated
DMAP: 4(N,N-dimethylamino)pyridine
DMF: dimethylformamide
EtOH: ethanol
MeOH: methanol
THF: tetrahydrofuran
$t_R$: retention time
LC-MS: liquid chromatography-mass spectrometry LC-MS spectra have been performed using the following chromatographic methods:

Method 1: Column Tracer Excel 120, ODSB 5 μm (10 mm×0.21 mm), temperature: 30° C., flow: 0.35 mL/min, eluent: A=acetonitrile, B=0.1% HCOOH, gradient: 0 min 10% A—10 min 90% A.

Method 2: Column X-Terra MS C18 5 μm (150 mm×2.1 mm), temperature: 30° C., flow: 0.40 mL/min, eluent:

A=acetonitrile, B=10 mM NH$_4$OAc (pH=6.80), gradient: 0 min 25% A—6 min 80% A—7.5 min 25% A.

REFERENCE EXAMPLE 1

1-(4-Fluorophenyl)-2-(4-pyridyl)ethanone a) 4-Fluoro-N-methoxy-N-methylbenzamide In a volumetric flask N,O-dimethylhydroxylamine hydrochloride (25.54 g, 261.8 mmol) and CH$_2$Cl$_2$ (443 mL) were introduced under argon atmosphere at 0° C. 4-Fluorobenzoyl chloride (34.59 g, 218.2 mmol) was added followed by the slow addition of triethylamine (48.13 g, 475.6 mmol). The reaction was stirred for 30 min at 5° C. and allowed to reach room temperature. It was washed with 5% aqueous citric acid (180 mL) and with 5% aqueous NaHCO$_3$ (180 mL). The aqueous phase was extracted with CH$_2$Cl$_2$. The organic phase was dried over Na$_2$SO$_4$ and concentrated to dryness, to afford 20.23 g of the desired compound (yield: 88%).

b) Title Compound

To a solution of diisopropylamine (23.4 mL, 165.7 mmol) in THF (250 mL), cooled to −78° C., BuLi (103.5 mL of a 1.6 M solution in hexane, 165.7 mmol) was added dropwise under argon atmosphere. After 5 minutes, a solution of 4-methylpyridine (10.28 g, 110.4 mmol) in THF (85 mL) was added over 20 min. The mixture was stirred at 0° C. for 15 min and a solution of 4-fluoro-N-methoxy-N-methylbenzamide (obtained in section a) in THF (85 mL) was added over 30 min period. The reaction was allowed to reach room temperature. Water (100 mL) and EtOAc (100 mL) were added and the mixture was stirred for 30 min. The organic phase was separated, dried over Na$_2$SO$_4$ and concentrated to dryness, to afford 24.32 g of the desired compound (yield: 100%).

$^1$H NMR (300 MHz, CDCl$_3$) δ (TMS): 4.29 (s, 2 H), 7.14-7.23 (complex signal, 4 H), 8.05 (m, 2 H), 8.59 (dd, J$_o$=1.6 Hz, J$_m$=4.4 Hz, 2 H).

REFERENCE EXAMPLE 2

2-(4-Pyridyl)-1-[3-(trifluoromethyl)phenyl]ethanone a) N-Methoxy-N-methyl-3-(trifluoromethyl)benzamide Following a similar procedure to that described in reference example 1 section a, but using 3-(trifluoromethyl)benzoyl chloride instead of 4-fluorobenzoyl chloride, the desired product was obtained (yield: 86%).

b) Title Compound

Following a similar procedure to that described in reference example 1 section b, but using N-methoxy-N-methyl-3-(trifluoromethyl)benzamide (obtained in section a of this example) instead of 4-fluoro-N-methoxy-N-methylbenzamide, the title compound was obtained (yield: 22%).

$^1$H NMR (300 MHz, CDCl$_3$) δ (TMS): 4.31 (s, 2 H), 7.20 (d, J=5.8 Hz, 2 H), 7.63 (t, J=7.8 Hz, 1 H), 7.84 (d, J=7.8 Hz, 1 H), 8.16 (d, J=7.9 Hz, 1 H), 8.24 (s, 1 H), 8.56 (d, J=5.8 Hz, 2 H).

REFERENCE EXAMPLE 3

1-Phenyl-2-(4-pyridyl)ethanone

A solution of diisopropylamine (22 mL, 15.03 mmol) in THF (200 mL) under argon atmosphere was cooled to −78° C. BuLi (96 mL of a 1.6 M solution in hexane, 153.0 mmol) was added dropwise. After 1 h, a solution of 4-methylpyridine (15.00 g, 161.1 mmol) in THF (75 mL) was added and allowed to warm to 0° C. At this temperature it was stirred for 30 minutes. It was cooled to −78° C. and benzonitrile (18.27 g, 177.2 mmol) in THF (75 mL) was added and stirred at −78° C. for 2 h. It was stirred at room temperature overnight. Water (225 mL) was added, it was cooled with a water-ice bath and adjusted to pH 1 with 48% HBr. The organic phase was separated. The aqueous phase was heated to reflux for 2 h, allowed to cool and extracted with diethyl ether. The aqueous phase was taken to neutral pH with 1 N NaOH and extracted with EtOAc. The organic phase was dried over Na$_2$SO$_4$ and concentrated to dryness, to afford 28.53 g of title compound (yield: 90%).

$^1$H NMR (300 MHz, CDCl$_3$) δ (TMS): 4.29 (s, 2 H), 7.20 (dd, J$_o$=1.6 Hz, J$_m$=4.4 Hz, 2 H), 7.49 (m, 2 H), 7.58 (m, 1 H), 8.00 (d, J=8.2 Hz, 2 H), 8.56 (dd, J$_o$=Hz, J$_m$=4.4 Hz, 2 H).

REFERENCE EXAMPLE 4

1-(4-Fluorophenyl)-2-(4-pyridyl)vinyl 4-fluorobenzoate

To a suspension of NaH (0.81 g, 18.6 mmol) in DMF (30 mL) under argon atmosphere and cooled to 0° C., a solution of 1-(4-fluorophenyl)-2-(4-pyridyl)ethanone (2.00 g, 9.3 mmol, obtained in reference example 1) in DMF (15 mL) was added and stirred to room temperature for 30 minutes. It was then cooled to 0° C. and a solution of 4-fluorobenzoyl chloride (2.95 g, 1.9 mmol) in DMF (10 mL) was added. It was stirred at room temperature overnight. Water was added and the solvent was evaporated off. The residue was dissolved in a mixture of CHCl$_3$ and water and the phases were separated. The aqueous phase was extracted with CHCl$_3$ (×3). The organic phase was washed with water (×2), dried over Na$_2$SO$_4$ and concentrated to dryness. The crude product obtained was purified by chromatography on silica gel using hexane-EtOAc mixtures of increasing polarity as eluent, to afford 0.98 g of the desired compound as a yellow solid (yield: 31%).

$^1$H NMR (300 MHz, CDCl$_3$) δ (TMS): 6.68 (s, 1 H), 7.11 (t, J=8.6 Hz, 2 H), 7.29 (t, J=8.6 Hz, 2 H), 7.39 (d, J=6.0 Hz, 2 H), 7.60 (dd, J$_o$=5.2 Hz, J$_m$=8.8 Hz, 2 H), 8.27 (dd, J$_o$=5.4 Hz, J$_m$=8.8 Hz, 2 H), 8.58 (d, J=6.0 Hz, 2 H)

REFERENCE EXAMPLE 5

1-Phenyl-2-(4-pyridyl)vinyl benzoate

Following a similar procedure to that described in reference example 4, but using 1-phenyl-2-(4-pyridyl)ethanone (obtained in reference example 3) instead of 1-(4-fluorophenyl)-2-(4-pyridyl)ethanone and benzoyl chloride instead of 4-fluorobenzoyl chloride, the title compound was obtained (yield: 62%).

$^1$H NMR (300 MHz, CDCl$_3$) δ (TMS): 6.72 (s, 1 H), 7.38-7.42 (complex signal, 5 H), 7.60-7.63 (complex signal, 4 H), 7.71 (t, J=7.4, 1 H), 8.23 (d, J=7.1 Hz, 2 H), 8.51 (dd, J$_o$=1.5 Hz, J$_m$=4.6 Hz, 2 H).

REFERENCE EXAMPLE 6

2-[2-(Methylsulfanyl)pyrimidin-4-yl]-1-[3-(trifluoromethyl)phenyl]ethanone a) 4-Methyl-2-(methylsulfanyl)pyrimidine To a solution of NaOH (7.46 g, 186.4 mmol) in water (120 mL), 4-methylpyrimidine-2-thiol hydrochloride (13.78 g, 84.7 mmol) was added and subsequently iodomethane (13.23 g, 93.2 mmol) was added dropwise under argon atmosphere. It was stirred at room temperature for 2 h. It was extracted with $CH_2Cl_2$ (×2). The organic phase was dried over $Na_2SO_4$ and concentrated to dryness. The crude product obtained was purified by chromatography on silica gel using hexane-EtOAc mixtures of increasing polarity as eluent, to afford 10.26 g of the desired compound (yield: 86%).

b) Title Compound

Following a similar procedure to that described in reference example 1 section b, but using N-methoxy-N-methyl-3-(trifluoromethyl)benzamide (obtained in section a of the reference example 2) instead of 4-fluoro-N-methoxy-N-methylbenzamide and 4-methyl-2-(methylsulfanyl)pyrimidine (obtained in section a of this example) instead of 4-methylpyridine, the title compound as a crude product was obtained that was directly used in the following reactions (yield: quantitative).

REFERENCE EXAMPLE 7

3-(Dimethylamino)-1-(4-fluorophenyl)-2-(4-pyridyl)prop-2-en-1-one

To a solution of 1-(4-fluorophenyl)-2-(4-pyridyl)ethanone (0.30 g, 1.4 mmol, obtained in reference example 1) in anhydrous THF (5 mL), dimethyl dimethylformamide acetal (0.27 g, 3.2 mmol) was added under argon atmosphere. This was stirred overnight at room temperature. The solvent was evaporated to afford 0.39 g of the title compound (yield: quantitative).

$^1$H NMR (300 MHz, $CDCl_3$) δ (TMS): 2.79 (s, 6 H), 6.97 (t, J=8.7 Hz, 2 H), 7.05 (dd, $J_o$=1.5 Hz, $J_m$=4.5 Hz, 2 H), 7.38 (s, 1 H), 7.45 (m, 2 H), 8.48 (dd, $J_o$=1.5 Hz, $J_m$=4.5 Hz, 2 H).

REFERENCE EXAMPLE 8

3-(Dimethylamino)-2-[2-(methylsulfanyl)pyrimidin-4-yl]-1-[3-(trifluoromethyl)phenyl]prop-2-en-1-one Following a similar procedure to that described in reference example 7, but using 2-[2-(methylsulfanyl)pyrimidin-4-yl]-1-[3-(trifluoromethyl)phenyl]ethanone (obtained in reference example 6) instead of 1-(4-fluorophenyl)-2-(4-pyridyl)ethanone, the desired compound was obtained in the form of a crude product that was directly used in the following reactions.

REFERENCE EXAMPLE 9

1-(6-Chloropyridin-3-yl)-2-(4-pyridyl)ethanone a) 6-Chloronicotinoyl chloride hydrochloride A solution of 6-chloronicotinic acid (10.00 g, 63.5 mmol) in $SOCl_2$ (37 mL) was heated to reflux for 2 h. The $SOCl_2$ was evaporated to dryness, to afford 12.56 g of the desired product (yield: 93%).

b) 6-Chloro-N-methoxy-N-methylnicotinamide

Following a similar procedure to that described in reference example 1 section a, but using 6-chloronicotinoyl chloride hydrochloride (obtained in section a of this example) instead of 4-fluorobenzoyl chloride, the desired compound was obtained (yield: 71%).

c) Title Compound

Following a similar procedure to that described in reference example 1 section b, but using 6-chloro-N-methoxy-N-methyinicotinamide (obtained in section b of this example) instead of 4-fluoro-N-methoxy-N-methylbenzamide, the title compound was obtained (yield: quantitative).

$^1$H NMR (300 MHz, $CDCl_3$) δ (TMS): 4.27 (s, 2 H), 7.18 (dd, $J_o$=1.5 Hz, $J_m$=4.5 Hz, 2 H), 7.45 (dd, $J_o$=0.6 Hz, $J_m$=8.4 Hz, 1 H), 8.20 (dd, $J_o$=2.5 Hz, $J_m$=8.3 Hz, 2 H s, 1 H), 8.56 (18 (dd, $J_o$=1.6 Hz, $J_m$=4.4 Hz, 2 H), 8.98 (d, J=2.4 Hz, 1 H).

REFERENCE EXAMPLE 10

2-(4-Fluorophenyl)-6-hydroxy-3,4'-bipyridine-5-carbonitrile

To a solution of 3-(dimethylamino)-1-(4-fluorophenyl)-2-(4-pyridyl)prop-2-en-1-one (12.77 g, 47.2 mmol, obtained in reference example 7) in DMF (175 mL), 2-cyanoacetamide (4.41 g, 52.0 mmol) was added under argon atmosphere. Then, sodium methoxide (5.35 g, 99.2 mmol) was added and heated to reflux for 1 hour. The mixture was allowed to cool, concentrated and diluted with water. The pH was adjusted to 4 with 1 N HCl. A precipitate was obtained that was filtered and dried to give 6.57 g of the desired compound as a solid (yield: 48%).

$^1$H NMR (300 MHz, $CDCl_3$+$CD_3OD$) δ (TMS): 4.20 (s, OH+NH+$CD_3OD$), 6.96 (dd, $J_o$=1.6 Hz, $J_m$=4.5 Hz, 2 H), 7.05 (t, J=8.7 Hz, 2 H), 7.23 (m, 2 H), 7.96 (s, 1 H), 8.39 (dd, $J_o$=1.4 Hz, $J_m$=4.6 Hz, 2 H).

REFERENCE EXAMPLE 11

2-Hydroxy-5-[2-(methylsulfanyl)pyrimidin-4-yl]-6-[3-(trifluoromethyl)phenyl]pyridine-3-carbonitrile Following a similar procedure to that described in reference example 10, but using 3-(dimethylamino)-2-[2-(methylsulfanyl)pyrimidin-4-yl]-1-[3-(trifluoromethyl)phenyl]prop-2-en-1-one (obtained in reference example 8) instead of 3-(dimethylamino)-1-(4-fluorophenyl)-2-(4-pyridyl)prop-2-en-1-one, the title compound was obtained (yield: 20%).

$^1$H NMR (300 MHz, $CDCl_3$+$CD_3OD$) δ (TMS): 3.28 (s, 3 H), 3.84 (s, OH+$CD_3OD$), 6.38 (d, J=5.4 Hz, 1 H), 7.42 (d, J=7.8 Hz, 1 H), 7.53 (t, J=7.8 Hz, 1 H), 7.61 (s, 1 H), 7.73 (d, J=7.8 Hz, 1 H), 8.18 (d, J=5.1 Hz, 1 H), 8.35 (s, 1 H).

REFERENCE EXAMPLE 12

6-Chloro-2-(4-fluorophenyl)-3,4'-bipyridine-5-carbonitrile

A mixture of 2-(4-fluorophenyl)-6-hydroxy-3,4'-bipyridine-5-carbonitrile (6.57 g, 22.5 mmol, obtained in reference example 10), $POCl_3$ (26.3 mL, 287.5 mmol) and DMF (0.37 mL) was heated to reflux under argon atmosphere for 2 h. It was cooled with an ice bath and basified by adding 30% aqueous $NH_3$. The precipitate obtained was filtered and washed with water. The product was purified by chromatography on silica gel using hexane-EtOAc mixtures of increasing polarity as eluent, to afford 3.86 g of the desired product as a yellow solid (yield: 55%).

$^1$H NMR (300 MHz, $CDCl_3$) δ (TMS): 7.00 (t, J=8.6 Hz, 2 H), 7.11 (dd, $J_o$=1.6 Hz, $J_m$=4.4 Hz, 2 H), 7.37 (m, 2 H), 7.98 (s, 1 H), 8.62 (dd, $J_o$=1.5 Hz, $J_m$=4.5 Hz, 2 H).

REFERENCE EXAMPLE 13

1-(6-Methylpyridin-3-yl)-2-(4-pyridyl)ethanone a) N-Methoxy-6,N-dimethyinicotinamide To a solution of 6-methylnicotinic acid (5.00 g, 36.5 mmol) in DMF (150 mL), 1-hydroxybenzotriazole (4.92 g, 36.5 mmol), N-ethyl-N-(3-dimethylaminopropyl)carbodiimide hydrochloride (8.38 g, 45.7 mmol) and 4-methylmorpholine (16.0 mL, 145.8 mmol) were added under argon atmosphere. The mixture was stirred at room temperature for 30 minutes after which N,O-dimethylhydroxylamine hydrochloride was added (3.55 g, 36.5 mmol). The reaction mixture was stirred at room temperature overnight. The solvent was evaporated off. The residue was dissolved in a mixture of $CHCl_3$ and 0.2 N $NaHCO_3$. The phases were separated and the aqueous phase was extracted with $CHCl_3$. The organic phase was dried over $Na_2SO_4$ and concentrated to dryness. The product was purified by chromatography on silica gel using hexane-EtOAc mixtures of increasing polarity as eluent, to afford 1.11 g of the desired product (yield: 29%).

b) Title Compound

Following a similar procedure to that described in reference example 1 section b, but using N-methoxy-6,N-dimethylnicotinamide (obtained in section a of this example) instead of 4-fluoro-N-methoxy-N-methylbenzamide, the title compound was obtained (yield: 87%).

$^1$H NMR (300 MHz, $CDCl_3$) δ (TMS): 2.64 (s, 3 H), 4.28 (s, 2 H), 7.20 (dd, $J_o$=1.4 Hz, $J_m$=4.6 Hz, 2 H), 7.28 (d, J=8.1 Hz, 1 H), 8.15 (dd, $J_o$=2.4 Hz, $J_m$=8.1 Hz, 1 H), 8.57 (dd, $J_o$=1.8 Hz, $J_m$=4.5 Hz, 2 H), 9.10 (d, J=2.4 Hz, 1 H).

REFERENCE EXAMPLE 14

2-Chloro-5-[2-(methylsulfanyl)pyrimidin-4-yl]-6-[3-(trifluoromethyl)phenyl]pyridine-3-carbonitrile Following a similar procedure to that described in reference example 12 but using 2-hydroxy-5-[2-(methylsulfanyl)pyrimidin-4-yl]-6-[3-(trifluoromethyl)phenyl]pyridine-3-carbonitrile (obtained in reference example 11) instead of 2-(4-fluorophenyl)-6-hydroxy-3,4'-bipyridine-5-carbonitrile, the title compound was obtained (yield: 44%).

$^1$H NMR (300 MHz, $CDCl_3$) δ (TMS): 2.48 (s, 3 H), 6.62 (d, J=5.1 Hz, 1 H), 7.51 (m, 2 H), 7.71 (d, J=7.2 Hz, 1 H), 7.82 (s, 1 H), 8.39 (d, J=5.1 Hz, 1 H), 8.42 (s, 1 H), 8.42 (s, 1 H).

REFERENCE EXAMPLE 15

3-Amino-5-(1-benzylpiperidin-4-yl)-2H-pyrazole a) Methyl 1-benzylpiperidine-4-carboxylate To a solution of methyl piperidine-4-carboxylate (10.00 g, 6.4 mmol) and triethylamine (10.32 g, 10.2 mmol) in $CHCl_3$ (100 mL), benzyl bromide (14.69 g, 8.6 mmol) was added under argon atmosphere while cooling with a water and ice bath. The mixture was stirred at room temperature overnight. $CHCl_3$ and water were added and the two phases were separated. The aqueous phase was extracted with $CHCl_3$. The organic phase was dried over $Na_2SO_4$ and concentrated to dryness, to afford 13.80 g of the desired compound as an orange solid (yield: 88%).

b) 3-(1-Benzylpiperidin-4-yl)-3-oxoproplononitrile

To a solution of BuLi (12.4 mL of a 1.6 M solution in hexane, 19.8 mmol) in THF (25 mL) cooled to −78° C., acetonitrile (1 mL) was added dropwise under argon atmosphere. After stirring the resulting suspension for 5 min at −78° C., a solution of methyl 1-benzylpiperidine-4-carboxylate (2.0 g, 8.1 mmol, obtained in the previous section) in THF (5 mL) was added dropwise and stirred for 30 min at −78° C. It was allowed to reach room temperature and stirred at this temperature overnight. 1 N HCl was added to adjust the pH to 7 and the aqueous phase was extracted with $CHCl_3$. The organic phase was dried over $Na_2SO_4$ and concentrated to dryness, to afford 1.92 g of the desired compound in a solid orange form (yield: 98%).

c) Title Compound

To a solution of 3-(1-benzylpiperidin-4-yl)-3-oxopropiononitrile (1.85 g, 7.6 mmol, obtained in the previous section) in EtOH (77 mL), hydrazine monohydrate (0.74 mL, 15.3 mmol) was added under argon atmosphere. The mixture was heated to reflux overnight. The solvent was evaporated and the residue was dissolved in a mixture of water-$CHCl_3$. The aqueous phase was extracted with $CHCl_3$. The organic phase was dried over $Na_2SO_4$ and concentrated to dryness. The crude product obtained was purified by chromatography on silica gel using hexane-EtOAc mixtures of increasing polarity as eluent, to afford 0.46 g of the desired compound (yield: 23%)

$^1$H NMR (300 MHz, $CD_3OD$) δ (TMS): 1.72 (m, 2 H), 1.90 (m, 2 H), 2.15 (m, 2 H), 2.56 (m, 1 H), 2.97 (m, 2 H), 3.57 (s, 2 H), 4.89 (broad s, $NH+NH_2+H_2O$), 5.43 (s, 1 H), 7.27-7.34 (complex signal, 5 H).

REFERENCE EXAMPLE 16

3-(Dimethylamino)-1-(4-fluorophenyl)-2-(4-pyridyl)but-2-en-1-one

Following a similar procedure to that described in reference example 7, but using dimethylacetamide dimethyl acetal instead of dimethylformamide dimethyl acetal, the desired compound was obtained in the form of a crude product that was directly used in the following reactions.

$^1$H NMR (300 MHz, $CDCl_3$) δ (TMS): 2.15 (s, 3 H), 3.00 (s, 6 H), 6.80 (m, 4 H), 7.45 (m, 2 H), 8.30 (d, J=8.0 Hz, 2 H).

REFERENCE EXAMPLE 17

2-(4-Fluorophenyl)-6-hydroxy-4-methyl-3,4'-bipyridine-5-carbonitrile

Following a similar procedure to that described in reference example 10, but using 3-(dimethylamino)-1-(4-fluorophenyl)-2-(4-pyridyl)but-2-en-1-one (obtained in reference example 16) instead of 3-dimethylamino-1-(4-fluorophenyl)-2-(4-pyridyl)prop-2-en-1-one, the title compound was obtained (yield: 21%).

$^1$H NMR (300 MHz, $CDCl_3$) δ (TMS): 1.55 (broad s, $OH+H_2O$), 2.30 (s, 3 H), 6.97 (m, 4 H), 7.25 (m, 2 H), 8.52 (m, 2 H).

REFERENCE EXAMPLE 18

6-Chloro-2-(4-fluorophenyl)-4-methyl-3,4'-bipyridine-5-carbonitrile

Following a similar procedure to that described in reference example 12, but using 2-(4-fluorophenyl)-6-hydroxy-4-methyl-3,4'-bipyridine-5-carbonitrile (obtained in reference example 17) instead of 2-(4-fluorophenyl)-6-hydroxy-3,4'-bipyridine-5-carbonitrile, the title compound was obtained (yield: 52%).

$^1$H NMR (300 MHz, CDCl$_3$) δ (TMS): 2.41 (s, 3 H), 6.90 (m, 2 H), 7.09 (d, J=9.0 Hz, 2 H), 7.25 (m, 2 H), 8.62 (m, J=4.0 Hz, 2 H).

REFERENCE EXAMPLE 19

1-(4-Fluorophenyl)-2-[2-(methylsulfanyl)pyrimidin-4-yl]ethanone

To a solution of 4-methyl-2-(methylsulfanyl)pyrimidine (21.00 g, 150.0 mmol, obtained in reference example 6, section a) and ethyl 4-fluorobenzoate (25.14 g, 150.0 mmol) in THF (300 mL) under argon atmosphere, a solution of sodium bis(trimethylsilyl)amide (150 mL of a 2 M solution in THF, 300 mmol) in THF (150 mL) was added dropwise while cooling with an ice-bath. It was stirred at room temperature for 2 h. Saturated NH$_4$Cl was added and the solvent was evaporated. The residue was taken up in a mixture of EtOAc and water and the phases were separated. The aqueous phase was reextracted with EtOAc. The combined organic phases were washed with brine, dried over Na$_2$SO$_4$ and concentrated to dryness, to afford 36.36 g of the title compound (yield: 93%).

$^1$H NMR (300 MHz, CDCl$_3$) δ (TMS): 2.52 (ketone: s, 3 H), 2.61 (enol: s, 3 H), 4.35 ketone: s, 2 H), 5.92 (enol: s, 1 H), 6.64 (enol: d, J=5.7 Hz, 1 H), 6.95 (ketone: d, J=5.1 Hz, 1 H), 7.08-7.19 (m, 2H), 7.83 (enol: m, 2 H), 8.07 (ketone-m, 2 H), 8.31 (enol: d, J=5.7 Hz, 1 H), 8.56 (ketone: d, J=5.1 Hz, 1 H).

REFERENCE EXAMPLE 20

3-(Dimethylamino)-1-(4-fluorophenyl)-2-[2-(methylsulfanyl)pyrimidin-4-yl]prop-2-en-1-one Following a similar procedure to that described in reference example 7, but using 1-(4-fluorophenyl)-2-[2-(methylsulfanyl)pyrimidin-4-yl]ethanone (obtained in reference example 19) instead of 1-(4-fluorophenyl)-2-(4-pyridyl)ethanone, the title compound was obtained.

$^1$H NMR (300 MHz, CDCl$_3$) δ (TMS): 2.50 (s, 3 H), 2.96 (s, 6 H), 6.20-8.20 (complex signal, 7 H).

REFERENCE EXAMPLE 21

6-(4-Fluorophenyl)-2-(hydroxy)-5-(2-methylsulfanylpyrimidin-4-yl)pyridine-3-carbonitrile Following a similar procedure to that described in reference example 10, but using 3-(dimethylamino)-1-(4-fluorophenyl)-2-[2-(methylsulfanyl)pyrimidin-4-yl]prop-2-en-1-one (obtained in reference example 20) instead of 3-(dimethylamino)-1-(4-fluorophenyl)-2-(4-pyridyl)prop-2-en-1-one, the title compound was obtained (yield: 91%).

LC-MS (method 1): t$_R$=7.09 min; m/z=338.9 [M+H]$^+$

REFERENCE EXAMPLE 22

2-Chloro-6-(4-fluorophenyl)-5-(2-methylsulfanylpyrimidin-4-yl)pyridine-3-carbonitrile A mixture of 6-(4-fluorophenyl)-2-(hydroxy)-5-(2-methylsulfanylpyrimidin-4-yl)pyridin-3-carbonitrile (48.84 g, 144.6 mmol, obtained in reference example 21), POCl$_3$ (166 mL, 1.8 mol) and DMF (2.2 mL) was heated to 100° C. for 2 h. It was allowed to cool to room temperature and concentrated. It was cooled with an acetone-CO$_2$ bath and EtOAc and ice were subsequently added. The organic phase was decanted, washed with saturated NaHCO$_3$, dried over Na$_2$SO$_4$ and concentrated to dryness. The crude obtained was purified by chromatography on silica gel using hexane-EtOAc mixtures of increasing polarity, to afford 31.00 g of the title compound (yield: 60%).

$^1$H NMR (300 MHz, CDCl$_3$) δ (TMS): 2.54 (s, 3 H), 6.60 (d, J=5.1 Hz, 1 H), 7.08 (t, J=8.5 Hz, 2 H), 7.44 (m, 2 H), 8.37 (d, J=5.1 Hz, 1 H), 8.39 (s, 1 H).

REFERENCE EXAMPLE 23

2-(2-Chloropyridin-4-yl)-1-(4-fluorophenyl)ethanone

Following a similar procedure to that described in reference example 19, but starting from 2-chloro-4-methylpyridine and ethyl 4-fluorobenzoate, the title compound was obtained.

LC-MS (method 1): t$_R$=7.96 min; m/z=250.0, 252.0 [M+H]$^+$

REFERENCE EXAMPLE 24

2-[2-(Methylsulfanyl)pyrimidin-4-yl]-1-phenylethanone

Following a similar procedure to that described in reference example 19, but starting from 4-methyl-2-(methylsulfanyl)pyrimidine (obtained in reference example 6, section a) and ethyl benzoate, the title compound was obtained.

$^1$H NMR (300 MHz, CDCl$_3$) δ (TMS): 2.52 (ketone: s, 3 H), 2.62 (enol: s, 3 H), 4.39 (ketone: s, 2 H), 5.99 (enol: s, 1 H), 6.65 (enol: d, J=5.7 Hz, 1 H), 6.98 (ketone: d, J=5.1 Hz, 1 H), 7.40-7.51 (m, 3 H), 7.85 (enol: m, 2 H), 8.03 (ketone: m, 2 H), 8.32 (enol: d, J=5.7 Hz, 1 H), 8.46 (ketone: d, J=5.1 Hz, 1 H).

REFERENCE EXAMPLE 25

3-(Dimethylamino)-2-[2-(methylsulfanyl)pyrimidin-4-yl]-1-phenylprop-2-en-1-one

Following a similar procedure to that described in reference example 7, but starting from 2-[2-(methylsulfanyl)pyrimidin-4-yl]-1-phenylethanone (obtained in reference example 24), the title compound was obtained.

$^1$H NMR (300 MHz, CDCl$_3$) δ (TMS): 2.50 (s, 3 H), 2.90 (s, 6 H), 6.20-8.00 (complex signal, 8 H).

REFERENCE EXAMPLE 26

2-Hydroxy-5-(2-methylsulfanylpyrimidin-4-yl)-6-phenylpyridine-3-carbonitrile

Following a similar procedure to that described in reference example 10, but using 3-(dimethylamino)-2-[2-(methylsulfanyl)pyrimidin-4-yl]-1-phenylprop-2-en-1-one (obtained in reference example 25) instead of 3-dimethylamino-1-(4-fluorophenyl)-2-(4-pyridyl)prop-2-en-1-one, the title compound was obtained.

LC-MS (method 1): t$_R$=6.90 min; m/z=320.9 [M+H]$^+$

REFERENCE EXAMPLE 27

1-[6-(4-Fluorophenyl)-2-hydroxy-5-(2-methylsulfanylpyrimidin-4-yl)pyridin-3-yl]ethanone Following a similar procedure to that described in reference example 10, but starting from 3-(dimethylamino)-1-(4-fluorophenyl)-2-[2-(methylsulfanyl)pyrimidin-4-yl]prop-2- en-1-one (obtained in reference example 20) and 3-oxobutyramide, the title compound was obtained.

$^1$H NMR (300 MHz, CDCl$_3$) δ (TMS): 2.43 (s, 3 H), 2.66 (enol: s, 3 H), 6.53 (d, J=5.1 Hz, 1 H), 7.12 (t, J=8.4 Hz, 2 H), 7.42 (m, 2 H), 8.29 (d, J=5.1 Hz, 1 H), 8.63 (s, 1 H).

REFERENCE EXAMPLES 28-29

Following a similar procedure to that described in reference example 12, but starting from the appropriate compounds in each case, the compounds in the following table were obtained:

| Reference example | Compound name | Starting compounds | Method | LC-MS $t_R$ (min) | m/z [M + H]$^+$ |
|---|---|---|---|---|---|
| 28 | 2-Chloro-5-(2-methylsulfanylpyrimidin-4-yl) 6-phenylpyridine-3-carbonitrile | Reference example 26 | 1 | 10.18 | 338.9 |
| 29 | 4-[6-Chloro-5-(1-chlorovinyl)-2-(4-fluorophenyl)pyridin-3-yl]-2-methylsulfanylpyrimidine | Reference example 27 | 1 | 11.62 | 391.9 393.9 395.9 |

REFERENCE EXAMPLE 30

1-(4-Fluorophenyl)-2-pyrimidin-4-ylethanone

To a suspension of NaH (2.26 g 50%, 47.7 mmol) in DMF (92 mL) under argon atmosphere and cooled to 0° C., 4-methylpyrimidine (3.00 g, 31.9 mmol) was added slowly. Then, ethyl 4-fluorobenzoate (6.40 g, 38.2 mmol) was added and it was stirred at room temperature overnight. Water was added and the solvent was evaporated. The residue was taken up in a mixture of EtOAc and brine. The phases were separated and the aqueous phase was reextracted with EtOAc. The combined organic phases were dried over Na$_2$SO$_4$ and concentrated to dryness. The crude product obtained by chromatography on silica gel using hexane-EtOAc mixtures of increasing polarity as eluent, to afford 3.30 g of the desired compound (yield: 48%).

$^1$H NMR (300 MHz, CDCl$_3$) δ (TMS): 4.11 (ketone: s, 2 H), 5.94 (enol: s, 1 H), 6.94 (enol: d, J=5.4 Hz, 1 H), 7.08-7.16 (m, 2 H), 7.37 (ketone: d, J=5.1 Hz, 1 H), 7.89 (enol: m, 2 H), 8.08 (ketone: m, 2 H), 8.42 (enol: d, J=5.4 Hz, 1 H), 8.69 (ketone: d, J=5.1 Hz, 1 H), 8.81 (enol: s, 1 H), 9.17 (ketone: s, 1 H).

Example 1

4,6-Bis(4-fluorophenyl)-5-(4-pyridyl)-1H-pyrazolo[3,4-b]pyridine

Method A

In a volumetric flask, 1-(4-fluorophenyl)-2-(4-pyridyl)ethanone (23.56 g, 109.4 mmol, obtained in reference example 1) and 2-methoxyethanol (150 mL) were introduced. A solution of 3-amino-2H-pyrazole (10.00 g, 120.3 mmol) in 2-methoxyethanol (170 mL) and 37% HCl (3.23 g, 32.8 mmol) were added under argon atmosphere. This was heated to reflux for 3 days. It was allowed to cool and concentrated. The solid obtained was dissolved in CHCl$_3$ (400 mL) and MeOH (50 mL) and washed with 0.1 N HCl (300 mL) and 1 N NaOH (300 mL). The organic phase was dried over Na$_2$SO$_4$ and concentrated to dryness, to afford 9.93 g of the desired product in solid cream form (yield: 47%)

Method B

To a solution of 3-amino-2H-pyrazole (60 mg, 71.8 mmol) in EtOH (2 mL) and 1 drop of 37% HCl, 1-(4-fluorophenyl)-2-(4-pyridyl)vinyl 4-fluorobenzoate (0.22 g, 65.0 mmol, obtained in reference example 4) was added under argon atmosphere. This was heated to reflux for 3 days. The mixture was diluted with CHCl$_3$ and MeOH. It was washed with saturated NaHCO$_3$. The aqueous phase was extracted with CHCl$_3$ (×2). The organic phase was dried over Na$_2$SO$_4$ and concentrated to dryness. The crude product obtained was purified by chromatography on silica gel using hexane-EtOAc mixtures of increasing polarity as eluent, to afford 58 mg of the desired product in a solid white form (yield: 23%).

$^1$H NMR (300 MHz, CDCl$_3$+CD$_3$OD) δ (TMS): 4.08 (s, NH+CD$_3$OD), 6.80-7.01 (complex signal, 6 H), 7.21 (m, 2 H), 7.28 (m, 2 H), 7.95 (s, 1 H), 8.27 (dd, J$_o$=1.4 Hz, J$_m$=4.6 Hz, 2 H).

Example 2

4,6-Diphenyl-5-(4-pyridyl)-1H-pyrazolo[3,4-b]pyridine

Following a similar procedure to that described in example 1 method B, but using 1-phenyl-2-(4-pyridyl)vinyl benzoate (obtained in reference example 5) instead of 1-(4-fluorophenyl)-2-(4-pyridyl)vinyl 4-fluorobenzoate, the title compound was obtained in solid white form (yield: 37%).

$^1$H NMR (300 MHz, CDCl$_3$) δ (TMS): 4.08 (s, NH+H$_2$O), 6.85 (d, J=6.0 Hz, 2 H), 7.12-7.31 (complex signal, 10 H), 7.98 (s, 1 H), 8.29 (d, J=5.8 Hz, 2 H).

Example 3

5-(4-Pyridyl)-4,6-bis[3-(trifluoromethyl)phenyl]-1H-pyrazolo[3,4-b]pyridine

Following a similar procedure to that described in example 1 method A, but using 2-(4-pyridyl)-1-[3-(trifluoromethyl)phenyl]ethanone (obtained in reference example 2) instead of 1-(4-fluorophenyl)-2-(4-pyridyl)ethanone, the title compound was obtained (yield: 10%).

$^1$H NMR (300 MHz, CDCl$_3$) δ (TMS): 1.57 (s, NH+H$_2$O), 6.86 (broad s, 2 H), 7.30-7.60 (complex signal, 8 H), 7.99 (s, 1 H), 8.35 (broad s, 2 H).

Example 4

4,6-Bis(4-fluorophenyl)-3-methyl-5-(4-pyridyl)-1H-pyrazolo[3,4-b]pyridine

Following a similar procedure to that described in example 1 method B, but using 3-amino-5-methyl-2H-pyrazole instead of 3-amino-2H-pyrazole, the title compound was obtained in solid white form (yield: 19%).

$^1$H NMR (300 MHz, CDCl$_3$+CD$_3$OD) δ (TMS): 2.03 (broad s, 3 H), 4.08 (s, NH+CD$_3$OD), 6.81 (m, 2 H), 6.96 (m, 2 H), 7.01 (m, 2 H), 7.04 (m, 2 H), 7.29 (m, 2 H), 8.23 (m, 2 H).

Example 5

4,6-Diphenyl-3-methyl-5-(4-pyridyl)-1H-pyrazolo[3,4-b]pyridine

Following a similar procedure to that described in example 1 method B, but using 3-amino-5-methyl-2H-pyrazole instead of 3-amino-2H-pyrazole and 1-phenyl-2-(4-pyridyl)vinyl benzoate (obtained in reference example 5) instead of 1-(4-fluorophenyl)-2-(4-pyridyl)vinyl 4-fluorobenzoate, the title compound was obtained in solid white form (yield: 16%).

$^1$H NMR (300 MHz, CDCl$_3$) δ (TMS): 2.02 (s, 3 H), 2.02 (s, NH+H$_2$O), 6.83 (dd, J$_o$=1.5 Hz, J$_m$=4.5 Hz, 2 H), 7.13 (m, 2 H), 7.23-7.33 (complex signal, 6 H), 8.25 (83 (dd, J$_o$=1.5 Hz, J$_m$=4.5 Hz, 2 H).

Example 6

2-Ethyl-4,6-bis(4-fluorophenyl)-5-(4-pyridyl)pyrazolo[3,4-b]pyridine

Example 7

1-Ethyl-4,6-bis(4-fluorophenyl)-5-(4-pyridyl)pyrazolo[3,4-b]pyridine

A suspension of 4,6-bis(4-fluorophenyl)-5-(4-pyridyl)-1H-pyrazolo[3,4-b]pyridine (0.39 g, 0.8 mmol, obtained in example 1), KOH (0.05 g, 0.8 mmol) and crown ether 18-C-6 (0.01 g, 0.03 mmol) in toluene (3 mL) was heated to 100° C. for 2 h. A solution of iodoethane (0.18 g, 1.2 mmol) in toluene (1 mL) was added and stirred at 100° C. for 2 days. It was allowed to cool, water and EtOAc were added and the phases were separated. The aqueous phase was extracted with EtOAc. The organic phase was dried over Na$_2$SO$_4$ and concentrated to dryness. The crude product obtained was purified by chromatography on silica gel using hexane-EtOAc mixtures of increasing polarity as eluent, to afford 0.20 g of 2-ethyl-4,6-bis(4-fluorophenyl)-5-(4-pyridyl)pyrazolo[3,4-b]pyridine (yield: 61%) and 28 mg of 1-ethyl-4,6-bis(4-fluorophenyl)-5-(4-pyridyl)pyrazolo[3,4-b]pyridine (yield: 9%).

Example 6: $^1$H NMR (300 MHz, CDCl3) δ (TMS): 1.68 (t, J=7.4 Hz, 3 H), 4.51 (c, J=7.2 Hz, 2 H), 6.82 (dd, J$_o$=1.6 Hz, J$_m$=4.4 Hz, 2 H), 6.89 (t, J=8.7 Hz, 2 H), 7.00 (t, J=8.7 Hz, 2 H), 7.15 (m, 2 H), 7.30 (m, 2 H), 7.78 (s, 1H), 8.31 (dd, J$_o$=1.6 Hz, J$_m$=4.5 Hz, 2 H).

Example 7: $^1$H NMR (300 MHz, CDCl$_3$) δ (TMS): 1.61 (t, J=7.4 Hz, 3 H), 4.67 (c, J=7.2 Hz, 2 H), 6.81 (dd, J$_o$=1.6 Hz, J$_m$=4.4 Hz, 2 H), 6.96 (t, J=8.7 Hz, 2 H), 7.01 (t, J=8.7 Hz, 2 H), 7.13 (m, 2 H), 7.29 (m, 2 H), 7.86 (s, 1H), 8.32 (dd, J$_o$=1.5 Hz, J$_m$=4.5 Hz, 2 H).

Example 8

4,6-Bis(4-fluorophenyl)-2-methyl-5-(4-pyridyl)pyrazolo[3,4-b]pyridine

Example 9

4,6-Bis(4-fluorophenyl)-1-methyl-5-(4-pyridyl)pyrazolo[3,4-b]pyridine

Following a similar procedure to that described in example 6 and 7, but using iodomethane instead of iodoethane, the title compounds were obtained.

Example 8: yield: 52%; $^1$H NMR (300 MHz, CDCl$_3$) δ (TMS): 4.25 (s, 3 H), 6.81 (d, J=5.3 Hz, 2 H), 6.95 (t, J=8.6 Hz, 2 H), 6.98 (t, J=8.5 Hz, 2 H), 7.12 (m, 2 H), 7.28 (m, 2 H), 7.77 (s, 1H), 8.29 (d, J=5.2 Hz, 2 H).

Example 9: yield: 5%; $^1$H NMR (300 MHz, CDCl$_3$) δ (TMS): 4.20 (s, 3 H), 6.81 (dd, J$_o$=1.5 Hz, J$_m$=4.5 Hz, 2 H), 6.90 (t, J=8.7 Hz, 2 H), 6.98 (t, J=8.6 Hz, 2 H), 7.12 (m, 2 H), 7.26 (m, 2 H), 7.84 (s, 1H), 8.29 (dd, J$_o$=1.5 Hz, J$_m$=4.5 Hz, 2 H).

Example 10

4,6-Bis(4-fluorophenyl)-2,3-dimethyl-5-(4-pyridyl)pyrazolo[3,4-b]pyridine

Example 11

4,6-Bis(4-fluorophenyl)-1,3-dimethyl-5-(4-pyridyl)pyrazolo[3,4-b]pyridine

Following a similar procedure to that described in examples 6 and 7, but using 4,6-bis(4-fluorophenyl)-3-methyl-5-(4-pyridyl)-1H-pyrazolo[3,4-b]pyridine (obtained in example 4) instead of 4,6-bis(4-fluorophenyl)-5-(4-pyridyl)-1H-pyrazolo[3,4-b]pyridine and iodomethane instead of iodoethane, the title compounds were obtained.

Example 10: yield: 53%; $^1$H NMR (300 MHz, CDCl$_3$) δ (TMS): 2.03 (s, 3 H), 4.13 (s, 3 H), 6.79 (dd, J$_o$=1.5 Hz, J$_m$=4.5 Hz, 2 H), 6.88 (t, J=8.8 Hz, 2 H), 6.98-7.11 (complex signal, 4 H), 7.30 (m, 2 H), 8.26 (dd, J$_o$=1.6 Hz, J$_m$=4.4 Hz, 2 H).

Example 11: yield: 30%; $^1$H NMR (300 MHz, CDCl$_3$+CD$_3$OD) δ (TMS): 2.01 (broad s, 3 H), 4.15 (broad s, 3 H), 6.81 (m, 2 H), 6.93 (m, 2 H), 7.00 (m, 2 H), 7.07 (m, 2 H), 7.30 (m, 2 H), 8.23 (m, 2 H).

Example 12

2-[2-[1-(tert-Butoxycarbonyl)piperidin-4-yl]ethyl]-4,6-bis(4-fluorophenyl)-5-(4-pyridyl)pyrazolo[3,4-b]pyridine Example 13

1-[2-[1-(tert-Butoxycarbonyl)piperidin-4-yl]ethyl]-4,6-bis(4-fluorophenyl)-5-(4-pyridyl)pyrazolo[3,4-b]pyridine a) 2-[1-(tert-Butoxycarbonyl)piperidin-4-yl]ethanol To a solution of 2-(4-piperidyl)ethanol (9.63 g, 74.5 mmol) in DMF (100 mL) at 0° C., di-tert-butyl dicarbonate (16.26 g, 74.5 mol) was added slowly. The mixture was stirred overnight at room temperature. The solvent was concentrated and the residue was dissolved in a mixture of EtOAc and water. The phases were separated. The organic phase was dried over Na$_2$SO$_4$ and concentrated to dryness, to afford 15.09 g of the desired product (yield: 88%).

b) 2-[1-(tert-Butoxycarbonyl)piperidin-4-yl]ethyl methanesulfonate

To a solution of 2-[1-(tert-butoxycarbonyl)piperidin-4-yl]ethanol (7.50 g, 32.7 mmol, obtained in section a) in CHCl$_3$ (180 mL), triethylamine (4.6 mL) was added under argon atmosphere and cooled to 0° C. Then, methanesulfonyl chloride (2.6 mL, 32.7 mmol) was added dropwise. The mixture was stirred overnight at room temperature. Water was added and the phases were separated. The aqueous phase was extracted with CHCl$_3$ (×3). The organic phase was dried over Na$_2$SO$_4$ and concentrated to dryness, to afford 11.18 g of the desired compound (yield: quantitative).

c) Title Compounds

Following a similar procedure to that described in example 6 and 7, but using 2-[1-(tert-butoxycarbonyl)piperidin-4-yl] ethyl methanesulfonate (obtained in section b) instead of iodoethane, the title compounds were obtained.

Example 12: yield: 14%; $^1$H NMR (300 MHz, CDCl$_3$) δ (TMS): 1.00-1.40 (complex signal, 3 H), 1.45 (s, 9 H), 1.70 (m, 2 H), 2.66 (m, 2 H), 2.05 (m, 2 H), 4.09 (m, 2 H), 4.90 (t, J=7.4 Hz, 2 H), 6.83 (dd, J$_o$=1.6 Hz, J$_m$=4.4 Hz, 2 H), 6.90 (t, J=8.7 Hz, 2 H), 7.00 (t, J=8.7 Hz, 2 H), 7.14 (m, 2 H), 7.28 (m, 2 H), 7.77 (s, 1 H), 8.31 (dd, J$_o$=1.6 Hz, J$_m$=4.4 Hz, 2 H).

Example 13: yield: 29%; $^1$H NMR (300 MHz, CDCl$_3$) δ (TMS): ): 1.00-1.40 (complex signal, 3 H), 1.46 (s, 9 H), 1.82 (m, 2 H), 1.98 (m, 2 H), 2.67 (m, 2 H), 4.08 (m, 2 H), 4.65 (t, J=7.0 Hz Hz, 2 H), 6.82 (dd, J$_o$=1.6 Hz, J$_m$=4.5 Hz, 2 H), 6.93 (t, J=8.7 Hz, 2 H), 7.01 (t, J=8.7 Hz, 2 H), 7.25 (m, 2 H), 7.28 (m, 2 H), 7.86 (s, 1 H), 8.32 (dd, J$_o$=1.5 Hz, J$_m$=4.5 Hz, 2 H).

Example 14

2-[1-(tert-Butoxycarbonyl)piperidin-4-yl]-4,6-bis(4-fluorophenyl)-3-methyl-5-(4-pyridyl)pyrazolo[3,4-b]pyridine Example 15

1-[1-(tert-Butoxycarbonyl)piperidin-4-yl]-4,6-bis(4-fluorophenyl)-3-methyl-5-(4-pyridyl)pyrazolo[3,4-b]pyridine a) 1-(tert-Butoxycarbonyl)piperidin-4-yl methanesulfonate Following a similar procedure to that described in examples 12 and 13 section b, but using (1-tert-butoxycarbonyl)piperidin-4-ol instead of 2-[1-(tert-butoxycarbonyl)piperidin-4-yl]ethanol, the desired compound was obtained (yield: 97%).

b) Title Compounds

Following a similar procedure to that described in examples 6 and 7, but using 4,6-bis(4-fluorophenyl)-3-methyl-5-(4-pyridyl)-1H-pyrazolo[3,4-b]pyridine (obtained in example 4) instead of 4,6-bis(4-fluorophenyl)-5-(4-pyridyl)-1H-pyrazolo[3,4-b]pyridine and 1-(tert-butoxycarbonyl)piperidin-4-yl methanesulfonate (obtained in section a) instead of iodoethane, the title compounds were obtained.

Example 14: yield: 13%; $^1$H NMR (300 MHz, CDCl$_3$) δ (TMS): 1.51 (s, 9 H), 1.97 (m, 2 H), 2.06 (s, 3 H), 2.45 (m, 2 H), 2.94 (m, 2 H), 4.35 (m, 3 H), 6.78 (d, J=6.0 Hz, 2 H), 6.87 (t, J=8.7 Hz, 2 H), 7.01 (t, J=8.6 Hz, 2 H), 7.10 (m, 2 H), 7.33 (m, 2 H), 8.26 (d, J=6.0 Hz, 2 H).

Example 15: yield: 52%; $^1$H NMR (300 MHz, CDCl$_3$) δ (TMS): 1.54 (s, 9H), 2.00 (s, 3 H), 2.00 (m, 2 H), 2.31 (m, 2 H), 2.99 (m, 2 H), 4.33 (m, 2 H), 5.10 (m, 1 H), 6.78 (dd, J$_o$=1.8 Hz, J$_m$=4.5 Hz, 2 H), 6.92 (t, J=8.7 Hz, 2 H), 6.99 (t, J=8.7 Hz, 2 H), 7.08 (m, 2 H), 7.30 (m, 2 H), 8.27 (dd, J$_o$=1.5 Hz, J$_m$=4.5 Hz, 2 H).

Example 16

2-(3-Chloropropyl)-4,6-bis(4-fluorophenyl)-5-(4-pyridyl)pyrazolo[3,4-b]pyridine

Example 17

1-(3-Chloropropyl)-4,6-bis(4-fluorophenyl)-5-(4-pyridyl)pyrazolo[3,4-b]pyridine

Following a similar procedure to that described in examples 6 and 7, but using 1-bromo-3-chloropropane instead of iodoethane, the title compounds were obtained.

Example 16: yield: 28%; $^1$H NMR (300 MHz, CDCl$_3$) δ (TMS): 2.54 (m, 2 H), 3.52 (t, J=6.0 Hz, 2 H), 4.61 (t, J=6.0 Hz, 2 H), 6.81 (dd, J$_o$=1.6 Hz, J$_m$=4.4 Hz, 2 H), 6.86 (t, J=8.8 Hz, 2 H), 6.98 (t, J=8.7 Hz, 2 H), 7.13 (m, 2 H), 7.28 (m, 2 H), 7.83 (s, 1 H), 8.29 (dd, J$_o$=1.5 Hz, J$_m$=4.5 Hz, 2 H).

Example 17: yield: 19%; $^1$H NMR (300 MHz, CDCl$_3$) δ (TMS): 2.51 (m, 2 H), 3.61 (t, J=6.3 Hz, 2 H), 4.78 (t, J=6.4 Hz, 2 H), 6.82 (dd, J$_o$=1.6 Hz, J$_m$=4.4 Hz, 2 H), 6.92 (t, J=8.7 Hz, 2 H), 7.01 (t, J=8.7 Hz, 2 H), 7.14 (m, 2 H), 7.26 (m, 2 H), 7.86 (s, 1 H), 8.32 (dd, J$_o$=1.6 Hz, J$_m$=4.4 Hz, 2 H).

Example 18

3-[4,6-Bis(4-fluorophenyl)-5-(4-pyridyl)pyrazolo[3,4-b]pirridin-2-yl]propan-1-ol Method A a) 4,6-Bis(4-fluorophenyl)-5-(4-pyridyl)-2-[3-(tetrahydropyran-2-yloxy)propyl]pyrazolo[3,4-b]pyridine A suspension of 4,6-bis(4-fluorophenyl)-5-(4-pyridyl)-1H-pyrazolo[3,4-b]pyridine (0.30 g, 0.8 mmol, obtained in example 1), KOH (0.05 g, 0.8 mmol) and crown ether 18-C-6 (0.01 g, 0.03 mmol) in toluene (10 mL) was heated to 100° C. for 1 h. 2-(3-Bromopropoxy)tetrahydropyran (0.17 g, 0.8 mmol) was added and stirred at 100° C. for 24 h. It was allowed to cool, water and EtOAc were added and the phases were separated. The aqueous phase was extracted with EtOAc. The organic phase was dried over Na$_2$SO$_4$ and concentrated to dryness. The crude product obtained was purified by chromatography on silica gel using hexane-EtOAc mixtures of increasing polarity as eluent, to afford 0.22 g of the desired compound (yield: 54%).

LC-MS (método 1): t$_R$=7.60 min; m/z=527.2 [M+H]$^+$.

b) Title Compound

A solution of 4,6-bis(4-fluorophenyl)-5-(4-pyridyl)-2-[3-(tetrahydropyran-2-yloxy)propyl]pyrazolo[3,4-b]pyridine (0.22 g, 0.42 mmol, obtained in section a) in a mixture 4:2:1 of AcOH:THF:H$_2$O (9 mL) was heated to a 55° C. for 3 h. It was allowed to cool and concentrated. Saturated NaHCO$_3$ and 1 N NaOH were added to the residue and it was extracted with EtOAc. The organic phase was dried over Na$_2$SO$_4$ and concentrated to dryness, to afford 0.15 g of the title compound (yield: 83%).

LC-MS (método 1): t$_R$=5.37 min; m/z=−443.1 [M+H]$^+$.

Example 18

3-[4,6-Bis(4-fluorophenyl)-5-(4-pyridyl)pyrazolo[3,4-b]pirridin-2-yl]propan-1-ol Example 19

3-[4,6-Bis(4-fluorophenyl)-5-(4-pyridyl)pyrazolo[3,4-b]pyridin-1-yl]propan-1-ol

Method B

Following a similar procedure to that described in examples 6 and 7, but using 3-iodopropanol instead of iodoethane, the title compounds were obtained.

Example 18: yield: 33%; $^1$H NMR (300 MHz, CDCl$_3$) δ (TMS): 1.58 (s, OH+H$_2$O), 2.17 (m, 2 H), 3.71 (m, 2 H), 4.63 (t, J=6.4 Hz, 2 H), 6.83 (dd, J$_o$=1.6 Hz, J$_m$=4.4 Hz, 2 H), 6.90 (t, J=8.7 Hz, 2 H), 7.00 (t, J=8.7 Hz, 2 H), 7.15 (m, 2 H), 7.29 (m, 2 H), 7.82 (s, 1 H), 8.33 (dd, J$_o$=1.5 Hz, J$_m$=4.5 Hz, 2 H).

Example 19: yield: 21%; ¹H NMR (300 MHz, CDCl$_3$) δ (TMS): 1.57 (s, OH+H$_2$O), 2.17 (m, J=5.9 Hz, 2 H), 3.58 (m, 2 H), 4.78 (t, J=6.0 Hz, 2 H), 6.82 (dd, J$_o$=1.5 Hz, J$_m$=4.5 Hz, 2 H), 6.94 (t, J=8.7 Hz, 2 H), 7.02 (t, J=8.7 Hz, 2 H), 7.15 (m, 2 H), 7.27 (m, 2 H), 7.90 (s, 1 H), 8.34 (dd, J$_o$=1.5 Hz, J$_m$=4.5 Hz, 2 H).

Example 20

2-[1-(tert-Butoxycarbonyl)piperidin-4-yl]-4,6-bis(4-fluorophenyl)-5-(4-pyridyl)pyrazolo[3,4-b]pyridine

EXAMPLE 21

1-[1-(tert-Butoxycarbonyl)piperidin-4-yl]-4,6-bis(4-fluorophenyl)-5-(4-pyridyl)pyrazolo[3,4-b]pyridine Following an analogous procedure to that described in examples 6 and 7, but using 1-(tert-butoxycarbonyl)piperidin-4-yl methanesulfonate (obtained in example 14 section a) instead of Iodoethane, the title compounds were obtained.

Example 20: yield: 30%; ¹H NMR (300 MHz, CDCl$_3$) δ (TMS): 1.48 (s, 9 H), 2.00-2.20 (m, 4 H), 2.87 (m, 2 H), 4.21 (m, 2 H), 4.50 (m, 1 H), 6.73 (dd, J$_o$=1.5 Hz, J$_m$=4.5 Hz, 2 H), 6.81 (t, J=8.7 Hz, 2 H), 6.92 (t, J=8.7 Hz, 2 H), 7.03 (m, 2 H), 7.20 (m, 2 H), 7.73 (s, 1 H), 8.23 (dd, J$_o$=1.4 Hz, J$_m$=4.4 Hz, 2 H).

Example 21: yield: 28%; ¹H NMR (300 MHz, CDCl$_3$) δ (TMS): 1.46 (s, 9 H), 2.10-2.30 (complex signal, 4 H), 2.96 (m, 2 H), 4.30 (m, 2 H), 4.60 (m, 1 H), 6.82 (dd, J$_o$=1.5 Hz, J$_m$=4.5 Hz, 2 H), 6.89 (t, J=8.7 Hz, 2 H), 7.00 (t, J=8.7 Hz, 2 H), 7.14 (m, 2 H), 7.31 (m, 2 H), 7.82 (s, 1 H), 8.31 (dd, J$_o$=1.5 Hz, J$_m$=4.5 Hz, 2 H).

Example 22

2-Methyl-4,6-diphenyl-5-(4-pyridyl)pyrazolo[3,4-b]pyridine

Example 23

1-Methyl-4,6-diphenyl-5-(4-pyridyl)pyrazolo[3,4-b]pyridine

To a suspension of 4,6-diphenyl-5-(4-pyridyl)-1H-pyrazolo[3,4-b]pyridine (0.10 g, 0.3 mmol, obtained in example 2) in acetone (1 mL), KOH (21 mg, 0.4 mmol) was added under argon atmosphere. Then, a solution of iodomethane (47 mg, 0.3 mmol) in acetone (0.1 mL) was added and stirred overnight at room temperature. Water was added and extracted with CHCl$_3$. The organic phase was dried over Na$_2$SO$_4$ and concentrated to dryness. The crude product obtained was purified by chromatography on silica gel using hexane-EtOAc mixtures of increasing polarity as eluent, to afford 47 mg of 2-methyl-4,6-diphenyl-5-(4-pyridyl)pyrazolo[3,4-b]pyridine (yield: 47%) and 38 mg of 1-methyl-4,6-diphenyl-5-(4-pirridyl)pyrazolo[3,4-b]pyridine (yield: 38%).

Example 22: ¹H NMR (300 MHz, CDCl$_3$) δ (TMS): 4.24 (s, 3 H), 6.83 (dd, J$_o$=1.5 Hz, J$_m$=4.5 Hz, 2 H), 7.16-7.21 (complex signal, 4 H), 7.26-7.31 (complex signal, 6 H), 7.77 (s, 1H), 8.24 (dd, J$_o$=1.5 Hz, J$_m$=4.5 Hz, 2 H).

Example 23: ¹H NMR (300 MHz, CDCl$_3$) δ (TMS): 4.23 (s, 3 H), 6.81 (dd, J$_o$=1.6 Hz, J$_m$=4.4 Hz, 2 H), 7.17 (m, 2 H), 7.22-7.32 (complex signal, 8 H), 7.89 (s, 1 H), 8.26 (dd, J$_o$=1.5 Hz, J$_m$=4.5 Hz, 2 H).

Example 24

4,6-Bis(4-fluorophenyl)-5-(4-pyridyl)-2-[2-(tetrahydropiran-2-yloxy)ethyl]pyrazolo[3,4-b]pyridine Following a similar procedure to that described in examples 6 and 7, but using 2-(2-bromoethoxy)tetrahydropyran instead of Iodoethane, the title compound was obtained (yield: 50%).

¹H NMR (300 MHz, CDCl$_3$) δ (TMS): 1.48-1.63 (complex signal, 6 H), 3.47 (m, 1 H), 3.67 (m, 1 H), 4.02 (m, 1 H), 4.22 (m, 1 H), 4.57 (m, 1 H), 4.65 (m, 2 H), 6.83 (dd, J$_o$=1.5 Hz, J$_m$=4.5 Hz, 2 H), 6.90 (t, J=8.7 Hz, 2 H), 7.00 (t, J=8.6 Hz, 2 H), 7.14 (m, 2 H), 7.31 (m, 2 H), 7.92 (s, 1 H), 8.32 (dd, J$_o$=1.5 Hz, J$_m$=4.5 Hz, 2 H).

Example 25

2-[4,6-Bis(4-fluorophenyl)-5-(4-pyridyl)pyrazolo[3,4-b]pyridin-1-yl]ethanol

Following a similar procedure to that described in examples 22 and 23, but using 4,6-bis(4-fluorophenyl)-5-(4-pyridyl)-1H-pyrazolo[3,4-b]pyridine (obtained in example 1) instead of 4,6-diphenyl-5-(4-pyridyl)-1H-pyrazolo[3,4-b]pyridine and 2-bromoethanol instead of iodomethane, the title compound was obtained.

¹H NMR (300 MHz, CDCl$_3$) δ (TMS): 4.19 (m, 2 H), 4.32 (m, OH), 4.77 (t, J=4.7 Hz, 2 H), 6.82 (dd, J$_o$=1.5 Hz, J$_m$=4.5 Hz, 2 H), 6.95 (t, J=8.7 Hz, 2 H), 7.02 (t, J=8.6 Hz, 2 H), 7.15 (m, 2 H), 7.26 (m, 2 H), 7.89 (s, 1 H), 8.34 (dd, J$_o$=1.6 Hz, J$_m$=4.5 Hz, 2 H).

Example 26

4,6-Bis(4-fluorophenyl)-2-(4-methylsuffanylbenzyl)-5-(4-pyridyl)pyrazolo[3,4-b]pyridine Example 27

4,6-Bis(4-fluorophenyl)-1-(4-methylsulfanylbenzyl)-5-(4-pyridyl)pyrazolo[3,4-b]pyridine a) 1-Chloromethyl-4-(methylsulfanyl)benzene A solution of thionyl chloride (0.2 mL, 3.2 mmol) in THF (9 mL) was added slowly to 4-(methylsulfanylphenyl)methanol (0.346 g, 2.2 mmol) under argon atmosphere. The mixture was stirred at room temperature for 2 days. Brine (9 mL) was added and the phases were separated. The organic phase was dried over Na$_2$SO$_4$ and concentrated to dryness, to afford 0.37 g of the desired compound (yield: 95%).

b) Title Compounds

In a volumetric flask, 4,6-bis(4-fluorophenyl)-5-(4-pyridyl)-1H-pyrazolo[3,4-b]pyridine (0.30 g, 78.0 mmol, obtained in example 1) and DMF (3.5 mL) were introduced under argon atmosphere. KOH (0.06 g, 1.1 mmol) was added followed by a solution of 1-chloromethyl-4-(methylsulfanyl)benzene (0.15 g, 0.9 mmol, obtained in section a) in DMF (0.4 mL). This was heated to 60° C. overnight. It was allowed to cool and concentrated. The residue was dissolved in a mixture of water and EtOAc. The two phases were separated. The organic phase was dried over Na$_2$SO$_4$ and concentrated to dryness. The crude product obtained was purified by chromatography on silica gel using hexane-EtOAc mixtures of increasing polarity as eluent, to afford 0.10 g of 4,6-bis(4-fluorophenyl)-2-(4-methylsulfanylbenzyl)-5-(4-pyridyl)

pyrazolo[3,4-b]pyridine (yield: 25%) and 0.19 g of 4,6-bis(4-fluorophenyl)-1-(4-methylsulfanylbenzyl)-5-(4-pyridyl)pyrazolo[3,4-b]pyridine (yield: 47%).

Example 26: $^1$H NMR (300 MHz, CDCl$_3$) δ (TMS): 2.50 (s, 3 H), 5.60 (s, 2 H), 6.84 (dd, $J_o$=1.5 Hz, $J_m$=4.5 Hz, 2 H), 6.92 (t, J=8.8 Hz, 2 H), 7.00 (t, J=8.7 Hz, 2 H), 7.05 (m, 2 H), 7.24-7.37 (complex signal, 6 H), 7.76 (s, 1 H), 8.34 (dd, $J_o$=1.5 Hz, $J_m$=4.5 Hz, 2 H).

Example 27: $^1$H NMR (300 MHz, CDCl$_3$) δ (TMS): 2.49 (s, 3 H), 5.77 (s, 2 H), 6.85 (dd, $J_o$=1.6 Hz, $J_m$=4.4 Hz, 2 H), 6.97 (t, J=8.8 Hz, 2 H), 7.03 (t, J=8.7 Hz, 2 H), 7.15 (m, 2 H), 7.24-7.33 (complex signal, 4 H), 7.42 (d, J=8.1 Hz, 2 H), 7.89 (s, 1 H), 8.36 (dd, $J_o$=1.5 Hz, $J_m$=4.5 Hz, 2 H).

Example 28

2-[1-(tert-Butoxycarbonyl)piperidin-4-ylmethyl]-4,6-bis(4-fluorophenyl)-5-(4-pyridyl)pyrazolo[3,4-b]pyridine Example 29

1-[1-(tert-Butoxycarbonyl)piperidin-4-ylmethyl]-4,6-bis(4-fluorophenyl)-5-(4-pyridyl)pyrazolo[3,4-b]pyridine a) (4-Piperidyl)methanol To a suspension of LiAlH$_4$ (10.10 g, 0.266 mol) in THF (150 mL) at 0° C., a solution of ethyl piperidine-4-carboxylate (18.13 g, 0.120 mol) in THF (300 mL) was added slowly. This was stirred at room temperature overnight. It was cooled with an ice bath and a mixture of water (14 mL) and THF (28 mL) was added slowly. Afterwards, a mixture of 15% aqueous NaOH (14 mL) and water (37 mL) was added followed by stirring at room temperature for 30 min. The precipitate obtained was filtered and the filtrate was concentrated, to afford 17.88 g of the desired compound (yield: quantitative).

b) [1-(tert-Butoxycarbonyl)piperidin-4-yl]methanol

Following a similar procedure to that described in Example 12 section a, but using (4-piperidyl)methanol (obtained in section a of this example), instead of 2-(4-piperidyl)ethanol, the title compound was obtained (yield: 77%).

c) [1-(tert-Butoxycarbonyl)piperidin-4-yl]methyl methanesulfonate

Following a similar procedure to that described in example 12 section b, but using [1-(tert-butoxycarbonyl)piperidin-4-yl]methanol (obtained in section b of this example) instead of 2-[1-(tert-butoxycarbonyl)piperidin-4-yl]ethanol, the title compound was obtained (yield: 71%).

d) Title Compounds

Following a similar procedure to that described in examples 26 and 27, but using [1-(tert-butoxycarbonyl)piperidin-4-yl]methyl methanesulfonate (obtained in section c) instead of 1-chloromethyl-4-(methylsulfanyl)benzene, the title compounds were obtained.

Example 28: yield: 22%; $^1$H NMR (300 MHz, CDCl$_3$) δ (TMS): 1.47 (s, 9 H), 1.63 (m, 2 H), 2.43 (m, 1 H), 2.72 (m, 2 H), 4.15 (m, 2 H), 4.33 (d, J=7.2 Hz, 2 H), 6.86 (dd, $J_o$=1.5 Hz, $J_m$=4.5 Hz, 2 H), 6.93 (t, J=8.7 Hz, 2 H), 7.04 (t, J=8.7 Hz, 2 H), 7.17 (m, 2 H), 7.33 (m, 2 H), 7.77 (s, 1 H), 8.35 (dd, $J_o$=1.6 Hz, $J_m$=4.4 Hz, 2 H).

Example 29: yield: 71%; $^1$H NMR (300 MHz, CDCl$_3$) δ (TMS): 1.20-1.8 (complex signal, 5 H), 1.49 (s, 9 H), 2.35 (m, 1 H), 2.74 (m, 2 H), 4.15 (m, 2 H), 4.54 (d, J=7.2 Hz, 2 H), 6.86 (dd, $J_o$=1.5 Hz, $J_m$=4.5 Hz, 2 H), 6.97 (t, J=8.7 Hz, 2 H), 7.04 (t, J=8.7 Hz, 2 H), 7.18 (m, 2 H), 7.28 (m, 2 H), 7.90 (s, 1 H), 8.36 (dd, $J_o$=1.6 Hz, $J_m$=4.5 Hz, 2 H).

Example 30

4,6-Bis(4-fluorophenyl)-2-[2-(morpholin-4-yl)ethyl]-5-(4-pyridyl)pyrazolo[3,4-b]pyridine Example 31

4,6-Bis(4-fluorophenyl)-1-[2-(morpholin-4-yl)ethyl]-5-(4-pyridyl)pyrazolo[3,4-b]pyridine Following a similar procedure to that described in examples 26 and 27, but using 4-(2-chloroethyl)morpholine hydrochloride instead of 1-chloromethyl-4-(methylsulfanyl)benzene and 2 equivalents of KOH, the title compounds were obtained.

Example 30: yield: 10%; $^1$H NMR (300 MHz, CDCl$_3$) δ (TMS): 2.55 (m, 4 H), 3.06 (t, J=6.4 Hz, 2 H), 3.70 (m, 4 H), 4.58 (t, J=6.4 Hz, 2 H), 6.86 (dd, $J_o$=1.6 Hz, $J_m$=4.4 Hz, 2 H), 6.93 (t, J=8.9 Hz, 2 H), 7.04 (t, J=8.7 Hz, 2 H), 7.16 (m, 2H), 7.31 (m, 2 H), 7.88 (s, 1 H), 8.35 (dd, $J_o$=1.5 Hz, $J_m$=4.5 Hz, 2 H).

Example 31: yield: 24%; $^1$H NMR (300 MHz, CDCl$_3$) δ (TMS): 2.63 (m, 4 H), 3.04 (t, J=6.9 Hz, 2 H), 3.69 (m, 4 H), 4.77 (t, J=6.8 Hz, 2 H), 6.86 (dd, $J_o$=1.5 Hz, $J_m$=4.5 Hz, 2 H), 6.96 (t, J=8.7 Hz, 2 H), 7.05 (t, J=8.7 Hz, 2 H), 7.18 (m, 2 H), 7.28 (m, 2 H), 7.90 (s, 1 H), 8.36 (dd, $J_o$=1.5 Hz, $J_m$=4.5 Hz, 2 H).

Example 32

Ethyl 2-[4,6-bis(4-fluorophenyl)-5-(4-pyridyl)pyrazolo[3,4-b]pyridin-2-yl]acetate Example 33

Ethyl 2-[4,6-bis(4-fluorophenyl)-5-(4-pyridyl)pyrazolo[3,4-b]pyridin-1-yl]acetate Following a similar procedure to that described in examples 26 and 27, but using ethyl bromoacetate instead of 1-chloromethyl-4-(methylsulfanyl)benzene, the title compounds were obtained.

Example 32: yield: 6%; $^1$H NMR (300 MHz, CDCl$_3$) δ (TMS): 1.32 (t, J=7.2 Hz, 3 H), 4.32 (c, J=7.2 Hz, 2 H), 5.27 (s, 2 H), 6.86 (dd, $J_o$=1.6 Hz, $J_m$=4.4 Hz, 2 H), 6.93 (t, J=8.7 Hz, 2 H), 7.03 (t, J=8.6 Hz, 2 H), 7.18 (m, 2 H), 7.32 (m, 2 H), 7.93 (s, 1 H), 8.35 (dd, $J_o$=1.5 Hz, $J_m$=4.5 Hz, 2 H).

Example 33: yield: 21%; $^1$H NMR (300 MHz, CDCl$_3$) δ (TMS): 1.32 (t, J=7 Hz, 3 H), 4.31 (c, J=6.9 Hz, 2 H), 5.42 (s, 2 H), 6.84 (dd, $J_o$=1.6 Hz, $J_m$=4.5 Hz, 2 H), 6.95 (t, J=8.7 Hz, 2 H), 7.05 (t, J=8.7 Hz, 2 H), 7.19 (m, 2 H), 7.28 (m, 2 H), 7.98 (s, 1 H), 8.36 (dd, $J_o$=1.5 Hz, $J_m$=4.5 Hz, 2 H).

Example 34

Ethyl 3-[4,6-Bis(4-fluorophenyl)-5-(4-pyridyl)pyrazolo[3,4-b]pyridin-2-yl]propionate Example 35

Ethyl 3-[4,6-bs(4-Fluorophenyl)-5-(4-pyridyl)pyrazolo[3,4-b]pyridin-1-yl]propionate Following a similar procedure to that described in examples 26 and 27, but using ethyl 3-bromopropionate instead of 1-chloromethyl-4-(methylsulfanyl)benzene, the title compounds were obtained.

Example 34: yield: 5%; $^1$H NMR (300 MHz, CDCl$_3$) δ (TMS): 1.26 (t, J=7.2 Hz, 3 H), 3.20 (t, J=6.3 Hz, 2 H), 4.31 (c, J=7.2 Hz, 2 H), 4.76 (t, J=6.3 Hz, 2 H), 6.85 (dd, J$_o$=1.6 Hz, J$_m$=4.4 Hz, 2 H), 6.93 (t, J=8.8 Hz, 2 H), 7.03 (t, J=8.5 Hz, 2 H), 7.16 (m, 2 H), 7.32 (m, 2 H), 7.92 (s, 1 H), 8.34 (dd, J$_o$=1.5Hz, J$_m$=4.5 Hz, H).

Example 35: yield: 3%; $^1$H NMR (300 MHz, CDCl$_3$) δ (TMS): 1.25 (t, J=7.2 Hz, 3 H), 3.10 (t, J=7.2 Hz, 2 H), 4.17 (c, J=7.1 Hz, 2 H), 4.94 (t, J=7.0 Hz, 2 H), 6.85 (dd, J$_o$=1.6 Hz, J$_m$=4.6 Hz, 2 H), 6.96 (t, J=8.6 Hz, 2 H), 7.04 (t, J=8.6 Hz, 2 H), 7.18 (m, 2 H), 7.31 (m, 2 H), 7.89 (s, 1 H), 8.36 (dd, J$_o$=1.5 Hz, J$_m$=4.5 Hz, 2 H).

Example 36

4,6-Bis(4-fluorophenyl)-2-(4-piperidyl)-5-(4-pyridyl)pyrazolo[3,4-b]pyridine

To a solution of 2-[1-(tert-butoxycarbonyl)piperidin-4-yl]-4,6-bis(4-fluorophenyl)-5-(4-pyridyl)pyrazolo[3,4-b]pyridine (0.62 g, 1.1 mmol, obtained in example 20) in CH$_2$Cl$_2$ (19 mL) under argon atmosphere and cooled to 0° C., trifluoroacetic acid (1.8 mL) was added. It was stirred at room temperature for 2.5 h. The solvent was evaporated. The residue was dissolved in CHCl$_3$ and washed with 1 N NaOH and brine. The organic phase was dried over Na$_2$SO$_4$ and concentrated to dryness, to afford 319 mg of the title compound (yield: 62%).

$^1$H NMR (300 MHz, CDCl$_3$) δ (TMS): 1.71 (broad s, NH+H$_2$O), 2.21 (m, 2 H), 2.34 (m, 2 H), 2.88 (m, 2 H), 3.35 (m, 2 H), 4.54 (m, 1 H), 6.87 (dd, J$_o$=1.5 Hz, J$_m$=4.5 Hz, 2 H), 6.95 (t, J=8.7 Hz, 2 H), 7.06 (t, J=8.6 Hz, 2 H), 7.18 (m, 2 H), 7.34 (m, 2 H), 7.88 (s, 1 H), 8.36 (dd, J$_o$=1.6 Hz, J$_m$=4.4 Hz, 2 H).

Example 37

4,6-Bis(4-fluorophenyl)-1-(4-piperidyl)-5-(4-pyridyl)pyrazolo[3,4-b]pyridine

Following a similar procedure to that described in example 36, but using 1-[1-(tert-butoxycarbonyl)piperidin-4-yl]-4,6-bis(4-fluorophenyl)-5-(4-pyridyl)pyrazolo[3,4-b]pyridine (obtained in example 21) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 29%).

$^1$H NMR (300 MHz, CDCl$_3$) δ (TMS): 1.62 (broad s, NH+H$_2$O), 2.13 (m, 2 H), 2.32 (m, 2 H), 2.92 (m, 2 H), 3.33 (m, 2 H), 4.52 (m, 1 H), 6.81 (dd, J$_o$=1.5 Hz, J$_m$=4.5 Hz, 2 H), 6.94 (t, J=8.7 Hz, 2 H), 7.01 (t, J=8.6 Hz, 2 H), 7.14 (m, 2 H), 7.27 (m, 2 H), 7.86 (s, 1 H), 8.32 (dd, J$_o$=1.4 Hz, J$_m$=4.4 Hz, 2 H).

Example 38

4,6-Bis(4-fluorophenyl)-2-(4-piperidylmethyl)-5-(4-pyridyl)pyrazolo[3,4b]pyridine Following a similar procedure to that described in example 36, but using 2-[1-(tert-butoxycarbonyl)piperidin-4-ylmethyl]-4,6-bis(4-fluorophenyl)-5-(4-pyridyl)pyrazolo[3,4-b]pyridine (obtained in example 28) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 13%).

$^1$H NMR (300 MHz, CDCl$_3$) δ (TMS): 1.30-1.80 (complex signal, 4 H), 1.63 (broad s, NH+H$_2$O), 2.38 (m, 1 H), 2.64 (m, 2 H), 3.14 (m, 2 H), 4.32 (d, J=7.2 Hz, 2 H), 6.86 (dd, J$_o$=1.6 Hz, J$_m$=4.4 Hz, 2 H), 6.93 (t, J=8.8 Hz, 2 H), 7.04 (t, J=8.6 Hz, 2 H), 7.18 (m, 2 H), 7.33 (m, 2 H), 7.78 (s, 1 H), 8.35 (dd, J$_o$=1.8 Hz, J$_m$=4.5 Hz, 2 H).

Example 39

4,6-Bis(4-fluorophenyl)-1-(4-piperidylmethyl)-5-(4-pyridyl)pyrazolo[3,4-b]pyridine Following a similar procedure to that described in example 36, but using 1-[1-(tert-butoxycarbonyl)piperidin-4-ylmethyl]4,6-bis(4-fluorophenyl)-5-(4-pyridyl)pyrazolo[3,4-b]pyridine (obtained in example 29) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 12%).

$^1$H NMR (300 MHz, CDCl$_3$) δ (TMS): 1.80-2.10 (complex signal, 4 H), 2.47 (m, 1 H), 3.0 (m, 3 H), 3.50 (m, 2 H), 4.63 (d, J=6.6, 2 H), 7.04 (t, J=8.4 Hz, 2 H), 7.12-7.16 (complex signal, 4 H), 7.22 (m, 2 H), 7.31 (m, 2 H), 7.95 (s, 1 H), 8.58 (d, J=6.6, 2 H).

Example 40

4,6-Bis(6-chloropyridin-3-yl)-5-(4-pyridyl)-1H-pyrazolo[3,4-b]pyridine

Following a similar procedure to that described in example 1 method A, but using 1-(6-chloropyridin-3-yl)2-(4-pyridyl)ethanone (obtained in reference example 9) instead of 1-(4-fluorophenyl)-2-(4-pyridyl)ethanone, the title compound was obtained (yield: 17%).

$^1$H NMR (300 MHz, CDCl$_3$) δ (TMS): 6.90 (dd, J$_o$=1.5 Hz, J$_m$=4.5 Hz, 2 H), 7.21 (d, J=8.4 Hz, 1 H), 7.30 (d, J=8.4 Hz, 1 H), 7.38 (dd, J$_o$=2.5 Hz, J$_m$=8.3 Hz, 1 H), 7.49 (dd, J$_o$=2.4 Hz, J$_m$=8.4 Hz, 1 H), 8.00 (s, 1 H), 8.36 (d, J=2.4 Hz, 1 H), 8.46-8.48 (complex signal, 3 H), 11.34 (broad s, 1 H).

Example 41

4,6-Bis(4-fluorophenl)-3-methyl-2-(4-piperidyl)-5-(4-pyridyl)pyrazolo[3,4-b]pyridine Following a similar procedure to that described in example 36, but using 2-[1-(tert-butoxycarbonyl)piperidin-4-yl]-4,6-bis(4-fluorophenyl)-3-methyl-5-(4-pyridyl)pyrazolo[3,4-b]pyridine (obtained in example 14) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 73%).

$^1$H NMR (300 MHz, CDCl$_3$) δ (TMS): 1.55 (broad s, NH+H$_2$O), (s, 3 H), 2.35 (m, 2 H), 3.34 (m, 2 H), 3.85 (m, 2 H), 4.73 (m, 2 H), 4.75 (m, 1 H), 6.78 (d, J=6.3 Hz, 2 H), 6.89 (t, J=8.6 Hz, 2 H), 7.03-7.19 (complex signal, 4 H), 7.29 (m, 2 H), 8.27 (d, J=6.0 Hz, 2 H).

Example 42

4,6-Bis(4-fluorophenyl)-3-methyl-1-(4-piperidyl)-5-(4-pyridyl)pyrazolo[3,4-b]pyridine Following a similar procedure to that described in example 36, but using 1-[1-(tert-butoxycarbonyl)piperidin-4-yl]-4,6-bis(4-fluorophenyl)-3-methyl-5-(4-pyridyl)pyrazolo[3,4-b]pyridine (obtained in example 15) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 59%).

¹H NMR (300 MHz, CDCl₃) δ (TMS): 1.55 (broad s, NH+H₂O), 2.01 (s, 3 H), 2.07 (m, 2 H), 2.29 (m, 2 H), 2.90 (m, 2 H), 3.32 (m, 2 H), 4.75 (m, 1 H), 6.78 (dd, $J_o$=1.6 Hz, $J_m$=4.4 Hz, 2 H), 6.93 (t, J=8.7 Hz, 2 H), 6.99 (t, J=8.7 Hz, 2 H), 7.08 (m, 2 H), 7.30 (m, 2 H), 8.27 (dd, $J_o$=1.6 Hz, $J_m$=4.4 Hz, 2 H).

Example 43

4,6-Bis(4-fluorophenyl)-2-[2-(4-piperidyl)ethyl]-5-(4-pyridyl)pyrazolo[3,4-b]pyridine Following a similar procedure to that described in example 36, but using 2-[2-[1-(tert-butoxycarbonyl)piperidin-4-yl]ethyl]-4,6-bis(4-fluorophenyl)-5-(4-pyridyl)pyrazolo[3,4-b]pyridine (obtained in example 12) instead of 2-[1-(tert-butoxycarbonyl)piperidin-4-yl]4,6-bis(4-fluorophenyl)-5-(4-pyridyl)pyrazolo[3,4-b]pyridine, the title compound was obtained (yield: 88%).

¹H NMR (300 MHz, CDCl₃) δ (TMS): 1.00-1.60 (complex signal, 3 H), 1.66 (s, NH+H₂O), 1.74 (m, 2 H), 2.03 (m, 2 H), 2.60 (m, 2 H), 3.10 (m, 2 H), 4.85 (t, J=7.2 Hz, 2 H), 6.82 (dd, $J_o$=1.5 Hz, $J_m$=4.5 Hz, 2 H), 6.89 (t, J=8.7 Hz, 2 H), 7.00 (t, J=8.7 Hz, 2 H), 7.13 (m, 2 H), 7.30 (m, 2 H), 7.76 (s, 1 H), 8.31 (dd, $J_o$=1.5 Hz, $J_m$=4.5 Hz, 2 H).

Example 44

2-[4,6-Bis(4-fluorophenyl)-5-(4-pyridyl)pyrazolo[3,4-b]pyridin-2yl]acetic acid

To a solution of ethyl 2-[4,6-bis(4-fluorophenyl)-5-(4-pyridyl)pyrazolo[3,4-b]pyridin-2-yl]acetate (0.09 g, 0.2 mmol, obtained in example 32) in EtOH (4.2 mL), a solution of KOH (0.09 g, 2.5 mmol) in water (0.5 mL) was added. This was heated to reflux for 1 h. It was allowed to cool and concentrated. The residue was dissolved in a mixture of EtOAc and water. The phases were separated. The aqueous phase was acidified and extracted with EtOAc. The combined organic phases were dried over Na₂SO₄ and concentrated to dryness, to afford 57 mg of title compound (yield: 66%).

¹H NMR (300 MHz, CDCl₃+CD₃OD) δ (TMS): 4.00 (broad s, 1 H+CD₃OD), 5.28 (broad s, 2 H), 6.92-7.05 (complex signal, 6 H), 7.15-7.30 (complex'signal, 4 H), 8.02 (broad s, 1 H), 8.26 (m, 2 H).

Example 45

2-[4,6-Bis(4-fluorophenyl)-5-(4-pyridyl)pyrazolo[3,4-b]pyridin-1-yl]acetic acid

Following a similar procedure to that described in example 44, but using ethyl 2-[4,6-bis(4-fluorophenyl)-5-(4-pyridyl)pyrazolo[3,4-b]pyridin-1-yl]acetate (obtained in example 33) instead of ethyl 2-[4,6-bis(4-fluorophenyl)-5-(4-pyridyl)pyrazolo[3,4-b]pyridin-2-yl]acetate, the title compound was obtained (yield: 96%).

¹H NMR (300 MHz, CDCl₃+CD₃OD) δ (TMS): 3.88 (broad s, 1H+CD₃OD), 5.32 (s, 2 H), 6.83 (dd, $J_o$=1.5 Hz, $J_m$=4.5 Hz, 2 H), 6.88 (t, J=8.7 Hz, 2 H), 6.98 (t, J=8.6 Hz, 2 H), 7.11 (m, 2 H), 7.20 (m, 2 H), 7.90 (s, 1 H), 8.21 (dd, $J_o$=1.5 Hz, $J_m$=4.5 Hz, 2H).

Example 46

3-[4,6-Bis(4-fluorophenyl)-5-(4-pyridyl)pyrazolo[3,4-b]pyridin-2-yl]propionic acid Following a similar procedure to that described in example 44, but using ethyl 3-[4,6-bis(4-fluorophenyl)-5-(4-pyridyl)pyrazolo[3,4-b]pyridin-2-yl]propionate (obtained in example 34) instead of ethyl 2-[4,6-bis(4-fluorophenyl)-5-(4-pyridyl)pyrazolo[3,4-b]pyridin-2-yl]acetate, the title compound was obtained (yield: 69%).

¹H NMR (300 MHz, CDCl₃+CD₃OD) δ (TMS): 3.08 (t, J=6.3 Hz, 2 H), 4.50 (broad s, 1H+CD₃OD), 4.72 (t, J=6.3 Hz, 2 H), 6.88 (dd, $J_o$=1.6 Hz, $J_m$=4.6 Hz, 2 H), 6.90 (t, J=8.7 Hz, 2 H), 6.99 (t, J=8.7 Hz, 2 H), 7.15 (m, 2 H), 7.23 (m, 2 H), 8.03 (s, 1 H), 8.21 (dd, $J_o$=1.5 Hz, $J_m$=4.5 Hz, 2 H).

Example 47

3-[4,6-Bis(4-fluorophenyl)-5-(4-pyridyl)pyrazolo[3,4-b]pyridin-1-yl]propionic acid Following a similar procedure to that described in example 44, but using ethyl 3-[4,6-bis(4-fluorophenyl)-5-(4-pyridyl)pyrazolo[3,4-b]pyridin-1-yl]propionate (obtained in example 35) instead of ethyl 2-[4,6-bis(4-fluorophenyl)-5-(4-pyridyl)pyrazolo[3,4-b]pyridin-2-yl]acetate, the title compound was obtained (yield: 88%).

¹H NMR (300 MHz, CDCl₃+CD₃OD) δ (TMS): 3.02 (t, J=7.2 Hz, 2 H), 4.50 (broad s, 1H+CD₃OD), 4.86 (t, J=7.3 Hz, 2 H), 6.87 (dd, $J_o$=1.5 Hz, $J_m$=4.5 Hz, 2 H), 6.91 (t, J=8.7 Hz, 2 H), 7.00 (t, J=8.7 Hz, 2 H), 7.12 (m, 2 H) 7.24 (m, 2 H), 7.84 (s, 1 H), 8.21 (dd, $J_o$=1.5 Hz, $J_m$=4.5 Hz, 2 H).

Example 48

2-[4,6-Bis(4-fluorophenyl)-5-(4-pyridyl)pyrazolo[3,4-b]pyridin-2-yl]-1-(morpholin-4-yl)ethanone To a solution of 2-[4,6-bis(4-fluorophenyl)-5-(4-pyridyl)pyrazolo[3,4-b]pyridin-2-yl]acetic acid (0.05 g, 0.1 mmol, obtained in example 44) in DMF (1 mL), N,N'-dicyclohexylcarbodiimide (0.02 g, 0.1 mmol) and 1-hydroxybenzotriazole (0.02 g, 0.1 mmol) were added under argon atmosphere. The mixture was stirred for 15 min and morpholine (0.01 g, 0.1 mmol) was added. This was stirred at room temperature for 2 days. EtOAc was added and the mixture was filtered. The filtrate was washed with saturated NaHCO₃. The organic phase was dried over Na₂SO₄ and concentrated to dryness. The crude product obtained was purified by chromatography on silica gel using EtOAc-MeOH mixtures of increasing polarity as eluent, to afford 18 mg of title compound (yield: 35%).

¹H NMR (300 MHz, CDCl₃) δ (TMS): 3.66-3.76 (complex signal, 8 H), 5.30 (s, 2 H), 6.82 (d, J=5.7 Hz, 2 H), 6.91 (t, J=8.8 Hz, 2 H), 6.99 (t, J=8.7 Hz, 2 H), 7.14 (m, 2 H), 7.28 (m, 2 H), 7.99 (s, 1 H), 8.32 (d, J=6.0 Hz, 2 H).

Example 49

2-[4,6-Bis(4-fluorophenyl)-5-(4-pyridyl)pyrazolo[3,4-b]pyridin-1-yl]acetamide

Following a similar procedure to that described in example 48, but using 2-[4,6-bis(4-fluorophenyl)-5-(4-pyridyl)pyrazolo[3,4-b]pyridin-1-yl]acetic acid (obtained in example 45) instead of 2-[4,6-bis(4-fluorophenyl)-5-(4-pyridyl)pyrazolo[3,4-b]pyridin-2-yl]acetic acid, and aqueous NH₃ instead of morpholine, the title compound was obtained (yield: 36%).

¹H NMR (300 MHz, CDCl₃) δ (TMS): 5.35 (s, 2 H), 5.56 (broad s, 1 H), 6.15 (broad s, 1 H), 6.85 (d, J=5.4 Hz, 2 H), 6.96 (t, J=8.6 Hz, 2 H), 7.06 (t, J=8.6 Hz, 2 H), 7.17 (m, 2 H), 7.29 (m, 2 H), 8.01 (s, 1 H), 8.38 (d, J=5.4 Hz, 2 H).

Example 50

2-[4,6-Bis(4-fluorophenyl)-5-(4-pyridyl)pyrazolo[3,4-b]pyridin-1-yl]-1-(morpholin-4-yl)ethanone Following a similar procedure to that described in example 48, but using 2-[4,6-bis(4-fluorophenyl)-5-(4-pyridyl)pyrazolo[3,4-b]pyridin-1-yl]acetic acid (obtained in example 45) instead of 2-[4,6-bis(4-fluorophenyl)-5-(4-pyridyl)pyrazolo[3,4-b]pyridin-2-yl]acetic acid, the title compound was obtained (yield: 60%).

$^1$H NMR (300 MHz, CDCl$_3$) δ (TMS): 3.67-3.70 (complex signal, 4 H), 3.75-3.81 (complex signal, 4 H), 5.50 (s, 2 H), 6.83 (dd, J$_o$=1.6 Hz, J$_m$=4.4 Hz, 2 H), 6.95 (t, J=8.7 Hz, 2 H), 7.04 (t, J=8.7 Hz, 2 H), 7.17 (m, 2 H), 7.27 (m, 2 H), 7.99 (s, 1 H), 8.35 (dd, J$_o$=1.6 Hz, J$_m$=4.4 Hz, 2 H)

Example 51

3-[4,6-Bis(4-fluorophenyl)-5-(4-pyridyl)pyrazolo[3,4-b]pyridin-2-yl]-1-(morpholin-4-yl)propan-1-one Following a similar procedure to that described in example 48, but using 3-[4,6-bis(4-fluorophenyl)-5-(4-pyridyl)pyrazolo[3,4-b]pyridin-2-yl]propionic acid (obtained in example 46) instead of 2-[4,6-bis(4-fluorophenyl)-5-(4-pyridyl)pyrazolo[3,4-b]pyridin-2-yl]acetic acid, the title compound was obtained (yield: 64%).

$^1$H NMR (300 MHz, CDCl$_3$) δ (TMS): 3.20 (t, J=6.0 Hz, 2 H), 3.45 (m, 2 H), 3.55-3.63 (complex signal, 6 H), 4.79 (t, J=6.1 Hz, 2 H), 6.81 (dd, J$_o$=1.6 Hz, J$_m$=4.4 Hz, 2 H), 6.90 (t, J=8.7 Hz, 2 H), 6.99 (t, J=8.7 Hz, 2 H), 7.13 (m, 2 H), 7.30 (m, 2 H), 7.94 (s, 1 H), 8.31 (dd, J$_o$=1.6 Hz, J$_m$=4.4 Hz, 2 H)

Example 52

3-[4,6-Bis(4-fluorophenyl)-5-(4-pyridyl)pyrazolo[3,4-b]pyridin-1-yl]-N-propylpropionamide Following a similar procedure to that described in example 48, but using 3-[4,6-bis(4-fluorophenyl)-5-(4-pyridyl)pyrazolo[3,4-b]pyridin-1-yl]propionic acid (obtained in example 47) instead of 2-[4,6-bis(4-fluorophenyl)-5-(4-pyridyl)pyrazolo[3,4-b]pyridin-2-yl]acetic acid, and propylamine instead of morpholine, the title compound was obtained (yield: 76%).

$^1$H NMR (300 MHz, CDCl$_3$) δ (TMS): 0.84 (t, J=7.3 Hz, 3 H), 1.42 (m, 2 H), 2.98 (t, J=6.7 Hz, 2 H), 3.18 (m, 2 H), 4.95 (t, J=6.7 Hz, 2 H), 6.05 (m, NH), 6.84 (dd, J$_o$=1.5 Hz, J$_m$=4.5 Hz, 2 H), 6.96 (t, J=8.7 Hz, 2 H), 7.04 (t, J=8.7 Hz, 2 H), 7.16 (m, 2 H), 7.32 (m, 2 H), 7.89 (s, 1 H), 8.36 (dd, J$_o$=1.5 Hz, J$_m$=4.5 Hz, 2 H).

Example 53

3-[4,6-Bis(4-fluorophenyl)-5-(4-pyridyl)pyrazolo[3,4-b]pyridin-1-yl]-1-(morpholin-4-yl)propan-1-one Following a similar procedure to that described in example 48, but using 3-[4,6-bis(4-fluorophenyl)-5-(4-pyridyl)pyrazolo[3,4-b]pyridin-1-yl]propionic acid (obtained in example 47) instead of 2-[4,6-bis(4-fluorophenyl)-5-(4-pyridyl)pyrazolo[3,4-b]pyridin-2-yl]acetic acid, the title compound was obtained (yield: 72%).

$^1$H NMR (300 MHz, CDCl$_3$) δ (TMS): 3.13 (t, J=7.3 Hz, 2 H), 3.49 (m, 2 H), 3.63-3.67 (complex signal, 6 H), 4.99 (t, J=7.3 Hz, 2 H), 6.84 (dd, J$_o$=1.4 Hz, J$_m$=4.4 Hz, 2 H), 6.96 (t, J=8.7 Hz, 2 H), 7.04 (t, J=8.7 Hz, 2 H), 7.16 (m, 2 H), 7.30 (m, 2 H), 7.89 (s, 1 H), 8.36 (dd, J$_o$=1.6 Hz, J$_m$=4.4 Hz, 2 H)

Example 54

4,6-Bis(4-fluorophenyl)-2-(4-methylsulfanylphenyl)-5-(4-pyridyl)pyrazolo[3,4-b]pyridine

Example 55

4,6-Bis(4-fluorophenyl)-1-(4-methylsulfanylphenyl)-5-(4-pyridyl)pyrazolo[3,4-b]pyridine In a volumetric flask molecular sieves of 4 Å (1 g, previously dried for 3 h at 200° C. under vacuum), 4,6-bis(4-fluorophenyl)-5-(4-pyridyl)-1H-pyrazolo[3,4-b]pyridine (0.30 g, 0.8 mmol, obtained in example 1), (4-methylsulfanylphenyl)boronic acid (0.26 g, 1.6 mmol), copper 11 acetate (0.28 g, 1.6 mmol), pyridine (0.12 g, 1.6 mmol), triethylamine (0.16 g, 1.6 mmol) and CH$_2$Cl$_2$ (22 mL) were introduced under argon atmosphere. This was stirred at room temperature for 2 days. It was filtered through celite and concentrated. The crude product obtained was purified by chromatography on silica gel using hexane-EtOAc mixtures of increasing polarity as eluent, to afford 40 mg of 4,6-bis(4-fluorophenyl)-2-(4-methylsulfanylphenyl)-5-(4-pyridyl)pyrazolo[3,4-b]pyridine (yield: 10%) and 90 mg of 4,6-bis(4-fluorophenyl)-1-(4-methylsulfanylphenyl)-5-(4-pyridyl)pyrazolo[3,4-b]pyridine (yield: 23%).

Example 54: $^1$H NMR (300 MHz, CDCl$_3$) δ (TMS): 2.46 (s, 3 H), 6.76 (dd, J$_o$=1.6 Hz, J$_m$=4.4 Hz, 2 H), 6.83 (t, J=8.7 Hz, 2 H), 6.95 (t, J=8.6 Hz, 2 H), 7.11 (m, 2 H), 7.26 (m, 2 H), 7.29 (d, J=8.7 Hz, 2 H), 7.83 (d, J=8.7 Hz, 2 H), 8.16 (s, 1 H), 8.26 (dd, J$_o$=1.6 Hz, J$_m$=4.4 Hz, 2 H).

Example 55: $^1$H NMR (300 MHz, CDCl$_3$) δ (TMS): 2.46 (s, 3 H), 6.76 (dd, J$_o$=1.5 Hz, J$_m$=4.5 Hz, 2 H), 6.86 (t, J=8.7 Hz, 2 H), 6.96 (t, J=8.7 Hz, 2 H), 7.08 (m, 2 H), 7.22 (m, 2 H), 7.34 (d, J=9.0 Hz, 2 H), 7.94 (s, 1 H), 8.23 (d, J=8.7 Hz, 2 H), 8.26 (dd, J$_o$=1.5 Hz, J$_m$=4.5 Hz, 2 H).

Example 56

4,6-Bis(4-fluorophenyl)-2-(4-methylsulfinylphenyl)-5-(4-pyridyl)pyrazolo[3,4-b]pyridine

Example 57

4,6-Bis(4-fluorophenyl)-2-(4-methylsulfonylphenyl)-5-(4-pyridyl)pyrazolo[3,4-b]pyridine To a solution of 4,6-bis(4-fluorophenyl)-2-(4-methylsulfanylphenyl)-5-(4-pyridyl)pyrazolo[3,4-b]pyridine (0.09 g, 0.2 mmol, obtained in example 54) in CH$_2$Cl$_2$ (3.5 mL), 3-chloroperbenzoic acid (0.04 g, 0.2 mmol) was added under argon atmosphere and stirred for 2 h at room temperature. CHCl$_3$ was added and washed with saturated NaHCO$_3$. The organic phase was dried over Na$_2$SO$_4$ and concentrated to dryness. The crude product obtained was purified by chromatography on silica gel using increasing polarity hexane-EtOAc mixtures as eluent, to afford 15 mg of 4,6-bis(4-fluorophenyl)-2-(4-methylsulfinylphenyl)-5-(4-pyridyl)pyrazolo[3,4-b]pyridine (yield: 16%) and 10 mg of 4,6-bis(4-fluorophenyl)-2-(4-methylsulfonylphenyl)-5-(4-pyridyl)pyrazolo[3,4-b]pyridine (yield: 11%)

Example 56: $^1$H NMR (300 MHz, CDCl$_3$) δ (TMS): 2.83 (s, 3 H), 6.90 (dd, J$_o$=1.5 Hz, J$_m$=4.5 Hz, 2 H), 6.96 (t, J=8.7 Hz, 2 H), 7.08 (t, J=8.7 Hz, 2 H), 7.24 (m, 2 H), 7.36 (m, 2 H), 7.75 (HA from an AB system, J=8.9 Hz, 2 H), 8.32 (H$_B$ from an AB system, J=8.9 Hz, 2 H), 8.38 (s, 1 H), 8.39 (dd, J$_o$=1.5 Hz, J$_m$=4.5 Hz, 2 H).

Example 57: $^1$H NMR (300 MHz, CDCl$_3$) δ (TMS): 3.16 (s, 3 H), 6.89 (dd, J$_o$=1.6 Hz, J$_m$=4.4 Hz, 2 H), 6.97 (t, J=8.7 Hz, 2 H), 7.09 (t, J=8.7 Hz, 2 H), 7.24 (m, 2 H), 7.36 (m, 2 H), 8.05 (H$_A$ from an AB system, J=9.0 Hz, 2 H), 8.38 (H$_B$ from an AB system, J=9.0 Hz, 2 H), 8.39 (dd, J$_o$=1.6 Hz, J$_m$=4.6 Hz, 2 H), 8.41 (s, 1 H).

Example 58

4,6-Bis(4-fluorophenyl)-1-(4-methylsulfinylphenyl)-5-(4-pyridyl)pyrazolo[3,4-b]pyridine Following a similar procedure to that described in example 56, but using 4,6-bis(4-fluorophenyl)-1-(4-methylsulfanylphenyl)-5-(4-pyridyl)pyrazolo[3,4-b]pyridine (obtained in example 55) instead of 4,6-bis(4-fluorophenyl)-2-(4-methylsulfanylphenyl)-5-(4-pyridyl)pyrazolo[3,4-b]pyridine, the title compound was obtained (yield: 70%).

$^1$H NMR (300 MHz, CDCl$_3$) δ (TMS): 2.82 (s, 3 H), 6.90 (dd, J$_o$=1.8 Hz, J$_m$=4.5 Hz, 2 H), 7.00 (t, J=8.7 Hz, 2 H), 7.09 (t, J=8.6 Hz, 2 H), 7.20 (m, 2 H), 7.35 (m, 2 H), 7.86 (dd, J$_o$=2.1 Hz, J$_m$=6.9 Hz, 2 H), 8.10 (s, 1 H), 8.41 (dd, J$_o$=1.5 Hz, J$_m$=4.5 Hz, 2 H), 8.69 (dd, J$_o$=1.8 Hz, J$_m$=6.9 Hz, 2 H).

Example 59

4,6-Bis(4-fluorophenyl)-2-(4-methylsulfinylbenzyl)-5-(4-pyridyl)pyrazolo[3,4-b]pyridine Example 60

4,6-Bis(4-fluorophenyl)-2-(4-methylsulfonylbenzyl)-5-(4-pyridyl)pyrazolo[3,4-b]pyridine Following a similar procedure to that described in example 56, but using 4,6-bis(4-fluorophenyl)-2-(4-methylsulfanylbenzyl)-5-(4-pyridyl)pyrazolo[3,4-b]pyridine (obtained in example 26) instead of 4,6-bis(4-fluorophenyl)-2-(4-methylsulfanylphenyl)-5-(4-pyridyl)pyrazolo[3,4-b]pyridine, the title compounds were obtained.

Example 59: yield: 48%; $^1$H NMR (300 MHz, CDCl$_3$) δ (TMS): 2.74 (s, 3 H), 5.70 (s, 2 H), 6.85 (dd, J$_o$=1.5 Hz, J$_m$=4.5 Hz, 2 H), 6.93 (t, J=8.8 Hz, 2 H), 7.02 (t, J=8.7 Hz, 2 H), 7.16 (m, 2 H), 7.32 (m, 2 H), 7.59 (H$_A$ from an AB system, J=8.2 Hz, 2 H), 7.68 (H$_B$ from an AB system, J=8.2 Hz, 2 H), 7.87 (s, 1 H), 8.39 (dd, J$_o$=1.5 Hz, J$_m$=4.5 Hz, 2 H).

Example 60: yield: 16%; $^1$H NMR (300 MHz, CDCl$_3$) δ (TMS): 3.07 (s, 3 H), 5.73 (s, 2 H), 6.85 (dd, J$_o$=1.6 Hz, J$_m$=4.4 Hz, 2 H), 6.93 (t, J=8.7 Hz, 2 H), 7.03 (t, J=8.8 Hz, 2 H), 7.16 (m, 2 H), 7.32 (m, 2 H), 7.61 (H$_A$ from an AB system, J=8.7 Hz, 2 H), 7.89 (s, 1 H), 7.97 (H$_B$ from an AB system, J=8.7 Hz, 2 H), 8.36 (dd, J$_o$=1.8 Hz, J$_m$=4.5 Hz, 2 H).

Example 61

4,6-Bis (4-fluorophenyl)-1-(4-methylsulfinylbenzyl)-5-(4-pyridyl)pyrazolo[3,4-b]pyridine Example 62

4,6-Bis(4-fluorophenyl)-1-(4-methylsulfonylbenzyl)-5-(4-pyridyl)pyrazolo[3,4-b]pyridine Following a similar procedure to that described in example 56, but using 4,6-bis(4-fluorophenyl)-1-(4-methylsulfanylbenzyl)-5-(4-pyridyl)pyrazolo[3,4-b]pyridine (obtained in example 27) instead of 4,6-bis(4-fluorophenyl)-2-(4-methylsulfanylphenyl)-5-(4-pyridyl)pyrazolo[3,4-b]pyridine, the title compounds were obtained.

Example 61: yield: 69%; $^1$H NMR (300 MHz, CDCl$_3$) δ (TMS): 2.71 (s, 3 H), 5.84 (s, 2 H), 6.83 (dd, J$_o$=1.5 Hz, J$_m$=4.5 Hz, 2 H), 6.94 (t, J=8.7 Hz, 2 H), 7.01 (t, J=8.6 Hz, 2 H), 7.13 (m, 2 H), 7.25 (m, 2 H), 7.61 (H$_A$ from an AB system, J=8.4 Hz, 2 H), 7.92 (H$_B$ from an AB system, J=8.4 Hz, 2 H), 7.91 (s, 1 H), 8.34 (dd, J$_o$=1.5 Hz, J$_m$=4.5 Hz, 2 H).

Example 62: yield: 4%; $^1$H NMR (300 MHz, CDCl$_3$) δ (TMS): 3.03 (s, 3 H), 5.87 (s, 2 H), 6.83 (d, J=6.0 Hz, 2 H), 6.94 (t, J=8.8 Hz, 2 H), 7.02 (t, J=8.7 Hz, 2 H), 7.14 (m, 2 H), 7.26 (m, 2 H), 7.60 (H$_A$ from an AB system, J=8.2 Hz, 2 H), 7.91 (s, 1 H), 7.93 (H$_B$ from an AB system, J=8.2 Hz, 2 H), 8.34 (d, J=6.3 Hz, 2 H).

Example 63

3-Chloro-4,6-bis(4-fluorophenyl)-5-(4-pyridyl)-1H-pyrazolo[3,4-b]pyridine

To a solution of 4,6-bis(4-fluorophenyl)-5-(4-pyridyl)-1H-pyrazolo[3,4-b]pyridine (0.20 g, 0.5 mmol, obtained in example 1) in DMF (5 mL), N-chlorosuccinimide (0.10 g, 0.8 mmol) was added under argon atmosphere and the mixture was heated to 60° C. for 5 h. It was washed with 1 N NaOH and extracted with CHCl$_3$ and EtOAc. The combined organic phases were dried over Na$_2$SO$_4$ and concentrated to dryness. The crude product obtained was purified by chromatography on silica gel using hexane-EtOAc mixtures of increasing polarity as eluent, to afford 171 mg of title compound (yield: 79%).

$^1$H NMR (300 MHz, CDCl$_3$) δ (TMS): 1.61 (broad s, NH+H$_2$O), 6.82 (dd, J$_o$=1.6 Hz, J$_m$=4.4 Hz, 2 H), 6.98 (t, J=8.7 Hz, 2 H), 7.03 (t, J=8.7 Hz, 2 H), 7.13 (m, 2 H), 7.29 (m, 2 H), 8.35 (dd, J$_o$=1.5 Hz, J$_m$=4.5 Hz, 2 H).

Example 64

3-Bromo-4,6-bis(4-fluorophenyl)-5-(4-pyridyl)-1H-pyrazolo[3,4-b]pyridine

To a suspension of 4,6-bis(4-fluorophenyl)-5-(4-pyridyl)-1H-pyrazolo[3,4-b]pyridine (1.00 g, 2.6 mmol, obtained in example 1) in CHCl$_3$ (10 mL), a solution of Br$_2$ (0.69 g, 4.3 mmol) in CHCl$_3$ (3 mL) was added under argon atmosphere. Acetonitrile (4 mL) was added and the mixture was stirred at room temperature for 2 days. The residue was concentrated, dissolved in CHCl$_3$ and washed with 1 N NaOH. A precipitate was formed, which was filtered and dissolved with MeOH. The solution was concentrated and washed with 1 N NaOH. It was extracted with EtOAc, dried over Na$_2$SO$_4$ and concentrated. This was treated with diethyl ether, the solvent was decanted and the product obtained was dried to afford 1.16 g of the title compound (yield: 97%).

$^1$H NMR (300 MHz, CD$_3$OD) δ (TMS): 4.78 (broad s, NH+CD$_3$OD), 6.89 (t, J=8.8 Hz, 2 H), 6.93-6.99 (complex signal, 4 H), 7.14 (m, 2 H), 7.27 (m, 2 H), 8.12 (dd, J$_o$=1.5 Hz, J$_m$=4.5 Hz, 2 H).

Example 65

4,6-Bis(4-fluorophenyl)-5-(4-pyridyl)-1H-pyrazolo[3,4-b]pyridine-3-carbonitrile

In a volumetric flask, 3-bromo-4,6-bis(4-fluorophenyl)-5-(4-pyridyl)-1H-pyrazolo[3,4-b]pyridine (0.20 g, 0.4 mmol, obtained in example 64), copper cyanide (I) (0.05 g, 0.6 mmol) and anhydrous 1-methyl-2-pyrrolidone (1 mL) were introduced under argon atmosphere and heated to reflux for 2 h. This was poured into a 10% aqueous solution of ethylendiamine (4 mL) and extracted with CHCl$_3$. Brine was added to the aqueous phase and it was extracted with EtOAc. The combined organic phases were dried over Na$_2$SO$_4$ and concentrated to dryness. The crude product obtained was purified by chromatography on silica gel using hexane-EtOAc mixtures of increasing polarity as eluent, to afford the title compound in a solid form (yield: quantitative).

$^1$H NMR (300 MHz, CDCl$_3$+CD$_3$OD) δ (TMS): 4.00 (broad s, NH+CD$_3$OD), 6.80-7.40 (complex signal, 12 H), 8.25 (m, 2 H).

Example 66

3-Bromo-4,6-bis(4-fluorophenyl)-1-methyl-5-(4-pyridyl)pyrazolo[3,4-b]pyridine

Following a similar procedure to that described in example 64, but using 4,6-bis(4-fluorophenyl)-1-methyl-5-(4-pyridyl)pyrazolo[3,4-b]pyridine (obtained in example 9) instead of 4,6-bis(4-fluorophenyl)-5-(4-pyridyl)-1H-pyrazolo[3,4-b]pyridine, the title compound was obtained (yield: 15%).

$^1$H NMR (300 MHz, CDCl$_3$) δ (TMS): 4.21 (s, 3 H), 6.78 (d, J=6.0 Hz, 2 H), 6.93-7.02 (complex signal, 4 H), 7.08 (m, 2 H), 7.27 (m, 2 H), 8.29 (d, J=6.0 Hz, 2 H).

Example 67

4,6-Bis(4-fluorophenyl)-5-(4-pyridyl)-1H-pyrazolo[3,4-b]pyridine-3-carboxamide

A solution of KOH (0.07 g, 1.3 mmol) in tBuOH (2.5 mL) was added under argon atmosphere to 4,6-bis(4-fluorophenyl)-5-(4-pyridyl)-1H-pyrazolo[3,4-b]pyridine-3-carbonitrile (0.05 g, 0.1 mmol, obtained in example 65) and heated to reflux overnight. Water and EtOAc were added and the phases were separated. The aqueous phase was extracted with EtOAc. The combined organic phases were dried over Na$_2$SO$_4$ and concentrated to dryness. The crude product obtained was purified by chromatography on silica gel using hexane-EtOAc mixtures of increasing polarity as eluent, to afford 15 mg of the title compound in solid form (yield: 28%)

$^1$H NMR (300 MHz, CDCl$_3$) δ (TMS): 1.56 (broad s, NH$_2$+H$_2$O), 6.80 (d, J=4.5 Hz, 2 H), 6.90-7.10 (complex signal, 6 H), 7.30 (m, 2 H), 8.30 (d, J=4.5 Hz, 2 H).

Example 68

3-Aminomethyl-4,6-bis(4-fluorophenyl)-5-(4-pyridyl)-1H-pyrazolo[3,4-b]pyridine

LiAlH$_4$ (0.06 g, 1.5 mmol) and anhydrous diethyl ether (2 mL) were introduced into a volumetric flask. The mixture was cooled with an ice bath and a solution of 4,6-bis(4-fluorophenyl)-5-(4-pyridyl)-1H-pyrazolo[3,4-b]pyridine-3-carbonitrile (0.15 g, 0.4 mmol, obtained in example 65) in diethyl ether (1 mL) was added dropwise. THF (2 mL) was added and the mixture was stirred at room temperature overnight. It was cooled with an ice bath and successively water (0.1 mL), THF (0.2 mL), a 15% aqueous NaOH (0.1 mL) and water (0.3 mL) were added. The precipitate obtained was filtered and washed with THF. The solvent of the filtrate was evaporated. The residue obtained was purified by chromatography on silica gel using hexane-EtOAc mixtures of increasing polarity as eluent, to afford 71 mg of the title compound in solid form (yield: 47%).

$^1$H NMR (300 MHz, CDCl$_3$) δ (TMS): 2.10 (broad s, NH$_2$+H$_2$O) 3.62 (s, 2 H), 6.80 (dd, J$_o$=1.5 Hz, J$_m$=4.5 Hz, 2 H), 6.93 (t, J=8.7 Hz, 2 H), 7.03 (t, J=8.6 Hz, 2 H), 7.11 (m, 2 H), 7.25 (m, 2 H), 8.30 (dd, J$_o$=1.5 Hz, J$_m$=4.5 Hz, 2 H).

Example 69

4,6-Bis(4-fluoro-3-nitrophenyl)-5-(4-pyridyl)-1H-pyrazolo[3,4-b]pyridine

To a solution of 4,6-bis(4-fluorophenyl)-5-(4-pyridyl)-1H-pyrazolo[3,4-b]pyridine (0.20 g, 0.5 mmol, obtained in example 1) in conc. H$_2$SO$_4$ (3 mL), 65% HNO$_3$ (0.1 mL, 0.2 mmol) was added under argon atmosphere. This was heated to 90° C. for 30 min. It was cooled with an ice bath and adjusted to pH=8 with 1 N NaOH. It was extracted with EtOAc. The organic phase was dried over Na$_2$SO$_4$ and concentrated to dryness. The crude product was purified by chromatography on silica gel using hexane-EtOAc mixtures of increasing polarity as eluent, to afford 69 mg of the title compound in solid form (yield: 28%).

$^1$H NMR (300 MHz, CDCl$_3$+CD$_3$OD) δ (TMS): 4.28 (s, NH+CD$_3$OD), 7.03 (dd, J$_o$=1.5 Hz, J$_m$=4.5 Hz, 2 H), 7.22 (dd, J$_o$=2.7 Hz, J$_m$=10.5 Hz, 1 H), 7.36 (dd, J$_o$=2.6 Hz, J$_m$=10.4 Hz, 1 H), 7.53 (m, 2 H), 7.99-8.01 (complex signal, 2 H), 8.13 (m, 1 H), 8.41 (dd, J$_o$=1.5 Hz, J$_m$=4.5 Hz, 2 H).

Example 70

3-Amino-6-(4-fluorophenyl)-5-(4-pyridyl)-1H-pyrazolo[3,4-b]pyridine

Following a similar procedure to that described in reference example 15 section c, but using 6-chloro-2-(4-fluorophenyl)-3,4'-bipyridine-5-carbonitrile (obtained in reference example 12) instead of 3-(1-benzylpiperidin-4-yl)-3-oxopropiononitrile, the title compound was obtained (yield: 41%).

$^1$H NMR (300 MHz, CD$_3$OD) δ (TMS): 4.38 (s, NH$_2$+CD$_3$OD), 7.05 (t, J=8.8 Hz, 2 H), 7.26 (dd, J$_o$=1.6 Hz, J$_m$=4.6 Hz, 2 H), 7.39 (m, 2 H), 8.27 (s, 1 H), 8.42 (dd, J$_o$=1.4 Hz, J$_m$=4.6 Hz, 2 H).

Example 71

3-Amino-6-(4-fluorophenyl)-1-methyl-5-(4-pyridyl)pyrazolo[3,4-b]pyridine

Following a similar procedure to that described in reference example 15 section c, but using 6-chloro-2-(4-fluorophenyl)-3,4'-bipyridine-5-carbonitrile (obtained in reference example 12) instead of 3-(1-benzylpiperidin-4-yl)-3-oxopropiononitrile and methylhydrazine instead of hydrazine monohydrate, the title compound was obtained (yield: 70%).

$^1$H NMR (300 MHz, CDCl$_3$) δ (TMS): 4.00 (s, 3 H), 4.17 (broad s, 2 H), 6.98 (t, J=8.7 Hz, 2 H), 7.09 (dd, J$_o$=1.5 Hz, J$_m$=4.5 Hz, 2 H), 7.37 (m, 2 H), 7.90 (s, 1 H), 8.50 (dd, J$_o$=1.5 Hz, J$_m$=4.5 Hz, 2 H).

Example 72

4-[6-(4-Fluorophenyl)-5-(4-pyridyl)-1H-pyrazolo[3,4-b]pyridin-4-yl]phenol

To a solution of 1-(4-fluorophenyl)-2-(4-pyridyl)ethanone (0.30 g, 1.4 mmol, obtained in reference example 1) in 2-methoxyethanol (2 mL), 3-amino-2H-pyrazole (0.13 g, 1.5 mmol), 4-hydroxybenzaldehyde (0.17 g, 1.4 mmol), 2-methoxyethanol (2 mL) and 37% HCl (0.04 g, 0.4 mmol) were added under argon atmosphere. The mixture was heated to reflux overnight. It was allowed to cool and concentrated. The solid obtained was dissolved in $CHCl_3$ and some drops of MeOH. Saturated $NaHCO_3$ was added and the aqueous phase was extracted 3 times with $CHCl_3$. The combined organic phases were dried over $Na_2SO_4$ and concentrated to dryness. The crude product was purified by chromatography on silica gel using hexane-EtOAc mixtures of increasing polarity as eluent, to afford 0.22 g of the desired compound (yield: 41%).

LC-MS (método 1): $t_R$=5.56 min; m/z=383.0 $[M+H]^+$.

Example 73

2-(2,2-Diethoxyethyl)-4,6-bis(4-fluorophenyl)-5-(4-pyridyl)pyrazolo[3,4-b]pyridine Example 74

1-(2,2-Diethoxyethyl)-4,6-bis(4-fluorophenyl)-5-(4-pyridyl)pyrazolo[3,4-b]pyridine In a volumetric flask 4,6-bis(4-fluorophenyl)-5-(4-pyridyl)-1H-pyrazolo[3,4-b]pyridine (0.20 g, 0.5 mmol, obtained in example 1), KOH (0.03 g, 0.5 mmol), 2-bromo-1,1-diethoxyethane (0.10 g, 0.5 mmol) and 1-methoxy-2-(2-methoxyethoxy)ethane (2 mL) were introduced under argon atmosphere. The mixture was heated to 100° C. and stirred at this temperature overnight. It was allowed to cool and a mixture of $H_2O$-EtOAc was added. The phases were separated and the aqueous phase was extracted with EtOAc. The combined organic phases were dried over $Na_2SO_4$ and concentrated to dryness. The crude product obtained was purified by chromatography on silica gel using hexane-EtOAc mixtures of increasing polarity as eluent, to afford 139 mg of 2-(2,2-diethoxyethyl)-4,6-bis(4-fluorophenyl)-5-(4-pyridyl) pyrazolo[3,4-b]pyridine (yield: 53%) and 60 mg of 1-(2,2-diethoxyethyl)-4,6-bis(4-fluorophenyl)-5-(4-pyridyl)pyrazolo[3,4-b]pyridine (yield: 24%).

Example 73: $^1$H NMR (300 MHz, $CDCl_3$) δ (TMS): 1.15 (t, J=7.0 Hz, 6 H), 3.50 (m, 2 H), 3.73 (m, 2 H), 4.49 (d, J=5.4 Hz, 2 H), 5.06 (t, J=5.4 Hz, 1 H), 6.83 (dd, $J_o$=1.4 Hz, $J_m$=4.4 Hz, 2 H), 6.90 (t, J=8.7 Hz, 2 H), 7.00 (t, J=8.6 Hz, 2 H), 7.14 (m, 2 H), 7.29 (m, 2 H), 7.85 (s, 1 H), 8.32 (dd, $J_o$=1.5 Hz, $J_m$=4.5 Hz, 2 H).

Example 74: $^1$H NMR (300 MHz, $CDCl_3$) δ (TMS): 1.21 (t, J=6.9 Hz, 6 H), 3.58 (m, 2 H), 3.82 (m, 2 H), 4.74 (d, J=5.7 Hz, 2 H), 5.19 (t, J=5.7 Hz, 1 H), 6.81 (dd, $J_o$=1.5 Hz, $J_m$=4.5 Hz, 2 H), 6.92 (t, J=8.7 Hz, 2 H), 7.01 (t, J=8.7 Hz, 2 H), 7.13 (m, 2 H), 7.25 (m, 2 H), 7.87 (s, 1 H), 8.32 (dd, $J_o$=1.5 Hz, $J_m$=4.5 Hz, 2 H).

Example 75

4,6-Bis(4-fluorophenyl)-1-methyl-5-(4-pyridyl)pyrazolo[3,4-b]pyridine-3-carbonitrile Following a similar procedure to that described in example 65, but using 3-bromo-4,6-bis(4-fluorophenyl)-1-methyl-5-(4-pyridyl)pyrazolo[3,4-b]pyridine (obtained in example 66) instead of 3-bromo-4,6-bis(4-fluorophenyl)-5-(4-pyridyl)-1H-pyrazolo[3,4-b]pyridine, the title compound was obtained (yield: 48%).

$^1$H NMR (300 MHz, $CDCl_3$) δ (TMS): 4.32 (s, 3 H), 6.81 (dd, $J_o$=1.5 Hz, $J_m$=4.5 Hz, 2 H), 6.96 (t, J=8.4 Hz, 2 H), 7.05 (t, J=8.4 Hz, 2 H), 7.13 (m, 2 H), 7.29 (m, 2 H), 8.35 (dd, $J_o$=1.5 Hz, $J_m$=4.5 Hz, 2 H).

Example 76

3-Bromo-6-(4-fluorophenyl)-5-(4-pyridyl)-1H-pyrazolo[3,4-b]pyridine

To a solution of 3-amino-6-(4-fluorophenyl)-5-(4-pyridyl)-1H-pyrazolo[3,4-b]pyridine (0.20 g, 0.7 mmol, obtained in example 70) in 48% HBr (1 mL) at 0° C., a solution of $NaNO_2$ (0.05 g, 0.7 mmol) in water (0.1 mL) was added dropwise over a period of 15 minutes maintaining the temperature at 0-5° C. The mixture was stirred for 15 min at this temperature. Then, a solution of CuBr (0.24 g, 1.7 mmol) in 48% HBr (1 mL) was added slowly at 0° C. The resulting solution was stirred for 3 h at 0° C. It was allowed to reach room temperature, neutralized at pH=7 with saturated sodium bicarbonate and a 30% aqueous $NH_3$. It was filtered and the solid was washed with a mixture of $CH_2Cl_2$ and water. The organic phase was washed with 1 N NaOH and the aqueous phase extracted with EtOAc. The combined organic phases were dried over $Na_2SO_4$ and concentrated to dryness. The crude product obtained was purified by chromatography on silica gel using $CHCl_3$-MeOH mixtures of increasing polarity as eluent, to afford 50 mg of the title compound (yield: 21%).

$^1$H NMR (300 MHz, $CDCl_3+CD_3OD$) δ (TMS): 4.24 (s, $NH+CD_3OD$), 6.92 (m, 2 H), 7.15 (m, 2 H), 7.29 (m, 2 H), 7.95 (s, 1 H), 8.39 (d, J=6.0 Hz, 2 H).

Example 77

6-Fluorophenyl-5-(4-pyridyl)-1H-pyrazolo[3,4-b] pyridine

3-Amino-6-(4-fluorophenyl)-5-(4-pyridyl)-1H-pyrazolo[3,4-b]pyridine (0.20 g, 0.7 mmol, obtained in example 70) and a solution of $H_3PO_2$ (0.2 mL, 2.0 mmol) in water (2 mL) were mixed and allowed to cool to 5° C. A solution of $NaNO_2$ (0.10 g, 1.4 mmol) in water (0.4 mL) was added dropwise. This was stirred for 30 min at 5° C., allowed to reach room temperature and stirred at room temperature for 4 h. It was neutralized with 1 N NaOH and extracted with $CHCl_3$. The combined organic phases were dried over $Na_2SO_4$ and concentrated to dryness. The crude product obtained was purified by chromatography on silica gel using increasing polarity hexane-EtOAc mixtures as eluent, to afford 63 mg of the title compound (yield: 33%).

$^1$H NMR (300 MHz, MeOH+$CDCl_3$) δ (TMS): 3.46 (s, $NH+CD_3OD$), 6.92 (t, J=8.6 Hz, 2 H), 7.07 (dd, $J_o$=1.6 Hz, $J_m$=4.4 Hz, 2 H), 7.26 (m, 2 H), 8.08 (s, 1 H), 8.09 (s, 1 H), 8.37 (dd, $J_o$=1.5 Hz, $J_m$=4.5 Hz, 2 H).

Example 78

N-Methyl-[3-[4,6-bis(4-fluorophenyl)-5-(4-pyridyl) pyrazolo[3,4-b]pyridin-2-yl]propyl]amine To a solution of 2-(3-chloropropyl)-4,6-bis(4-fluorophenyl)-5-(4-pyridyl)pyrazolo[3,4-b]pyridine (0.07 g, 0.1 mmol, obtained in example 16) in acetonitrile (0.3 mL), methylamine (1.8 mL of a 33% solution in EtOH, 14.6 mmol) was added under argon atmosphere. This was heated to 60° C. for 3 days, adding methylamine (0.9 mL and 3.6 mL of a 33% solution in EtOH) after 24 and 48 h respectively. The organic phase was dried over $Na_2SO_4$ and concentrated to dryness. The crude product obtained was purified by silica gel EtOAc-MeOH mixtures of using increasing polarity as eluent, to afford 24 mg of the title compound in solid form (yield: 29%).

¹H NMR (300 MHz, CDCl₃) δ (TMS): 2.00 (broad s, NH+H₂O), 2.53 (m, 2 H), 2.61 (s, 3 H), 2.99 (t, J=6.7 Hz, 2 H), 4.67 (t, J=6.4 Hz, 2 H), 6.82 (dd, J$_o$=1.5 Hz, J$_m$=4.5 Hz, 2 H), 6.90 (t, J=8.7 Hz, 2 H), 7.00 (t, J=8.6 Hz, 2 H), 7.13 (m, 2 H), 7.27 (m, 2 H), 7.90 (s, 1 H), 8.32 (dd, J$_o$=1.5 Hz, J$_m$=4.5 Hz, 2 H).

Example 79

[4,6-Bis(4-fluorophenyl)-5-(4-pyridyl)pyrazolo[3,4-b]pyridin-2-yl]methanol

A suspension of 4,6-bis(4-fluorophenyl)-5-(4-pyridyl)-1H-pyrazolo[3,4-b]pyridine (0.20 g, 0.5 mmol, obtained in example 1) in 30-40% aqueous formaldehyde (0.9 mL) was stirred at 130° C. under argon atmosphere for 4 h. The solvent was concentrated and the residue was dissolved in a mixture of CHCl₃ and water and the phases were separated. The organic phase was dried over Na₂SO₄ and concentrated to dryness. The crude product obtained was purified on chromatography on silica gel using hexane-EtOAc mixtures of increasing polarity as eluent, to afford 140 mg of the title compound in solid form (yield: 65%).

¹H NMR (300 MHz, CDCl₃) δ (TMS): 3.5 (t, 1 H, OH), 6.11 (d, J=J=7.8 Hz, 2 H), 6.85 (dd, J$_o$=1.8 Hz, J$_m$=4.5 Hz, 2 H), 6.97 (t, J=8.7 Hz, 1 H), 7.08 (t, J=8.7 Hz, 1 H), 7.16 (m, 2 H), 7.31 (m, 2 H), 7.97 (s, 1 H), 8.37 (dd, J$_o$=1.6 Hz, J$_m$=4.3 Hz, 2 H).

Example 80

2-[4,6-Bis(4-fluorophenyl)-5-(4-pyridyl)pyrazolo[3,4-b]pyridin-2-yl]-N,N-dimethylacetamide Example 81

2-[4,6-Bis(4-fluorophenyl)-5-(4-pyridyl)pyrazolo[3,4-b]pyridin-1-yl]-N,N-dimethylacetamide Following a similar procedure to that described in examples 73 and 74, but using 2-chloro-N,N-dimethylacetamide instead of 2-bromo-1,1-diethoxyethane, the title compounds were obtained.

Example 80: yield: 10%

Example 81: yield 32%; ¹H NMR (300 MHz, CDCl₃) δ (TMS): 3.01 (s, 3 H), 3.18 (s, 3 H), 5.47 (s, 2 H), 6.79 (dd, J$_o$=1.5 Hz, J$_m$=4.5 Hz, 2 H), 6.91 (t, J=8.7 Hz, 1 H), 7.01 (t, J=8.6 Hz, 1 H), 7.15 (m, 2 H), 7.23 (m, 2 H), 7.95 (s, 1 H), 8.31 (dd, J$_o$=1.6 Hz, J$_m$=4.3 Hz, 2 H).

Example 82

4,6-Bis(4-fluorophenyl)-2-[2-(2-methoxyethoxy)ethyl]-5-(4-pyridyl)pyrazolo[3,4-b]pyridine Example 83

4,6-Bis(4-fluorophenyl)-1-[2-(2-methoxyethoxy)ethyl]-5-(4-pyridyl)pyrazolo[3,4-b]pyridine Following a similar procedure to that described in examples 6 and 7, but using 1-bromo-2-(2-methoxyethoxy)ethane instead of iodoethane, the title compounds were obtained.

Example 82: yield: 27%; ¹H NMR (300 MHz, CDCl₃) δ (TMS): 3.28 (s, 3 H), 3.45 (m, 2 H), 3.57 (m, 2 H), 4.05 (t, J=5.1 Hz, 2 H), 4.63 (t, J=5.1 Hz, 2 H), 6.82 (dd, J$_o$=1.5 Hz, J$_m$=4.5 Hz, 2 H), 6.89 (t, J=8.7 Hz, 2 H), 6.99 (t, J=8.7 Hz, 2 H), 7.14 (m, 2 H), 7.29 (m, 2 H), 7.93 (s, 1 H), 8.31 (dd, J$_o$=1.6 Hz, J$_m$=4.4 Hz, 2 H).

Example 83: yield: 19%; ¹H NMR (300 MHz, CDCl₃) δ (TMS): 3.32 (s, 3 H), 3.50 (m, 2 H), 3.68 (m, 2 H), 4.08 (t, J=6.0 Hz, 2 H), 4.81 (t, J=6.0 Hz, 2 H), 6.81 (dd, J$_o$=1.4 Hz, J$_m$=4.4 Hz, 2 H), 6.92 (t, J=8.7 Hz, 2 H), 7.01 (t, J=8.6 Hz, 2 H), 7.13 (m, 2 H), 7.26 (m, 2 H), 7.86 (s, 1 H), 8.32 (dd, J$_o$=1.5 Hz, J$_m$=4.5 Hz, 2 H), Example 84

4,6-Bis(4-fluorophenyl)-2-[3-(morpholin-4-yl)propyl]-5-(4-pyridyl)pyrazolo[3,4-b]pyridine a) 3-[4,6-Bis(4-fluorophenyl)-5-(4-pyridyl)pyrazolo[3,4-b]pyridin-2-yl]propyl methanesulfonate Following a similar procedure to that described in example 12 section b, but using 3-[4,6-bis(4-fluorophenyl)-5-(4-pyridyl)pyrazolo[3,4-b]pyridin-2-yl]propan-1-ol (obtained in example 18) instead of 2-[1-(tert-butoxycarbonyl)piperidin-4-yl]ethanol, the desired compound was obtained (yield: quantitative).

b) Title Compound

In a volumetric flask, 3-[4,6-bis(4-fluorophenyl)-5-(4-pyridyl)pyrazolo[3,4-b]pyridin-2-yl]propyl methanesulfonate (0.10 g, 0.2 mmol, obtained in section a), NaI (0.003 g, 0.02 mmol), morpholine (0.03 g, 0.4 mmol) and 1,2-dimethoxyethane (2 mL) were introduced under argon atmosphere. The mixture was heated to 90° C. and stirred at this temperature overnight. A mixture of water and EtOAc was added. The phases were separated. The aqueous phase was extracted with EtOAc. The organic phase was dried over Na₂SO₄ and concentrated to dryness. The crude product obtained was purified by chromatography on silica gel using increasing polarity mixtures of EtOAc-MeOH as eluent, to afford 37 mg of the title compound (yield: 36%).

¹H NMR (300 MHz, CDCl₃) δ (TMS): 2.27 (m, 2 H), 2.30-2.43 (complex signal, 6 H), 3.69 (m, 4 H), 4.53 (t, J=6.6 Hz, 2 H), 6.83 (dd, J$_o$=1.6 Hz, J$_m$=4.4 Hz, 2 H), 6.89 (t, J=8.7 Hz, 2 H), 7.00 (t, J=8.6 Hz, 2 H), 7.14 (m, 2 H), 7.31 (m, 2 H), 7.81 (s, 1 H), 8.32 (dd, J$_o$=1.6 Hz, J$_m$=4.4 Hz, 2 H).

Example 85

4,6-Bis(6-chloropyridin-3-yl)-2-methyl-5-(4-pyridyl)pyrazolo[3,4-b]pyridine

ECAMPLE 86

4,6-Bis(6-chloropyridin-3-yl)-1-methyl-5-(4-pyridyl)pyrazolo[3,4-b]pyridine

Following a similar procedure to that described in examples 73 and 74, but using 4,6-bis(6-chloropyridin-3-yl)-5-(4-pyridyl)-1H-pyrazolo[3,4-b]pyridine (obtained in example 40) instead of 4,6-bis(4-fluorophenyl)-5-(4-pyridyl)-1H-pyrazolo[3,4-b]pyridine and iodomethane instead of 2-bromo-1,1-diethoxyethane, the title compounds were obtained.

Example 85: yield: 26%; ¹H NMR (300 MHz, CDCl₃) δ (TMS): 1.56 (s, NH+H₂O), 4.32 (s, 3 H), 6.88 (dd, J$_o$=1.5 Hz, J$_m$=4.5 Hz, 2 H), 7.19 (d, J=8.4 Hz, 1 H), 7.31 (m, 2 H), 7.58 (dd, J$_o$=2.4 Hz, J$_m$=8.4 Hz, 1 H), 7.84 (s, 1 H), 8.37 (dd, J$_o$=2.4 Hz, J$_m$=6.9 Hz, 2 H), 8.43 (dd, J$_o$=1.6 Hz, J$_m$=4.4 Hz, 2 H).

Example 86: yield: 27%; ¹H NMR (300 MHz, CDCl₃) δ (TMS): 1.57 (s, NH+H₂O), 4.26 (s, 3 H), 6.88 (dd, J$_o$=1.8 Hz, J$_m$=4.5 Hz, 2 H), 7.20 (d, J=8.4 Hz, 1 H), 7.29 (d, J=8.1 Hz, 1 H), 7.35 (dd, J$_o$=2.4 Hz, J$_m$=8.1 Hz, 1 H), 7.50 (dd, J$_o$=2.6 Hz, J$_m$=8.2 Hz, 1 H), 7.91 (s, 1 H), 8.34 (d, J=2.1 Hz, 1 H), 8.43-8.45 (complex signal, 3 H)

Example 87

4,6-Bis(6-chloropyridin-3-yl)-3-methyl-5-(4-pyridyl)-1H-pyrazolo[3,4-b]pyridine

Following a similar procedure to that described in example 1 method A, but using 1-(6-chloropyridin-3-yl)-2-(4-pyridyl)ethanone (obtained in example reference 9) instead of 1-(4-fluorophenyl)-2-(4-pyridyl)ethanone and 3-amino-5-methyl-2H-pyrazole instead of 3-amino-2H-pyrazole, the title compound was obtained (yield: 9%).

¹H NMR (300 MHz, CDCl₃+CD₃OD) δ (TMS): 2.09 (s, 3 H), 3.51 (s, NH+H₂O), 6.92 (m, 2 H), 7.23 (d, J=8.4 Hz, 1 H), 7.32 (m, 1 H), 7.51 (m, 1 H), 7.54 (dd, J$_o$=2.4 Hz, J$_m$=8.4 Hz, 1 H), 8.26 (broad s, 1 H), 8.35-8.38 (complex signal, 3 H).

Example 88

4,6-Bis(6-methylpyridin-3-yl)-5-(4-pyridyl)-1H-pyrazolo[3,4-b]pyridine

Following a similar procedure to that described in example 1 method A, but using 1-(6-methylpyridin-3-yl)-2-(4-pyridyl)ethanone (obtained in reference example 13) instead of 1-(4-fluorophenyl)-2-(4-pyridyl)ethanone, the title compound was obtained (yield: 23%).

¹H NMR (300 MHz, CDCl₃) δ (TMS): 1.59 (s, NH+H₂O), 2.59 (s, 6 H), 6.90 (dd, J$_o$=1.5 Hz, J$_m$=4.5 Hz, 2 H), 6.99 (d, J=8.1 Hz, 1 H), 7.09 (d, J=7.8 Hz, 1 H), 7.33 (m, 2 H), 7.99 (s, 1 H), 8.39 (dd, J$_o$=1.5 Hz, J$_m$=4.5 Hz, 2 H), 8.47 (d, J=2.1 Hz, 1 H), 8.80 (broad s, 1 H).

Example 89

4,6-Bis(4-fluorophenyl)-2-(2-phthalimidoethyl)-5-(4-pyridyl)pyrazolo[3,4-b]pyridine Following a similar procedure to that described in examples 6 and 7, but using N-(2-bromoethyl)phthalimide instead of iodomethane, the title compound was obtained (yield: 29%).

¹H NMR (300 MHz, CDCl₃) δ (TMS): 4.32 (t, J=6.1 Hz, 2 H), 4.76 (t, J=6.0 Hz, 2 H), 6.81 (dd, J$_o$=1.6 Hz, J$_m$=4.4 Hz, 2 H), 6.88 (t, J=8.7 Hz, 2 H), 6.95 (t, J=8.6 Hz, 2 H), 7.07 (m, 2 H), 7.25 (m, 2 H), 7.50 (m, 2 H), 7.61 (s, 1 H), 7.71 (m, 2 H), 8.32 (dd, J$_o$=1.6 Hz, J$_m$=4.4 Hz, 2 H).

Example 90

2-(2-Aminoethyl)-4,6-bis(4-fluorophenyl)-5-4-pyridyl)pyrazolo[3,4-b]pyridine

To a solution of 4,6-bis(4-fluorophenyl)-2-(2-phthalimidoethyl)-5-(4-pyridyl)pyrazolo[3,4-b]pyridine (0.09 g, 0.2 mmol, obtained in example 89) in EtOH (2 mL), hydrazine monohydrate (0.02 g, 0.3 mmol) was added and the mixture was heated to reflux for 3 h. A mixture of water and EtOAc was added. The phases were separated. The aqueous phase was extracted with EtOAc. The organic phase was dried over Na₂SO₄ and concentrated to dryness. The crude product obtained was purified by chromatography on silica gel using CHCl₃-MeOH mixtures of increasing polarity as eluent, to afford 57 mg of the title compound (yield: 83%).

¹H NMR (300 MHz, CDCl₃) δ (TMS): 1.57 (s, NH₂+H₂O), 3.38 (t, J=5.7 Hz, 2 H), 4.49 (t, J=5.5 Hz, 2 H), 6.83 (dd, J$_o$=1.5 Hz, J$_m$=4.5 Hz, 2 H), 6.90 (t, J=8.8 Hz, 2 H), 7.00 (t, J=8.7 Hz, 2 H), 7.15 (m, 2 H), 7.31 (m, 2 H), 7.85 (s, 1 H), 8.32 (dd, J$_o$=1.6 Hz, J$_m$=4.6 Hz, 2 H).

Example 91

2-[4,6-Bis(4-fluorophenyl)-5-(4-pyridyl)pyrazolo[3,4-b]pyridin-2-yl]ethanol

A solution of 4,6-bis(4-fluorophenyl)-5-(4-pyridyl)-2-[2-(tetrahydropyran-2-yloxy)ethyl]pyrazolo[3,4-b]pyridine (1.08 g, 2.09 mmol, obtained in example 24) in a 4:2:1 mixture of AcOH:THF:H₂O (42 mL) was heated to 55° C. overnight. The mixture was allowed to cool and basified with saturated NaHCO₃ and extracted with EtOAc. The organic phase was dried over Na₂SO₄ and concentrated to dryness. The crude product obtained was purified by chromatography on silica gel using hexane-EtOAc mixtures of increasing polarity as eluent, to afford 0.78 g of the title compound (yield: 87%).

¹H NMR (300 MHz, CDCl₃) δ (TMS): 1.61 (broad s, OH+H₂O), 4.21 (t, J=4.7 Hz, 2 H), 4.58 (t, J=4.7 Hz, 2 H), 6.83 (dd, J$_o$=1.6 Hz, J$_m$=4.4 Hz, 2 H), 6.91 (t, J=8.7 Hz, 2 H), 7.01 (t, J=8.6 Hz, 2 H), 7.14 (m, 2 H), 7.27 (m, 2 H), 7.87 (s, 1 H), 8.33 (dd, J$_o$=1.6 Hz, J$_m$=4.5 Hz, 2 H).

Example 92

6-(4-Fluorophenyl)-2-methyl-5-(4-pyridyl)pyrazolo[3,4-b]pyridine

Following a similar procedure to that described in examples 6 and 7, but using 6-fluorophenyl-5-(4-pyridyl)-1H-pyrazolo[3,4-b]pyridine (obtained in example 77) instead of 4,6-bis(4-fluorophenyl)-5-(4-pyridyl)-1H-pyrazolo[3,4-b]pyridine and iodomethane instead of iodoethane, the title compound was obtained (yield: 35%).

¹H NMR (300 MHz, CDCl₃) δ (TMS): 1.56 (broad s, NH+H₂O), 4.31 (s, 3 H), 6.95 (t, J=8.7 Hz, 2 H), 7.11 (d, J=6.0 Hz, 2 H), 7.41 (m, 2 H), 8.01 (s, 1 H), 8.06 (s, 1 H), 8.51 (d, J=6.0 Hz, 2 H).

Example 93

4,6-Bis(4-fluorophenyl)-2-(3-phthalimidopropyl)-5-(4-pyridyl)pyrazolo[3,4-b]pyridine Following a similar procedure to that described in examples 6 and 7, but using N-(3-bromopropyl)phthalimide instead of iodoethane, the title compound was obtained (yield: 31%).

¹H NMR (300 MHz, CDCl₃) δ (TMS): 2.54 (q, J=6.4 Hz, 2 H), 3.79 (t, J=6.2 Hz, 2 H), 4.50 (t, J=6.6 Hz, 2 H), 6.82 (dd, J$_o$=1.5 Hz, J$_m$=4.5 Hz, 2 H), 6.89 (t, J=8.7 Hz, 2 H), 7.02 (t, J=8.7 Hz, 2 H), 7.17 (m, 2 H), 7.28 (m, 2 H), 7.71 (m, 2 H), 7.83 (m, 2 H), 7.93 (s, 1 H), 8.32 (dd, J$_o$=1.6 Hz, J$_m$=4.5 Hz, 2 H).

Example 94

2-[4,6-Bis(4-fluorophenyl)-5-(4-pyridyl)pyrazolo[3,4-b]pyridin-2-yl]acetaldehyde In a volumetric flask, 2-(2,2-diethoxyethyl)-4,6-bis(4-fluorophenyl)-5-(4-pyridyl)pyrazolo[3,4-b]pyridine (0.31 g, 0.6 mmol, obtained in example 73) and 1 N HCl (2.6 mL) were introduced. The mixture was heated to 100° C. for 1 hour. It was allowed to cool, adjusted to pH=7 and extracted with EtOAc. The organic phase was dried over $Na_2SO_4$ and concentrated to dryness. The crude product obtained was purified by chromatography on silica gel using hexane-EtOAc mixtures of increasing polarity eluent, to afford 166 mg of the title compound (yield: 65%).

$^1$H NMR (300 MHz, CDCl$_3$) δ (TMS): 5.26 (s, 2 H), 6.83 (dd, $J_o$=1.4 Hz, $J_m$=4.4 Hz, 2 H), 6.91 (t, J=8.5 Hz, 2 H), 7.00 (t, J=8.8 Hz, 2 H), 7.15 (m, 2 H), 7.30 (m, 2 H), 7.88 (s, 1 H), 8.31 (m, 2 H), 9.85 (s, 1 H).

Example 95

2-(3-Aminopropyl)-4,6-bis(4-fluorophenyl)-5-(4-pyridyl)pyrazolo[3,4-b]pyridine

Following a similar procedure to that described in example 90, but using 4,6-bis(4-fluorophenyl)-2-(3-phthalimidopropyl)-5-(4-pyridyl)pyrazolo[3,4-b]pyridine (obtained in example 93) instead of 4,6-bis(4-fluorophenyl)-2-(2-phthalimidoethyl)-5-(4-pyridyl)pyrazolo[3,4-b]pyridine, the title compound was obtained (yield: 49%).

$^1$H NMR (300 MHz, CDCl$_3$) δ (TMS): 1.54 (s, NH$_2$+H$_2$O), 2.19 (m, 2 H), 2.76 (t, J=6.7 Hz, 2 H), 4.57 (t, J=6.7 Hz, 2 H), 6.83 (dd, $J_o$=1.6 Hz, $J_m$=4.4 Hz, 2 H), 6.90 (t, J=8.7 Hz, 2 H), 7.00 (t, J=8.7 Hz, 2 H), 7.13 (m, 2 H), 7.30 (m, 2 H), 7.81 (s, 1 H), 8.32 (dd, $J_o$=1.5 Hz, $J_m$=4.5 Hz, 2 H).

Example 96

N-[4,6-Bis(4-fluorophenyl)-5-(4-pyridyl)-1H-pyrazolo[3,4-b]pyridin-3-ylmethyl]-1-(tert-butoxycarbonyl)piperidine-4-carboxamide Following a similar procedure to that described in example 48, but using 1-(tert-butoxycarbonyl)piperidine-4-carboxylic acid instead of 2-[4,6-bis(4-fluorophenyl)-5-(4-pyridyl)pyrazolo[3,4-b]pyridin-2-yl]acetic acid and 3-aminomethyl-4,6-bis(4-fluorophenyl)-5-(4-pyridyl)-1H-pyrazolo[3,4-b]pyridine (obtained in example 68) instead of morpholine, the title compound was obtained (yield: 26%).

Example 97

N-[4,6-Bis(4-fluorophenyl)-5-(4-pyridyl)-1H-pyrazolo[3,4-b]pyridin-3-ylmethyl]piperidine-4-carboxamide Following a similar procedure to that described in example 36, but using N-[4,6-bis(4-fluorophenyl)-5-(4-pyridyl)-1H-pyrazolo[3,4-b]pyridin-3-ylmethyl]-1-(tert-butoxycarbonyl)piperidine-4-carboxamide (obtained in example 96) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 63%).

$^1$H NMR (300 MHz, CDCl$_3$) δ (TMS): 1.40-1.90 (complex signal, 3 H+H$_2$O), 2.18 (m, 2 H), 2.63 (m, 2 H), 3.13 (m, 2 H), 4.15 (d, J=5.1 Hz, 2 H), 5.20 (broad s, 1H, NH), 6.20 (broad s, 1 H, NH), 6.78 (dd, $J_o$=1.5 Hz, $J_m$=4.5 Hz, 2 H), 6.94 (t, J=8.7 Hz, 2 H), 7.03 (t, J=8.7 Hz, 2 H), 7.08-7.14 (complex signal, 4 H), 8.30 (dd, $J_o$=1.6 Hz, $J_m$=4.4 Hz, 2 H).

Example 98

2-(3-Benzyloxypropyl)-4,6-bis(4-fluorophenyl)-5-(4-pyridyl)pyrazolo[3,4-b]pyridine

Example 99

1-(3-Benzyloxypropyl)-4,6-bis(4-fluorophenyl)-5-(4-pyridyl)pyrazolo[3,4-b]pyridine Following a similar procedure to that described in examples 6 and 7, but using 3-bromopropanol benzylic ether instead of iodoethane, the title compounds were obtained.

Example 98: yield: 43%; $^1$H NMR (300 MHz, CDCl$_3$) δ (TMS): 2.38 (m, 2 H), 3.48 (t, J=5.6 Hz, 2 H), 4.44 (s, 2 H), 4.57 (t, J=6.7 Hz, 2 H), 6.82 (dd, J=1.5 Hz, $J_m$=4.5 Hz, 2 H), 6.89 (t, J=8.7 Hz, 2 H), 6.99 (t, J=8.7 Hz, 2 H), 7.10 (m, 2 H), 7.26-7.32 (complex signal, 7 H), 7.73 (s, 1 H), 8.32 (dd, $J_o$=1.8 Hz, $J_m$=4.5 Hz, 2 H).

Example 99: yield: 20%; $^1$H NMR (300 MHz, CDCl$_3$) δ (TMS): 2.19 (m, 2 H), 3.58 (t, J=6.1 Hz, 2 H), 4.48 (s, 2 H), 4.75 (t, J=6.9 Hz, 2 H), 6.81 (dd, $J_o$=1.5 Hz, $J_m$=4.5 Hz, 2 H), 6.90 (t, J=8.7 Hz, 2 H), 7.01 (t, J=8.6 Hz, 2 H), 7.12 (m, 2 H), 7.24-7.33 (complex signal, 7 H), 7.86 (s, 1 H), 8.32 (dd, $J_o$=1.6 Hz, $J_m$=4.4 Hz, 2 H).

Example 100

N,N-Diethyl-[2-[4,6-bis(4-fluorophenyl)-5-(4-pyridyl)pyrazolo[3,4-b]pyridin-2-yl]ethyl]amine

Example 101

N,N-Diethyl-[2-[4,6-bis(4-fluorophenyl)-5-(4-pyridyl)pyrazolo[3,4-b]pyridin-1-yl]ethyl]amine Following a similar procedure to that described in examples 6 and 7, but using N-(2-chloroethyl)diethylamine hydrochloride instead of iodoethane and 2 equivalents of KOH, the title compounds were obtained.

Example 100: yield: 5%; $^1$H NMR (300 MHz, CDCl$_3$) δ (TMS): 0.99 (t, J=7.2 Hz, 6 H), 2.56 (c, J=7.1 Hz, 4 H), 3.08 (t, J=6.5 Hz, 2 H), 4.48 (t, J=6.5 Hz, 2 H), 6.82 (dd, $J_o$=1.5 Hz, $J_m$=4.5 Hz, 2 H), 6.89 (t, J=8.8 Hz, 2 H), 7.00 (t, J=8.6 Hz, 2 H), 7.14 (m, 2 H), 7.29 (m, 2 H), 7.85 (s, 1 H), 8.32 (dd, $J_o$=1.5 Hz, $J_m$=4.5 Hz, 2 H).

Example 101: yield: 73%; $^1$H NMR (300 MHz, CDCl$_3$) δ (TMS): 1.05 (t, J=7.2 Hz, 6 H), 2.66 (c, J=7.2 Hz, 4 H), 3.09 (t, J=7.2 Hz, 2 H), 4.69 (t, J=7.2 Hz, 2 H), 6.82 (dd, $J_o$=1.5 Hz, $J_m$=4.5 Hz, 2 H), 6.92 (t, J=8.7 Hz, 2 H), 6.98 (t, J=8.7 Hz, 2 H), 7.14 (m, 2 H), 7.26 (m, 2 H), 7.85 (s, 1 H), 8.32 (dd, $J_o$=1.5 Hz, $J_m$=4.5 Hz, 2 H).

Example 102

4,6-Bis(4-fluorophenyl)-5-(4pyridyl)-2-(3-pyridylmethyl)pyrazolo[3,4-b]pyridine

Example 103

4,6-Bis(4-fluorophenyl)-5-(4-pyridyl)-1-(3-pyridylmethyl)pyrazolo[3,4-b]pyridine Following a similar procedure to that described in examples 6 and 7, but using 3-chloromethylpyridine hydrochloride instead of iodoethane, the title compounds were obtained.

Example 102: yield: 16% $^1$H NMR (300 MHz, CDCl$_3$) δ (TMS): 5.63 (s, 2 H), 6.81 (dd, $J_o$=1.8 Hz, $J_m$=4.5 Hz, 2 H), 6.90 (t, J=8.8 Hz, 2 H), 6.99 (t, J=8.7 Hz, 2 H), 7.10 (m, 2 H), 7.31 (m, 2 H), 7.82 (m, 2 H), 8.32 (dd, $J_o$=1.5 Hz, $J_m$=4.5 Hz, 2 H), 8.61 (dd, $J_o$=1.5 Hz, $J_m$=4.8 Hz, 2 H), 8.68 (s, 1 H).
Example 103: yield: 22%; $^1$H NMR (300 MHz, CDCl$_3$) δ (TMS): 5.80 (s, 2 H), 6.81 (dd, $J_o$=1.5 Hz, $J_m$=4.5 Hz, 2 H), 6.94 (t, J=8.6 Hz, 2 H), 7.01 (t, J=8.7 Hz, 2 H), 7.13 (m, 2 H), 7.27 (m, 2 H), 7.79 (m, 1 H), 7.88 (s, 1 H), 8.32 (dd, $J_o$=1.4 Hz, $J_m$=4.4 Hz, 2 H), 8.56 (d, J=5.0 Hz, 2 H), 8.75 (s, 1 H).

Example 104

N,N-Dimethyl-[3-[4,6-bis(4-fluorophenyl)-5-(4-pyridyl)pyrazolo[3,4-b]pyridin-2-yl]propyl]amine Example 105

N,N-Dimethyl-[3-[4,6-bis(4-fluorophenyl)-5-(4-pyridyl)pyrazolo[3,4-b]pyridin-1-yl]propyl]amine Following a similar procedure to that described in examples 6 and 7, but using N-(3-chloropropyl)dimethylamine hydrochloride instead of iodoethane, the title compounds were obtained.
Example 104: 22%; $^1$H NMR (300 MHz, CDCl$_3$) δ (TMS): 2.21-2.29 (complex signal, 10 H), 4.51 (t, J=6.6 Hz, 2 H), 6.82 (dd, $J_o$=1.6 Hz, $J_m$=4.4 Hz, 2 H), 6.89 (t, J=8.8 Hz, 2 H), 7.00 (t, J=8.7 Hz, 2 H), 7.14 (m, 2 H), 7.30 (m, 2 H), 7.81 (s, 1 H), 8.31 (dd, $J_o$=1.6 Hz, $J_m$=4.4 Hz, 2 H).
Example 105: yield: 19%; $^1$H NMR (300 MHz, CDCl$_3$) δ (TMS): 2.18-2.27 (complex signal, 8 H), 2.43 (t, J=7.2 Hz, 2 H), 4.65 (t, J=7.1 Hz, 2 H), 6.82 (dd, $J_o$=1.5 Hz, $J_m$=4.5 Hz, 2 H), 6.93 (t, J=8.8 Hz, 2 H), 7.01 (t, J=8.7 Hz, 2 H), 7.14 (m, 2 H), 7.27 (m, 2 H), 7.86 (s, 1 H), 8.32 (dd, $J_o$=1.5 Hz, $J_m$=4.5 Hz, 2 H).

Example 106

1-[2-[4,6-Bis(4-fluorophenyl)-5-(4-pyridyl)pyrazolo[3,4-b]pyridin-2-yl]ethyl]piperidin-4-ol In a volumetric flask, 2-[4,6-bis(4-fluorophenyl)-5-(4-pyridyl)pyrazolo[3,4-b]pyridin-2-yl]acetaldehyde (0.08 g, 0.2 mmol, obtained in example 94), sodium triacetoxyborohydride (0.08 g, 0.4 mmol), 4-hydroxypiperidine (0.02 g, 0.2 mmol) and 1,2-dichloroethane (3 mL) were introduced under argon atmosphere. The mixture was stirred overnight at room temperature. It was concentrated and a mixture of water and EtOAc were added. The phases were separated. The aqueous phase was extracted with EtOAc. The organic phase was dried over Na$_2$SO$_4$ and concentrated to dryness. The crude product obtained was purified by chromatography on silica gel using increasing polarity mixtures of EtOAc-MeOH as eluent, to afford 19 mg of the title compound (yield: 20%).
$^1$H NMR (300 MHz, CDCl$_3$) δ (TMS): 1.57 (broad s 1 H+OH+H$_2$O), 1.85 (m, 2 H), 2.05 (m, 2 H), 2.30 (m, 2 H), 2.80 (m, 2 H), 3.01 (m, 2 H), 4.54 (m, 2 H), 6.83 (dd, $J_o$=1.5 Hz, $J_m$=4.5 Hz, 2 H), 6.90 (t, J=8.6 Hz, 2 H), 7.01 (t, J=8.6 Hz, 2 H), 7.14 (m, 2 H), 7.29 (m, 2 H), 7.85 (s, 1 H), 8.34 (dd, $J_o$=1.6 Hz, $J_m$=4.4 Hz, 2 H).

Example 107

3-[4,6-Bis(4-fluorophenyl)-5-(4-pyridyl)pyrazolo[3,4-b]pyridin-2-yl]-2-hydroxypropan-1-ol Example 108

3-[4,6-Bis(4-fluorophenyl)-5-(4-pyridyl)pyrazolo[3,4-b]pyridin-1-yl]-2-hydroxypropan-1-ol Following a similar procedure to that described in examples 6 and 7, but using 3-bromopropane-1,2-diol instead of iodoethane, the title compounds were obtained.

Example 107: yield: 17%; $^1$H NMR (300 MHz, CDCl$_3$) δ (TMS): 3.49 (s, 1H, OH), 3.72 (m, 2 H), 4.32 (m, 1 H), 4.60 (m, 2 H), 5.30 (s, 1 H, OH), 6.83 (dd, $J_o$=1.6 Hz, $J_m$=4.4 Hz, 2 H), 6.91 (t, J=8.7 Hz, 2 H), 7.01 (t, J=8.6 Hz, 2 H), 7.14 (m, 2 H), 7.28 (m, 2 H), 7.88 (s, 1 H), 8.32 (dd, $J_o$=1.6 Hz, $J_m$=4.4 Hz, 2 H).
Example 108: yield: 26%; $^1$H NMR (300 MHz, CDCl$_3$) δ (TMS): 3.65 (m, 2 H), 4.26 (m, 1 H), 4.78 (m, 2 H), 5.30 (s, 2 H, OH), 6.82 (dd, $J_o$=1.5 Hz, $J_m$=4.5 Hz, 2 H), 6.94 (t, J=8.6 Hz, 2 H), 7.03 (t, J=8.7 Hz, 2 H), 7.14 (m, 2 H), 7.28 (m, 2 H), 7.91 (s, 1 H), 8.34 (dd, $J_o$=1.5 Hz, $J_m$=4.5 Hz, 2 H).

Example 109

4,6-Bis(4-fluorophenyl)-5-(4-pyridyl)-2-(4-pyridylmethyl)pyrazolo[3,4-b]pyridine Example 110

4,6-Bis(4-fluorophenyl)-5-(4-pyridyl)-1-(4-pyridylmethyl)pyrazolo[3,4-b]pyridine Following a similar procedure to that described in examples 6 and 7, but using 4-chloromethylpyridine hydrochloride instead of iodoethane, the title compounds were obtained.
Example 109: yield: 29%; $^1$H NMR (300 MHz, CDCl$_3$) δ (TMS): 5.63 (s, 2 H), 6.83 (dd, $J_o$=1.5 Hz, $J_m$=4.5 Hz, 2 H), 6.90 (t, J=8.7 Hz, 2 H), 6.99 (t, J=8.7 Hz, 2 H), 7.12 (m, 2 H), 7.23-7.33 (complex signal, 4 H), 7.84 (s, 1 H), 8.32 (dd, $J_o$=1.5 Hz, $J_m$=4.5 Hz, 2 H), 8.61 (dd, $J_o$=1.5 Hz, $J_m$=4.8 Hz, 2 H).
Example 110: yield: 15%; 5.80 (s, 2 H), 6.82 (dd, $J_o$=1.5 Hz, $J_m$=4.5 Hz, 2 H), 6.93 (t, J=8.7 Hz, 2 H), 7.00 (t, J=8.7 Hz, 2 H), 7.14 (m, 2 H), 7.20-7.26 (complex signal, 4 H), 7.93 (s, 1 H), 8.34 (dd, $J_o$=1.5 Hz, $J_m$=4.5 Hz, 2 H), 8.61 (dd, $J_o$=1.5 Hz, $J_m$=4.8 Hz, 2 H).

Example 111

N-(tert-Butoxycarbonyl)-[1-[3-[4,6-bis(4-fluorophenyl)-5-(4-pyridyl)pyrazolo[3,4-b]pyridin-2-yl]propyl]piperidin-4-yl]amine To a solution of 3-[4,6-bis(4-fluorophenyl)-5-(4-pyridyl)pyrazolo[3,4-b]pyridin-2-yl]propyl methanesulfonate (0.15 g, 0.3 mmol, obtained in example 84 section a) in acetonitrile (2 mL), N-(tert-butoxycarbonyl)-N-(4-piperidyl)amine (0.12 g, 0.6 mmol) was added under argon atmosphere and heated to 60° C. overnight. A mixture of CHCl$_3$ and saturated NaHCO$_3$ were added. The phases were separated. The aqueous phase was extracted with CHCl$_3$. The organic phase was dried over Na$_2$SO$_4$ and concentrated to dryness. The crude product obtained was purified by chromatography on silica gel using increasing polarity mixtures of EtOAc-MeOH as eluent, to afford 40 mg of the title compound (yield: 22%).
$^1$H NMR (300 MHz, CDCl$_3$) δ (TMS): 1.44 (broad s, 2 H+NH$_2$+H$_2$O), 1.95 (m, 2 H), 2.06 (m, 2 H), 2.25 (m, 2 H), 2.35 (m, 2 H), 3.46 (m, 2 H), 4.40 (m, 1 H), 4.51 (t, 2 H), 6.83 (d, J=6.0 Hz, 2 H), 6.90 (t, J=8.7 Hz, 2 H), 7.00 (t, J=8.7 Hz, 2 H), 7.14 (m, 2 H), 7.29 (m, 2 H), 7.80 (s, 1 H), 8.32 (d, J=6.0 Hz, 2 H).

Example 112

2-[1-(tert-Butoxycarbonyl)piperidin-4-yl]-6-(4-fluorophenyl)-5-(4-pyridyl)pyrazolo[3,4-b]pyridine

Example 113

1-[1-(tert-Butoxycarbonyl)piperidin-4-yl]-6-(4-fluorophenyl)-5-(4-pyridyl)pyrazolo[3,4-b]pyridine Following a similar procedure to that described in examples 6 and 7, but using 6-fluorophenyl-5-(4-pyridyl)-1H-pyrazolo[3,4-b]pyridine (obtained in example 77) instead of 4,6-bis(4-fluorophenyl)-5-(4-pyridyl)-1H-pyrazolo[3,4-b]pyridine and 1-(tert-butoxycarbonyl)piperidin-4-yl methanesulfonate (obtained in example 14 section a) instead of iodoethane, the title compounds were obtained.

Example 112: yield: 26%; $^1$H NMR (300 MHz, CDCl$_3$) δ (TMS): 1.50 (s, 9 H), 2.17-2.32 (complex signal, 2 H), 2.99 (m, 2 H), 4.33 (m, 2 H), 4.60 (m, 1 H), 6.95 (t, J=8.7 Hz, 2 H), 7.11 (dd, J$_o$=1.5 Hz, J$_m$=4.5 Hz, 2 H), 7.41 (m, 2 H), 8.06 (s, 1 H), 8.07 (s, 1 H), 8.52 (dd, J$_o$=1.6 Hz, J$_m$=4.4 Hz, 2 H).

Example 113: yield: 55%; $^1$H NMR (300 MHz, CDCl$_3$) δ (TMS): 1.50 (s, 9 H), 2.04 (m, 2 H), 2.30 (m, 2 H), 3.00 (m, 2 H), 4.42 (m, 2 H), 5.10 (m, 1 H), 7.00 (t, J=8.6 Hz, 2 H), 7.10 (dd, J$_o$=1.6 Hz, J$_m$=4.5 Hz, 2 H), 7.37 (m, 2 H), 8.07 (s, 1 H), 8.10 (s, 1 H), 8.52 (dd, J$_o$=1.8 Hz, J$_m$=4.5 Hz, 2 H).

Example 114

3-Methyl-4,6-bis(6-methylpyridin-3-yl)-5-(4-pyridyl)-1H-pyrazolo[3,4-b]pyridine

Following a similar procedure to that described in example 1 method A, but using 1-(6-methylpyridin-3-yl)-2-(4-pyridyl)ethanone (obtained in reference example 13) instead of 1-(4-fluorophenyl)-2-(4-pyridyl)ethanone and 3-amino-5-methyl-2H-pyrazole instead of 3-amino-2H-pyrazole, the title compound was obtained (yield: 24%).

$^1$H NMR (300 MHz, CDCl$_3$) δ (TMS): 2.07 (s, 3 H), 2.54 (s, 3 H), 2.57 (s, 3 H), 6.85 (m, 2 H), 6.99 (d, J=8.1 Hz, 1 H), 7.08 (d, J=8.1 Hz, 1 H), 7.30 (m, 1 H), 8.10 (dd, J$_o$=2.4 Hz, J$_m$=8.1 Hz, 1 H), 8.32 (dd, J$_o$=1.5 Hz, J$_m$=4.5 Hz, 2 H), 8.38 (s, 1 H), 8.57 (s, 1 H), 10.74 (broad s, NH).

Example 115

1-[3-[4,6-Bis(4-fluorophenYl)-5-(4-pyridyl)pyrazolo[3,4-b]pyridin-2-yl]propyl]piperidin-4-one In a volumetric flask, 3-[4,6-bis(4-fluorophenyl)-5-(4-pyridyl)pyrazolo[3,4-b]pyridin-2-yl]propyl methanesulfonate (0.15 g, 0.3 mmol, obtained in example 84 section a), NaI (0.008 g, 0.06 mmol), 4-piperidone monohydrate hydrochloride (0.04 g, 0.3 mmol), K$_2$CO$_3$ (0.07 g, 0.5 mmol) and DMF (2 mL) were introduced under argon atmosphere. The mixture was heated to 60° C. for 24 h. It was allowed to cool and a mixture of water and EtOAc was added. The phases were separated. The aqueous phase was extracted with EtOAc. The organic phase was dried over Na$_2$SO$_4$ and concentrated to dryness. The crude product obtained was purified by chromatography on silica gel using EtOAc-MeOH mixtures of increasing polarity as eluent, to afford 16 mg of the title compound (yield: 10%).

$^1$H NMR (300 MHz, CDCl$_3$) δ (TMS): 1.57 (broad s,4 H+H$_2$O), 2.30 (m, 2 H), 2.42 (m, 2 H), 2.48 (m, 2 H), 2.73 (t, 2 H), 4.55 (t, 2 H), 6.83 (d, J=6.0 Hz, 2 H), 6.90 (t, J=8.7 Hz, 2 H), 7.00 (t, J=8.6 Hz, 2 H), 7.18 (m, 2 H), 7.27 (m, 2 H), 7.82 (s, 1 H), 8.32 (d, J=6.0 Hz, 2 H).

Example 116

N-(tert-Butoxycarbonyl)-[1-[2-[4,6-bis(4-fluorophenyl)-5-(4-pyridyl)pyrazolo[3,4-]pyridin-2-yl]ethyl]piperidin-4-yl]amine a) 2-[4,6-Bis(4-fluorophenyl)-5-(4-pyridyl)pyrazolo[3,4-b]pyridin-2-yl]ethyl methanesulfonate Following a similar procedure to that described in example 12 section b, but using 2-[4,6-bis(4-fluorophenyl)-5-(4-pyridyl)pyrazolo[3,4-b]pyridin-2-yl]ethanol (obtained in example 91) instead of 2-[1-(tert-butoxycarbonyl)piperidin-4-yl]ethanol, the desired compound was obtained (yield: quantitative).

b) Title compound

Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in section a) instead of 3-[4,6-bis(4-fluorophenyl)-5-(4-pyridyl)pyrazolo[3,4-b]pyridin-2-yl]propyl methanesulfonate the desired compound was obtained (yield: 66%).

$^1$H NMR (300 MHz, CDCl$_3$) δ (TMS): 1.44 (s, 9 H), 1.57 (broad s, 1 H+NH+H$_2$O), 1.90 (m, 2 H), 2.22 (m, 2 H), 2.82 (m, 2 H), 3.01 (t, J=6.6 Hz, 2 H), 3.45 (m, 1 H), 4.40 (m, 1 H), 4.52 (t, J=6.5 Hz, 2 H), 6.82 (d, J=5.7 Hz, 2 H), 6.89 (t, J=8.7 Hz, 2 H), 7.01 (t, J=8.6 Hz, 2 H), 7.14 (m, 2 H), 7.29 (m, 2 H), 7.82 (s, 1 H), 8.31 (dd, J$_o$=1.5 Hz, J$_m$=4.5 Hz, 2 H).

Example 117

N-Methyl-[1-[2-[4,6-bis(4-fluorophenyl)-5-(4-pyridyl)pyrazolo[3,4-b]pyridin-2-yl]ethyl]piperidin-4-yl]amine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and N-methyl-N-(piperidin-4-yl)amine instead of N-(tert-butoxycarbonyl)-N-(4-piperidyl)amine, the desired compound was obtained (yield: 50%).

$^1$H NMR (300 MHz, CDCl$_3$) δ (TMS): 1.61 (broad s, 1 H+NH+H$_2$O), 2.28 (s, 3 H), 2.41 (m, 4 H), 2.57 (m, 4 H), 3.03 (t, J=6.5 Hz, 2 H), 4.55 (t, J=6.5 Hz, 2 H), 6.83 (dd, J$_o$=1.5 Hz, J$_m$=4.5 Hz, 2 H), 6.90 (t, J=8.7 Hz, 2 H), 7.01 (t, J=8.7 Hz, 2 H), 7.14 (m, 2 H), 7.29 (m, 2 H), 7.85 (s, 1 H), 8.32 (dd, J$_o$=1.5 Hz, J$_m$=4.5 Hz, 2 H).

Example 118

[1-[3-[4,6-Bis(4-fluorophenyl)-5-(4-pyridyl)pyrazolo[3,4-b]pyridin-2-yl]propyl]piperidin-4-yl]amine Following a similar procedure to that described in example 36, but using N-(tert-butoxycarbonyl)-[1-[3-[4,6-bis(4-fluorophenyl)-5-(4-pyridyl)pyrazolo[3,4-b]pyridin-2-yl]propyl]piperidin-4-yl]amine (obtained in example 111) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 89%).

$^1$H NMR (300 MHz, CDCl$_3$) δ (TMS): 1.35 (m, 2 H), 1.62 (broad s NH$_2$+H$_2$O), 1.85 (m, 2 H), 2.03 (m, 2 H), 2.25 (m, 2

H), 2.36 (m, 2 H), 2.70 (m, 1 H), 2.82 (m, 2 H), 4.52 (d, J=6.6 Hz, 2 H), 6.83 (dd, $J_o$=1.5 Hz, $J_m$=4.5 Hz, 2 H), 6.90 (t, J=8.7 Hz, 2 H), 7.00 (t, J=8.6 Hz, 2 H), 7.13 (m, 2 H), 7.29 (m, 2 H), 7.81 (s, 1 H), 8.31 (dd, $J_o$=1.6 Hz, $J_m$=4.4 Hz, 2 H).

Example 119

2-[1-[2-[4,6-Bis(4-fluorophenyl)-5-(4-pyridyl)pyrazolo[3,4-b]pyridin-2-yl]ethyl]piperidin-4-yl]ethanol Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 2-(4-piperidyl)ethanol instead of N-(tert-butoxycarbonyl)-N-(4-piperidyl)amine, the desired compound was obtained (yield: 50%).
$^1$H NMR (300 MHz, CDCl$_3$) δ (TMS): 1.48-1.53 (complex signal, 5 H), 2.11 (m, 2 H), 2.88 (m, 2 H), 2.99 (m, 2 H), 3.70 (t, J=6.5 Hz, 2 H), 4.55 (t, J=6.5 Hz, 2 H), 6.83 (dd, $J_o$=1.5 Hz, $J_m$=4.5 Hz, 2 H), 6.89 (t, J=8.7 Hz, 2 H), 7.00 (t, J=8.6 Hz, 2 H), 7.14 (m, 2 H), 7.29 (m, 2 H), 7.86 (s, 1 H), 8.32 (dd, $J_o$=1.5 Hz, $J_m$=4.5 Hz, 2 H).

Example 120

[1-[2-[4,6-Bis(4-fluorophenyl)-5-(4-pyridyl)pyrazolo[3,4-b]pyridin-2-yl]ethyl]piperidin-4-yl]amine Following a similar procedure to that described in example 36, but using N-(tert-butoxycarbonyl)-[1-[2-[4,6-bis(4-fluorophenyl)-5-(4-pyridyl)pyrazolo[3,4-b]pyridin-2-yl]ethyl]piperidin-4-yl]amine (obtained in example 116) instead of 2-[1-(tert-butoxycarbonyl)piperidin-4-yl]4,6-bis(4-fluorophenyl)-5-(4-pyridyl)pyrazolo[3,4-b]pyridine, the title compound was obtained (yield: 77%).
$^1$H NMR (300 MHz, CDCl$_3$) δ (TMS): 1.38 (m, 2 H), 1.78 (broad s, 2 H+NH$_2$+H$_2$O), 2.18 (m, 2 H), 2.75 (m, 1 H), 2.84 (m, 2 H), 3.02 (t, J=6.3 Hz, 2 H), 4.54 (t, J=6.5 Hz, 2 H), 6.82 (d, J=5.7 Hz, 2 H), 6.89 (t, J=8.7 Hz, 2 H), 7.00 (t, J=8.6 Hz, 2 H), 7.14 (m, 2 H), 7.29 (m, 2 H), 7.84 (s, 1 H), 8.31 (d, J=6.0 Hz, 2 H).

Example 121

6-(4-Fluorophenyl)-2-(4-piperidyl)-5-(4-pyridyl)pyrazolo[3,4-b]pyridine

Following a similar procedure to that described in example 36, but using 2-[1-(tert-butoxycarbonyl)piperidin-4-yl]-6-(4-fluorophenyl)-5-(4-pyridyl)pyrazolo[3,4-b]pyridine (obtained in example 112) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 77%).
$^1$H NMR (300 MHz, CDCl$_3$) δ (TMS): 1.89 (m, NH+H$_2$O), 2.25 (m, 2 H), 2.30 (m, 2 H), 2.89 (m, 2 H), 3.34 (m, 2 H), 4.60 (m, 1 H), 6.95 (t, J=8.7 Hz, 2 H), 7.11 (dd, $J_o$=1.5 Hz, $J_m$=4.5 Hz, 2 H), 7.40 (m, 2 H), 8.07 (s, 1 H), 8.08 (s, 1 H), 8.51 (dd, $J_o$=1.6 Hz, $J_m$=4.4 Hz, 2 H).

Example 122

6-(4-Fluorophenyl)-1-(4-piperidyl)-5-(4-pyridyl)pyrazolo[3,4-b]pyridine

Following a similar procedure to that described in example 36, but using 1-[1-(tert-butoxycarbonyl)piperidin-4-yl]-6-(4-fluorophenyl)-5-(4-pyridyl)pyrazolo[3,4-b]pyridine (obtained in example 113) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: quantitative).
$^1$H NMR (300 MHz, CDCl$_3$) δ (TMS): 1.60 (m, NH+H$_2$O), 2.42 (m, 2 H), 2.67 (m 2 H), 3.28 (m, 2 H), 3.72 (m, 2 H), 5.28 (m, 1 H), 7.00 (t, J=8.7 Hz, 2 H), 7.11 (dd, $J_o$=1.5 Hz, $J_m$=4.5 Hz, 2 H), 7.37 (m, 2 H), 8.10 (s, 1 H), 8.12 (s, 1 H), 8.54 (dd, $J_o$=1.6 Hz, $J_m$=4.4 Hz, 2 H).

Example 123

3-Amino-5-[2-(methylsulfanyl)pyrimidin-4-yl]-6-[3-(trifluoromethyl)phenyl]-1H-pyrazolo[3,4-b]pyridine Following a similar procedure to that described in reference example 15 section c, but using 2-chloro-5-[2-(methylsulfanyl)pyrimidin-4-yl]-6-[3-(trifluoromethyl)phenyl]pyridine-3-carbonitrile (obtained in reference example 14) instead of 3-(1-benzylpiperidin-4-yl)-3-oxopropiononitrile, the title compound was obtained (yield: 78%).
$^1$H NMR (300 MHz, CDCl$_3$) δ (TMS): 2.44 (s, 3 H), 4.32 (broad s, NH$_2$), 6.61 (d, J=5.1 Hz, 1 H), 7.44-7.84 (complex signal, 2 H), 7.65 (d, J=7.2 Hz, 1 H), 7.84 (s, 1 H), 8.30 (d, J=5.1 Hz, 1 H), 8.40 (s, 1 H), 9.55 (broad s, NH).

Example 124

4,6-Bis(4-fluorophenyl)-2-[3-[1-(tert-butoxycarbonyl)piperazin-4-yl]propyl]-5-(4-pyridyl)pyrazolo[3,4-b]pyridine Following a similar procedure to that described in example 84 section b, but using 1-(tert-butoxycarbonyl)piperazine instead of morpholine and adding triethylamine (1.5 equivalents), the desired compound was obtained (yield: 14%).
$^1$H NMR (300 MHz, CDCl$_3$) δ (TMS): 2.66 (m, 2 H), 2.98 (m, 4 H), 3.10 (m, 2 H), 3.66-3.74 (complex signal, 4 H), 4.66 (m, 2 H), 6.85 (dd, $J_o$=1.5 Hz, $J_m$=4.5 Hz, 2 H), 6.91 (t, J=8.7 Hz, 2 H), 7.00 (t, J=8.7 Hz, 2 H), 7.14 (m, 2 H), 7.28 (m, 2 H), 7.98 (s, 1 H), 8.32 (dd, $J_o$=1.5 Hz, $J_m$=4.5 Hz, 2 H).

Example 125

4,6-Bis(4-fluorophenyl)-2-[3-(piperazin-1-yl)propyl]-5-(4-pyridyl)pyrazolo[3,4-b]pyridine Following a similar procedure to that described in example 36, but using 4,6-bis(4-fluorophenyl)-2-[3-[1-(tert-butoxycarbonyl)piperazin-4-yl]propyl]-5-(4-pyridyl)pyrazolo[3,4-b]pyridine (obtained in example 124) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: quantitative).
$^1$H NMR (300 MHz, CDCl$_3$) δ (TMS): 1.78 (broad s, 2 H+NH+H$_2$O), 2.26 (m, 2 H), 2.40-2.59 (complex signal, 6 H), 3.04 (m, 2 H), 4.52 (m, 2 H), 6.83 (dd, $J_o$=1.5 Hz, $J_m$=4.5 Hz, 2 H), 6.90 (t, J=8.7 Hz, 2 H), 7.00 (t, J=8.7 Hz, 2 H), 7.14 (m, 2 H), 7.29 (m, 2 H), 7.80 (s, 1 H), 8.31 (dd, $J_o$=1.5 Hz, $J_m$=4.5 Hz, 2 H).

Example 126

5-[2-(Methylsulfanyl)pyrimidin-4-yl]-6-[3-(trifluoromethyl)phenyl]-1H-pyrazolo[3,4-b]pyridine Following a similar procedure to that described in example 77, but using 3-amino-5-[2-(methylsulfanyl)pyrimidin-4-yl]-6-[3-(trifluoromethyl)phenyl]-1H-pyrazolo[3,4-b]pyridine (obtained in example 123) instead of 3-amino-6-(4-fluorophenyl)-5-(4-pyridyl)-1H-pyrazolo[3,4-b]pyridine, the title compound was obtained (yield: 34%).

$^1$H NMR (300 MHz, CDCl$_3$) δ (TMS): 1.55 (broad s, NH+H$_2$O), 6.70 (d, J=5.1 Hz, 1 H), 7.50 (m, 2 H), 7.72 (m, 1 H), 7.86 (s, 1 H), 8.24 (s, 1 H), 8.35 (d, J=5.1 Hz, 1 H), 8.54 (s, 1 H).

Example 127

5-[2-(Methylsulfonyl)pyrimidin-4-yl]-6-[3-(trifluoromethyl)phenyl]-1H-pyrazolo[3,4-b]pyridine Following a similar procedure to that described in example 56, but using 5-[2-(methylsulfanyl)pyrimidin-4-yl]-6-[3-(trifluoromethyl)phenyl]-1H-pyrazolo[3,4-b]pyridine (obtained in example 126) instead of 4,6-bis(4-fluorophenyl)-2-(4-methylsulfanylphenyl)-5-(4-pyridyl)pyrazolo[3,4-b]pyridine and 2 equivalents of m-chloroperbenzoic acid, the title compound was obtained (yield: quantitative).

$^1$H NMR (300 MHz, CDCl$_3$) δ (TMS): 1.56 (broad s, NH+H$_2$O), 3.22 (s, 3 H), 7.21 (d, J=5.1 Hz, 1 H), 7.49 (d, J=4.8 Hz, 2 H), 7.71 (m, 1 H), 7.84 (s, 1 H), 8.30 (s, 1 H), 8.71 (m, 2 H).

Example 128

(1S)-N-(1-Phenylethyl)-[4-[6-[3-(trifluoromethyl)phenyl]-1H-pyrazolo[3,4-b]pyridin-5-yl]pyrimidin-2-yl]amine A mixture of 5-[2-(methylsulfonyl)pyrimidin-4-yl]-6-[3-(trifluoromethyl)phenyl]-1H-pyrazolo[3,4-b]pyridine (0.55 g, 0.13 mmol, obtained in example 127) and (1S)-1-phenylethylamine (0.16 g, 1.3 mmol) was heated to 100° C. for 1 h. It was allowed to cool and the crude product obtained was purified by chromatography on silica gel using increasing polarity mixtures of EtOAc-hexane as eluent, to afford 10 mg of the title compound (yield: 16%).

$^1$H NMR (300 MHz, CDCl$_3$+CD$_3$OD) δ (TMS): 1.50 (d, 3 H), 3.80 (broad s, 2 NH+H$_2$O), 6.30 (d, 1 H), 7.20-7.40 (complex signal, 6 H), 7.50 (d, 1 H), 7.68 (d, 1 H), 7.76 (d, 1 H), 7.83 (s, 1 H), 8.08 (d, 1 H), 8.15 (s, 1 H), 8.24 (broad s, 1 H).

Example 129

1-[3-[4,6-Bis(4-fluorophenyl)-5-(4-pyridyl)pyrazolo[3,4-b]pyridin-2-yl]propyl]piperidin-4-ol Following a similar procedure to that described in example 111, but using piperidin-4-ol instead of N-(tert-butoxycarbonyl)-N-(4-piperidyl)amine, the desired compound was obtained (yield: 39%).

$^1$H NMR (300 MHz, CDCl$_3$) δ (TMS): 1.57 (m, 2 H), 1.88-2.50 (complex signal, 5 H+OH+H$_2$O), 2.75 (m, 2 H), 3.44-3.51 (complex signal, 4 H), 4.52 (t, J=6.6 Hz, 2 H), 6.83 (dd, J$_o$=1.6 Hz, J$_m$=4.4 Hz, 2 H), 6.89 (t, J=8.7 Hz, 2 H), 7.00 (t, J=8.6 Hz, 2 H), 7.14 (m, 2 H), 7.34 (m, 2 H), 7.82 (s, 1 H), 8.32 (dd, J$_o$=1.5 Hz, J$_m$=4.5 Hz, 2 H).

Example 130

2-[1-[3-[4,6-Bis(4-fluorophenyl)-5-(4-pyridyl)pyrazolo[3,4-b]pyridin-2-yl]propyl]piperidin-4-yl]ethanol Following a similar procedure to that described in example 111, but using 2-(4-piperidyl)ethanol instead of N-(tert-butoxycarbonyl)-N-(4-piperidyl)amine, the desired compound was obtained (yield: 44%).

$^1$H NMR (300 MHz, CDCl$_3$) δ (TMS): 1.20-2.00 (broad s, 8 H+OH+H$_2$O), 2.50 (m, 1 H), 2.85 (m, 1 H), 3.50 (m, 1 H), 3.70 (m, 4 H), 4.59 (m, 2 H), 6.83 (d, J=6.0 Hz, 2 H), 6.90 (t, J=8.7 Hz, 2 H), 7.00 (t, J=8.6 Hz, 2 H), 7.14 (m, 2 H), 7.30 (m, 2 H), 7.89 (s, 1 H), 8.32 (d, J=6.0 Hz, 2 H).

Example 131

4,6-Bis(4-fluorophenyl)-3-(4-piperidyl)-5-(4-pyridyl)-1H-pyrazolo[3,4-b]pyridine a) 3-(1-Benzylpiperidin-4-yl)-4,6-bis(4-fluorophenyl)-5-(4-pyridyl)-1H-pyrazolo[3,4-b]pyridine Following a similar procedure to that described in example 1 method A, but using 3-amino-5-(1-benzylpiperidin-4-yl)-2H-pyrazole (obtained in reference example 15) instead of 3-amino-2H-pyrazole, the title compound was obtained (yield: 6%).

b) Title Compound

To a solution of 3-(1-benzylpiperidin-4-yl)-4,6-bis(4-fluorophenyl)-5-(4-pyridyl)-1H-pyrazolo[3,4-b]pyridine (23 mg, 0.04 mmol, obtained in the previous section) in MeOH (1 mL), Pd/C and a solution of HCOONH$_4$ (0.01 g, 0.2 mmol) in water (0.06 mL) were added under argon atmosphere. The mixture was heated to reflux for 5 h. It was filtered through celite and concentrated. The residue was dissolved in CHCl$_3$ and washed with saturated NaHCO$_3$, to afford 2 mg of the title compound (yield: 10%).

$^1$H NMR (300 MHz, CDCl$_3$) δ (TMS): 1.10-1.90 (broad s, 7 H), 2.23 (m, 2 H), 2.99 (m, 2 H), 6.80 (dd, J$_o$=1.6 Hz, J$_m$=4.4 Hz, 2 H), 6.92 (t, J=8.7 Hz, 2 H), 7.02 (t, J=8.7 Hz, 2 H), 7.12 (m, 2 H), 7.28 (m, 2 H), 8.28 (dd, J$_o$=1.5 Hz, J$_m$=4.5 Hz, 2 H).

Example 132

6-(4-Fluorophenyl)-5-(4-pyridyl)-1H-pyrazolo[3,4-b]pyridine-3-carbonitrile

Following a similar procedure to that described in example 65, but using 3-bromo-6-(4-fluorophenyl)-5-(4-pyridyl)-1H-pyrazolo[3,4-b]pyridine (obtained in example 76) instead of 3-bromo-4,6-bis(4-fluorophenyl)-5-(4-pyridyl)-1H-pyrazolo[3,4-b]pyridine, the title compound was obtained (yield: 38%).

Example 133

2-[2-[[1-(tert-Butoxycarbonyl)piperidin-4-yl]amino]ethyl]-4,6-bis(4-fluorophenyl)-5-(4-pyridyl)pyrazolo[3,4-b]pyridine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and [N-(tert-butoxycarbonyl)piperidin-4-yl]amine instead of N-(tert-butoxycarbonyl)-N-(4-piperidyl)amine, the desired compound was obtained (yield: 40%).

$^1$H NMR (300 MHz, CDCl$_3$) δ (TMS): 1.20 (m, 2 H), 1.45 (s, 9 H), 1.55 (broad s NH+H$_2$O), 1.83 (m, 2 H), 2.65 (m, 1 H), 2.77 (m, 2 H), 3.31 (t, 2 H), 4.02 (m, 2 H), 4.53 (t, 2 H), 6.82 (dd, J$_o$=1.5 Hz, J$_m$=4.5 Hz, 2 H), 6.90 (t, J=8.8 Hz, 2 H), 7.00 (t, J=8.7 Hz, 2 H), 7.13 (m, 2 H), 7.28 (m, 2 H), 7.84 (s, 1 H), 8.32 (dd, J$_o$=1.5 Hz, J$_m$=4.5 Hz, 2 H).

Example 134

4,6-Bis(4-fluorophenyl)-2-[2-[(4-piperidyl)amino]ethyl]-5-(4-pyridyl)pyrazolo[3,4-b]pyridine Following a similar procedure to that described in example 36, but using 2-[2-[[1-(tert-butoxycarbonyl)piperidin-4-yl]

amino]ethyl]-4,6-bis(4-fluorophenyl)-5-(4-pyridyl)pyrazolo [3,4-b]pyridine (obtained in example 133) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 97%).

$^1$H NMR (300 MHz, CDCl$_3$) δ (TMS): 1.30 (m, 2 H), 1.70 (broad s, 2 NH+H$_2$O), 1.85 (m, 2 H), 2.61 (m, 3 H), 3.09 (m, 2 H), 3.31 (t, J=5.7 Hz, 2 H), 4.53 (t, J=5.7 Hz, 2 H), 6.82 (dd, J$_o$=1.6 Hz, J$_m$=4.4 Hz, 2 H), 6.90 (t, J=8.8 Hz, 2 H), 7.00 (t, J=8.7 Hz, 2 H), 7.14 (m, 2 H), 7.29 (m, 2 H), 7.85 (s, 1 H), 8.32 (dd, J$_o$=1.6 Hz, J$_m$=4.4 Hz, 2 H).

Example 135

N-(2-Methoxyethyl)-[2-[4,6-bis(4-fluorophenyl)-5-(4-pyridyl)pyrazolo[3,4-b]pyridin-2-yl]ethyl]amine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 2-methoxyethylamine instead of N-(tert-butoxycarbonyl)-N-(4-piperidyl)amine, the desired compound was obtained (yield: 63%).

$^1$H NMR (300 MHz, CDCl$_3$) δ (TMS): 1.57 (broad s, NH+H$_2$O), 2.81 (t, J=5.1 Hz, 2 H), 3.30 (t, J=5.8 Hz, 2 H), 3.31 (s, 3 H), 3.45 (t, J=5.1 Hz, 2 H), 4.55 (t, J=5.7 Hz, 2 H), 6.82 (dd, J$_o$=1.8 Hz, J$_m$=4.5 Hz, 2 H), 6.89 (t, J=8.7 Hz, 2 H), 7.00 (t, J=8.7 Hz, 2 H), 7.14 (m, 2 H), 7.29 (m, 2 H), 7.85 (s, 1 H), 8.32 (dd, J$_o$=1.5 Hz, J$_m$=4.5 Hz, 2 H).

Example 136

1-[4-[2-[4,6-Bis(4-fluorophenyl)-5-(4-pyridyl)pyrazolo[3,4-b]pyridin-2-yl]ethyl]piperazin-1-yl]ethanone Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 1-(piperazin-1-yl)ethanone instead of N-(tert-butoxycarbonyl)-N-(4-piperidyl)amine, the desired compound was obtained (yield: 50%).

$^1$H NMR (300 MHz, CDCl$_3$) δ (TMS): 2.07 (s, 3 H), 2.50 (m, 4 H), 3.07 (t, J=6.3 Hz, 2 H), 3.41 (t, J=4.9 Hz, 2 H), 3.57 (t, J=4.9 Hz, 2 H), 4.55 (t, J=6.3 Hz, 2 H), 6.82 (dd, J$_o$=1.5 Hz, J$_m$=4.5 Hz, 2 H), 6.90 (t, J=8.7 Hz, 2 H), 7.00 (t, J=8.6 Hz, 2 H), 7.14 (m, 2 H), 7.29 (m, 2 H), 7.82 (s, 1 H), 8.32 (dd, J$_o$=1.5 Hz, J$_m$=4.5 Hz, 2 H).

Example 137

3-[4,6-Diphenyl-5-(4-pyridyl)pyrazolo[3,4-b]pyridin-2-yl]propan-1-ol

Example 138

3-[4,6-Diphenyl-5-(4-pyridyl)pyrazolo[3,4-b]pyridin-1-yl]propan-1-ol

Following a similar procedure to that described in examples 6 and 7, but using 4,6-diphenyl-5-(4-pyridyl)-1H-pyrazolo[3,4-b]pyridine (obtained in example 2) instead of 4,6-bis(4-fluorophenyl)-5-(4-pyridyl)-1H-pyrazolo[3,4-b]pyridine and 3-iodopropanol instead of iodoethane, the title compounds were obtained.

Example 137: yield: 44%; $^1$H NMR (300 MHz, CDCl$_3$) δ (TMS): 1.56 (s, OH+H$_2$O), 2.25 (m, 2 H), 3.70 (m, 2 H), 4.62 (t, J=6.3 Hz, 2 H), 6.83 (dd, J$_o$=1.6 Hz, J$_m$=4.6 Hz, 2 H), 7.17-7.34 (complex signal, 10 H), 7.84 (s, 1 H), 8.26 (dd, J$_o$=1.5 Hz, J$_m$=4.5 Hz, 2 H).

Example 138: yield: 27%; $^1$H NMR (300 MHz, CDCl$_3$) δ (TMS): 1.58 (s, OH+H$_2$O), 2.15 (m, 2 H), 3.59 (m, 2 H), 4.79 (t, J=6.0 Hz, 2 H), 6.83 (dd, J$_o$=1.6 Hz, J$_m$=4.4 Hz, 2 H), 7.17 (m, 2 H), 7.21-7.33 (complex signal, 8 H), 7.91 (s, 1 H), 8.27 (dd, J$_o$=1.5 Hz, J$_m$=4.5 Hz, 2 H).

Example 139

2-Ethyl-4,6-diphenyl-5-(4-pyridyl)pyrazolo[3,4-b]pyridine

Example 140

1-Ethyl-4,6-diphenyl-5-(4-pyridyl)pyrazolo[3,4-b]pyridine

Following a similar procedure to that described in examples 6 and 7, but using 4,6-diphenyl-5-(4-pyridyl)-1H-pyrazolo[3,4-b]pyridine (obtained in example 2) instead of 4,6-bis(4-fluorophenyl)-5-(4-pyridyl)-1H-pyrazolo[3,4-b]pyridine, the title compounds were obtained.

Example 139: yield: 12%; $^1$H NMR (300 MHz, CDCl$_3$) δ (TMS): 1.67 (t, J=7.3 Hz, 3 H), 4.50 (c, J=7.3 Hz, 2 H), 6.83 (dd, J$_o$=1.5 Hz, J$_m$=4.5 Hz, 2 H), 7.15-7.34 (complex signal, 10 H), 7.80 (s, 1H), 8.25 (dd, J$_o$=1.5 Hz, J$_m$=4.5 Hz, 2 H).

Example 140: yield: 21%; $^1$H NMR (300 MHz, CDCl$_3$) δ (TMS): 1.61 (t, J=7.2 Hz, 3 H), 4.68 (c, J=7.2 Hz, 2 H), 6.82 (dd, J$_o$=1.5 Hz, J$_m$=4.5 Hz, 2 H), 7.17 (m, 2 H), 7.23-7.32 (complex signal, 8 H), 7.88 (s, 1H), 8.26 (dd, J$_o$=1.5 Hz, J$_m$=4.5 Hz, 2 H).

Example 141

4,6-Diphenyl-2-(2-phthalimidoethyl)-5-(4-pyridyl) pyrazolo[3,4-b]pyridine

Following a similar procedure to that described in examples 6 and 7, but using 4,6-diphenyl-5-(4-pyridyl)-1H-pyrazolo[3,4-b]pyridine (obtained in example 2) instead of 4,6-bis(4-fluorophenyl)-5-(4-pyridyl)-1H-pyrazolo[3,4-b]pyridine and N-(2-bromoethyl)phthalimide instead of iodoethane, the title compound was obtained (yield: 31%).

$^1$H NMR (300 MHz, CDCl$_3$) δ (TMS): 4.32 (t, J=6.1 Hz, 2 H), 4.75 (t, J=6.1 Hz, 2 H), 6.82 (dd, J$_o$=1.5 Hz, J$_m$=4.5 Hz, 2 H), 7.11 (m, 2 H), 7.18-7.32 (complex signal, 7 H), 7.73 (m, 2 H), 7.80 (s, 1 H), 7.83 (m, 2 H), 8.25 (dd, J$_o$=1.5 Hz, J$_m$=4.5 Hz, 2 H).

Example 142

2-(2-Aminoethyl)-4,6-diphenyl-5-(4-pyridyl)pyrazolo[3,4-b]pyridine

Following a similar procedure to that described in example 90, but using 2-(2-phthalimidoethyl)-4,6-diphenyl-5-(4-pyridyl)pyrazolo[3,4-b]pyridine (obtained in example 141) instead of 4,6-bis(4-fluorophenyl)-2-(2-phthalimidoethyl)-5-(4-pyridyl)pyrazolo[3,4-b]pyridine, the title compound was obtained (yield: 51%).

$^1$H NMR (300 MHz, CDCl$_3$) δ (TMS): 1.50 (s, NH$_2$+H$_2$O), 3.37 (t, J=5.5 Hz, 2 H), 4.48 (t, J=5.4 Hz, 2 H), 6.83 (dd, J$_o$=1.5 Hz, J$_m$=4.5 Hz, 2 H), 7.17-7.34 (complex signal, 10 H), 7.86 (s, 1 H), 8.25 (dd, J$_o$=1.5 Hz, J$_m$=4.5 Hz, 2 H).

Example 143

2-Allyl-4,6-bis(4-fluorophenyl)-5-(4-pyridyl)pyrazolo[3,4-b]pyridine

Example 144

1-Allyl-4,6-bis(4fluorophenyl)-5-(4-pyridyl)pyrazolo[3,4-b]pyridine

Following a similar procedure to that described in examples 6 and 7, but using allyl bromide instead of iodoethane, the title compounds were obtained.

Example 143: yield: 33%; $^1$H NMR (300 MHz, CDCl$_3$) δ (TMS): 5.08 (d, J=6.3 Hz, 2 H), 5.40 (m, 2 H), 6.16 (m, 1 H), 6.82 (dd, J$_o$=1.5 Hz, J$_m$=4.5 Hz, 2 H), 6.89 (t, J=8.7 Hz, 2 H), 7.00 (t, J=8.6 Hz, 2 H), 7.13 (m, 2 H), 7.30 (m, 2 H), 7.78 (s, 1 H), 8.34 (dd, J$_o$=1.5 Hz, J$_m$=4.5 Hz, 2 H).

Example 144: yield: 10%; $^1$H NMR (300 MHz, CDCl$_3$) δ (TMS): 5.22-5.34 (complex signal, 4 H), 6.14 (m, 1 H), 6.81 (dd, J$_o$=1.5 Hz, J$_m$=4.5 Hz, 2 H), 6.93 (t, J=8.7 Hz, 2 H), 7.01 (t, J=8.6 Hz, 2 H), 7.14 (m, 2 H), 7.29 (m, 2 H), 7.87 (s, 1 H), 8.32 (dd, J$_o$=1.5 Hz, J$_m$=4.5 Hz, 2 H).

Example 145

1-[2-[4,6-Bis(4-fluorophenyl)-5-(4-pyridyl)pyrazolo[3,4-b]pyridin-2-yl]ethyl]piperidin-4-one Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 4-piperidone monohydrate hydrochloride instead of N-(tert-butoxycarbonyl)-N-(4-piperidyl)amine and adding triethylamine (3 equivalents), the desired product was obtained (yield: 18%).

$^1$H NMR (300 MHz, CDCl$_3$) δ (TMS): 2.41 (t, J=6.0 Hz, 4 H), 2.84 (t, J=6.0 Hz, 4 H), 3.20 (t, J=6.4 Hz, 2 H), 4.58 (t, J=6.4 Hz, 2 H), 6.83 (d, J=6.0 Hz, 2 H), 6.90 (t, J=8.7 Hz, 2 H), 7.00 (t, J=8.6 Hz, 2 H), 7.14 (m, 2 H), 7.30 (m, 2 H), 7.85 (s, 1 H), 8.32 (d, J=6.0 Hz, 2 H).

Example 146

3-Aminomethyl-6-(4-fluorophenyl)-5-(4-pyridyl)-1H-pyrazolo[3,4-b]pyridine

Following a similar procedure to that described in example 68, but using 6-(4-fluorophenyl)-5-(4-pyridyl)-1H-pyrazolo[3,4-b]pyridine-3-carbonitrile (obtained in example 132) instead of 4,6-bis(4-fluorophenyl)-5-(4-pyridyl)-1H-pyrazolo[3,4-b]pyridine-3-carbonitrile, the title compound was obtained (yield: 22%).

$^1$H NMR (300 MHz, CDCl$_3$+CD$_3$OD) δ (TMS): 4.24 (s, 2 H), 4.25 (broad s, NH+NH$_2$+CD$_3$OD), 6.95 (m, 2 H), 7.16 (m, 2 H), 7.29 (m, 2 H), 8.25 (broad s, 1 H), 8.38 (broad s, 2 H).

Example 147

3-Amino-6-(4-fluorophenyl)-4-methyl-5-(4-pyridyl)-1H-pyrazolo[3,4-b]pyridine

Following a similar procedure to that described in reference example 15 section c, but using 6-chloro-2-(4-fluorophenyl)-4-methyl-3,4'-bipyridine-5-carbonitrile (obtained in reference example 18) instead of 3-(1-benzylpiperidin-4-yl)-3-oxopropiononitrile, the title compound was obtained (yield: 27%).

$^1$H NMR (300 MHz, CDCl$_3$) δ (TMS): 1.56 (broad s, NH+NH$_2$+H$_2$O), 2.51 (s, 3 H), 6.80-7.20 (complex signal, 4 H), 7.22 (m, 2 H), 8.55 (d, J=8.0 Hz, 2 H).

Example 148

3-[N-[2-[4,6-Bis(4-fluorophenyl)-5-(4-pyridyl)pyrazolo[3,4-b]pyridin-2-yl]ethyl]amino]propan-1-ol Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 3-amino-1-propanol instead of N-(tert-butoxycarbonyl)-N-(4-piperidyl)amine, the desired compound was obtained (yield: 57%).

$^1$H NMR (300 MHz, CDCl$_3$) δ (TMS): 1.50-1.80 (complex signal, 2 H+NH+OH+H$_2$O), 2.91 (t, J=5.7 Hz, 2 H), 3.31 (t, J=5.4 Hz, 2 H), 3.77 (t, J=5.4 Hz, 2 H), 4.54 (t, J=5.4 Hz, 2 H), 6.82 (dd, J$_o$=1.5 Hz, J$_m$=4.5 Hz, 2 H), 6.90 (t, J=8.7 Hz, 2 H), 7.00 (t, J=8.7 Hz, 2 H), 7.15 (m, 2 H), 7.29 (m, 2 H), 7.82 (s, 1 H), 8.31 (dd, J$_o$=1.8 Hz, J$_m$=4.5 Hz, 2 H).

Example 149

N-Ethyl-[2-[4,6-bis(4-fluorophenyl)-5-(4-pyridyl)pyrazolo[3,4-b]pyridin-2-yl]ethyl]amine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 of section a) instead of 3-[4,6-bis(4-fluorophenyl)-5-(4-pyridyl)pyrazolo[3,4-b]pyridin-2-yl]propyl methanesulfonate and ethylamine instead of N-(tert-butoxycarbonyl)-N-(4-piperidyl)amine, the desired compound was obtained (yield: 58%).

$^1$H NMR (300 MHz, CDCl$_3$) δ (TMS): 1.09 (t, J=7.0 Hz, 3 H), 1.71 (broad s, NH+H$_2$O), 2.70 (c, J=7.1 Hz, 2 H), 3.29 (t, J=5.7 Hz, 2 H), 4.56 (t, J=5.7 Hz, 2 H), 6.82 (dd, J$_o$=1.5 Hz, J$_m$=4.5 Hz, 2 H), 6.90 (t, J=8.7 Hz, 2 H), 7.00 (t, J=8.7 Hz, 2 H), 7.14 (m, 2 H), 7.29 (m, 2 H), 7.84 (s, 1 H), 8.32 (dd, J$_o$=1.5 Hz, J$_m$=4.5 Hz, 2 H).

Example 150

2-[N-[2-[4,6-Bis(4-fluorophenyl)-5-(4-pyridyl)pyrazolo[3,4-b]pyridin-2-yl]ethyl]amino]ethanol Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 2-aminoethanol instead of N-(tert-butoxycarbonyl)-N-(4-piperidyl)amine, the desired compound was obtained (yield: 54%).

$^1$H NMR (300 MHz, CDCl$_3$) δ (TMS): 1.70 (broad s, NH+OH+H$_2$O), 2.82 (t, J=5.3 Hz, 2 H), 3.32 (t, J=5.6 Hz, 2 H), 3.62 (t, J=5.3 Hz, 2 H), 4.55 (t, J=5.6 Hz, 2 H), 6.83 (dd, J$_o$=1.5 Hz, J$_m$=4.5 Hz, 2 H), 6.90 (t, J=8.7 Hz, 2 H), 7.00 (t, J=8.6 Hz, 2 H), 7.14 (m, 2 H), 7.29 (m, 2 H), 7.83 (s, 1 H), 8.31 (dd, J$_o$=1.8 Hz, J$_m$=4.5 Hz, 2 H).

Example 151

N-[(2-Pyridyl)methyl]-[2-[4,6-bis(4-fluorophenyl)-5-(4-pyridyl)pyrazolo[3,4-b]pyridin-2-yl]ethyl]amine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and (2-pyridyl)methylamine instead of N-(tert-butoxycarbonyl)-N-(4-piperidyl)amine, the desired compound was obtained (yield: 52%).

$^1$H NMR (300 MHz, CDCl$_3$) δ (TMS): 1.62 (broad s, NH+H$_2$O), 3.33 (t, J=5.7 Hz, 2 H), 3.92 (s, 2 H), 4.58 (t, J=5.7 Hz, 2 H), 6.83 (dd, J$_o$=1.8 Hz; J$_m$=4.5 Hz, 2 H), 6.90 (t, J=8.7 Hz, 2 H), 6.99 (t, J=8.6 Hz, 2 H), 7.14 (m, 4 H), 7.29 (m, 2 H), 7.60 (m, 1 H), 7.86 (s, 1 H), 8.31 (dd, J$_o$=1.5 Hz, J$_m$=4.5 Hz, 2 H), 8.51 (m, 1 H).

Example 152

N-[(2-Thienyl)methyl]-[2-[4,6-bis(4-fluorophenyl)-5-(4-pyridyl)pyrazolo[3,4-b]pyridin-2-yl]ethyl]amine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl and (2-thienyl)methylamine instead of N-(tert-butoxycarbonyl)-N-(4-piperidyl)amine, the desired compound was obtained (yield: 25%).

$^1$H NMR (300 MHz, CDCl$_3$) δ (TMS): 1.55 (broad s, NH+H$_2$O) 3.32 (t, J=5.6 Hz, 2 H), 4.00 (s, 2 H), 4.54 (t, J=5.6 Hz, 2 H), 6.83 (dd, J$_o$=1.5 Hz, J$_m$=4.5 Hz, 2 H), 6.90 (t, J=8.7 Hz, 2 H), 6.91 (m, 1 H), 7.00 (t, J=8.6 Hz, 2 H), 7.16 (m, 3 H), 7.29 (m, 3 H), 7.86 (s, 1 H), 8.32 (dd, J$_o$=1.5 Hz, J$_m$=4.5 Hz, 2 H).

Example 153

1-[2-[4,6-Bis(4-fluorophenyl)-5-(4-pyridyl)pyrazolo[3,4-b]pyridin-2-yl]ethyl]piperidine-4-carboxamide Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and piperidine-4-carboxamide instead of N-(tert-butoxycarbonyl)-N-(4-piperidyl)amine, the desired compound was obtained (yield: 75%).

$^1$H NMR (300 MHz, CDCl$_3$) δ (TMS): 1.61-1.76 (complex signal, 5 H), 1.84 (m, 2 H), 2.91 (m, 2 H), 3.01 (t, J=6.3 Hz, 2 H), 4.52 (t, J=6.3 Hz, 2 H), 5.27 (broad s, NH), 5.41 (broad s, NH), 6.83 (dd, J$_o$=1.5 Hz, J$_m$=4.5 Hz, 2 H), 6.89 (t, J=8.7 Hz, 2 H), 7.02 (t, J=8.6 Hz, 2 H), 7.14 (m, 2 H), 7.30 (m, 2 H), 7.83 (s, 1 H), 8.32 (dd, J$_o$=1.4 Hz, J$_m$=4.6 Hz, 2 H).

Example 154

4,6-Bis(4-fluorophenyl)-2-[2-(pyrrolidin-1-yl)ethyl]-5-(4-pyridyl)pyrazolo[3,4-b]pyridine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and pyrrolidine instead of N-(tert-butoxycarbonyl)-N-(4-piperidyl)amine, the desired compound was obtained (yield: 75%).

$^1$H NMR (300 MHz, CDCl$_3$) δ (TMS): 1.77 (m, 4 H), 2.55 (m, 4 H), 3.17 (t, J=6.6 Hz, 2 H), 4.58 (t, J=6.6 Hz, 2 H), 6.82 (dd, J$_o$=1.5 Hz, J$_m$=4.5 Hz, 2 H), 6.89 (t, J=8.7 Hz, 2 H), 7.00 (t, J=8.7 Hz, 2 H), 7.14 (m, 2 H), 7.29 (m, 2 H), 7.84 (s, 1 H), 8.31 (dd, J$_o$=1.5 Hz, J$_m$=4.5 Hz, 2 H).

Example 155

(3R)-1-[2-[4,6-Bis(4-fluorophenyl)-5-(4-pyridyl)pyrazolo[3,4-b]pyridin-2-yl]ethyl]pyrrolidin-3-ol Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and (3R)-3-pyrrolidinol instead of N-(tert-butoxycarbonyl)-N-(4-piperidyl)amine, the desired compound was obtained (yield: 52%).

$^1$H NMR (300 MHz, CDCl$_3$) δ (TMS): 1.69 (broad s, 1H+OH+H$_2$O), 2.14 (m, 1 H), 2.40 (m, 1 H), 2.58 (m, 1 H), 2.69 (m, 1 H), 2.94 (m, 1 H), 3.20 (t, J=6.4 Hz, 2 H), 4.32 (m, 1 H), 4.57 (t, J=6.4 Hz, 2 H), 6.83 (dd, J$_o$=1.5 Hz, J$_m$=4.5 Hz, 2 H), 6.89 (t, J=8.7 Hz, 2 H), 7.00 (t, J=8.6 Hz, 2 H), 7.14 (m, 2 H), 7.29 (m, 2 H), 7.82 (s, 1 H), 8.32 (dd, J$_o$=1.5 Hz, J$_m$=4.5 Hz, 2 H).

Example 156

2-[N-[2-[4,6-Bis(4-fluorophenyl)-5-(4-pyridyl)pyrazolo[3,4-b]pyridin-2-yl]ethyl]-N-methylamino]ethanol Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 2-(methylamino)ethanol instead of N-(tert-butoxycarbonyl)-N-(4-piperidyl)amine, the desired compound was obtained (yield: 71%).

$^1$H NMR (300 MHz, CDCl$_3$) δ (TMS): 1.56 (broad s, OH+H$_2$O), 2.34 (s, 3 H), 2.60 (t, J=5.2 Hz, 2 H), 3.14 (t, J=6.0 Hz, 2 H), 3.53 (t, J=5.2 Hz, 2 H), 4.53 (t, J=6.0 Hz, 2 H), 6.83 (dd, J$_o$=1.8 Hz, J$_m$=4.5 Hz, 2 H), 6.89 (t, J=8.7 Hz, 2 H), 7.00 (t, J=8.6 Hz, 2 H), 7.14 (m, 2 H), 7.29 (m, 2 H), 7.81 (s, 1 H), 8.31 (dd, J$_o$=1.5 Hz, J$_m$=4.5 Hz, 2 H).

Example 157

4,6-Bis(4-fluorophenyl)-5-(4-pyridyl)-2-[2-(1,2,3,4-tetrahydroisoquinolin-2-yl)ethyl]pyrazolo[3,4-b]pyridine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 1,2,3,4-tetrahydroisoquinoline instead of N-(tert-butoxycarbonyl)-N-(4-piperidyl)amine, the desired compound was obtained (yield: 57%).

$^1$H NMR (300 MHz, CDCl$_3$) δ (TMS): 2.78-2.85 (complex signal, 4 H), 3.20 (t, J=6.3 Hz, 2 H), 3.72 (s, 2 H), 4.63 (t, J=6.3 Hz, 2 H), 6.81 (dd, J$_o$=1.5 Hz, J$_m$=4.5 Hz, 2 H), 6.86-

7.17 (complex signal, 10 H), 7.30 (m, 2 H), 7.86 (s, 1 H), 8.31 (dd, $J_o$=1.5 Hz, $J_m$=4.5 Hz, 2 H).

Example 158

4,6-Bis(4-fluorophenyl)-2-[2-(4-phenylpiperazin-1-yl)ethyl]-5-(4-pyridyl)pyrazolo[3,4-b]pyridine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 1-phenylpiperazine instead of N-(tert-butoxycarbonyl)-N-(4-piperidyl)amine, the desired compound was obtained (yield: 71%).

$^1$H NMR (300 MHz, CDCl$_3$) δ (TMS): 2.69 (m, 4 H), 3.10 (t, J=6.4 Hz, 2 H), 3.16 (m, 4 H), 4.59 (t, J=6.4 Hz, 2 H), 6.82 (dd, $J_o$=1.8 Hz, $J_m$=4.5 Hz, 2 H), 6.86-7.02 (complex signal, 9 H), 7.14 (m, 2 H), 7.29 (m, 2 H), 7.86 (s, 1 H), 8.32 (dd, $J_o$=1.5 Hz, $J_m$=4.5 Hz, 2 H).

Example 159

4,6-Bis(4-fluorophenyl)-2-[2-[4-(1-piperidyl)piperidin-1-yl]ethyl]-5-(4-pyridyl)pyrazolo[3,4-b]pyridine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 4-piperidinopiperidine instead of N-(tert-butoxycarbonyl)-N-(4-piperidyl)amine, the desired compound was obtained (yield: 51%).

$^1$H NMR (300 MHz, CDCl$_3$) δ (TMS): 1.40-1.60 (complex signal, 8 H), 1.78 (m, 2 H), 2.04-2.22 (complex signal, 3 H), 2.48 (m, 4 H), 2.96 (m, 4 H), 4.52 (t, J=6.4 Hz, 2 H), 6.82 (dd, $J_o$=1.5 Hz, $J_m$=4.5 Hz, 2 H), 6.89 (t, J=8.7 Hz, 2 H), 7.00 (t, J=8.6 Hz, 2 H), 7.13 (m, 2 H), 7.29 (m, 2 H), 7.85 (s, 1 H), 8.31 (dd, $J_o$=1.5 Hz, $J_m$=4.5 Hz, 2 H).

Example 160

3-[N-[2-[4,6-Bis(4-fluorophenyl)-5-(4-pyridyl)pyrazolo[3,4-b]pyridin-2-yl]ethyl]-N-methylamino]propiononitrile Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 3-(methylamino)propiononitrile instead of N-(tert-butoxycarbonyl)-N-(4-piperidyl)amine, the desired compound was obtained (yield: 50%).

$^1$H NMR (300 MHz, CDCl$_3$) δ (TMS): 2.35 (complex signal, 5 H), 2.71 (t, J=6.4 Hz, 4 H), 3.13 (t, J=5.9 Hz, 2 H), 4.50 (t, J=5.9 Hz, 2 H), 6.83 (dd, $J_o$=1.6 Hz, $J_m$=4.4 Hz, 2 H), 6.90 (t, J=8.7 Hz, 2 H), 6.99 (t, J=8.7 Hz, 2 H), 7.17 (m, 2 H), 7.31 (m, 2 H), 7.87 (s, 1 H), 8.32 (dd, $J_o$=1.5 Hz, $J_m$=4.5 Hz, 2 H).

Example 161

N-Methyl-[2-[4,6-bis(4-fluorophenyl)-5-(4-pyridyl)pyrazolo[3,4-b]pyridin-2-yl]ethyl]amine Following a similar procedure to that described in example 111, but using 2-[4,6-bis(4-fluorophenyl)-5-(4-pyridyl)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and methylamine instead of N-(tert-butoxycarbonyl)-N-(4-piperidyl)amine, the desired compound was obtained (yield: 51%).

$^1$H NMR (300 MHz, CDCl$_3$) δ (TMS): 1.61 (broad s, NH+H$_2$O), 3.25 (t, J=5.6 Hz, 2 H), 4.57 (t, J=5.6 Hz, 2 H), 6.82 (dd, $J_o$=1.5 Hz, $J_m$=4.5 Hz, 2 H), 6.90 (t, J=8.7 Hz, 2 H), 7.00 (t, J=8.6 Hz, 2 H), 7.14 (m, 2 H), 7.29 (m, 2 H), 7.84 (s, 1 H), 8.31 (dd, $J_o$=1.5 Hz, $J_m$=4.5 Hz, 2 H).

Example 162

2-[2-[4-(tert-Butoxycarbonyl)piperazin-1-yl]ethyl]-4,6-(4-fluorophenyl)-5-(4-pyridyl)pyrazolo[3,4-b]pyridine Following a similar procedure to that described in example 111, but using 2-[4,6-bis(4-fluorophenyl)-5-(4-pyridil)pyrazolo[3,4-b]pyridin-2-yl]ethyl methanesulfonate (obtained in example 116 section a) instead of 3-[4,6-bis(4-fluorophenyl)-5-(4-pyridyl)pyrazolo[3,4-b]pyridin-2-yl]propyl methanesulfonate and 1-(tert-butoxycarbonyl)piperazine instead of N-(tert-butoxycarbonyl)-N-(4-piperidyl)amine, the desired compound was obtained (yield: 63%).

$^1$H NMR (300 MHz, CDCl$_3$) δ (TMS): 1.45 (s, 9 H), 2.46 (m, 4 H), 3.05 (t, J=6.4 Hz, 2 H), 3.40 (m, 4 H), 4.54 (t, J=6.4 Hz, 2 H), 6.82 (dd, $J_o$=1.6 Hz, $J_m$=4.4 Hz, 2 H), 6.89 (t, J=8.7 Hz, 2 H), 7.00 (t, J=8.6 Hz, 2 H), 7.15 (m, 2 H), 7.30 (m, 2 H), 7.86 (s, 1 H), 8.33 (dd, $J_o$=1.5 Hz, $J_m$=4.5 Hz, 2 H).

Example 163

4,6-Bis(4-fluorophenyl)-2-[2-(piperazin-1-yl)ethyl]-5-(4-pyridyl)pyrazolo[3,4-b]pyridine Following a similar procedure to that described in example 36, but using 2-[2-[4-(tert-butoxycarbonyl)piperazin-1-yl]ethyl]-4,6-bis(4-fluorophenyl)-5-(4-pyridyl)pyrazolo[3,4-b]pyridine (obtained in example 162) instead of 2-[1-(tert-butoxycarbonyl)piperidin-4-yl]-4,6-bis(4-fluorophenyl)-5-(4-pyridyl)pyrazolo[3,4-b]pyridine, the title compound was obtained (yield: 62%).

$^1$H NMR (300 MHz, CDCl$_3$) δ (TMS): 1.56 (broad s, NH+H$_2$O), 2.45 (m, 4 H), 2.85 (m, 4 H), 3.00 (t, J=6.4 Hz, 2 H), 4.55 (t, J=6.4 Hz, 2 H), 6.82 (dd, $J_o$=1.6 Hz, $J_m$=4.4 Hz, 2 H), 6.89 (t, J=8.7 Hz, 2 H), 7.03 (t, J=8.7 Hz, 2 H), 7.14 (m, 2 H), 7.30 (m, 2 H), 7.86 (s, 1 H), 8.32 (dd, $J_o$=1.5 Hz, $J_m$=4.5 Hz, 2 H).

Example 164

4,6-Bis(4-fluorophenyl)-5-(4-pyridyl)-2-vinylpyrazolo[3,4-b]pyridine

A solution of 2-[4,6-bis(4-fluorophenyl)-5-(4-pyridyl)pyrazolo[3,4-b]pyridin-2-yl]ethyl methanesulfonate (0.15 g, 0.3 mmol, obtained in example 116 section a) and KOH (0.02 g, 0.3 mmol) in toluene (4 mL) was heated to 100° C. reflux overnight. Water and EtOAc were added and the phases were separated. The aqueous phase was saturated with NaCl (solid) and extracted with EtOAc. The combined organic phases were dried over Na$_2$SO$_4$ and concentrated to dryness. The crude product obtained was purified by chromatography on silica gel using hexane-EtOAc mixtures of increasing polarity as eluent, to afford 110 mg of the title compound (yield: 90%).

¹H NMR (300 MHz, CDCl₃) δ (TMS): 5.27 (dd, J$_{gem}$=1.8 Hz, J$_{vec}$=8.7 Hz, 1 H), 6.22 (dd, J$_{gem}$=1.4 Hz, J$_{vec}$=15.4 Hz, 1 H), 6.83 (dd, J$_o$=1.5 Hz, J$_m$=4.5 Hz, 2 H), 6.91 (t, J=8.7 Hz, 2 H), 7.01 (t, J=8.6 Hz, 2 H), 7.15 (m, 2 H), 7.17-7.34 (complex signal, 3 H), 7.90 (s, 1 H), 8.33 (dd, J$_o$=1.5 Hz, J$_m$=4.5 Hz, 2 H).

Example 165

2-[N-[2-[4,6-Bis-(4-fluorophenyl)-5-(4-pyridyl)pyrazolo[3,4-b]pyridin-2-yl]ethyl]-N-(2-hydroxyethyl)amino]ethanol Following a similar procedure to that described in example 111, but using 2-[4,6-bis-(4-fluorophenyl)-5-(4-pyridyl)pyrazolo[3,4-b]pyridin-2-yl]ethyl methanesulfonate (obtained in example 116 section a) instead of 3-[4,6-bis-(4-fluorophenyl)-5-(4-pyridyl)pyrazolo[3,4-b]pyridin-2-yl]propyl methanesulfonate and 2-(2-hydroxyethylamino)ethanol instead of N-(tert-butoxycarbonyl)-N-(4-piperidyl)amine, the desired compound was obtained (yield: 51%).

¹H NMR (300 MHz, CDCl₃) δ (TMS): 1.50 (broad s, 2 OH+H₂O), 2.73 (t, J=5.0 Hz, 4H), 3.21 (t, J=5.6 Hz, 2 H), 3.52 (t, J=5.0 Hz, 4 H), 4.54 (t, J=5.4 Hz, 2 H), 6.82 (dd, J$_o$=1.5 Hz, J$_m$=4.5 Hz, 2 H), 6.89 (t, J=8.7 Hz, 2 H), 6.99 (t, J=8.7 Hz, 2 H), 7.13 (m, 2 H), 7.29 (m, 2 H), 7.89 (s, 1 H), 8.32 (dd, J$_o$=1.8 Hz, J$_m$=4.5 Hz, 2 H).

Example 166

N-Cyclopropyl-[2-[4,6-bis(4-fluorophenyl)-5-(4-pyridyl)pyrazolo[3,4-b]pyridin-2-yl]ethyl]amine Following a similar procedure to that described in example 111, but using 2-[4,6-bis-(4-fluorophenyl)-5-(4-pyridyl)pyrazolo[3,4-b]pyridin-2-yl]ethyl methanesulfonate (obtained in example 116 section a) instead of 3-[4,6-bis-(4-fluorophenyl)-5-(4-pyridyl)pyrazolo[3,4-b]pyridin-2-yl]propyl methanesulfonate and cyclopropylamine instead of N-(tert-butoxycarbonyl)-N-(4-piperidyl)amine, the desired compound was obtained (yield: 47%).

¹H NMR (300 MHz, CDCl₃) δ (TMS): 0.30 (m, 2 H), 0.45 (m, 2 H), 1.60 (broad s, NH+H₂O), 2.20 (m, 1 H), 3.36 (t, J=5.7 Hz, 2 H), 4.55 (t, J=5.7 Hz, 2 H), 6.82 (dd, J$_o$=1.5 Hz, J$_m$=4.5 Hz, 2 H), 6.90 (t, J=8.7 Hz, 2 H), 7.00 (t, J=8.6 Hz, 2 H), 7.14 (m, 2 H), 7.30 (m, 2 H), 7.82 (s, 1 H), 8.32 (dd, J$_o$=1.5 Hz, J$_m$=4.5 Hz, 2 H).

Example 167

N-[2-[4,6-Bis(4-fluorophenyl)-5-(4-pyridyl)pyrazolo[3,4-b]pyridin-2-yl]ethyl]acetamide Following a similar procedure to that described in reference example 1 section a, but using acetyl chloride instead of 4-fluorobenzoyl chloride and 2-(2-aminoethyl)-4,6-bis(4-fluorophenyl)-5-(4-pyridyl)pyrazolo[3,4-b]pyridine (obtained in example 90) instead of N,O-dimethylhydroxylamine, the desired compound was obtained (yield: 48%).

¹H NMR (300 MHz, CDCl₃) δ (TMS): 1.98 (s, 3 H), 3.95 (m, 2 H), 4.58 (t, J=5.4 Hz, 2 H), 6.47 (m, NH), 6.83 (d, J=9.0 Hz, 2 H), 6.91 (t, J=8.7 Hz, 2 H), 7.01 (t, J=8.6 Hz, 2 H), 7.14 (m, 2 H), 7.28 (m, 2 H), 7.82 (s, 1 H), 8.33 (d, J=9.0 Hz, 2 H).

Example 168

N-[2-[4,6-Bis(4-fluorophenyl)-5-(4-pyridyl)pyrazolo[3,4-b]pyridin-2-yl]ethyl]-N'-isopropylurea To a solution of 2-(2-aminoethyl)-4,6-bis(4-fluorophenyl)-5-(4-pyridyl)pyrazolo[3,4-b]pyridine (0.06 g, 0.15 mmol, obtained in example 90) in DMF (1 mL), isopropylisocyanate (0.02 g, 0.18 mmol) was added under argon atmosphere. This was stirred at room temperature for 2 days. The solvent was concentrated again and diethyl ether was added to the residue obtained. The solvent was concentrated, to afford 38 mg of title compound in solid form (yield: 50%).

¹H NMR (300 MHz, CDCl₃) δ (TMS): 1.05 (d, J=6.3 Hz, 6 H), 3.84 (m, 3 H), 4.22 (m, NH), 4.58 (t, J=5.4 Hz, 2 H), 5.30 (m, NH), 6.82 (dd, J$_o$=1.4 Hz, J$_m$=4.6 Hz, 2 H), 6.91 (t, J=8.7 Hz, 2 H), 7.00 (t, J=8.6 Hz, 2 H), 7.13 (m, 2 H), 7.28 (m, 2 H), 7.84 (s, 1 H), 8.32 (dd, J$_o$=1.5 Hz, J$_m$=4.5 Hz, 2 H).

Example 169

N-[2-[4,6-Bis(4-fluorophenyl)-5-(4-pyridyl)pyrazolo[3,4-b]pyridin-2-yl]ethyl]methanesulfonamide To a solution of 2-(2-aminoethyl)-4,6-bis(4-fluorophenyl)-5-(4-pyridyl)pyrazolo[3,4-b]pyridine (0.06 g, 0.15 mmol, obtained in example 90) and DMAP (0.001 g, 0.0058 mmol) in pyridine (0.6 mL), methanesulfonyl chloride (0.017 mL, 0.22 mmol) was added under argon atmosphere and cooled with an ice bath (0.017 mL, 0.22 mmol). This was stirred overnight at room temperature. The solvent was concentrated. The residue was dissolved in CHCl₃ and saturated NaHCO₃ was added. The phases were separated. The organic phase was dried over Na₂SO₄ and concentrated. The crude product obtained was purified by chromatography on silica gel using EtOAc as solvent, and 70 mg of the title compound was obtained (yield: 95%).

¹H NMR (300 MHz, CDCl₃) δ (TMS): 2.99 (s, 3 H), 3.86 (m, 2 H), 4.64 (t, J=5.3 Hz, 2 H), 5.33 (m, NH), 6.83 (dd, J=1.5 Hz, J$_m$=4.5 Hz, 2 H), 6.91 (t, J=8.7 Hz, 2 H), 7.01 (t, J=8.7 Hz, 2 H), 7.14 (m, 2 H), 7.29 (m, 2 H), 7.88 (s, 1 H), 8.33 (dd, J$_o$=1.5 Hz, J$_m$=4.5 Hz, 2 H).

EXAMPLES 170-178

Following a similar procedure to that described in example 72, but starting from the appropriate compounds in each case, the compounds in the following table were obtained:

| | | | | LC-MS | |
| --- | --- | --- | --- | --- | --- |
| Example | Compound name | Starting compounds | Method | t$_R$ (min) | m/z [M + H]⁺ |
| 170 | 6-(4-Fluorophenyl)-4-(4-piperidyl)-5-(4-pyridyl)-1H-pyrazolo[3,4-b]pyridine | Reference example 1, 3-amino-2H-pyrazole and 1-(tert-butoxycarbonyl)-piperidine-4-carbaldehyde | 1 | 3.34 | 374.1 |

-continued

| Example | Compound name | Starting compounds | LC-MS Method | $t_R$ (min) | m/z [M + H]$^+$ |
|---|---|---|---|---|---|
| 171 | 6-(4-Fluorophenyl)-4-(2-furyl)-5-(4-pyridyl)-1H-pyrazolo[3,4-b]pyridine | Reference example 1, 3-amino-2H-pyrazole and furan-2-carbaldehyde | 1 | 5.72 | 357.1 |
| 172 | 6-(4-Fluorophenyl)-4-(1H-imidazol-4-yl)-5-(4-pyridyl)-1H-pyrazolo[3,4-b]pyridine | Reference example 1, 3-amino-2H-pyrazole and 2H-pyrazole-3-carbaldehyde | 1 | 3.25 | 357.1 |
| 173 | 4-(5-Bromothien-2-yl)-6-(4-fluorophenyl)-5-(4-pyridyl)-1H-pyrazolo[3,4-b]pyridine | Reference example 1, 3-amino-2H-pyrazole and 5-bromothiophene-2-carbaldehyde | 1 | 7.46 | 450.9 452.9 |
| 174 | 4,6-Bis(4-fluorophenyl)-5-(2-methylsulfanylpyrimidin-4-yl)-1H-pyrazolo[3,4-b]pyridine | Reference example 19, 3-amino-2H-pyrazole and 4-fluorobenzaldehyde | 1 | 9.11 | 432.2 |
| 175 | 5-(2-Chloropyridin-4-yl)-4,6-bis(4-fluorophenyl)-1H-pyrazolo[3,4-b]pyridine | Reference example 23, 3-amino-2H-pyrazole and 4-fluorobenzaldehyde | 1 | 8.99 | 419.0 421.0 |
| 176 | 6-(4-Fluorophenyl)-4-(2-phenylethyl)-5-(4-pyridyl)-1H-pyrazolo[3,4-b]pyridine | Reference example 1, 3-amino-2H-pyrazole and 3-phenylpropionaldehyde | 1 | 6.52 | 395.0 |
| 177 | 4-(6-Chloropyridin-3-yl)-6-(4-fluorophenyl)-5-(4-pyridyl)-1H-pyrazolo[3,4-b]pyridine | Reference example 1, 6-chloropyridine-3-carbaldehyde and amino-2H-pyrazole | 1 | 5.50 | 402.0 404.0 |
| 178 | 4-(3,4-Dichlorophenyl)-1-ethyl-6-(4-fluorophenyl)-5-(4-pyridyl)pyrazolo[3,4-b]pyridine | Reference example 1, 3,4-dichlorobenzaldehyde and 3-amino-2-ethylpyrazole | 1 | 10.56 | 462.9 464.9 |

Example 179

6-(4-Flurophenyl)-4-(1-methylpiperidin-4-yl)-5-(4-pyridyl)-1H-pyrazolo[3,4-b]pyridine To a suspension of 6-(4-fluorophenyl)-4-(4-piperidyl)-5-(4-pyridyl)-1H-pyrazolo[3,4-b]pyridine (0.24 g, 0.6 mmol, obtained in example 170) in formic acid (0.64 mL), 35-40% aqueous formaldehyde (0.96 mL) was added. It was heated to 70-80° C. for 24 h. It was allowed to cool and 1 N NaOH was added. It was extracted with CHCl$_3$ and the combined organic phases were dried over Na$_2$SO$_4$ and concentrated to dryness. The crude product obtained was purified by chromatography on silica gel using CHCl$_3$—MeOH—NH$_3$ mixtures of increasing polarity as eluent, to afford 47 mg of the desired compound (yield: 19%).

LC-MS (method 1): $t_R$=3.28 min; m/z=388.1 [M+H]$^+$.

Example 180

3-Amino-6-(4-fluorophenyl)-5-(2-methylsulfanylpyrimidin-4-yl)-1H-pyrazolo[3,4-b]pyridine Following a similar procedure to that described in reference example 15 section c, but using 2-chloro-6-(4-fluorophenyl)-5-(2-methylsulfanylpyrimidin-4-yl)pyridine-3-carbonitrile (obtained in reference example 22) instead of 3-(1-benzylpiperidin-4-yl)-3-oxopropiononitrile, the title compound was obtained.

LC-MS (method 1): $t_R$=6.70 min; m/z=353.0 [M+H]$^+$.

Example 181

6-(4-Fluorophenyl)-5-(2-methylsulfanylpyrimidin-4-yl)-1H-pyrazolo[3,4-b]pyridine To a solution of 3-amino-6-(4-fluorophenyl)-5-(2-methylsulfanylpyrimidin-4-yl)-1H-pyrazolo[3,4-b]pyridine (10.00 g, 28.4 mmol, obtained in example 180) in AcOH (52 mL), water (22 mL) and HCl conc. (5.7 mL), cooled to 0° C., a solution of NaNO$_2$ (2.30 g, 33.4 mmol) in water (7.5 mL) was added dropwise. It was stirred for 30 min at 0° C., and H$_3$PO$_2$ (50% aqueous solution, 56.8 mL) was added slowly. It was stirred at 0° C. for 6 h. It was allowed to cool to room temperature, basified at 0° C. by slow addition of 6 N NaOH hasta pH=8 and was extracted with EtOAc. The combined organic phases were dried over Na$_2$SO$_4$ and concentrated to dryness. The crude product obtained was purified by chromatography on silica gel using hexane-EtOAc mixtures of increasing polarity as eluent, to afford 4.00 g of the title compound (yield: 42%)

LC-MS (method 1): $t_R$=7.80 min; m/z=338.0 [M+H]$^+$.

EXAMPLES 182-193

Following a similar procedure to that described in examples 6 and 7, but starting from the appropriate compounds in each case, the compounds in the following table were obtained:

| Example | Compound name | Starting compounds | Method | LC-MS $t_R$ (min) | m/z $[M + H]^+$ |
|---|---|---|---|---|---|
| 182 | 4,6-Diphenyl-5-(4-pyridyl)-2-[2-(tetrahydropyran-2-yloxy)ethyl]-pyrazolo[3,4-b]pyridine | Example 2 and 2-(2-bromoethoxy)tetrahydropyran | 1 | 6.70 | 477.1 |
| 183 | 6-(4-Fluorophenyl)-4-(2-furyl)-2-methyl-5-(4-pyridyl)pyrazolo[3,4-b]pyridine | Example 171 and iodomethane | 1 | 5.32 | 371.1 |
| 184 | 6-(4-Fluorophenyl)-2-methyl-4-(1-methyl-1H-imidazol-4-yl)-5-(4-pyridyl)pyrazolo[3,4-b]pyridine | Example 172 and iodomethane (2 equivalents) | 1 | 3.66 | 385.2 |
| 185 | 6-(4-Fluorophenyl)-5-(2-methylsulfanylpyrimidin-4-yl)-2-[2-(tetrahydropyran-2-yloxy)ethyl]-pyrazolo[3,4-b]pyridine | Example 181 and 2-(2-bromoethoxy)-tetrahydropyran | 1 | 8.79 | 466.1 |
| 186 | 6-(4-Fluorophenyl)-5-(2-methylsulfanylpyrimidin-4-yl)-2-[3-(tetrahydropyran-2-yloxy)propyl]-pyrazolo[3,4-b]pyridine | Example 181 and 2-(3-bromopropoxy)-tetrahydropyran | 1 | 9.11 | 480.2 |
| 187 | 4,6-Bis(4-fluorophenyl)-5-(2-methylsulfanylpyrimidin-4-yl)2-[3-(tetrahydropyran-2-yloxy)propyl]-pyrazolo[3,4-b]pyridine | Example 174 and 2-(3-bromopropoxy)-tetrahydropyran | 1 | 10.26 | 574.2 |
| 188 | 4-(5-Bromothien-2-yl)-6-(4-fluoro-phenyl)-2-methyl-5-(4-pyridyl)-1H-pyrazolo[3,4-b]pyridine | Example 173 and iodomethane | 1 | 6.94 | 464.9 466.9 |
| 189 | 6-(4-Fluorophenyl)-2-methyl-5-(2-methylsulfanylpyrimidin-4-yl)pyrazolo[3,4-b]pyridine | Example 181 and iodomethane | 1 | 7.29 | 352.0 |
| 190 | 5-(2-Chloropyridin-4-yl)-4,6-bis(4-fluorophenyl)-2-methylpyrazolo-[3,4-b]pyridine | Example 175 and iodomethane | 1 | 8.55 | 433.0 435.0 |
| 191 | 6-(4-Fluorophenyl)-4-(2-phenyl-ethyl)-5-(4-pyridyl)-2-[3-(tetrahydropyran-2-yloxy)propyl]-pyrazolo[3,4-b]pyridine | Example 176 and 2-(3-bromopropoxy)-tetrahydropyran | 1 | 7.74 | 537.0 |
| 192 | 4-(6-Chloropyridin-3-yl)-6-(4-fluorophenyl)-5-(4-pyridyl)-2-[3-(tetrahydropyran-2-yloxy)propyl]-pyrazolo[3,4-b]pyridine | Example 177 and 2-(3-bromopropoxy)-tetrahydropyran | 1 | 9.05 | 544.2 546.2 |
| 193 | 4-(6-Chloropyridin-3-yl)-6-(4-fluorophenyl)-2-methyl-5-(4-pyridyl)pyrazolo[3,4-b]pyridine | Example 177 and iodomethane | 1 | 5.34 | 416.1 418.1 |

Example 194

5-(2-Methylsulfanylpyrimidin-4-yl)-2-[3-(tetrahydropyran-2-yloxy)propyl]-6-(3-trifluoromethylphenyl)pyrazolo[3,4-b]pyridine Following a similar procedure to that described in examples 6 and 7, but starting from 5-[2-(methylsulfanyl)pyrimidin-4-yl]-6-[3-(trifluoromethyl)phenyl]-1H-pyrazolo[3,4-b]pyridine (obtained in example 126) and 2-(3-bromopropoxy)tetrahydropyran, the title compound was obtained.

$^1$H NMR (300 MHz, CDCl$_3$) δ (TMS): 1.50-1.90 (m, 4 H), 2.40 (complex signal, 5 H), 3.37-3.50 (m, 4 H), 3.85 (m, 2 H), 4.53 (m, 1 H), 4.65 (m, 2 H), 6.68 (d, J=5.1 Hz, 1 H), 7.40 (t, J=7.8 Hz, 1 H), 7.52 (d, J=7.6 Hz, 1 H), 7.61 (d, J=7.5 Hz, 1 H), 7.93 (s, 1 H), 8.13 (s, 1 H), 8.32 (d, J=5.1 Hz, 1 H), 8.49 (s, 1 H).

Example 195

6-(4-Fluorophenyl)-2-methyl-5-(4-pyridyl)-4-[5-(3-pyridyl)thien-2-yl]pyrazolo[3,4-b]pyridine A suspension of 4-(5-bromothien-2-yl)-6-(4-fluorophenyl)-2-methyl-5-(4-pyridyl)-1H-pyrazolo[3,4-b]pyridine (0.10 g, 0.2 mmol, obtained in example 188), 3-pyridylboronic acid (0.04 g, 0.3 mmol), K$_2$CO$_3$ (0.06 g, 0.4 mmol), Pd(PPh$_3$)$_4$ (0.017 g, 0.01 mmol), 1,2-dimethoxyethane (1.31 mL) and water (0.04 mL) was heated at 80° C. under argon atmosphere overnight. It was allowed to cool and diluted with CHCl$_3$ and water. The combined organic phases were dried over Na$_2$SO$_4$ and concentrated to dryness. The crude product obtained was purified by chromtography on silica gel using hexane-EtOAc mixtures of increasing polarity as eluent, to afford 35 mg of the desired compound (yield: 50%).

LC-MS (method 1): $t_R$=5.42 min; m/z=464.0 [M+H]$^+$.

EXAMPLES 196-202

Following a similar procedure to that described in example 91 but using the adequate starting compounds in each case, the compounds in the following table were obtained:

| Example | Compound name | Starting compound | Method | LC-MS $t_R$ (min) | m/z $[M + H]^+$ |
|---|---|---|---|---|---|
| 196 | 2-[4,6-Diphenyl-5-(4-pyridyl)pyrazolo-[3,4-b]pyridin-2-yl]ethanol | Example 182 | 1 | 4.67 | 393.0 |
| 197 | 3-[5-(2-Methylsulfanylpyrimidin-4-yl)-6-(3-trifluoromethylphenyl)pyrazolo-[3,4-b]pyridin-2-yl]propan-1-ol | Example 194 | 1 | 7.67 | 446.0 |
| 198 | 2-[6-(4-Fluorophenyl)-5-(2-methyl-sulfanylpyrimidin-4-yl)pyrazolo[3,4-b]pyridin-2-yl]ethanol | Example 185 | 1 | 6.58 | 382.0 |
| 199 | 3-[6-(4-Fluorophenyl)-5-(2-methyl-sulfanylpyrimidin-4-yl)pyrazolo[3,4-b]pyridin-2-yl]propan-1-ol | Example 186 | 1 | 6.79 | 396.1 |
| 200 | 3-[4,6-Bis(4-fluorophenyl)-5-(2-methyl-sulfanylpyrimidin-4-yl)pyrazolo[3,4-b]pyridin-2-yl]propan-1-ol | Example 187 | 1 | 8.10 | 490.2 |
| 201 | 3-[6-(4-Fluorophenyl)-4-(2-phenylethyl)-5-(4-pyridyl)pyrazolo[3,4-b]pyridin-2-yl]propan-1-ol | Example 191 | 1 | 5.80 | 453.2 |
| 202 | 3-[4-(6-Chloropyridin-3-yl)-6-(4-fluorophenyl)-5-(4-pyridyl)pyrazolo-[3,4-b]pyridin-2-yl]propan-1-ol | Example 192 | 1 | 5.88 | 460.2 462.2 |

EXAMPLES 203-207

Following a similar procedure to that described in example 56 but using the adequate starting compounds in each case, the compounds in the following table were obtained:

| Example | Compound name | Starting compound | Method | LC-MS $t_R$ (min) | m/z $[M + H]^+$ |
|---|---|---|---|---|---|
| 203 | 6-(4-Fluorophenyl)-2-methyl-5-(2-methylsulfonylpyrimidin-4-yl)pyrazolo[3,4-b]pyridine | Example 189 | 1 | 5.76 | 384.0 |
| 204 | 3-[5-(2-Methylsulfonylpyrimidin-4-yl)-6-(3-trifluoromethylphenyl)pyrazolo-[3,4-b]pyridin-2-yl]propan-1-ol | Example 197 | 1 | 6.39 | 478.0 |
| 205 | 2-[6-(4-Fluorophenyl)-5-(2-methyl-sulfonylpyrimidin-4-yl)pyrazolo[3,4-b]pyridin-2-yl]ethanol | Example 198 | 1 | 5.28 | 414.0 |
| 206 | 3-[6-(4-Fluorophenyl)-5-(2-methyl-sulfonylpyrimidin-4-yl)pyrazolo[3,4-b]pyridin-2-yl]propan-1-ol | Example 199 | 1 | 5.46 | 428.0 |
| 207 | 3-[4,6-Bis(4-fluorophenyl)-5-(2-methyl-sulfonylpyrimidin-4-yl)pyrazolo[3,4-b]pyridin-2-yl]propan-1-ol | Example 200 | 1 | 6.76 | 522.2 |

Example 208

N-Cyclopropylmethyl-[4-[6-[3-(trifluoromethyl)phenyl]-1H-pyrazolo[3,4-b]pyridin-5-yl]pyrimidin-2-yl]amine A solution of 5-[2-(methylsulfonyl)pyrimidin-4-yl]-6-[3-(trifluoromethyl)phenyl]-1H-pyrazolo[3,4-b]pyridine (90 mg, 0.2 mmol, obtained in example 127) and (cyclopropylmethyl)amine (75 mg, 1.0 mmol) in THF (2 mL) was heated in a closed vessel at 60° C. overnight. It was allowed to cool and concentrated. The crude product obtained was purified by chromatography on silica gel using hexane-EtOAc mixtures of increasing polarity as eluent, to afford 57 mg of the desired compound (yield: 67%).

LC-MS (method 1): $t_R$=8.12 min; m/z=411.0 [M+H]$^+$.

Following a similar procedure to that described in example 208 but using the adequate starting compounds in each case, the compounds in the following table were obtained:

| Example | Compound name | Starting compounds | LC-MS Method | $t_R$ (min) | m/z [M + H]⁺ |
|---|---|---|---|---|---|
| 209 | (1S)-3-[5-[2-(1-Phenylethylamino)-pyrimidin-4-yl]-6-(3-trifluoromethylphenyl)pyrazolo[3,4-b]pyridin-2-yl]propan-1-ol | Example 204 and (1S)-1-phenylethylamine | 1 | 9.11 | 519.1 |
| 210 | N-Cyclopropylmethyl-[4-[6-(4-fluorophenyl)-2-methylpyrazolo[3,4-b]pyridin-5-yl]pyrimidin-2-yl]amine | Example 203 and (cyclopropylmethyl)amine | 1 | 6.43 | 375.1 |
| 211 | 2-[5-[2-[(Cyclopropylmethyl)-amino]pyrimidin-4-yl]-6-(4-fluorophenyl)pyrazolo[3,4-b]pyridin-2-yl]ethanol | Example 205 and (cyclopropylmethyl)amine | 1 | 5.85 | 405.1 |
| 212 | 3-[5-[2-[(Cyclopropylmethyl)-amino]pyrimidin-4-yl]-6-(4-fluorophenyl)pyrazolo[3,4-b]pyridin-2-yl]propan-1-ol | Example 206 and (cyclopropylmethyl)amine | 1 | 6.06 | 419.1 |
| 213 | 3-[5-[2-[(Cyclopropylmethyl)amino]-pyrimidin-4-yl]-4,6-bis(4-fluorophenyl)pyrazolo[3,4-b]pyridin-2-yl]propan-1-ol | Example 207 and (cyclopropylmethyl)amine | 1 | 7.63 | 513.3 |

Example 214

4-[4-[4,6-Bis(4-fluorophenyl)-2-methylpyrazolo[3,4-b]pyridin-5-yl]pyridin-2-ylamino]benzenesulfonamide A mixture of 5-(2-chloropyridin-4-yl)-4,6-bis(4-fluorophenyl)-2-methylpyrazolo[3,4-b]pyridine (100 mg, 0.23 mmol, obtained in example 190) and 4-aminobenzenesulfonamide (46 mg, 0.27 mmol) was heated at 190° C. overnight. It was allowed to cool and the crude product obtained was purified by chromatography on silica gel using EtOAc as eluent, to afford 23 mg of the desired compound (yield: 17%).
LC-MS (method 1): $t_R$=6.91 min; m/z=569.0 [M+H]⁺.

EXAMPLES 215-230

Following a similar procedure to that described in example 72 but using the adequate starting compounds in each case, the compounds in the following tables were obtained:

| Example | Compound name | Starting compounds | LC-MS Method | $t_R$ (min) | m/z [M + H]⁺ |
|---|---|---|---|---|---|
| 215 | 4,6-Bis(4-fluorophenyl)-5-(4-pyridyl)pyrazolo-[3,4-b]pyridin-3-ol | Reference example 1, 5-amino-1H-pirazol-3-ol and 4-fluorobenzaldehyde | 1 | 5.02 | 401.1 |
| 216 | 6-(4-Fluorophenyl)-4-(3H-imidazol-4-yl)-5-(4-pyridyl)-1H-pyrazolo[3,4-b]pyridine | Reference example 1, 3-amino-2H-pyrazole and 3H-imidazol-4-carbaldehyde | 1 | 3.23 | 357.1 |
| 217 | 6-(4-Fluorophenyl)-4-(1H-pyrazol-3-yl)-5-(4-pyridyl)-1H-pyrazolo[3,4-b]pyridine | Reference example 1, 3-amino-2H-pyrazole and 2H-pyrazole-3-carbaldehyde | 1 | 4.24 | 357.1 |
| 218 | 3-[6-(4-Fluorophenyl)-5-(4-pyridyl)-1H-pyrazolo-[3,4-b]pyridin-4-yl]phenol | Reference example 1, 3-amino-2H-pyrazole and 3-hydroxybenzaldehyde | 1 | 4.99 | 383.1 |
| 219 | 4-Cyclopropyl-6-(4-fluorophenyl)-5-(4-pyridyl)-1H-pyrazolo[3,4-b]pyridine | Reference example 1, 3-amino-2H-pyrazole and cyclopropanecarbaldehyde | 1 | 4.99 | 331.1 |
| 220 | 6-(4-Fluorophenyl)-4-(5-methylfuran-2-yl)-5-(4-pyridyl)-1H-pyrazolo[3,4-b]pyridine | Reference example 1, 3-amino-2H-pyrazole and 5-methylfuran-2-carbaldehyde | 1 | 8.45 | 445 |
| 221 | 4-(5-Bromofuran-2-yl)-6-(4-fluorophenyl)-5-(4-pyridyl)-1H-pyrazolo[3,4-b]pyridine | Reference example 1, 3-amino-2H-pyrazole and 5-methylfuran-2-carbaldehyde | 1 | 7.02 | 435.0 437.0 |

| Example | Compound name | Starting compounds | Method | $t_R$ (min) | m/z [M + H]$^+$ |
|---|---|---|---|---|---|
| 222 | 4-(4-Benzyloxyphenyl)-6-(4-fluorophenyl)-2-methyl-5-pyrimidin-4-yl-1H-pyrazolo[3,4-b]pyridine | Reference example 30, 3-amino-2H-pyrazole and 4-benzyloxybenzaldehyde | 1 | 9.05 | 474.1 |
| 223 | 4-(4-Benzyloxyphenyl)-6-(4-fluorophenyl)-5-(2-methylsulfanylpyrimidin-4-yl)-1H-pyrazolo[3,4-b]pyridine | Reference example 19, 3-amino-2H-pyrazole and 4-benzyloxybenzaldehyde | 1 | 10.52 | 520.1 |
| 224 | 6-(4-Fluorophenyl)-4-propyl-5-(4-pyridyl)-1H-pyrazolo[3,4-b]pyridine | Reference example 1, 3-amino-2H-pyrazole and butyraldehyde | 1 | 5.42 | 333.0 |
| 225 | 4-(3-Benzyloxyphenyl)-6-(4-fluorophenyl)-5-(4-pyridyl)-1H-pyrazolo[3,4-b]pyridine | Reference example 1, 3-amino-2H-pyrazole and 3-benzyloxybenzaldehyde | 1 | 8.00 | 473.2 |
| 226 | 5-(2-Chloropyridin-4-yl)-6-(4-fluorophenyl)-1H-pyrazolo[3,4-b]pyridine | Reference example 23, 3-amino-2H-pyrazole and paraformaldehyde | 1 | 7.73 | 325.2 327.2 |
| 227 | 4-[6-(4-Fluorophenyl)-5-(4-pyridyl)-1H-pyrazolo[3,4-b]pyridin-4-yl]butan-1-ol | Reference example 1, 3-amino-2H-pyrazole and 5-hydroxypentanal | 1 | 4.23 | 363.2 |
| 228 | 4-Benzyl-6-(4-fluorophenyl)-5-(4-pyridyl)-1H-pyrazolo[3,4-b]pyridine | Reference example 1, 3-amino-2H-pyrazole and phenylacetaldehyde | 1 | 6.37 | 381.2 |

| Example | Compound name | Starting compounds | $^1$H NMR(300MHz, CDCl$_3$) δ (TMS) |
|---|---|---|---|
| 229 | 4-(4-Benzyloxyphenyl)-6-(4-fluorophenyl)-2-methyl-5-(4-pyridyl)-1H-pyrazolo[3,4-b]pyridine | Reference example 1, 3-amino-2H-pyrazole and 4-benzyloxybenzaldehyde | 5.06(s, 2H), 6.85(dd, J$_o$=1.5Hz, J$_m$=4.5Hz, 2H), 6.91(m, 4H), 6.95(m, 2H), 7.23-7.40(m, 7H), 8.01(s, 1H), 8.35(dd, J$_o$=1.5Hz, J$_m$=4.5Hz, 2H), 10.62(broad s, 1H, NH). |
| 230 | 4,6-Bis(4-fluorophenyl)-5-pyrimidin-4-yl-1H-pyrazolo[3,4-b]pyridine | Reference example 30, 3-amino-2H-pyrazole and 4-fluorobenzaldehyde | 6.92-7.08(complex signal, 5H), 7.23(m, 2H), 7.32(m, 2H), 7.99(s, 1H), 8.45(d, J=5.1Hz, 1H), 9.03(s, 1H), 11.40(broad s, 1H, NH). |

Example 231

[(2S)-2-[4,6-Bis(4-fluorophenyl)-5-(4-pyridyl)pyrazolo[3,4-b]pyridin-2-yl]ethyl]pyrrolidine-2-carboxamide a) [(2S)-2-[4,6-Bis(4-fluorophenyl)-5-(4-pyridyl)pyrazolo[3,4-b]pyridin-2-yl]ethyl]-1-(benzyloxycarbonyl)pyrrolidine-2-carboxamide Following a similar procedure to that described in example 48, but starting from 2-(2-aminoethyl)-4,6-bis(4-fluorophenyl)-5-(4-pyridyl)pyrazolo[3,4-b]pyridine (obtained in example 90) and (2S)-1-(benzyloxycarbonyl)pyrrolidine-2-carboxylic acid, the desired compound was obtained.

LC-MS (method 1): $t_R$=7.13 min; m/z=659.3 [M+H]$^+$.

b) Title Compound

Following a similar procedure to that described in example 269, but starting from [2-[4,6-bis(4-fluorophenyl)-5-(4-pyridyl)pyrazolo[3,4-b]pyridin-2-yl]ethyl]-1-(benzyloxycarbonyl)pyrrolidine-2-carboxamide (obtained in section a), the title compound was obtained.

LC-MS (method 1): $t_R$=4.35 min; m/z=525.2 [M+H]$^+$.

Example 232

2-[2-(4,6-Diphenyl-5-(4-pyridyl)pyrazolo[3,4-b]pyridin-2-yl)ethylamino]ethanol a) 2-[4,6-Diphenyl-5-(4-pyridyl)pyrazolo[3,4-b]pyridin-2-yl]ethyl methanesulfonate Following a similar procedure to that described in example 12 section b, but starting from 2-[4,6-diphenyl-5-(4-pyridyl)pyrazolo[3,4-b]pyridin-2-yl]ethanol (obtained in example 196), the desired compound was obtained.

$^1$H NMR (300 MHz, CDCl$_3$) δ (TMS): 2.94 (s, 3 H), 4.76 (m, 2 H), 4.85 (m, 2 H), 6.88 (d, J$_o$=1.5 Hz, J$_m$=4.5 Hz, 2 H), 7.15-7.90 (complex signal, 10 H), 8.27 (s, 1H), 8.28 (dd, J$_o$=1.5 Hz, J$_m$=4.5 Hz, 2 H).

b) Title Compound

Following a similar procedure to that described in example 111, but starting from 2-[4,6-diphenyl-5-(4-pyridyl)pyrazolo[3,4-b]pyridin-2-yl]ethyl methanesulfonate (obtained in section a) and 2-amino-1-ethanol, the desired compound was obtained.

LC-MS (method 1): $t_R$=3.89 min; m/z=436.1 [M+H]$^+$.

Example 233

6-(4-Fluorophenyl)-2-methyl-4-(3-pyridyl)-5-(4-pyridyl)pyrazolo[3,4-b]pyridine

To a solution of 4-(6-chloropyridin-3-yl)-6-(4-fluorophenyl)-2-methyl-5-(4-pyridyl)pyrazolo[3,4-b]pyridine (74 mg, 0.2 mmol, obtained in example 193) in AcOH (1 mL), Zn (72 mg, 1.1 mmol) was added under argon atmosphere and the mixture was heated to reflux overnight. It was allowed to cool and concentrated. The residue was treated with saturated NaHCO$_3$ and it was extracted with CHCl$_3$. The organic phase was dried over Na$_2$SO$_4$ and concentrated to dryness. The crude product obtained was purified by chromatography on silica gel using hexane-EtOAc-MeOH mixtures of increasing polarity, to afford 2.4 mg of the title compound (yield: 4%)

LC-MS (method 1): $t_R$=4.02 min; m/z=382.2 [M+H]$^+$.

EXAMPLES 234-235

Following a similar procedure to that described in reference example 15 section c, but starting from the appropriate compounds in each case, the compounds in the following table were obtained:

Example 238

5-(2-Methoxypyrimidin-4-yl)-6-(3-trifluoromethylphenyl)-1H-pyrazolo[3,4-b]pyridine To a solution of 5-[2-(methylsulfonyl)pyrimidin-4-yl]-6-[3-(trifluoromethyl)phenyl]-1H-pyrazolo[3,4-b]pyridine (90 mg, 0.2 mmol, obtained in example 127) in MeOH (5 mL) in a closed vessel, sodium methoxide (11 mg, 0.2 mmol) was added and heated to 60° C. for 24 h. Then, sodium methoxide (11 mg, 0.2 mmol) was added and it was stirred at 60° C. for 2 h more. It was allowed to cool and was concentrated. EtOAc and buffer (pH=5.3) were added. The phases were separated and the organic phase was washed with water, dried over Na$_2$SO$_4$ and concentrated to dryness. The crude product obtained was purified by chromatography on silica gel using hexane-EtOAc mixtures at 50%, to afford 38 mg of the title compound (yield: 47%)

LC-MS (method 1): $t_R$=7.71 min; m/z=372.0 [M+H]$^+$.

EXAMPLES 239-242

Following a similar procedure to that described in reference example 1 section a, but starting from the appropriate compounds in each case, the compounds in the following table were obtained:

| Example | Compound name | Starting compounds | LC-MS Method | $t_R$ (min) | m/z [M + H]$^+$ |
|---|---|---|---|---|---|
| 234 | 6-(4-Fluorophenyl)-3-methyl-5-(2-methylsulfanylpyrimidin-4-yl)-1H-pyrazolo[3,4-b]pyridine | Reference example 29 and hydrazine monohydrate | 1 | 8.57 | 352.0 |
| 235 | 3-Amino-5-(2-methylsulfanylpyrimidin-4-yl)-6-phenyl-1H-pyrazolo[3,4-b]pyridine | Reference example 28 and hydrazine monohydrate | 1 | 6.55 | 335.0 |

EXAMPLES 236-237

Following a similar procedure to that described in example 77, but starting from the appropriate compounds in each case, the compounds in the following table were obtained:

| Example | Compound name | Starting compound | LC-MS Method | $t_R$ (min) | m/z [M + H]$^+$ |
|---|---|---|---|---|---|
| 236 | 5-(2-Methylsulfanylpyrimidin-4-yl)-6-phenyl-1H-pyrazolo[3,4-b]pyridine | Example 235 | 1 | 7.54 | 320.0 |
| 237 | 6-(4-Fluorophenyl)-4-methyl-5-(2-methylsulfanylpyrimidin-4-yl)-1H-pyrazolo[3,4-b]pyridine | Example 147 | 1 | 4.42 | 305.0 |

| Example | Compound name | Starting compound | LC-MS Method | $t_R$ (min) | m/z [M + H]$^+$ |
|---|---|---|---|---|---|
| 239 | N-[2-[4,6-(Diphenyl)-5-(4-pyridyl)pyrazolo[3,4-b]pyridin-2-yl]ethyl]acetamide | Example 142 and acetyl chloride | 1 | 5.34 | 434.1 |
| 240 | N-[3-[4,6-Bis(4-fluorophenyl)-5-(4-pyridyl)pyrazolo[3,4-b]pyridin-2-yl]propyl]acetamide | Example 95 and acetyl chloride | 1 | 5.31 | 484.1 |
| 241 | N-[2-(4,6-Diphenyl-5-(4-pyridyl)pyrazolo[3,4-b]pyridin-2-yl]ethyl]-N-(2-hydroxyethyl)-acetamide | Example 232 and acetyl chloride | 1 | 5.27 | 478.1 |
| 242 | N-[2-[4,6-Bis(4-fluorophenyl)-5-(4-pyridyl)pyrazolo[3,4-b]pyridin-2-yl]ethyl]propionamide | Example 90 and propionyl chloride | 1 | 5.39 | 484.1 |

Example 243

N-[3-[4,6-Bis(4-fluorophenyl)-5-(4-pyridyl)pyrazolo[3,4-b]pyridin-2-yl]propyl]methanesulfonamide Following a similar procedure to that described in example 169, but starting from 2-(3-aminopropyl)-4,6-bis(4-fluorophenyl)-5-(4-pyridyl)pyrazolo[3,4-b]pyridine (obtained in example 95), the desired compound was obtained.

LC-MS (method 1): $t_R$=5.79 min; m/z=520.1 [M+H]$^+$.

Example 244

5-(2-Aminopyrimidin-4-yl)-6-(3-trifluoromethylphenyl)-1H-pyrazolo[3,4-b]pyridine A solution of THF (20 mL) saturated with NH$_3$ (g) at –20° C. was added over 5-[2-(methylsulfonyl)pyrimidin-4-yl]-6-[3-(trifluoromethyl)phenyl]-1H-pyrazolo[3,4-b]pyridine (90 mg, 0.2 mmol, obtained in example 127) in a closed vessel. It was stirred at room temperature for 2 days and concentrated. The crude product obtained was purified by chromatography on silica gel using hexane-EtOAc mixtures of increasing polarity as eluent, to afford 7 mg of the title compound (yield: 9%)

LC-MS (method 1): $t_R$=6.01 min; m/z=357.0 [M+H]$^+$.

Example 245

N-[5-(2-Methylsulfanylpyrimidin-4-yl)-6-(3-trifluoromethylphenyl)-1H-pyrazolo[3,4-b]pyridin-3-yl]acetamide A solution of 3-amino-5-[2-(methylsulfanyl)pyrimidin-4-yl]-6-[3-(trifluoromethyl)phenyl]-1H-pyrazolo[3,4-b]pyridine (200 mg, 0.5 mmol, obtained in example 123) and acetyl chloride (39 mg, 0.5 mmol) in pyridine (10 mL) was stirred at room temperature for 3 h. It was concentrated and the residue was taken up in a mixture of EtOAc and 1 N NaOH. The organic phase was dried over Na$_2$SO$_4$ and concentrated to dryness. The crude product obtained was purified by chromatography on silica gel using hexane-EtOAc mixtures of increasing polarity as eluent, to afford 78 mg of the title compound (yield: 37%)

LC-MS (method 1): $t_R$=8.55 min; m/z=445.0 [M+H]$^+$.

Example 246

N-Cyclopropylmethyl-[4-[3-benzyloxycarbonylamino-6-(3-trifluoromethylphenyl)-1H-pyrazolo[3,4-b]pyridin-5-yl]pyrimidin-2-yl]amine a) N-Benzyloxycarbonyl-[5-(2-methylsulfanylpyrimidin-4-yl)-6-(3-trifluoromethylphenyl)-1H-pyrazolo[3,4-b]pyridin-3-yl]amine Following a similar procedure to that described in example 245, but starting from 3-amino-5-[2-(methylsulfanyl)pyrimidin-4-yl]-6-[3-(trifluoromethyl)phenyl]-1H-pyrazolo[3,4-b]pyridine (obtained in example 123) and benzyl chloroformate, the desired compound was obtained.

LC-MS (method 1): $t_R$=10.00 min; m/z=537.1 [M+H]$^+$.

b) N-Benzyloxycarbonyl-[5-(2-methylsulfonylpyrimidin-4-yl)-6-(3-trifluoromethylphenyl)-1H-pyrazolo[3,4-b]pyridin-3-yl]amine Following a similar procedure to that described in example 56, but starting from N-benzyloxycarbonyl-[5-(2-methylsulfanylpyrimidin-4-yl)-6-(3-trifluoromethylphenyl)-1H-pyrazolo[3,4-b]pyridin-3-yl]amine (obtained in section a), the desired compound was obtained.

LC-MS (method 1): $t_R$=8.47 min; m/z=567.1 [M+H]$^+$.

c) Title Compound

Following a similar procedure to that described in example 208, but starting from N-benzyloxycarbonyl-[5-(2-methylsulfonylpyrimidin-4-yl)-6-(3-trifluoromethylphenyl)-1H-pyrazolo[3,4-b]pyridin-3-yl]amine (obtained in section b) and (cyclopropylmethyl)amine, the desired compound was obtained.

LC-MS (method 1): $t_R$=9.44 min; m/z 560.3 [M+H]$^+$.

Example 247

N-[2-[4,6-Bis(4-fluorophenyl)-5-(4-pyridyl)pyrazolo[3,4-b]pyridin-2-yl]ethyl]-2-hydroxyacetamide Following a similar procedure to that described in example 48, but starting from 2-(2-aminoethyl)-4,6-bis(4-fluorophenyl)-5-(4-pyridyl)pyrazolo[3,4-b]pyridine (obtained in example 90) and hydroxyacetic acid, the title compound was obtained.

LC-MS (method 1): $t_R$=4.84 min; m/z=486.1 [M+H]$^+$.

Example 248

N-[2-[4,6-Bis(4-fluorophenyl)-5-(4-pyridyl)pyrazolo[3,4-b]pyridin-2-yl]ethyl]piperidine-4-carboxamide a) N-[2-[4,6-Bis(4-fluorophenyl)-5-(4-pyridyl)pyrazolo[3,4-b]pyridin-2-yl]ethyl]-1-(tert-butoxycarbonyl)piperidine-4-carboxamide Following a similar procedure to that described in example 48, but starting from 2-(2-aminoethyl)-4,6-bis(4-fluorophenyl)-5-(4-pyridyl)pyrazolo[3,4-b]pyridine (obtained in example 90) and 1-(tert-butoxycarbonyl)piperidine-4-carboxylic acid, the desired compound was obtained.

b) Title Compound

Following a similar procedure to that described in example 36, but starting from N-[2-[4,6-bis(4-fluorophenyl)-5-(4-pyridyl)pyrazolo[3,4-b]pyridin-2-yl]ethyl]-1-(tert-butoxycarbonyl)piperidine-4-carboxamide (obtained in section a), the title compound was obtained.

LC-MS (method 1): $t_R$=4.29 min; m/z=539.2 [M+H]$^+$.

Example 249

N-[2-[4,6-Bis(4-fluorophenyl)-5-(4-pyridyl)pyrazolo[3,4-b]pyridin-2-yl]ethyl]-2-(methylamino)acetamide a) N-[2-[4,6-Bis(4-fluorophenyl)-5-(4-pyridyl)pyrazolo[3,4-b]pyridin-2-yl]ethyl]-2-chloroacetamide Following a similar procedure to that described in reference example 1 section a, but starting from 2-(2-aminoethyl)-4,6-bis(4-fluorophenyl)-5-(4-pyridyl)pyrazolo[3,4-b]pyridine (obtained in example 90) and chloroacetyl chloride, the title compound was obtained.

LC-MS (method 1): $t_R$=5.72 min; m/z 504.1, 506.1 [M+H]$^+$.

b) Title Compound

Following a similar procedure to that described in example 78, but starting from N-[2-[4,6-bis(4-fluorophenyl)-5-(4-pyridyl)pyrazolo[3,4-b]pyridin-2-yl]ethyl]-2-chloroacetamide (obtained in section a) and methylamine, the title compound was obtained.

LC-MS (method 1): $t_R$=4.28 min; m/z=499.2 [M+H]$^+$.

Example 250

N-[2-[4,6-Bis(4-fluorophenyl)-5-(4-pyridyl)pyrazolo[3,4-b]pyridin-2-yl]ethyl]-2-(2-hydroxyethylamino)acetamide Following a similar procedure to that described in example 78, but starting from N-[2-[4,6-bis(4-fluorophenyl)-5-(4-pyridyl)pyrazolo[3,4-b]pyridin-2-yl]ethyl]-2-chloroacetamide (obtained in example 249 section a) and 2-aminoethanol, the title compound was obtained.

LC-MS (method 1): $t_R$=4.29 min; m/z=529.2 [M+H]$^+$.

Example 251

N-[2-[4,6-Bis(4-fluorophenyl)-5-(4-pyridyl)pyrazolo[3,4-b]pyridin-2-yl]ethyl]nicotinamide a) Nicotinoyl Chloride Hydrochloride A solution of nicotinic acid (0.50 g, 4.0 mmol) and POCl$_3$ (5 mL) was heated at reflux for 1.5 h and concentrated. The product obtained was directly used in the next reaction.

b) Title Compound

Following a similar procedure to that described in example 245, but starting from 2-(2-aminoethyl)-4,6-bis(4-fluorophenyl)-5-(4-pyridyl)pyrazolo[3,4-b]pyridine (obtained in example 90) and nicotinoyl chloride hydrichloride (obtained in section a), the title compound was obtained.

LC-MS (method 1): $t_R$=5.25 min; m/z=533.1 [M+H]$^+$.

EXAMPLES 252-265

Following a similar procedure to that described in examples 6 and 7, but starting from the appropriate compounds in each case, the compounds in the following table were obtained:

| Example | Compound name | Starting compound | Method | $t_R$ (min) | m/z [M + H]$^+$ |
|---|---|---|---|---|---|
| 252 | 4-(4-Benzyloxyphenyl)-6-(4-fluorophenyl)-2-methyl-5-(4-pyridyl)-pyrazolo[3,4-b]pyridine | Example 229 and iodomethane | 1 | 7.53 | 487.1 |
| 253 | 6-(4-Fluorophenyl)-5-(2-methylsulfanylpyrimidin-4-yl)-2-methyl-pyrazolo[3,4-b]pyridine | Example 181 and iodomethane | 1 | 7.13 | 352.1 |
| 254 | 6-(4-Fluorophenyl)-2,4-dimethyl-5-(4-pyridyl)pyrazolo[3,4-b]pyridine | Example 237 and iodomethane | 1 | 4.11 | 319.00 |
| 255 | 4-(4-Benzyloxyphenyl)-6-(4-fluorophenyl)-2-methyl-5-(2-methylsulfanyl-pyrimidin-4-yl)pyrazolo[3,4-b]pyridine | Example 223 and iodomethane | 1 | 10.16 | 534.2 |
| 256 | 2-(1-Benzylpyrrolidin-2-ylmethyl)-4,6-bis(4-fluorophenyl)-5-(4-pyridyl)-pyrazolo[3,4-b]pyridine | Example 1 and 1-benzyl-2-chloromethyl-pyrrolidine | 1 | 6.10 | 558.2 |
| 257 | 4-(4-Benzyloxyphenyl)-6-(4-fluorophenyl)-2-methyl-5-pyrimidin-4-ylpyrazolo[3,4-b]pyridine | Example 222 and iodomethane | 1 | 8.72 | 488.2 |

-continued

| Example | Compound name | Starting compound | LC-MS Method | $t_R$ (min) | m/z [M + H]$^+$ |
|---|---|---|---|---|---|
| 258 | 6-(4-Fluorophenyl)-2-methyl-4-(5-methylfuran-2-yl)-5-(4-pyridyl)-pyrazolo[3,4-b]pyridine | Example 220 and iodomethane | 1 | 5.85 | 385.0 |
| 259 | 4-(5-Bromofuran-2-yl)-6-(4-fluorophenyl)-2-methyl-5-(4-pyridyl)-pyrazolo[3,4-b]pyridine | Example 221 and iodomethane | 1 | 6.48 | 449.1 451.1 |
| 260 | 6-(4-Fluorophenyl)-2-methyl-4-propyl-5-(4-pyridyl)pyrazolo[3,4-b]pyridine | Example 224 and iodomethane | 1 | 4.88 | 347.0 |
| 261 | 4-(3-Benzyloxyphenyl)-6-(4-fluorophenyl)-2-methyl-5-(4-pyridyl)-pyrazolo[3,4-b]pyridine | Example 225 and iodomethane | 1 | 7.79 | 487.0 |
| 262 | 6-(4-Fluorophenyl)-4-(2-phenyl)ethyl-2-methyl-5-(4-pyridyl)pyrazolo[3,4-b]pyridine | Example 176 and iodomethane | 1 | 5.94 | 409.0 |
| 263 | 5-(2-Chloropyridin-4-yl)-6-(4-fluorophenyl)-2-methylpyrazolo[3,4-b]pyridine | Example 226 and iodomethane | 1 | 7.30 | 339.2 341.2 |
| 264 | 4-Benzyl-6-(4-fluorophenyl)-2-methyl-5-(4-pyridyl)pyrazolo[3,4-b]pyridine | Example 228 and iodomethane | 1 | 5.95 | 395.2 |
| 265 | 4-[6-(4-Fluorophenyl)-2-methyl-5-(4-pyridyl)pyrazolo[3,4-b]pyridin-4-yl]butan-1-ol | Example 227 and iodomethane | 1 | 3.69 | 377.2 |

Example 266

4-[6-(4-Fluorophenyl)-2-methyl-5-(4-pyridyl)pyrazolo[3,4-b]pyridin-4-yl]phenol

To a solution of 4-(4-benzyloxyphenyl)-6-(4-fluorophenyl)-2-methyl-5-(4-pyridyl)pyrazolo[3,4-b]pyridine (112 mg, 0.2 mmol, obtained in example 252) in EtOH (13 mL), 10% Pd/C (20 mg) was added and it was hydrogenated under atmospheric pressure at room temperature for 2 days. It was filtered through celite, washed with EtOH and concentrated. The crude product obtained was purified by chromatography on silica gel using hexane-EtOAc-MeOH mixtures of increasing polarity as eluent, to afford 61 mg of the title compound (yield: 67%)

LC-MS (method 1): $t_R$=4.65 min; m/z=397.1 [M+H]$^+$.

Example 267

N-[6-(4-Fluorophenyl)-5-(2-methylsulfanylpyrimidin-4-yl)-1H-pyrazolo[3,4-b]pyridin-3-yl]acetamide Following a similar procedure to that described in example 245, but starting from 3-amino-6-(4-fluorophenyl)-5-(2-methylsulfanylpyrimidin-4-yl)pyrazolo[3,4-b]pyridine (obtained in example 180) and acetyl chloride, the title compound was obtained.

LC-MS (method 1): $t_R$=7.01 min; m/z=395.1 [M+H]$^+$.

Example 268

N-[5-[2-[(Cyclopropylmethyl)amino]pyrimidin-4-yl]-6-(4-fluorophenyl)-1H-pyrazolo[3,4-b]pyridin-3-yl]acetamide a) N-[6-(4-Fluorophenyl)-5-(2-methylsulfonylpyrimidin-4-yl)-1H-pyrazolo[3,4-b]pyridin-3-yl]acetamide and N-[6-(4-fluorophenyl)-5-(2-methylsulfonylpyrimidin-4-yl)-1H-pyrazolo[3,4-b]pyridin-3-yl]acetamide 7-oxide Following a similar procedure to that described in example 56, but starting from N-[6-(4-fluorophenyl)-5-(2-methylsulfanylpyrimidin-4-yl)-1H-pyrazolo[3,4-b]pyridin-3-yl]acetamide (obtained in example 267) and using 2 equivalents of m-chloroperbenzoic acid, the title compounds were obtained.

N-[6-(4-Fluorophenyl)-5-(2-methylsulfonylpyrimidin-4-yl)-1H-pyrazolo[3,4-b]pyridin-3-yl]acetamide: LC-MS (method 1): $t_R$=5.64 min; m/z=427.1 [M+H]$^+$.

N-[6-(4-Fluorophenyl)-5-(2-methylsulfonylpyrimidin-4-yl)-1H-pyrazolo[3,4-b]pyridin-3-yl]acetamide 7-oxide: LC-MS (method 1): $t_R$=4.44 min; m/z=443.0 [M+H]$^+$.

b) Title Compound

Following a similar procedure to that described in example 208, but starting from N-[6-(4-fluorophenyl)-5-(2-methylsulfonylpyrimidin-4-yl)-1H-pyrazolo[3,4-b]pyridin-3-yl]acetamide (obtained in section a) and (cyclopropylmethyl)amine, the title compound was obtained.

LC-MS (method 1): $t_R$=6.19 min; m/z=418.1 [M+H]$^+$.

Example 269

3-[6-(4-Fluorophenyl)-4-(2-furyl)-5-(4-pyridyl)pyrazolo[3,4-b]pyridin -2-yl]propan-1-ol a) 6-(4-Fluorophenyl)-4-(2-furyl)-5-(4-pyridyl)-2-[3-(tetrahydropyran-2-yloxy)propyl]pyrazolo[3,4-b]pyridine Following a similar procedure to that described in examples 6 and 7, but starting from 6-(4-fluorophenyl)-4-(2-furyl)-5-(4-pyridyl)-1H-pyrazolo[3,4-b]pyridine (obtained in example 171) and 2-(3-bromopropoxy)tetrahydropyran, the desired compound was obtained.

LC-MS (method 1): $t_R$=7.19 min; m/z=499.2 [M+H]$^+$.

b) Title Compound

Following a similar procedure to that described in example 91, but starting from 6-(4-fluorophenyl)-4-(2-furyl)-5-(4-pyridyl)-2-[3-(tetrahydropyran-2-yloxy)propyl]pyrazolo[3,4-b]pyridine (obtained in section a), the title compound was obtained.

LC-MS (method 1): $t_R$=5.05 min; m/z=415.1 [M+H]$^+$.

Following a similar procedure to that described in example 269, but starting from the appropriate compounds in each case, the compounds in the following table were obtained:

|  |  |  |  | LC-MS | |
|---|---|---|---|---|---|
| Example | Compound name | Starting compound | Method | $t_R$ (min) | m/z $[M + H]^+$ |
| 270 | 2-[4-(4-Benzyloxyphenyl-6-(4-fluorophenyl)-5-(4-pyridyl)-pyrazolo[3,4-b]pyridin-2-yl]ethanol | Example 229 and 2-(2-bromoethoxy)-tetrahydropyran | 1 | 6.76 | 517.2 |
| 271 | 3-[4-(4-Benzyloxyphenyl)-6-(4-fluorophenyl)-5-(4-pyridyl)-pyrazolo[3,4-b]pyridin-2-yl]propan-1-ol | Example 229 and 2-(3-bromopropoxy)-tetrahydropyran | 1 | 6.91 | 531.2 |
| 272 | 3-[6-(4-Fluorophenyl)-4-(5-methylfuran-2-yl)-5-(4-pyridyl)-pyrazolo[3,4-b]pyridin-2-yl]propan-1-ol | Example 220 and 2-(3-bromopropoxy)-tetrahydropyran | 1 | 5.42 | 429.1 |
| 273 | 3-[4-Cyclopropyl-6-(4-fluorophenyl)-5-(4-pyridyl)-pyrazolo[3,4-b]pyridin-2-yl]propan-1-ol | Example 219 and 2-(3-bromopropoxy)-tetrahydropyran | 1 | 4.40 | 389.1 |
| 274 | 3-[4-(5-Bromothien-2-yl)-6-(4-fluorophenyl)-5-(4-pyridyl)-pyrazolo[3,4-b]pyridin-2-yl]propan-1-ol | Example 173 and 2-(3-bromopropoxy)-tetrahydropyran | 1 | 6.25 | 508.9 510.9 |
| 275 | 3-[6-(4-Fluorophenyl)-4-propyl-5-(4-pyridyl)pyrazolo[3,4-b]pyridin-2-yl]propan-1-ol | Example 224 and 2-(3-bromopropoxy)-tetrahydropyran | 1 | 4.90 | 391.2 |
| 276 | 3-[4,6-Bis(4-fluorophenyl)-5-pyrimidin-4-ylpyrazolo[3,4-b]pyridin-2-yl]propan-1-ol | Example 230 and 2-(3-bromopropoxy)-tetrahydropyran | 1 | 6.56 | 444.2 |
| 277 | 3-[4-(3-Benzyloxyphenyl)-6-(4-fluorophenyl)-5-(4-pyridyl)-pyrazolo[3,4-b]pyridin-2-yl]propan-1-ol | Example 225 and 2-(3-bromopropoxy)-tetrahydropyran | 1 | 7.03 | 531.3 |
| 278 | 3-[4-Benzyl-6-(4-fluorophenyl)-5-(4-pyridyl)pyrazolo[3,4-b]pyridin-2-yl]propan-1-ol | Example 228 and 2-(3-bromopropoxy)-tetrahydropyran | 1 | 5.27 | 439.2 |

EXAMPLES 279-285

Following a similar procedure to that described in example 268, but starting from the appropriate compound and a suitable amine in each case, the compounds in the following table were obtained:

|  |  |  |  |  | LC-MS | |
|---|---|---|---|---|---|---|
| Example | Compound name | Starting compound | Amine | Method | $t_R$ (min) | m/z $[M + H]^+$ |
| 279 | (1S)-N-(1-Phenylethyl)-[4-[6-(4-fluorophenyl)-3-methyl-1H-pyrazolo[3,4-b]pyridin-5-yl]pyrimidin-2-yl]amine | Example 234 | (1S)-1-Phenylethyl-amine | 1 | 9.32 | 425.1 |
| 280 | N-Cyclopropylmethyl-4-[6-(4-fluorophenyl)-3-methyl-1H-pyrazolo[3,4-b]pyridin-5-yl]pyrimidin-2-yl]amine | Example 234 | (Cyclopropyl-methyl)amine | 2 | 5.54 | 373.2 |
| 281 | 1-[4-[6-(4-Fluorophenyl)-2-methylpyrazolo[3,4-b]pyridin-5-yl]pyrimidin-2-ylamino]propan-2-ol | Example 253 | 1-Amino-propan-2-ol | 1 | 4.73 | 379.2 |
| 282 | N-Cyclopropylmethyl-4-[6-[phenyl-1H-pyrazolo[3,4-b]pyridin-5-yl]pyrimidin-2-yl]amine | Example 236 | (Cyclopropyl-methyl)amine | 1 | 7.53 | 343.1 |
| 283 | 2-[4-[6-(4-Fluorophenyl)-2-methylpyrazolo[3,4-b]pyridin-5-yl]pyrimidin-2-ylamino]propan-1-ol | Example 253 | 2-Aminopropan-1-ol | 1 | 4.74 | 379.1 |

-continued

| Example | Compound name | Starting compound | Amine | LC-MS Method | t$_R$ (min) | m/z [M + H]$^+$ |
|---|---|---|---|---|---|---|
| 284 | 4-[4-[6-(4-Fluorophenyl)-2-methylpyrazolo[3,4-b]pyridin-5-yl]pyrimidin-2-ylamino]butan-1-ol | Example 253 | 4-Aminobutan-1-ol | 1 | 4.61 | 393.2 |
| 285 | (1S)-N-(1-Phenylethyl)-[4-[6-phenyl-1H-pyrazolo(3,4-b]pyridin-5-yl]pyrimidin-2-il]amine | Example 236 | (1S)-1-Phenylethyl-amine | 1 | 8.10 | 393.1 |

EXAMPLES 286-290

Following a similar procedure to that described in example 208, but starting from the appropriate compounds in each case, the compounds in the following table were obtained:

| Example | Compound name | Starting compounds | Method | t$_R$ (min) | m/z [M + H]$^+$ |
|---|---|---|---|---|---|
| 286 | N-(3-Methoxypropyl)-[4-[6-(3-trifluoromethylphenyl)-1H-pyrazolo-[3,4-b]pyridin-5-yl]pyrimidin-2-yl]amine | Example 127 and 3-methoxy-propylamine | 1 | 7.14 | 429.1 |
| 287 | 3-[4-[6-(3-Trifluoromethylphenyl)-1H-pyrazolo[3,4-b]pyridin-5-yl]pyrimidin-2-ylamino]propan-1-ol | Example 127 and 3-amino-propan-1-ol | 1 | 5.91 | 415.1 |
| 288 | 3-[4-[6-(4-Fluorophenyl)-2-(3-hydroxy-propyl)pyrazolo[3,4-b]pyridin-5-yl]pyrimidin-2-ylamino]propan-1-ol | Example 206 and 3-amino-propan-1-ol | 1 | 4.55 | 423.1 |
| 289 | N-Ethyl-[4-[6-(3-trifluoromethyl-phenyl)-1H-pyrazolo[3,4-b]pyridin-5-yl]pyrimidin-2-yl]amine | Example 127 and ethylamine | 1 | 7.21 | 385.0 |
| 290 | N-Benzyl-[4-[6-(3-trifluoromethyl-phenyl)-1H-pyrazolo[3,4-b]pyridin-5-yl]pyrimidin-2-yl]amine | Example 127 and benzylamine | 1 | 8.86 | 447.1 |

Example 291

4-[5-[2-[(Cyclopropylmethyl)amino]pyrimidin-4-yl]-6-(4-fluorophenyl)-2-methylpyrazolo[3,4-b]pyridin-4-yl]phenol a) 4-(4-Benzyloxyphenyl)-6-(4-fluorophenyl)-5-(2-methylsulfonylpyrimidin-4-yl)-2-methylpyrazolo[3,4-b]pyridine Following a similar procedure to that described in example 56, but starting from 4-(4-benzyloxyphenyl)-6-(4-fluorophenyl)-2-methyl-5-(2-methylsulfanylpyrimidin-4-yl)pyrazolo[3,4-b]pyridine (obtained in example 255), the desired compound was obtained.

LC-MS (method 1): t$_R$=8.77 min; m/z=566.2 [M+H]$^+$.

b) 4-[6-(4-Fluorophenyl)-5-(2-methylsulfonylpyrimidin-4-yl)-2-methylpyrazolo[3,4-b]pyridin-4-yl]phenol Following a similar procedure to that described in example 266, but starting from 4-(4-benzyloxyphenyl)-6-(4-fluorophenyl)-2-methyl-5-(2-methylsulfonylpyrimidin-4-yl)pyrazolo[3,4-b]pyridine (obtained in section a), the desired compound was obtained.

LC-MS (method 1): t$_R$=6.17 min; m/z=476.1 [M+H]$^+$.

c) Title Compound

Following a similar procedure to that described in example 128, but starting from 4-[6-(4-fluorophenyl)-5-(2-methylsulfonylpyrimidin-4-yl)-2-methylpyrazolo[3,4-b]pyridin-4-yl]phenol (obtained in section b) and (cyclopropylmethyl)amine, the title compound was obtained.

LC-MS (method 1): t$_R$=6.62 min; m/z=467.2 [M+H]$^+$.

EXAMPLES 292-295

Following a similar procedure to that described in example 266, but starting from the appropriate compounds in each case, the compounds in the following table were obtained:

| | | | LC-MS | |
|---|---|---|---|---|
| Example | Compound name | Starting compound | Method | $t_R$ (min) | m/z [M + H]+ |
| 292 | 4-[6-(4-Fluorophenyl)-2-(3-hydroxy-propyl)-5-(4-pyridyl)pyrazolo[3,4-b]pyridin-4-yl]phenol | Example 271 | 1 | 4.41 | 441.1 |
| 293 | 4-[6-(4-Fluorophenyl)-2-methyl-5-pyrimidin-4-yl)pyrazolo[3,4-b]pyridin-4-yl]phenol | Example 257 | 1 | 5.71 | 398.1 |
| 294 | 3-[6-(4-Fluorophenyl)-2-(3-hydroxy-propyl)-5-(4-pyridyl)pyrazolo[3,4-b]pyridin-4-yl]phenol | Example 277 | 1 | 4.54 | 441.2 |
| 295 | 3-[6-(4-Fluorophenyl)-2-methyl-5(4-pyridyl)pyrazolo]3,4-b]pyridin-4-yl]phenol | Example 261 | 1 | 4.74 | 397.0 |

Example 296

4,6-Bis(4-fluorophenyl)-5-(4-pyridyl)-2-(pyrrolidin-2-ylmethyl)pyrazolo[3,4-b]pyridine To a solution of 2-(1-benzylpyrrolidin-2-ylmethyl)-4,6-bis(4-fluorophenyl)-5-(4-pyridyl)pyrazolo[3,4-b]pyridine (83 mg, 0.1 mmol, obtained in example 259) in EtOH (6.9 mL), 10% Pd/C (8 mg) and formic acid (0.34 mL) were added and heated a reflux for 2 h. It was allowed to cool and filtered through celite, washed with EtOH and concentrated. The crude product obtained was purified by chromatography on silica gel using hexane-EtOAc-MeOH—NH$_3$ of increasing polarity as eluent, to afford 40 mg of the title compound (yield: 57%)

LC-MS (method 1): $t_R$=4.98 min; m/z=468.1 [M+H]+.

Example 297

4-[4-[6-(4-Fluorophenyl)-2-methylpyrazolo[3,4-b]pyridin-5-yl]pyridin-2-ylamino]benzenesulfonamide Following a similar procedure to that described in example 214, but starting from 5-(2-chloropyridin-4-yl)-6-(4-fluorophenyl)-2-methylpyrazolo[3,4-b]pyridine (obtained in example 263) and 4-aminobenzenesulfonamide, the title compound was obtained.

LC-MS (method 1): $t_R$=5.36 min; m/z=475.3 [M+H]+.

Example 298

N-[5-[2-[(Cyclopropylmethyl)amino]pyrimidin-4-yl]-6-(4-fluorophenyl)-1H-pyrazolo[3,4-b]pyridin-3-yl]acetamide 7-oxide Following a similar procedure to that described in example 208, but starting from N-[6-(4-fluorophenyl)-5-(2-methylsulfonylpyrimidin-4-yl)-1H-pyrazolo[3,4-b]pyridin-3-yl]acetamide 7-oxide (obtained in example 268 section a) and (cyclopropylmethyl)amine, the title compound was obtained.

LC-MS (method 1): $t_R$=5.45 min; m/z=434.2 [M+H]+.

Example 299

N-[6-(4-Fluorophenyl)-5-(4-pyridyl)-1H-pyrazolo[3,4-b]pyridin-3-yl]isonicotinamide a) Isonicotinoyl Chloride Hydrochloride A solution of isonicotinic acid (0.10 g, 0.8 mmol) and thionyl chloride (1 mL) were heated to reflux for 2 h and concentrated. The product obtained was used immediately in the following step.

b) Title Compound

In a volumetric flask, 3-amino-6-(4-fluorophenyl)-5-(4-pyridyl)-1H-pyrazolo[3,4-b]pyridine (0.20 g, 0.7 mmol, obtained in example 70), isonicotinoyl chloride hydrochloride (0.12 g, 0.7 mmol, obtained in section a) and pyridine (1 mL) were introduced under argon atmosphere. This was stirred at room temperature for 2 days. It was concentrated and the residue dissolved in a mixture of CHCl$_3$ and 1 N HCl. The phases were separated and the aqueous phase was extracted with CHCl$_3$ (×2). The aqueous phase was basified by slow addition of 1 N NaOH. Brine was added and extracted with CHCl$_3$ and EtOAc. The organic phase was dried over Na$_2$SO$_4$ and concentrated to dryness. The crude product obtained was purified by chromatography on silica gel using CHCl$_3$-MeOH mixtures of increasing polarity as eluent, to afford 98 mg of the title compound (yield: 68%).

LC-MS (method 1): $t_R$=4.21 min; m/z=411.1 [M+H]+.

The invention claimed is:

1. A compound of general formula I

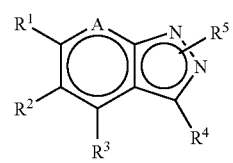

wherein:
A represents N or N+O−;
R$^1$ represents phenyl or Het optionally substituted with one or more substituents selected from R$^a$ and R$^b$;
R$^2$ represents Het optionally substituted with one or more substituents selected from R$^a$ and R$^b$;
R$^3$ represents H, Cy optionally substituted with one or more substituents selected from R$^a$ and R$^b$, or R$^3$ represents C$_{1-6}$alkyl optionally substituted with one or more substituents selected from R$^b$ and Cy*, wherein Cy* can be optionally substituted with one or more substituents selected from R$^b$ and R$^c$;
R$^4$ represents H, R$^a$, halogen, —OR$^{a'}$, —OCOR$^a$, —OSO$_2$R$^a$, —OCONR$^a$R$^{a'}$, —NO$_2$, —CN, —COR$^{a'}$, —CO$_2$R$^{a'}$, —CONR$^a$R$^{a'}$, —NR$^a$R$^{a'}$, —NR$^{a'}$COR$^{a'}$, —NR$^{a'}$CONR$^a$R$^{a'}$, —NR$^{a'}$CO$_2$R$^a$, —NR$^{a'}$SO$_2$R$^a$, —SR$^{a'}$, —SOR$^{a'}$, —SO$_2$R$^a$ or —SO$_2$NR$^a$R$^{a'}$;
R$^5$ can be placed on either of the 2 N of the pyrazole ring of formula I and represents H or R$^f$;

each $R^a$ independently represents $C_{1-6}$alkyl, $C_{2-6}$alkenyl, $C_{2-6}$alkynyl or Cy, wherein the groups $C_{1-6}$alkyl, $C_{2-6}$alkenyl or $C_{2-6}$alkynyl can be optionally substituted with one or more substituents selected from $R^b$ and Cy*, and wherein any of the groups Cy or Cy* can be optionally substituted with one or more substituents selected from $R^b$ and $R^c$;

each $R^{a'}$ independently represents H or $R^a$;

each $R^b$ independently represents halogen, —$OR^{c'}$, —$OCOR^c$, —$OSO_2R^c$, —$OCONR^{c'}R^{c'}$, —$NO_2$, —CN, —$COR^{c'}$, —$CO_2R^{c'}$, —$CONR^{c'}R^{c'}$, —$CONR^{c'}NR^{c'}R^{c'}$, —$NR^{c'}R^{c'}$, —$NR^{c'}COR^{c'}$, —$NR^{c'}CONR^{c'}R^{c'}$, —$NR^{c'}CO_2R^c$, —$NR^{c'}SO_2R^c$, —$SR^{c'}$, —$SOR^c$, —$SO_2R^c$, —$SO_2NR^{c'}R^{c'}$, —$C(NR^{c'})NR^{c'}R^{c'}$, —$C(NSO_2NR^{c'}R^{c'})NR^{c'}R^{c'}$, —$C(NOR^{c'})R^{c'}$, —$C(NNR^{c'}R^{c'})R^{c'}$, —$NR^{c'}C(NR^{c'})NR^{c'}R^{c'}$ or —$NR^{c'}C(NCN)NR^{c'}R^{c'}$;

each $R^c$ independently represents $C_{1-6}$alkyl, $C_{2-6}$alkenyl, $C_{2-6}$alkynyl or Cy, wherein all these groups can be optionally substituted with one or more substituents $R^d$;

each $R^{c'}$ independently represents H or $R^c$;

each $R^d$ independently represents halogen, $R^e$, —$OR^{e'}$, —$OCOR^e$, —$OSO_2R^e$, —$OCONR^eR^{e'}$, —$NO_2$, —CN, —$COR^{e'}$, —$CO_2R^{e'}$, —$CONR^eR^{e'}$, —$CONR^{e'}NR^eR^{e'}$, —$NR^eR^{e'}$, —$NR^{e'}COR^{e'}$, —$NR^{e'}CONR^eR^{e'}$, —$NR^{e'}CO_2R^e$, —$NR^{e'}SO_2R^e$, 'SR$^{e'}$, —$SOR^e$, —$SO_2R^e$, —$SO_2NR^eR^{e'}$, —$C(NR^{e'})NR^eR^{e'}$, —$C(NSO_2NR^eR^{e'})NR^eR^{e'}$, —$C(NOR^{e'})R^{e'}$, —$C(NNR^eR^{e'})R^{e'}$, —$NR^{e'}C(NR^{e'})NR^eR^{e'}$, —$NR^{e'}C(NCN)NR^eR^{e'}$ or Cy optionally substituted with one or more substituents selected from halogen, $R^e$, —$OR^{e'}$, —$OCOR^e$, —$OSO_2R^e$, —$OCONR^eR^{e'}$, —$NO_2$, —CN, —$COR^{e'}$, —$CO_2R^{e'}$, —$CONR^eR^{e'}$, —$CONR^{e'}NR^eR^{e'}$, —$NR^eR^{e'}$, —$NR^{e'}COR^{e'}$, —$NR^{e'}CONR^eR^{e'}$, —$NR^{e'}CO_2R^e$, —$NR^{e'}SO_2R^e$, —$SR^{e'}$, —$SOR^e$, —$SO_2R^e$, —$SO_2NR^eR^{e'}$, —$C(NR^{e'})NR^eR^{e'}$, —$C(NSO_2NR^eR^{e'})NR^eR^{e'}$, —$C(NOR^{e'})R^{e'}$, —$C(NNR^eR^{e'})R^{e'}$, —$NR^{e'}C(NR^{e'})NR^eR^{e'}$ and —$NR^{e'}C(NCN)NR^eR^{e'}$;

each $R^e$ independently represents $C_{1-6}$alkyl or halo$C_{1-6}$alkyl;

each $R^{e'}$ independently represents H or $R^e$;

$R^f$ represents $C_{1-6}$alkyl, $C_{2-6}$alkenyl, $C_{2-6}$alkynyl or Cy, wherein the groups $C_{1-6}$alkyl, $C_{2-6}$alkenyl or $C_{2-6}$alkynyl can be optionally substituted with one or more substituents selected from $R^g$ and Cy*, and wherein any of the groups Cy or Cy* can be optionally substituted with one or more substituents selected from $R^g$ and $R^a$;

each $R^g$ independently represents halogen, —$OR^{a'}$, —$OCOR^a$, —$OSO_2R^a$, —$OCONR^aR^{a'}$, —$NO_2$, —CN, —$COR^{a'}$, —$CO_2R^{a'}$, —$CONR^aR^{a'}$, —$CONR^{a'}NR^aR^{a'}$, —$NR^aR^{a'}$, —$NR^{a'}COR^{a'}$, —$NR^{a'}CONR^aR^{a'}$, —$NR^{a'}CO_2R^a$, —$NR^{a'}SO_2R^a$, —$SR^{a'}$, —$SOR^{a'}$, —$SO_2R^a$, —$SO_2NR^aR^a$, —$C(NR^{a'})NR^aR^{a'}$, —$C(NSO_2NR^aR^{a'})NR^aR^{a'}$, —$C(NOR^{a'})R^{a'}$, —$C(NNR^aR^{a'})R^{a'}$, —$NR^{a'}C(NR^{a'})NR^aR^{a'}$ or —$NR^{a'}C(NCN)NR^aR^{a'}$;

Het in the above definitions represents pyridine, pyrazine, pyrimidine, pyridazine, 2(1H)-pyridone, 2(1H)-pyrazinone, 2(1H)-pyrimidinone or 2(1H)-pyridazinone;

Cy or Cy* in the above definitions represent a partially unsaturated, saturated or aromatic 3- to 7-membered monocyclic or 8- to 12-membered bicyclic carbocyclic ring, which optionally contains from 1 to 4 heteroatoms selected from N, S and O, which can optionally contain 1 or 2 oxo groups when the ring is saturated or partially unsaturated, and wherein said ring or rings can be bonded to the rest of the molecule through a carbon or a nitrogen atom;

with the proviso that when $R^3$ and $R^5$ both represent H and $R^2$ represents Het optionally substituted with one or more substituents selected from halogen, —CN, —$CF_3$, —OH, —$NO_2$, —$OR^6$, —$NR^6R^6$, —$OCF_3$, $C_{1-6}$alkyl, $C_{2-6}$alkenyl, $C_{2-6}$alkynyl and Cy, wherein Cy can be optionally substituted with one or more substituents selected from $R^b$ and $R^c$, and wherein $R^6$ represents $C_{1-6}$alkyl, then $R^4$ is not —$NR^{a'}COR^a$, —$NHCONHR^a$ or —$NHCO_2R^a$; and the salts thereof.

2. A compound according to claim 1 wherein A represents N.

3. A compound according to claim 2 wherein $R^5$ can be placed on either of the 2 N of the pyrazole ring of formula I and represents H or $R^a$.

4. A compound according to claim 1 wherein $R^1$ represents pyridine or phenyl, wherein either of these groups can be optionally substituted with one or more substituents selected from $R^a$ and $R^b$.

5. A compound according to claim 4 wherein $R^1$ represents phenyl optionally substituted with one or more substituents selected from $R^a$ and $R^b$.

6. A compound according to claim 5 wherein $R^1$ represents phenyl optionally substituted with one or more substituents selected from halogen, —$OR^{c'}$, —$NO_2$, —CN, —$CONR^cR^{c'}$, —$NR^cR^{c'}$ and $C_{1-6}$alkyl optionally substituted with one or more substituents selected from halogen, —$OR^{c'}$, —$COR^{c'}$, —$NR^cR^{c'}$ and —$NR^{c'}COR^{c'}$.

7. A compound according to claim 6 wherein $R^1$ represents phenyl optionally substituted with one or more substituents selected from halogen and halo$C_{1-6}$alkyl.

8. A compound according to claim 1 wherein $R^2$ represents pyridine or pyrimidine, either of which can be optionally substituted with one or more substituents selected from $R^a$ and $R^b$.

9. A compound according to claim 8 wherein $R^2$ represents 4-pyridine or 4-pyrimidine, either of which can be optionally substituted with one or more substituents selected from $R^a$ and $R^b$.

10. A compound according to claim 9 wherein $R^2$ represents 4-pyridine or 4-pyrimidine, either of which can be optionally substituted with one or more substituents selected from halogen, —$OR^{c'}$, —$NR^cR^{c'}$, —$SR^{c'}$ and —$SO_2R^c$.

11. A compound according to claim 10 wherein $R^2$ represents 4-pyridine.

12. A compound according to claim 10 wherein $R^2$ represents 4-pyrimidine substituted with —$NR^cR^{c'}$, wherein in $R^2$:

each $R^{c'}$ independently represents H or $R^c$;

each $R^c$ independently represents $C_{1-6}$alkyl optionally substituted with one or more substituents selected from Cy and —$OR^{e'}$; and each $R^{e'}$ independently represents H or $R^{e'}$.

13. A compound according to claim 1 wherein $R^3$ represents H or Cy optionally substituted with one or more substituents selected from $R^a$ and $R^b$.

14. A compound according to claim 13 wherein $R^3$ represents H, heteroaryl or phenyl, wherein either the heteroaryl or phenyl can be optionally substituted with one or more substituents selected from $R^a$ and $R^b$, and wherein heteroaryl represents an aromatic 5- or 6-membered monocyclic or 8- to 12-membered bicyclic ring, which contains from 1 to 4 heteroatoms selected from N, S and O and which can be bonded to the rest of the molecule through a carbon or a nitrogen atom.

15. A compound according to claim 14 wherein $R^3$ represents heteroaryl or phenyl, either of which can be optionally substituted with one or more substituents selected from $R^a$ and $R^b$.

16. A compound according to claim 15 wherein $R^3$ represents monocyclic heteroaryl or phenyl, either of which can be optionally substituted with one or more substituents selected from halogen, —$NO_2$, —$OR^{c'}$, $C_{1-6}$alkyl and Cy, wherein $C_{1-6}$alkyl can be optionally substituted with one or more substituents selected from $R^b$ and Cy*, and wherein any of the groups Cy or Cy* can optionally substituted with one or more substituents selected from $R^b$ and $R^c$.

17. A compound according to claim 16 wherein $R^3$ represents monocyclic heteroaryl or phenyl, either of which can be optionally substituted with one or more substituents selected from halogen, —$NO_2$, —$OR^{c'}$, $C_{1-6}$alkyl, halo$C_{1-6}$alkyl and Cy, and wherein in $R^3$:
each $R^{c'}$ independently represents H or $R^c$;
each $R^c$ independently represents $C_{1-6}$alkyl optionally substituted with one or more substituents $R^d$; and
each $R^d$ independently represents Cy.

18. A compound according to claim 1 wherein $R^4$ represents H, $R^a$ halogen, —$OR^{a'}$, —CN, —$CONR^{a'}R^a$, —$NR^{a'}R^{a'}$ or —$NR^{a'}COR^{a'}$.

19. A compound according to claim 18 wherein $R^4$ represents H.

20. A compound according to claim 1 wherein $R^5$ represents H or $R^5$ represents $R^a$ and is placed on the N at position 2 of the pyrazole ring.

21. A compound according to claim 20 wherein $R^5$ represents $R^a$.

22. A compound according to claim 20 wherein $R^a$ in $R^5$ represents $C_{1-6}$alkyl, $C_{2-6}$alkenyl or Cy, wherein the groups $C_{1-6}$alkyl or $C_{2-6}$alkenyl can be optionally substituted with one or more substituents selected from $R^b$ and Cy*, and wherein any of the groups Cy or Cy* can be optionally substituted with one or more substituents selected from $R^b$ and $R^c$.

23. A compound according to claim 22 wherein each $R^b$ in $R^5$ independently represents halogen, —$OR^{c'}$, —$COR^{c'}$, —$CO_2R^{c'}$, —$CONR^{c'}R^{c'}$, —$NR^{c'}R^{c'}$, —$NR^{c'}COR^{c'}$, —$NR^{c'}CONR^{c'}R^{c'}$, —$NR^{c'}SO_2R^{c'}$, —$SR^{c'}$, —$SOR^{c'}$ or —$SO_2R^{c'}$.

24. A compound according to claim 23 wherein in $R^5$:
each $R^b$ independently represents —$OR^{c'}$, —$COR^{c'}$, —$CONR^{c'}R^{c'}$, —$NR^{c'}R^{c'}$, —$NR^{c'}COR^{c'}$, —$NR^{c'}CONR^{c'}R^{c'}$, —$NR^{c'}SO_2R^{c'}$, —$SOR^{c'}$ or —$SO_2R^{c'}$;
each $R^{c'}$ independently represents H or $R^c$;
each $R^c$ independently represents Cy or $C_{1-6}$alkyl, either of which can be optionally substituted with one or more substituents selected from $R^d$;
each $R^d$ independently represents $R^e$, —$OR^{e'}$, —$NR^{e'}R^{e'}$, —CN, —$COR^{e'}$, —$SR^{e'}$, —$SOR^{e'}$ or Cy.

25. A compound according to claim 21 wherein $R^a$ in $R^5$ represents $C_{1-6}$alkyl optionally substituted with one or more substituents selected from —$OR^{c'}$, —$COR^{c'}$, —$CONR^{c'}R^{c'}$, —$NR^{c'}R^{c'}$, —$NR^{c'}COR^{c'}$, —$NR^{c'}CONR^{c'}R^{c'}$, —$NR^{c'}SO_2R^{c'}$ and Cy* optionally substituted with one or more substituents selected from $R^c$; wherein in $R^5$:
each $R^{c'}$ independently represents H or $R^c$;
each $R^c$ independently represents Cy or $C_{1-6}$alkyl, either of which can be optionally substituted with one or more substituents selected from $R^d$;
each $R^d$ independently represents —$OR^{e'}$, —$NR^{e'}R^{e'}$, —CN, —$COR^{e'}$, —$SR^{e'}$, —$SOR^{e'}$ or Cy;
each $R^{e'}$ independently represents H or $R^e$; and
each $R^e$ independently represents $C_{1-6}$alkyl.

26. A compound according to claim 1, wherein:
A represents N;
$R^1$ represents phenyl optionally substituted with one of more substituents selected from halogen, —$OR^{c'}$, —$NO_2$, —CN, —$CONR^{c'}R^{c'}$, —$NR^{c'}R^{c'}$ and $C_{1-6}$alkyl optionally substituted with one or more substituents selected from halogen, —$OR^{c'}$, —$COR^{c'}$, —$NR^{c'}R^{c'}$ and —$NR^{c'}COR^{c'}$;
$R^2$ represents 4-pyridine or 4-pyrimidine, wherein either of which can be optionally substituted with one or more substituents selected from halogen, —$OR^{c'}$, —$NR^{c'}R^{c'}$, —$SR^{c'}$ and —$SO_2R^{c'}$, and
$R^3$ represents H, heteroaryl or phenyl, wherein either the heteroaryl or phenyl can be optionally substituted with one or more substituents selected from $R^a$ and $R^b$, and wherein heteroaryl represents an aromatic 5- or 6-membered monocyclic or 8- to 12-membered bicyclic ring, which contains from 1 to 4 heteroatoms selected from N, S and O and which can be bonded to the rest of the molecule through a carbon or a nitrogen atom.

27. A compound according to claim 26, wherein $R^5$ represents H or $R^5$ represents $R^a$ and is placed on the N at position 2 of the pyrazole ring.

28. A compound according to claim 27, wherein $R^2$ represents 4-pyridine.

29. A compound according to claim 27, wherein $R^2$ represents 4-pyrimidine substituted with —$NR^{c'}R^{c'}$, wherein in $R^2$:
each $R^{c'}$ independently represents H or $R^c$;
each $R^c$ independently represents $C_{1-6}$alkyl optionally substituted with one or more substituents selected from Cy and —$OR^{e'}$; and
each $R^{e'}$ independently represents H or $R^e$.

30. A compound according to claim 1 selected from:
4,6-bis(4-fluorophenyl)-5-(4-pyridyl)-1H-pyrazolo[3,4-b]pyridine;
4,6-diphenyl-5-(4-pyridyl)-1H-pyrazolo[3,4-b]pyridine;
5-(4-pyridyl)-4,6-bis[3-(trifluoromethyl)phenyl]-1H-pyrazolo[3,4-b]pyridine;
4,6-bis(4-fluorophenyl)-3-methyl-5-(4-pyridyl)-1H-pyrazolo[3,4-b]pyridine;
3-methyl-4,6-diphenyl-5-(4-pyridyl)-1H-pyrazolo[3,4-b]pyridine;
2-ethyl-4,6-bis(4-fluorophenyl)-5-(4-pyridyl)pyrazolo[3,4-b]pyridine;
1-ethyl-4,6-bis(4-fluorophenyl)-5-(4-pyridyl)pyrazolo[3,4-b]pyridine;
4,6-bis(4-fluorophenyl)-2-methyl-5-(4-pyridyl)pyrazolo[3,4-b]pyridine;
4,6-bis(4-fluorophenyl)-1-methyl-5-(4-pyridyl)pyrazolo[3,4-b]pyridine;
4,6-bis(4-fluorophenyl)-2,3-dimethyl-5-(4-pyridyl)pyrazolo[3,4-b]pyridine;
4,6-bis(4-fluorophenyl)-1,3-dimethyl-5-(4-pyridyl)pyrazolo[3,4-b]pyridine;
2-[2-[1-(tert-butoxycarbonyl)piperidin-4-yl]ethyl]-4,6-bis(4-fluorophenyl)-5-(4-pyridyl)pyrazolo[3,4-b]pyridine;
1-[2-[1-(tert-butoxycarbonyl)piperidin-4-yl]ethyl]-4,6-bis(4-fluorophenyl)-5-(4-pyridyl)pyrazolo[3,4-b]pyridine;
2-[1-(tert-butoxycarbonyl)piperidin-4-yl]-4,6-bis(4-fluorophenyl)-3-methyl-5-(4-pyridyl)pyrazolo[3,4-b]pyridine;
1-[1-(tert-butoxycarbonyl)piperidin-4-yl]-4,6-bis(4-fluorophenyl)-3-methyl-5-(4-pyridyl)pyrazolo[3,4-b]pyridine;

2-(3-chloropropyl)-4,6-bis(4-fluorophenyl)-5-(4-pyridyl)pyrazolo[3,4-b]pyridine;
1-(3-chloropropyl)-4,6-bis(4-fluorophenyl)-5-(4-pyridyl)pyrazolo[3,4-b]pyridine;
3-[4,6-bis(4-fluorophenyl)-5-(4-pyridyl)pyrazolo[3,4-b]pyridin-2-yl]propan-1-ol;
3-[4,6-bis(4-fluorophenyl)-5-(4-pyridyl)pyrazolo[3,4-b]pyridin-1-yl]propan-1-ol;
2-[1-(tert-butoxycarbonyl)piperidin-4-yl]-4,6-bis(4-fluorophenyl)-5-(4-pyridyl)pyrazolo[3,4-b]pyridine;
1-[1-(tert-butoxycarbonyl)piperidin-4-yl]-4,6-bis(4-fluorophenyl)-5-(4-pyridyl)pyrazolo[3,4-b]pyridine;
2-methyl-4,6-diphenyl-5-(4-pyridyl)pyrazolo[3,4-b]pyridine;
1-methyl-4,6-diphenyl-5-(4-pyridyl)pyrazolo[3,4-b]pyridine;
4,6-bis(4-fluorophenyl)-5-(4-pyridyl)-2-[2-(tetrahydropyran-2-yloxy)ethyl]-pyrazolo[3,4-b]pyridine;
2-[4,6-bis(4-fluorophenyl)-5-(4-pyridyl)pyrazolo[3,4-b]pyridin-1-yl]ethanol;
4,6-bis(4-fluorophenyl)-2-(4-methylsulfanylbenzyl)-5-(4-pyridyl)pyrazolo[3,4-b]pyridine;
4,6-bis(4-fluorophenyl)-1-(4-methylsulfanylbenzyl)-5-(4-pyridyl)pyrazolo[3,4-b]pyridine;
2-[1-(tert-butoxycarbonyl)piperidin-4-ylmethyl]-4,6-bis(4-fluorophenyl)-5-(4-pyridyl)pyrazolo[3,4-b]pyridine;
1-[1-(tert-butoxycarbonyl)piperidin-4-ylmethyl]-4,6-bis(4-fluorophenyl)-5-(4-pyridyl)pyrazolo[3,4-b]pyridine;
4,6-bis(4-fluorophenyl)-2-[2-(morpholin-4-yl)ethyl]-5-(4-pyridyl)pyrazolo[3,4-b]pyridine;
4,6-bis(4-fluorophenyl)-1-[2-(morpholin-4-yl)ethyl]-5-(4-pyridyl)pyrazolo[3,4-b]pyridine;
ethyl 2-[4,6-bis(4-fluorophenyl)-5-(4-pyridyl)pyrazolo[3,4-b]pyridin-2-yl]acetate;
ethyl 2-[4,6-bis(4-fluorophenyl)-5-(4-pyridyl)pyrazolo[3,4-b]pyridin-1-yl]acetate;
ethyl 3-[4,6-bis(4-fluorophenyl)-5-(4-pyridyl)pyrazolo[3,4-b]pyridin-2-yl]propionate;
ethyl 3-[4,6-bis(4-fluorophenyl)-5-(4-pyridyl)pyrazolo[3,4-b]pyridin-1-yl]propionate;
4,6-bis(4-fluorophenyl)-2-(4-piperidyl)-5-(4-pyridyl)pyrazolo[3,4-b]pyridine;
4,6-bis(4-fluorophenyl)-1-(4-piperidyl)-5-(4-pyridyl)pyrazolo[3,4-b]pyridine;
4,6-bis(4-fluorophenyl)-2-(4-piperidylmethyl)-5-(4-pyridyl)pyrazolo[3,4-b]pyridine;
4,6-bis(4-fluorophenyl)-1-(4-piperidylmethyl)-5-(4-pyridyl)pyrazolo[3,4-b]pyridine;
4,6-bis(6-chloropyridin-3-yl)-5-(4-pyridyl)-1H-pyrazolo[3,4-b]pyridine;
4,6-bis(4-fluorophenyl)-3-methyl-2-(4-piperidyl)-5-(4-pyridyl)pyrazolo[3,4-b]pyridine;
4,6-bis(4-fluorophenyl)-3-methyl-1-(4-piperidyl)-5-(4-pyridyl)pyrazolo[3,4-b]pyridine;
4,6-bis(4-fluorophenyl)-2-[2-(4-piperidyl)ethyl]-5-(4-pyridyl)pyrazolo[3,4-b]pyridine;
2-[4,6-bis(4-fluorophenyl)-5-(4-pyridyl)pyrazolo[3,4-b]pyridin-2-yl]acetic acid;
2-[4,6-bis(4-fluorophenyl)-5-(4-pyridyl)pyrazolo[3,4-b]pyridin-1-yl]acetic acid;
3-[4,6-bis(4-fluorophenyl)-5-(4-pyridyl)pyrazolo[3,4-b]pyridin-2-yl]propionic acid;
3-[4,6-bis(4-fluorophenyl)-5-(4-pyridyl)pyrazolo[3,4-b]pyridin-1-yl]propionic acid;
2-[4,6-bis(4-fluorophenyl)-5-(4-pyridyl)pyrazolo[3,4-b]pyridin-2-yl]-1-(morpholin-4-yl)ethanone;
2-[4,6-bis(4-fluorophenyl)-5-(4-pyridyl)pyrazolo[3,4-b]pyridin-1-yl]acetamide;
2-[4,6-bis(4-fluorophenyl)-5-(4-pyridyl)pyrazolo[3,4-b]pyridin-1-yl]-1-(morpholin-4-yl)ethanone;
3-[4,6-bis(4-fluorophenyl)-5-(4-pyridyl)pyrazolo[3,4-b]pyridin-2-yl]-1-(morpholin-4-yl)propan-1-one;
3-[4,6-bis(4-fluorophenyl)-5-(4-pyridyl)pyrazolo[3,4-b]pyridin-1-yl]-N-propylpropionamide;
3-[4,6-bis(4-fluorophenyl)-5-(4-pyridyl)pyrazolo[3,4-b]pyridin-1-yl]-1-(morpholin-1-yl)propan-1-one;
4,6-bis(4-fluorophenyl)-2-(4-methylsulfanylphenyl)-5-(4-pyridyl)pyrazolo[3,4-b]pyridine;
4,6-bis(4-fluorophenyl)-1-(4-methylsulfanylphenyl)-5-(4-pyridyl)pyrazolo[3,4-b]pyridine;
4,6-bis(4-fluorophenyl)-2-(4-methylsulfinylphenyl)-5-(4-pyridyl)pyrazolo[3,4-b]pyridine;
4,6-bis(4-fluorophenyl)-2-(4-methylsulfonylphenyl)-5-(4-pyridyl)pyrazolo[3,4-b]pyridine;
4,6-bis(4-fluorophenyl)-1-(4-methylsulfinylphenyl)-5-(4-pyridyl)pyrazolo[3,4-b]pyridine;
4,6-bis(4-fluorophenyl)-2-(4-methylsulfinylbenzyl)-5-(4-pyridyl)pyrazolo[3,4-b]pyridine;
4,6-bis(4-fluorophenyl)-2-(4-methylsulfonylbenzyl)-5-(4-pyridyl)pyrazolo[3,4-b]pyridine;
4,6-bis(4-fluorophenyl)-1-(4-methylsulfinylbenzyl)-5-(4-pyridyl)pyrazolo[3,4-b]pyridine;
4,6-bis(4-fluorophenyl)-1-(4-methylsulfonylbenzyl)-5-(4-pyridyl)pyrazolo[3,4-b]pyridine;
3-chloro-4,6-bis(4-fluorophenyl)-5-(4-pyridyl)-1H-pyrazolo[3,4-b]pyridine;
3-bromo-4,6-bis(4-fluorophenyl)-5-(4-pyridyl)-1H-pyrazolo[3,4-b]pyridine;
4,6-bis(4-fluorophenyl)-5-(4-pyridyl)-1H-pyrazolo[3,4-b]pyridine-3-carbonitrile;
3-bromo-4,6-bis(4-fluorophenyl)-1-methyl-5-(4-pyridyl)pyrazolo[3,4-b]pyridine;
4,6-bis(4-fluorophenyl)-5-(4-pyridyl)-1H-pyrazolo[3,4-b]pyridine-3-carboxamide;
3-aminomethyl-4,6-bis(4-fluorophenyl)-5-(4-pyridyl)-1H-pyrazolo[3,4-b]pyridine;
4,6-bis(4-fluoro-3-nitrophenyl)-5-(4-pyridyl)-1H-pyrazolo[3,4-b]pyridine;
3-amino-6-(4-fluorophenyl)-5-(4-pyridyl)-1H-pyrazolo[3,4-b]pyridine;
3-amino-6-(4-fluorophenyl)-1-methyl-5-(4-pyridyl)pyrazolo[3,4-b]pyridine;
4-[6-(4-fluorophenyl)-5-(4-pyridyl)-1H-pyrazolo[3,4-b]pyridin-4-yl]phenol;
2-(2,2-diethoxyethyl)-4,6-bis(4-fluorophenyl)-5-(4-pyridyl)pyrazolo[3,4-b]pyridine;
1-(2,2-diethoxyethyl)-4,6-bis(4-fluorophenyl)-5-(4-pyridyl)pyrazolo[3,4-b]pyridine;
4,6-bis(4-fluorophenyl)-1-methyl-5-(4-pyridyl)pyrazolo[3,4-b]pyridine-3-carbonitrile;
3-bromo-6-(4-fluorophenyl)-5-(4-pyridyl)-1H-pyrazolo[3,4-b]pyridine;
6-fluorophenyl-5-(4-pyridyl)-1H-pyrazolo[3,4-b]pyridine;
N-methyl-[3-[4,6-bis(4-fluorophenyl)-5-(4-pyridyl)pyrazolo[3,4-b]pyridin-2-yl]propyl]amine;
[4,6-bis(4-fluorophenyl)-5-(4-pyridyl)pyrazolo[3,4-b]pyridin-2-yl]methanol;
2-[4,6-bis(4-fluorophenyl)-5-(4-pyridyl)pyrazolo[3,4-b]pyridin-2-yl]-N,N-dimethylacetamide;
2-[4,6-bis(4-fluorophenyl)-5-(4-pyridyl)pyrazolo[3,4-b]pyridin-1-yl]-N,N-dimethylacetamide;

4,6-bis(4-fluorophenyl)-2-[2-(2-methoxyethoxy)ethyl]-5-(4-pyridyl)pyrazolo[3,4-b]pyridine;
4,6-bis(4-fluorophenyl)-1-[2-(2-methoxyethoxy)ethyl]-5-(4-pyridyl)pyrazolo[3,4-b]pyridine;
4,6-bis(4-fluorophenyl)-2-[3-(morpholin-4-yl)propyl]-5-(4-pyridyl)pyrazolo[3,4-b]pyridine;
4,6-bis(6-chloropyridin-3-yl)-2-methyl-5-(4-pyridyl)pyrazolo[3,4-b]pyridine;
4,6-bis(6-chloropyridin-3-yl)-1-methyl-5-(4-pyridyl)pyrazolo[3,4-b]pyridine;
4,6-bis(6-chloropyridin-3-yl)-3-methyl-5-(4-pyridyl)-1H-pyrazolo[3,4-b]pyridine;
4,6-bis(6-methylpyridin-3-yl)-5-(4-pyridyl)-1H-pyrazolo[3,4-b]pyridine;
4,6-bis(4-fluorophenyl)-2-(2-phtalimidoethyl)-5-(4-pyridyl)pyrazolo[3,4-b]pyridine;
2-(2-aminoethyl)-4,6-bis(4-fluorophenyl)-5-(4-pyridyl)pyrazolo[3,4-b]pyridine;
2-[4,6-bis(4-fluorophenyl)-5-(4-pyridyl)pyrazolo[3,4-b]pyridin-2-yl]ethanol;
6-(4-fluorophenyl)-2-methyl-5-(4-pyridyl)pyrazolo[3,4-b]pyridine;
4,6-bis(4-fluorophenyl)-2-(3-phtalimidopropyl)-5-(4-pyridyl)pyrazolo[3,4-b]pyridine;
2-[4,6-bis(4-fluorophenyl)-5-(4-pyridyl)pyrazolo[3,4-b]pyridin-2-yl]acetaldehyde;
2-(3-aminopropyl)-4,6-bis(4-fluorophenyl)-5-(4-pyridyl)pyrazolo[3,4-b]pyridine;
N-[4,6-bis(4-fluorophenyl)-5-(4-pyridyl)-1H-pyrazolo[3,4-b]pyridin-3-ylmethyl]-1-(tert-butoxycarbonyl)piperidine-4-carboxamide;
N-[4,6-bis(4-fluorophenyl)-5-(4-pyridyl)-1H-pyrazolo[3,4-b]pyridin-3-ylmethyl]-1H-piperidine-4-carboxamide;
2-(3-benzyloxypropyl)-4,6-bis(4-fluorophenyl)-5-(4-pyridyl)pyrazolo[3,4-b]pyridine;
1-(3-benzyloxypropyl)-4,6-bis(4-fluorophenyl)-5-(4-pyridyl)pyrazolo[3,4-b]pyridine;
N,N-diethyl-[2-[4,6-bis(4-fluorophenyl)-5-(4-pyridyl)pyrazolo[3,4-b]pyridin-2-yl]ethyl]amine;
N,N-diethyl-[2-[4,6-bis(4-fluorophenyl)-5-(4-pyridyl)pyrazolo[3,4-b]pyridin-1-yl]ethyl]amine;
4,6-bis(4-fluorophenyl)-5-(4-pyridyl)-2-(3-pyridylmethyl)pyrazolo[3,4-b]pyridine;
4,6-bis(4-fluorophenyl)-5-(4-pyridyl)-1-pyridin-3-ylmethylpyrazolo[3,4-b]pyridine;
N,N-dimethyl-[3-[4,6-bis(4-fluorophenyl)-5-(4-pyridyl)-pyrazolo[3,4-b]pyridin-2-yl]propyl]amine;
N,N-dimethyl-[3-[4,6-bis(4-fluorophenyl)-5-(4-pyridyl)-pyrazolo[3,4-b]pyridin-1-yl]propyl]amine;
1-[2-[4,6-bis(4-fluorophenyl)-5-(4-pyridyl)pyrazolo[3,4-b]pyridin-2-yl]ethyl]piperidin-4-ol;
3-[4,6-bis(4-fluorophenyl)-5-(4-pyridyl)pyrazolo[3,4-b]pyridin-2-yl]-2-hydroxypropan-1-ol;
3-[4,6-bis(4-fluorophenyl)-5-(4-pyridyl)pyrazolo[3,4-b]pyridin-1-yl]-2-hydroxypropan-1-ol;
4,6-bis(4-fluorophenyl)-5-(4-pyridyl)-2-(4-pyridylmethyl)pyrazolo[3,4-b]pyridine;
4,6-bis(4-fluorophenyl)-5-(4-pyridyl)-1-(4-pyridylmethyl)pyrazolo[3,4-b]pyridine;
N-(tert-butoxycarbonyl)-[1-[3-[4,6-bis(4-fluorophenyl)-5-(4-pyridyl)pyrazolo[3,4-b]pyridin-2-yl]propyl]piperidin-4-yl]amine;
2-[1-(tert-butoxycarbonyl)piperidin-4-yl]-6-(4-fluorophenyl)-5-(4-pyridyl)pyrazolo[3,4-b]pyridine;
1-[1-(tert-butoxycarbonyl)piperidin-4-yl]-6-(4-fluorophenyl)-5-(4-pyridyl)pyrazolo[3,4-b]pyridine;
3-methyl-4,6-bis(6-methylpyridin-3-yl)-5-(4-pyridyl)-1H-pyrazolo[3,4-b]pyridine;
1-[3-[4,6-bis(4-fluorophenyl)-5-(4-pyridyl)pyrazolo[3,4-b]pyridin-2-yl]-propyl]piperidin-4-one;
N-(tert-butoxycarbonyl)-[1-[2-[4,6-bis(4-fluorophenyl)-5-(4-pyridyl)pyrazolo[3,4-b]pyridin-2-yl]ethyl]piperidin-4-yl]amine;
N-methyl-[1-[2-[4,6-bis(4-fluorophenyl)-5-(4-pyridyl)-pyrazolo[3,4-b]pyridin-2-yl]ethyl]piperidin-4-yl]amine;
[1-[3-[4,6-bis(4-fluorophenyl)-5-(4-pyridyl)pyrazolo[3,4-b]pyridin-2-yl]propyl]piperidin-4-yl]amine;
2-[1-[2-[4,6-bis(4-fluorophenyl)-5-(4-pyridyl)pyrazolo[3,4-b]pyridin-2-yl]ethyl]piperidin-4-yl]ethanol;
[1-[2-[4,6-bis(4-fluorophenyl)-5-(4-pyridyl)pyrazolo[3,4-b]pyridin-2-yl]ethyl]piperidin-4-yl]amine;
6-(4-fluorophenyl)-2-(4-piperidyl)-5-(4-pyridyl)pyrazolo[3,4-b]pyridine;
6-(4-fluorophenyl)-1-(4-piperidyl)-5-(4-pyridyl)pyrazolo[3,4-b]pyridine;
3-amino-5-[2-(methylsulfanyl)pyrimidin-4-yl]-6-[3-(trifluoromethyl)phenyl]-1H-pyrazolo[3,4-b]pyridine;
2-[3-[1-(4-tert-butoxycarbonyl)piperazin-1-yl]propyl]-4,6-bis(4-fluorophenyl)-5-(4-pyridyl)pyrazolo[3,4-b]pyridine;
4,6-bis(4-fluorophenyl)-2-[3-(1-piperazin-1-yl)propyl]-5-(4-pyridyl)pyrazolo[3,4-b]pyridine;
5-[2-(methylsulfanyl)pyrimidin-4-yl]-6-[3-(trifluoromethyl)phenyl]-1H-pyrazolo[3,4-b]pyridine;
5-[2-(methylsulfonyl)pyrimidin-4-yl]-6-[3-(trifluoromethyl)phenyl]-1H-pyrazolo[3,4-b]pyridine;
(1S)-N-(1-phenylethyl)-[4-[6-[3-(trifluoromethyl)phenyl]-1H-pyrazolo[3,4-b]pyridin-5-yl]pyrimidin-2-yl]amine;
1-[3-[4,6-bis(4-fluorophenyl)-5-(4-pyridyl)pyrazolo[3,4-b]pyridin-2-yl]propyl]piperidin-4-ol;
2-[1-[3-[4,6-bis(4-fluorophenyl)-5-(4-pyridyl)pyrazolo[3,4-b]pyridin-2-yl]propyl]piperidin-4-yl]ethanol;
4,6-bis(4-fluorophenyl)-3-(4-piperidyl)-5-(4-pyridyl)-1H-pyrazolo[3,4-b]pyridine;
6-(4-fluorophenyl)-5-(4-pyridyl)-1H-pyrazolo[3,4-b]pyridine-3-carbonitrile;
2-[2-[[1-(tert-butoxycarbonyl)piperidin-4-yl]amino]ethyl]-4,6-bis(4-fluorophenyl)-5-(4-pyridyl)pyrazolo[3,4-b]pyridine;
4,6-bis(4-fluorophenyl)-2-[2-[(4-piperidyl)amino]ethyl]-5-(4-pyridyl)pyrazolo[3,4-b]pyridine;
N-(2-methoxyethyl)-[2-[4,6-bis(4-fluorophenyl)-5-(4-pyridyl)pyrazolo[3,4-b]pyridin-2-yl]ethyl]amine;
1-[4-[2-[4,6-bis(4-fluorophenyl)-5-(4-pyridyl)pyrazolo[3,4-b]pyridin-2-yl]ethyl]piperazin-1-yl]ethanone;
3-[4,6-diphenyl-5-(4-pyridyl)pyrazolo[3,4-b]pyridin-2-yl]propan-1-ol;
3-[4,6-diphenyl-5-(4-pyridyl)pyrazolo[3,4-b]pyridin-1-yl]propan-1-ol;
2-ethyl-4,6-diphenyl-5-(4-pyridyl)pyrazolo[3,4-b]pyridine;
1-ethyl-4,6-diphenyl-5-(4-pyridyl)pyrazolo[3,4-b]pyridine;
4,6-diphenyl-2-(2-phtalimidoethyl)-5-(4-pyridyl)pyrazolo[3,4-b]pyridine;
2-(2-aminoethyl)-4,6-diphenyl-5-(4-pyridyl)pyrazolo[3,4-b]pyridine;
2-allyl-4,6-bis(4-fluorophenyl)-5-(4-pyridyl)pyrazolo[3,4-b]pyridine;
1-allyl-4,6-bis(4-fluorophenyl)-5-(4-pyridyl)pyrazolo[3,4-b]pyridine;

1-[2-[4,6-bis(4-fluorophenyl)-5-(4-pyridyl)pyrazolo[3,4-b]pyridin-2-yl]ethyl]piperidin-4-one;
3-aminomethyl-6-(4-fluorophenyl)-5-(4-pyridyl)-1H-pyrazolo[3,4-b]pyridine;
3-amino-6-(4-fluorophenyl)-4-methyl-5-(4-pyridyl)-1H-pyrazolo[3,4-b]pyridine;
3-[N-[2-[4,6-bis(4-fluorophenyl)-5-(4-pyridyl)pyrazolo[3,4-b]pyridin-2-yl]ethyl]amino]propan-1-ol;
N-ethyl-[2-[4,6-bis(4-fluorophenyl)-5-(4-pyridyl)pyrazolo[3,4-b]pyridin-2-yl]ethyl]amine;
2-[N-[2-[4,6-bis(4-fluorophenyl)-5-(4-pyridyl)pyrazolo[3,4-b]pyridin-2-yl]ethyl]amino]ethanol;
N-[(2-pyridyl)methyl]-[2-[4,6-bis(4-fluorophenyl)-5-(4-pyridyl)pyrazolo[3,4-b]pyridin-2-yl]ethyl]amine;
N-[(2-thienyl)methyl]-[2-[4,6-bis(4-fluorophenyl)-5-(4-pyridyl)pyrazolo[3,4-b]pyridin-2-yl]ethyl]amine;
1-[2-[4,6-bis(4-fluorophenyl)-5-(4-pyridyl)pyrazolo[3,4-b]pyridin-2-yl]ethyl]piperidine-4-carboxamide;
4,6-bis(4-fluorophenyl)-2-[2-(pyrrolidin-1-yl)ethyl]-5-(4-pyridyl)pyrazolo[3,4-b]pyridine;
(3R)-1-[2-[4,6-bis(4-fluorophenyl)-5-(4-pyridyl)pyrazolo[3,4-b]pyridin-2-yl]ethyl]pyrrolidin-3-ol;
2-[N-[2-[4,6-bis(4-fluorophenyl)-5-(4-pyridyl)pyrazolo[3,4-b]pyridin-2-yl]ethyl]-N-methylamino]ethanol;
4,6-bis(4-fluorophenyl)-5-(4-pyridyl)-2-[2-(1,2,3,4-tetrahydroisoquinolin-2-yl)ethyl]pyrazolo[3,4-b]pyridine;
4,6-bis(4-fluorophenyl)-2-[2-(4-phenylpiperazin-1-yl)ethyl]-5-(4-pyridyl)pyrazolo[3,4-b]pyridine;
4,6-bis(4-fluorophenyl)-2-[2-[4-(1-piperidyl)piperidin-1-yl]ethyl]-5-(4-pyridyl)pyrazolo[3,4-b]pyridine;
3-[N-[2-[4,6-bis(4-fluorophenyl)-5-(4-pyridyl)pyrazolo[3,4-b]pyridin-2-yl]ethyl]-N-methylamino]propononitrue;
N-methyl-[2-[4,6-bis(4-fluorophenyl)-5-(4-pyridyl)pyrazolo[3,4-b]pyridin-2-yl]ethyl]amine;
2-[2-[4-(tert-butoxycarbonyl)piperazin-1-yl]ethyl]-4,6-bis(4-fluorophenyl)-5-(4-pyridyl)pyrazolo[3,4-b]pyridine;
4,6-bis(4-fluorophenyl)-2-[2-(piperazin-1-yl)ethyl]-5-(4-pyridyl)pyrazolo[3,4-b]pyridine;
4,6-bis(4-fluorophenyl)-5-(4-pyridyl)-2-vinylpyrazolo[3,4-b]pyridine;
2-[N-[2-[4,6-bis(4-fluorophenyl)-5-(4-pyridyl)pyrazolo[3,4-b]pyridin-2-yl]ethyl]-N-(2-hydroxyethyl)amino]ethanol;
N-cyclopropyl-[2-[4,6-bis(4-fluorophenyl)-5-(4-pyridyl)pyrazolo[3,4-b]pyridin-2-yl]ethyl]amine;
N-[2-[4,6-bis(4-fluorophenyl)-5-(4-pyridyl)pyrazolo[3,4-b]pyridin-2-yl]ethyl]acetamide;
N-[2-[4,6-bis(4-fluorophenyl)-5-(4-pyridyl)pyrazolo[3,4-b]pyridin-2-yl]ethyl]-n'-isopropylurea;
N-[2-[4,6-bis(4-fluorophenyl)-5-(4-pyridyl)pyrazolo[3,4-b]pyridin-2-yl]ethyl]methanesulfonamide;
6-(4-fluorophenyl)-4-(4-piperidyl)-5-(4-pyridyl)-1H-pyrazolo[3,4-b]pyridine;
6-(4-fluorophenyl)-4-(2-furyl)-5-(4-pyridyl)-1H-pyrazolo[3,4-b]pyridine;
6-(4-fluorophenyl)-4-(1H-imidazol-4-yl)-5-(4-pyridyl)-1H-pyrazolo[3,4-b]pyridine;
4-(5-bromothien-2-yl)-6-(4-fluorophenyl)-5-(4-pyridyl)-1H-pyrazolo[3,4-b]pyridine;
4,6-bis(4-fluorophenyl)-5-(2-methylsulfanylpyrimidin-4-yl)-1H-pyrazolo[3,4-b]pyridine;
5-(2-chloropyridin-4-yl)-4,6-bis(4-fluorophenyl)-1H-pyrazolo[3,4-b]pyridine;
6-(4-fluorophenyl)-4-(2-phenylethyl)-5-(4-pyridyl)-1H-pyrazolo[3,4-b]pyridine;
4-(6-chloropyridin-3-yl)-6-(4-fluorophenyl)-5-(4-pyridyl)-1H-pyrazolo[3,4-b]pyridine;
4-(3,4-dichlorophenyl)-1-ethyl-6-(4-fluorophenyl)-5-(4-pyridyl)pyrazolo[3,4-b]pyridine;
6-(4-fluorophenyl)-4-(1-methylpiperidin-4-yl)-5-(4-pyridyl)-1H-pyrazolo[3,4-b]pyridine;
3-amino-6-(4-fluorophenyl)-5-(2-methylsulfanylpyrimidin-4-yl)-1H-pyrazolo[3,4-b]pyridine;
6-(4-fluorophenyl)-5-(2-methylsulfanylpyrimidin-4-yl)-1H-pyrazolo[3,4-b]pyridine;
4,6-diphenyl-5-(4-pyridyl)-2-[2-(tetrahydropyran-2-yloxy)ethyl]pyrazolo[3,4-b]pyridine;
6-(4-fluorophenyl)-4-(2-furyl)-2-methyl-5-(4-pyridyl)pyrazolo[3,4-b]pyridine;
6-(4-fluorophenyl)-2-methyl-4-(1-methyl-1H-imidazol-4-yl)-5-(4-pyridyl)pyrazolo[3,4-b]pyridine;
6-(4-fluorophenyl)-5-(2-methylsulfanylpyrimidin-4-yl)-2-[2-(tetrahydropyran-2-yloxy)ethyl]pyrazolo[3,4-b]pyridine;
6-(4-fluorophenyl)-5-(2-methylsulfanylpyrimidin-4-yl)-2-[3-(tetrahydropyran-2-yloxy)propyl]pyrazolo[3,4-b]pyridine;
4,6-bis(4-fluorophenyl)-5-(2-methylsulfanylpyrimidin-4-yl)-2-[3-(tetrahydropyran-2-yloxy)propyl]pyrazolo[3,4-b]pyridine;
4-(5-bromothien-2-yl)-6-(4-fluorophenyl)-2-methyl-5-(4-pyridyl)-1H-pyrazolo[3,4-b]pyridine;
6-(4-fluorophenyl)-2-methyl-5-(2-methylsulfanylpyrimidin-4-yl)pyrazolo[3,4-b]pyridine;
5-(2-chloropyridin-4-yl)-4,6-bis(4-fluorophenyl)-2-methylpyrazolo[3,4-b]pyridine;
6-(4-fluorophenyl)-4-(2-phenylethyl)-5-(4-pyridyl)-2-[3-(tetrahydropyran-2-yloxy)propyl]pyrazolo[3,4-b]pyridine;
4-(6-chloropyridin-3-yl)-6-(4-fluorophenyl)-5-(4-pyridyl)-2-[3-(tetrahydropyran-2-yloxy)propyl]pyrazolo[3,4-b]pyridine;
4-(6-chloropyridin-3-yl)-6-(4-fluorophenyl)-2-methyl-5-(4-pyridyl)pyrazolo[3,4-b]pyridine;
5-(2-methylsulfanyl pyrimidin-4-yl)-2-[3-(tetrahydropyran-2-yloxy)propyl]-6-(3-trifluoromethylphenyl)pyrazolo[3,4-b]pyridine;
6-(4-fluorophenyl)-2-methyl-5-(4-pyridyl)-4-[5-(3-pyridyl)thien-2-yl]pyrazolo[3,4-b]pyridine;
2-[4,6-diphenyl-5-(4-pyridyl)pyrazolo[3,4-b]pyridin-2-yl]ethanol;
3-[5-(2-methylsulfanylpyrimidin-4-yl)-6-(3-trifluoromethyl phenyl)pyrazolo[3,4-b]pyridin-2-yl]propan-1-ol;
2-[6-(4-fluorophenyl)-5-(2-methylsulfanylpyrimidin-4-yl)pyrazolo[3,4-b]pyridin-2-yl]ethanol;
3-[6-(4-fluorophenyl)-5-(2-methylsulfanylpyrimidin-4-yl)pyrazolo[3,4-b]pyridin-2-yl]propan-1-ol;
3-[4,6-bis(4-fluorophenyl)-5-(2-methylsulfanylpyrimidin-4-yl)pyrazolo[3,4-b]pyridin-2-yl]propan-1-ol;
3-[6-(4-fluorophenyl)-4-(2-phenylethyl)-5-(4-pyridyl)pyrazolo[3,4-b]pyridin-2-yl]propan-1-ol;
3-[4-(6-chloropyridin-3-yl)-6-(4-fluorophenyl)-5-(4-pyridyl)pyrazolo[3,4-b]pyridin-2-yl]propan-1-ol;
6-(4-fluorophenyl)-2-methyl-5-(2-methylsulfonylpyrimidin-4-yl)pyrazolo[3,4-b]pyridine;
3-[5-(2-methylsulfonylpyrimidin-4-yl)-6-(3-trifluoromethylphenyl)pyrazolo[3,4-b]pyridin-2-yl]propan-1-ol;
2-[6-(4-fluorophenyl)-5-(2-methylsulfonylpyrimidin-4-yl)pyrazolo[3,4-b]pyridin-2-yl]ethanol;

3-[6-(4-fluorophenyl)-5-(2-methylsulfonylpyrimidin-4-yl)pyrazolo[3,4-b]pyridin-2-yl]propan-1-ol;
3-[4,6-bis(4-fluorophenyl)-5-(2-methylsulfonylpyrimidin-4-yl)pyrazolo[3,4-b]pyridin-2-yl]propan-1-ol;
N-cyclopropylmethyl-[4-[6-[3-(trifluoromethyl)phenyl]-1H-pyrazolo[3,4-b]pyridin-5-yl]pyrimidin-2-yl]amine;
(1S)-3-[5-[2-(1-phenylethylamino)pyrimidin-4-yl]-6-(3-trifluoromethylphenyl)pyrazolo[3,4-b]pyridin-2-yl]propan-1-ol;
N-cyclopropylmethyl-[4-[6-(4-fluorophenyl)-2-methylpyrazolo[3,4-b]pyridin-5-yl]pyrimidin-2-yl]amine;
2-[5-[2-[(cyclopropylmethyl)amino]pyrimidin-4-yl]-6-(4-fluorophenyl)pyrazolo[3,4-b]pyridin-2-yl]ethanol;
3-[5-[2-[(cyclopropylmethyl)amino]pyrimidin-4-yl]-6-(4-fluorophenyl)pyrazolo[3,4-b]pyridin-2-yl]propan-1-ol;
3-[5-[2-[(cyclopropylmethyl)amino]pyrimidin-4-yl]-4,6-bis(4-fluorophenyl)pyrazolo[3,4-b]pyridin-2-yl]propan-1-ol;
4-[4-[4,6-bis(4-fluorophenyl)-2-methylpyrazolo[3,4-b]pyridin-5-yl]pyridin-2-ylamino]benzenesulfonamide;
4,6-bis(4-fluorophenyl)-5-(4-pyridyl)pyrazolo[3,4-b]pyridin-3-ol;
6-(4-fluorophenyl)-4-(3H-imidazol-4-yl)-5-(4-pyridyl)-1H-pyrazolo[3,4-b]pyridine;
6-(4-fluorophenyl)-4-(1H-pyrazol-3-yl)-5-(4-pyridyl)-1H-pyrazolo[3,4-b]pyridine;
3-[6-(4-fluorophenyl)-5-(4-pyridyl)-1H-pyrazolo[3,4-b]pyridin-4-yl]phenol;
4-cyclopropyl-6-(4-fluorophenyl)-5-(4-pyridyl)-1H-pyrazolo[3,4-b]pyridine;
6-(4-fluorophenyl)-4-(5-methylfuran-2-yl)-5-(4-pyridyl)-1H-pyrazolo[3,4-b]pyridine;
4-(5-bromofuran-2-yl)-6-(4-fluorophenyl)-5-(4-pyridyl)-1H-pyrazolo[3,4-b]pyridine;
4-(4-benzyloxyphenyl)-6-(4-fluorophenyl)-5-pyrimidin-4-yl-1H-pyrazolo[3,4-b]pyridine;
4-(4-benzyloxyphenyl)-6-(4-fluorophenyl)-5-(2-methylsulfanylpyrimidin-4-yl)-1H-pyrazolo[3,4-b]pyridine;
6-(4-fluorophenyl)-4-propyl-5-(4-pyridyl)-1H-pyrazolo[3,4-b]pyridine;
4-(3-benzyloxyphenyl)-6-(4-fluorophenyl)-5-(4-pyridyl)-1H-pyrazolo[3,4-b]pyridine;
5-(2-chloropyridin-4-yl)-6-(4-fluorophenyl)-1H-pyrazolo[3,4-b]pyridine;
4-[6-(4-fluorophenyl)-5-(4-pyridyl)-1H-pyrazolo[3,4-b]pyridin-4-yl]butan-1-ol;
4-benzyl-6-(4-fluorophenyl)-5-(4-pyridyl)-1H-pyrazolo[3,4-b]pyridine;
4-(4-benzyloxyphenyl)-6-(4-fluorophenyl)-5-(4-pyridyl)-1H-pyrazolo[3,4-b]pyridine;
4,6-bis(4-fluorophenyl)-5-pyrimidin-4-yl-1H-pyrazolo[3,4-b]pyridine;
[(2S)-2-[4,6-bis(4-fluorophenyl)-5-(4-pyridyl)pyrazolo[3,4-b]pyridin-2-yl]ethyl]pyrroldine-2-carboxamide;
2-[2-(4,6-diphenyl-5-(4-pyridyl)pyrazolo[3,4-b]pyridin-2-yl)ethylamino]ethanol;
6-(4-fluorophenyl)-2-methyl-4-(3-pyridyl)-5-(4-pyridyl)pyrazolo[3,4-b]pyridine;
6-(4-fluorophenyl)-3-methyl-5-(2-methylsulfanylpyrimidin-4-yl)-1H-pyrazolo[3,4-b]pyridine;
3-amino-5-(2-methylsulfanylpyrimidin-4-yl)-6-phenyl-1H-pyrazolo[3,4-b]pyridine;
5-(2-methylsulfanylpyrimidin-4-yl)-6-phenyl-1H-pyrazolo[3,4-b]pyridine;
6-(4-fluorophenyl)-4-methyl-5-(2-methylsulfanylpyrimidin-4-yl)-1H-pyrazolo[3,4-b]pyridine;
5-(2-methoxypyrimidin-4-yl)-6-(3-trifluoromethylphenyl)-1H-pyrazolo[3,4-b]pyridine;
N-[2-[4,6-(diphenyl)-5-(4-pyridyl)pyrazolo[3,4-b]pyridin-2-yl]ethyl]acetamide;
N-[3-[4,6-bis(4-fluorophenyl)-5-(4-pyridyl)pyrazolo[3,4-b]pyridin-2-yl]propyl]acetamide;
N-[2-(4,6-diphenyl-5-(4-pyridyl)pyrazolo[3,4-b]pyridin-2-yl)ethyl]-N-(2-hydroxyethyl)acetamide;
N-[2-[4,6-bis(4-fluorophenyl)-5-(4-pyridyl)pyrazolo[3,4-b]pyridin-2-yl]ethyl]propionamide;
N-[3-[4,6-bis(4-fluorophenyl)-5-(4-pyridyl)pyrazolo[3,4-b]pyridin-2-yl]propyl]methanesulfonamide;
5-(2-aminopyrimidin-4-yl)-6-(3-trifluoromethylphenyl)-1H-pyrazolo[3,4-b]pyridine;
N-[5-(2-methylsulfanylpyrimidin-4-yl)-6-(3-trifluoromethylphenyl)-1H-pyrazolo[3,4-b]pyridin-3-yl]acetamide;
N-cyclopropylmethyl-[4-[3-benzyloxycarbonylamino-6-(3-trifluoromethylphenyl)-1H-pyrazolo[3,4-b]pyridin-5-yl]pyrimidin-2-yl]amine;
N-[2-[4,6-bis(4-fluorophenyl)-5-(4-pyridyl)pyrazolo[3,4-b]pyridin-2-yl]ethyl]-2-hydroxyacetamide;
N-[2-[4,6-bis(4-fluorophenyl)-5-(4-pyridyl)pyrazolo[3,4-b]pyridin-2-yl]ethyl]piperidine-4-carboxamide;
N-[2-[4,6-bis(4-fluorophenyl)-5-(4-pyridyl)pyrazolo[3,4-b]pyridin-2-yl]ethyl]-2-(methylamino)acetamide;
N-[2-[4,6-bis(4-fluorophenyl)-5-(4-pyridyl)pyrazolo[3,4-b]pyridin-2-yl]ethyl]-2-(2-hydroxyethylamino)acetamide;
N-[2-[4,6-bis(4-fluorophenyl)-5-(4-pyridyl)pyrazolo[3,4-b]pyridin-2-yl]ethyl]nicotinamide;
4-(4-benzyloxyphenyl)-6-(4-fluorophenyl)-2-methyl-5-(4-pyridyl)pyrazolo[3,4-b]pyridine;
6-(4-fluorophenyl)-5-(2-methylsulfanylpyrimidin-4-yl)-2-methylpyrazolo[3,4-b]pyridine;
6-(4-fluorophenyl)-2,4-dimethyl-5-(4-pyridyl)pyrazolo[3,4-b]pyridine;
4-(4-benzyloxyphenyl)-6-(4-fluorophenyl)-2-methyl-5-(2-methylsulfanylpyrimidin-4-yl)pyrazolo[3,4-b]pyridine;
2-(1-benzylpyrrolidin-2-ylmethyl)-4,6-bis(4-fluorophenyl)-5-(4-pyridyl)pyrazolo[3,4-b]pyridine;
4-(4-benzyloxyphenyl)-6-(4-fluorophenyl)-2-methyl-5-pyrimidin-4-ylpyrazolo[3,4-b]pyridine;
6-(4-fluorophenyl)-2-methyl-4-(5-methylfuran-2-yl)-5-(4-pyridyl)pyrazolo[3,4-b]pyridine;
4-(5-bromofuran-2-yl)-6-(4-fluorophenyl)-2-methyl-5-(4-pyridyl)pyrazolo[3,4-b]pyridine;
6-(4-fluorophenyl)-2-methyl-4-propyl-5-(4-pyridyl)pyrazolo[3,4-b]pyridine;
4-(3-benzyloxyphenyl)-6-(4-fluorophenyl)-2-methyl-5-(4-pyridyl)pyrazolo[3,4-b]pyridine;
6-(4-fluorophenyl)-2-methyl-4-(2-phenylethyl)-5-(4-pyridyl)pyrazolo[3,4-b]pyridine;
5-(2-chloropyridin-4-yl)-6-(4-fluorophenyl)-2-methylpyrazolo[3,4-b]pyridine;
4-benzyl-6-(4-fluorophenyl)-2-methyl-5-(4-pyridyl)pyrazolo[3,4-b]pyridine;
4-[6-(4-fluorophenyl)-2-methyl-5-(4-pyridyl)pyrazolo[3,4-b]pyridin-4-yl]butan-1-ol;
4-[6-(4-fluorophenyl)-2-methyl-5-(4-pyridyl)pyrazolo[3,4-b]pyridin-4-yl]phenol;
N-[6-(4-fluorophenyl)-5-(2-methylsulfanylpyrimidin-4-yl)-1H-pyrazolo[3,4-b]pyridin-3-yl]acetamide;
N-[5-[2-[(cyclopropylmethyl)amino]pyrimidin-4-yl]-6-(4-fluorophenyl)-1H-pyrazolo[3,4-b]pyridin-3-yl]acetamide;

3-[6-(4-fluorophenyl)-4-(2-furyl)-5-(4-pyridyl)pyrazolo [3,4-b]pyridin-2-yl]propan-1-ol;
2-[4-(4-benzyloxyphenyl)-6-(4-fluorophenyl)-5-(4-pyridyl)pyrazolo[3,4-b]pyridin-2-yl]ethanol; 3-[4-(4-benzyloxyphenyl)-6-(4-fluorophenyl)-5-(4-pyridyl)pyrazolo[3,4-b]pyridin-2-yl]propan-1-ol;
3-[6-(4-fluorophenyl)-4-(5-methylfuran-2-yl)-5-(4-pyridyl)pyrazolo[3,4-b]pyridin-2-yl]propan-1-ol;
3-[4-cyclopropyl-6-(4-fluorophenyl)-5-(4-pyridyl)pyrazolo[3,4-b]pyridin-2-yl]propan-1-ol;
3-[4-(5-bromothien-2-yl)-6-(4-fluorophenyl)-5-(4-pyridyl)pyrazolo[3,4-b]pyridin-2-yl]propan-1-ol;
3-[6-(4-fluorophenyl)-4-propyl-5-(4-pyridyl)pyrazolo[3,4-b]pyridin-2-yl]propan-1-ol;
3-[4,6-bis(4-fluorophenyl)-5-pyrimidin-4-ylpyrazolo[3,4-b]pyridin-2-yl]propan-1-ol;
3-[4-(3-benzyloxyphenyl)-6-(4-fluorophenyl)-5-(4-pyridyl)pyrazolo[3,4-b]pyridin-2-yl]propan-1-ol;
3-[4-benzyl-6-(4-fluorophenyl)-5-(4-pyridyl)pyrazolo[3,4-b]pyridin-2-yl]propan-1-ol;
(1S)-N-(1-phenylethyl)-[4-[6-(4-fluorophenyl)-3-methyl-1H-pyrazolo[3,4-b]pyridin-5-yl]pyrimidin-2-yl]amine;
N-cyclopropylmethyl-[4-[6-(4-fluorophenyl)-3-methyl-1H-pyrazolo[3,4-b]pyridin-5-yl]pyrimidin-2-yl]amine;
1-[4-[6-(4-fluorophenyl)-2-methylpyrazolo[3,4-b]pyridin-5-yl]pyrimidin-2-ylamino]propan-2-ol;
N-cyclopropylmethyl-[4-[6-phenyl-1H-pyrazolo[3,4-b]pyridin-5-yl]pyrimidin-2-yl]amine;
2-[4-[6-(4-fluorophenyl)-2-methylpyrazolo[3,4-b]pyridin-5-yl]pyrimidin-2-ylamino]propan-1-ol;
4-[4-[6-(4-fluorophenyl)-2-methyl-pyrazolo[3,4-b]pyridin-5-yl]pyrimidin-2-ylamino]butan-1-ol;
(1S)-N-(1-phenylethyl)-[4-[6-phenyl-1H-pyrazolo[3,4-b]pyridin-5-yl]pyrimidin-2-yl]amine;
N-(3-methoxypropyl)-[4-[6-(3-trifluoromethylphenyl)-1H-pyrazolo[3,4-b]pyridin-5-yl]pyrimidin-2-yl]amine;
3-[4-[6-(3-trifluoromethylphenyl)-1H-pyrazolo[3,4-b]pyridin-5-yl]pyrimidin-2-ylamino]propan-1-ol;
3-[4-[6-(4-fluorophenyl)-2-(3-hydroxypropyl)pyrazolo[3,4-b]pyridin-5-yl]pyrimidin-2-ylamino]propan-1-ol;
N-ethyl-[4-[6-(3-trifluoromethylphenyl)-1H-pyrazolo[3,4-b]pyridin-5-yl]pyrimidin-2-yl]amine;
N-benzyl-[4-[6-(3-trifluoromethylphenyl)-1H-pyrazolo[3,4-b]pyridin-5-yl]pyrimidin-2-yl]amine;
4-[5-[2-[(cyclopropylmethyl)amino]pyrimidin-4-yl]-6-(4-fluorophenyl)-2-methylpyrazolo[3,4-b]pyridin-4-yl]phenol;
4-[6-(4-fluorophenyl)-2-(3-hydroxypropyl)-5-(4-pyridyl)pyrazolo[3,4-b]pyridin-4-yl]phenol;
4-[6-(4-fluorophenyl)-2-methyl-5-pyrimidin-4-ylpyrazolo[3,4-b]pyridin-4-yl]phenol;
3-[6-(4-fluorophenyl)-2-(3-hydroxypropyl)-5-(4-pyridyl)pyrazolo[3,4-b]pyridin-4-yl]phenol;
3-[6-(4-fluorophenyl)-2-methyl-5-(4-pyridyl)pyrazolo[3,4-b]pyridin-4-yl]phenol;
4,6-bis(4-fluorophenyl)-5-(4-pyridyl)-2-(pyrrolidin-2-ylmethyl)pyrazolo[3,4-b]pyridine;
4-[4-[6-(4-fluorophenyl)-2-methylpyrazolo[3,4-b]pyridin-5-yl]pyridin-2-ylamino]benzenesulfonamide;
N-[5-[2-[(cyclopropylmethyl)amino]pyrimidin-4-yl]-6-(4-fluorophenyl)-1H-pyrazolo[3,4-b]pyridin-3-yl]acetamide 7-oxide; and
N-[6-(4-fluorophenyl)-5-(4-pyridyl)-1H-pyrazolo[3,4-b]pyridin-3-yl]isonicotinamide;
or a salt thereof.

31. Process for preparing a compound of formula I according to claim 1, which comprises:

(a) reacting a ketone of formula IV

wherein $R^1$ and $R^2$ have the same meaning as in claim 1, with an aminopyrazole of formula V and an aldehyde of formula VI

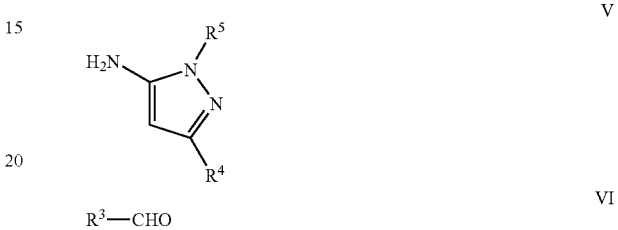

wherein $R^3$, $R^4$ and $R^5$ have the same meaning as in claim 1, to obtain a compound of formula I; or (b) reacting a ketone of formula IV or an enolate of formula VII

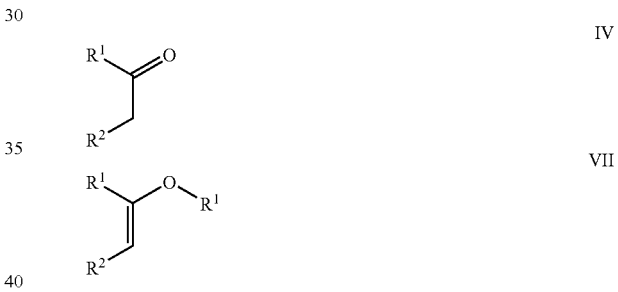

wherein $R^1$ and $R^2$ have the same meaning as in claim 1, with an aminopyrazole of formula Va

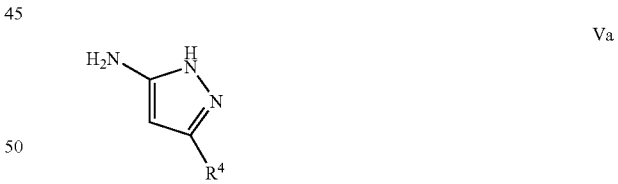

wherein $R^4$ has the same meaning as in claim 1, to obtain a compound of formula I wherein $R^5$ represents H and $R^3$ has the same meaning as $R^1$; or (c) treating a compound of formula XIX

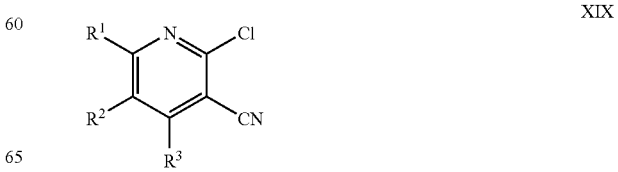

wherein $R^1$, $R^2$ and $R^3$ have the same meaning as in claim 1, with a hydrazine of formula VIIIa $$NH_2\text{—}NHR^5 \qquad \text{VIIIa}$$

wherein $R^5$ has the same meaning as in claim 1 to obtain a compound of formula I wherein $R^4$ represents $NH_2$; or (d) converting, in one or a plurality of steps, a compound of formula I into another compound of formula I.

32. The process of claim 31 which further comprises reacting said compound of formula I with a base or an acid to provide the corresponding salt.

33. A pharmaceutical composition which comprises an effective amount of a compound of formula I according to claim 1 or a pharmaceutically acceptable salt thereof and one or more pharmaceutically acceptable excipients.

* * * * *

UNITED STATES PATENT AND TRADEMARK OFFICE
CERTIFICATE OF CORRECTION

PATENT NO. : 7,468,376 B2
APPLICATION NO. : 10/547232
DATED : December 23, 2008
INVENTOR(S) : Almansa Rosales et al.

It is certified that error appears in the above-identified patent and that said Letters Patent is hereby corrected as shown below:

Title page (12), "Rosales et al." should be -- Almansa Rosales et al. --

Col. 38, lines 14-15, "3-[4,6-Bis(4-fluorophenyl)-5-(4-pyridyl)pyrazolo[3,4-b]pirridin-2-yl]propan-1-ol" should be -- 3-[4,6-Bis(4-fluorophenyl)-5-(4-pyridyl)pyrazolo[3,4-b]pyridin-2-yl]propan-1-ol --.

Col. 38, lines 50-51, "3-[4,6-Bis(4-fluorophenyl)-5-(4-pyridyl)pyrazolo[3,4-b]pirridin-2-yl]propan-1-ol" should be -- 3-[4,6-Bis(4-fluorophenyl)-5-(4-pyridyl)pyrazolo[3,4-b]pyridin-2-yl]propan-1-ol --

Claim 1, Col. 103, line 26, "'SR$^e$'" should be -- -SR$^e$' --

Claim 12, Col. 104, line 55, "H or R$^e$'" should be -- H or R$^e$ --

Col. 5, line 25, Col. 13, line 60, and Claim 31, col. 116, line 36, the Formula VII

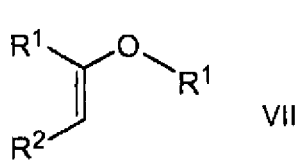  should be  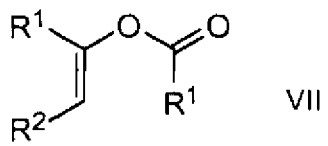

Signed and Sealed this

Seventh Day of July, 2009

JOHN DOLL
*Acting Director of the United States Patent and Trademark Office*